(12) United States Patent
Gu et al.

(10) Patent No.: US 11,459,323 B2
(45) Date of Patent: Oct. 4, 2022

(54) MONOCYCLIC β-LACTAM COMPOUND FOR TREATING BACTERIAL INFECTION

(71) Applicant: MEDSHINE DISCOVERY INC., Jiangsu (CN)

(72) Inventors: Lianghu Gu, Shanghai (CN); Wei Luo, Shanghai (CN); Zhigang Huang, Shanghai (CN); Charles Z. Ding, Shanghai (CN); Cheng Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 118 days.

(21) Appl. No.: 16/965,086

(22) PCT Filed: Jan. 29, 2019

(86) PCT No.: PCT/CN2019/073699
§ 371 (c)(1),
(2) Date: Jul. 27, 2020

(87) PCT Pub. No.: WO2019/144969
PCT Pub. Date: Aug. 1, 2019

(65) Prior Publication Data
US 2021/0115035 A1    Apr. 22, 2021

(30) Foreign Application Priority Data

Jan. 29, 2018 (CN) .......................... 201810084282.6
Mar. 12, 2018 (CN) .......................... 201810201654.9

(51) Int. Cl.
*C07D 417/14* (2006.01)
*A61P 31/04* (2006.01)

(52) U.S. Cl.
CPC ............ *C07D 417/14* (2013.01); *A61P 31/04* (2018.01)

(58) Field of Classification Search
CPC .............................. C07D 417/14; A61P 31/04
USPC ...................................................... 514/210.15
See application file for complete search history.

(56) References Cited

U.S. PATENT DOCUMENTS

| 5,290,929 A | 3/1994 | Koster et al. |
| 2015/0266867 A1 | 9/2015 | Aulakh et al. |

FOREIGN PATENT DOCUMENTS

| EP | 484881 A2 | 5/1992 |
| EP | 531976 A1 | 3/1993 |
| WO | WO-2002022613 A1 | 3/2002 |
| WO | WO-2007065288 A2 | 6/2007 |
| WO | WO-2008116813 A2 | 10/2008 |
| WO | WO-2010070523 A1 | 6/2010 |
| WO | WO-2013110643 A1 | 8/2013 |
| WO | WO-2015148379 A1 | 10/2015 |
| WO | WO-2017050218 A1 | 3/2017 |
| WO | WO-2017106064 A1 | 6/2017 |
| WO | WO-2017155765 A1 | 9/2017 |
| WO | WO-2017206947 A1 | 12/2017 |
| WO | WO-2018065636 A1 | 4/2018 |

OTHER PUBLICATIONS

Nature, 2017, 543, 15.
Clin. Inf. Dis., 2009, 48, 1-12.
Rev. Infect. Dis., 1985, 7, 579-593.
Apr. 28, 2020 International Search Report issued in International Patent Application No. PCT/CN2019/073699.

(Continued)

*Primary Examiner* — Kahsay Habte
(74) *Attorney, Agent, or Firm* — Harness, Dickey & Pierce, P.L.C.

(57) ABSTRACT

Disclosed are a class of new monocyclic β-lactam compounds, an isomer thereof or pharmaceutically acceptable salts thereof, and a pharmaceutical composition comprising the compounds, and the use of same in preparing drugs for treating diseases associated with bacterial infection. Specifically disclosed are the compounds as shown in formula (I') and formula (II'), isomers thereof or pharmaceutically acceptable salts thereof.

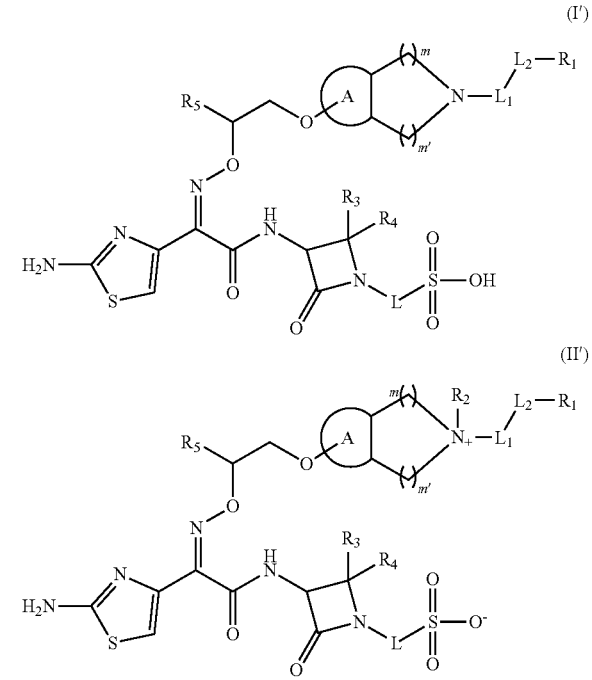

20 Claims, 2 Drawing Sheets

(56) References Cited

OTHER PUBLICATIONS

Apr. 28, 2020 Written Opinion of the International Searching Authority issued in International Patent Application No. PCT/CN2019/073699.
Berge et al., "Pharmaceutical Salts", *Journal of Pharmaceutical Science* 66: 1-19 (1977).
*Remington: Science and Practice of Pharmacy*, 21st Edition, Lippincott, Williams & Wilkins (2005).
Drugs Jul. 1997; 54 (1): 117-140, "*Cefpirome A Review of its Antibacterial Activity, Pharmacokinetic Properties and Clinical Efficacy in the Treatment of Severe Nosocomial Infections and Febrile Neutropenia*", L. R. Wiseman and H. M. Lamb, Adis International Limited, Auckland, New Zealand.
Bioorganic & Medicinal Chemistry 16 (2008) 1632-1647, "*A novel series of parenteral cephalosporins exhibiting potent activities against both Pseudomonas aeruginosa and other Gram-negative pathogens. Part 2: Synthesis and structure-activity relationships*", K. Yamawaki et al.
First Chinese Office Action issued in Chinese Patent Application No. 201980006879.1 dated Feb. 8, 2022.
Extended European Search Report issued in European Patent Application No. EP19743987.0 dated Nov. 17, 2020.

MONOCYCLIC β-LACTAM COMPOUND FOR TREATING BACTERIAL INFECTION

CROSS-REFERENCE TO RELATED APPLICATIONS

This application is a 371 National Phase of International Application No. PCT/CN2019/073699, filed Jan. 29, 2019, which claims the benefit of Chinese Patent Application No. CN 201810084282.6, filed Jan. 29, 2018 and Chinese Patent Application No. CN 201810201654.9, filed Mar. 12, 2018. The entire disclosures of the above applications are incorporated herein by reference.

FIELD OF INVENTION

The present invention relates to the field of medicine, and in particular to a class of monocyclic β-lactam compounds, an isomer thereof or pharmaceutically acceptable salts thereof, and a pharmaceutical composition comprising the compounds, and a use of same in preparing drugs for treating diseases associated with bacterial infection. Specifically it relates to compounds as shown in formula (I') or formula (II'), isomers thereof or pharmaceutically acceptable salts thereof.

PRIOR ARTS

Public health experts and officials generally believe that the emergence and spread of drug-resistant bacteria is one of the major public health issues in the $21^{st}$ century. The frequency of antimicrobial resistance and its relationship with serious infectious diseases have increased at an alarming rate. Resistance to nosocomial pathogens is becoming increasingly common and particularly disturbing. 50% to 60% of the more than 2 million nosocomial infections that occur in the United States each year are caused by antibiotic-resistant bacteria. The high rate of resistance to commonly used antibacterial drugs increases the morbidity, mortality and cost associated with nosocomial infections. The number of patients dying from incurable nosocomial infections continuously grows, and now the worldwide number of deaths due to drug-resistant bacteria reach 700,000 each year, if new therapeutic drugs or treatment programs are not developed, this number will be increased to 10 million by 2050 (Nature, 2017, 543, 15). The treatment options available for infections caused by multi-drug resistant Gram-negative bacteria (including Enterobacteriaceae and non-fermentative bacteria) are particularly limited, what makes the situation more serious is that few compounds can break through the bacterial resistance in the research and development pipeline of the medical industry (Clin. Inf. Dis., 2009, 48, 1-12).

Over the past few decades, a very successful and well-tolerated class of β-lactam antibiotics has been the main basis for the treatment of infections caused by Gram-negative pathogens. Among them, the third-generation cephalosporins, carbapenems and monocyclic lactams are widely used to treat infections caused by Gram-negative bacteria. However, the emergence of more and more lactamases and other drug resistance mechanisms seriously jeopardizes the medium-term availability of the current compounds in these subclasses, especially extended spectrum lactamases (ESBLs) and carbapenemases are important driving forces for drug resistant, so there is an urgent need for new β-lactam antibiotics that can break through drug resistance to fill the gap.

Aztreonam is the only monocyclic β-lactam approved by the FDA worldwide and the second analog (tigemonam) sold only in the Japanese market, the value of monocyclic β-lactam antibiotics is far from being excavated (Rev. Infect. Dis., 1985, 7, 579-593). On the other hand, the resistance of bacteria makes the permeability of aztreonam worse, enhances the efflux effect, and reduces the bacteriostatic spectrum. In order to increase the permeability of monocyclic β-lactam to bacteria, Basilea (WO 2007065288), Naeja Pharmaceuticals (WO 2002022613) and Squibb & Sons (U.S. Pat. No. 5,290,929, EP 531976, EP 484881) introduce iron carriers uptake system on the monocyclic β-lactam molecules. Recently, Pfizer has re-examined the monocyclic β-lactam carrying a sulfonylaminocarbonyl activated group at the N1-position (WO 2010070523). In addition, in WO 2008116813, Basilea describes a combined treatment method using monocyclic β-lactam and carbapenems. Each of AiCuris (WO 2013110643) and Novartis (WO 2015148379) respectively reported researches for enhancing the activity by modifying the substituent group on the Aztreonam molecule, the structural formula of the compounds are shown below, where the group A is an aromatic ring structure connected with guanyl and guanidyl. Novartis (WO 2017050218) also reported a patent of salt form of one of these compounds, which are all currently in the preclinical or clinical development stage.

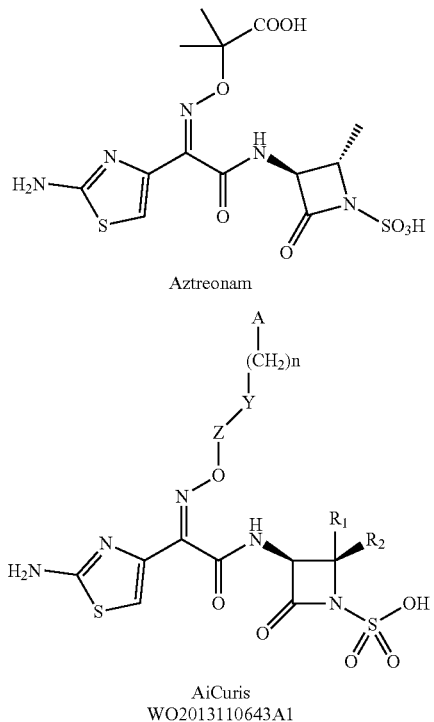

Aztreonam

AiCuris
WO2013110643A1

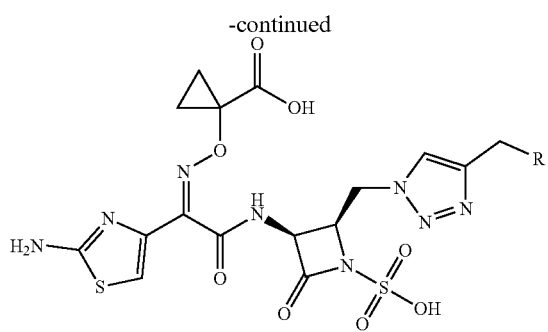

Novartis
WO2015148379A1

Content of the Present Invention

The present disclosure provides a compound of formula (I') or formula (II'), an isomer thereof or a pharmaceutically acceptable salt thereof, (I')

(II')

wherein,
ring A is selected from phenyl or 5-6 membered heteroaryl;
each of m and m' is independently selected from 1 or 2;
each of $L_1$ and $L_2$ is independently selected from single bond, —NH—, —C(=NH)—, —C(=NR$_6$)NH—, —CH=N— or —(CH$_2$)$_n$—;
$R_6$ is selected from H or 3-6 membered heterocycloalkyl optionally substituted by one, two or three R;
n is selected from 1, 2, 3 or 4;
$R_1$ is selected from H, NH$_2$, C$_{1-6}$ alkyl, C$_{1-6}$ heteroalkyl, C$_{3-6}$ cycloalkyl or 3-6 membered heterocycloalkyl, where each of the C$_{1-6}$ alkyl, C$_{1-6}$ heteroalkyl, C$_{3-6}$ cycloalkyl and 3-6 membered heterocycloalkyl is independently optionally substituted by one, two or three R;

R is selected from F, Cl, Br, I, CH$_3$, N$_2$,

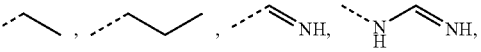

or 5-6 membered heterocycloalkyl, where each of CH$_3$, NH$_2$,

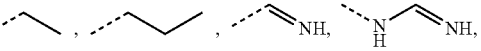

and 5-6 membered heterocycloalkyl is independently optionally substituted by one, two or three R';
R' is selected from F, Cl, Br, I, CH$_3$, NH$_2$,

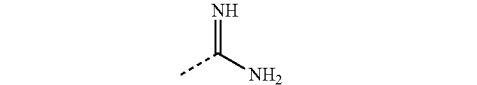

$R_2$ is selected from C$_{1-3}$ alkyl;
each of $R_3$ and $R_4$ is independently selected from H or C$_{1-3}$ alkyl optionally substituted by one, two or three R;
L is selected from single bond or —O—;
$R_5$ is selected from: H, COOH, OH, C(=O)NH$_2$, C(=O)CH$_3$ or C(=O)OCH$_3$;
the "hetero" represents for heteroatom or heteroatom group, the "hetero" in the 5-6 membered heteroaryl, C$_{1-6}$ heteroalkyl, 3-6 membered heterocycloalkyl, 5-6 membered heterocycloalkyl is independently selected from N, —NH—, —C(=NH)—, —C(=NH)NH—, —O—, —S—, N, =O, =S and —C(=O)—;
in any one of the cases above, the number of the heteroatom or heteroatom group is independently selected from 1, 2 or 3.

In some embodiments of the present disclosure, R is selected from F, Cl, Br, I, CH$_3$, NH$_2$, In some embodiments of the present disclosure, $R_1$ is selected from H, NH$_2$, C$_{1-4}$ alkyl, C$_{1-4}$ heteroalkyl, C$_{3-6}$ cycloalkyl and 3-6 membered heterocycloalkyl, where each of the C$_{1-4}$ alkyl, C$_{1-4}$ heteroalkyl, C$_{3-6}$ cycloalkyl, 3-6 membered heterocycloalkyl is independently optionally substituted by one, two or three R.

In some embodiments of the present disclosure, $R_1$ is selected from H, $NH_2$, $CH_3$, $OCH_2CH_3$,

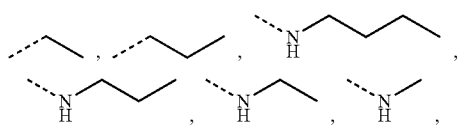

cyclohexyl, pyrrolidinyl, piperidinyl and piperazinyl, where each of the $NH_2$, $CH_3$, $OCH_2CH_3$,

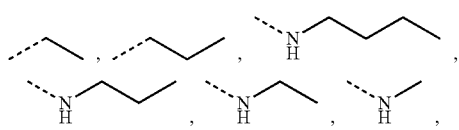

cyclohexyl, pyrrolidinyl, piperidinyl and piperazinyl is independently optionally substituted by one, two or three R.

In some embodiments of the present disclosure, $R_1$ is selected from: H, $CH_3$, $OCH_2CH_2(NH_2)$, $NH_2$,

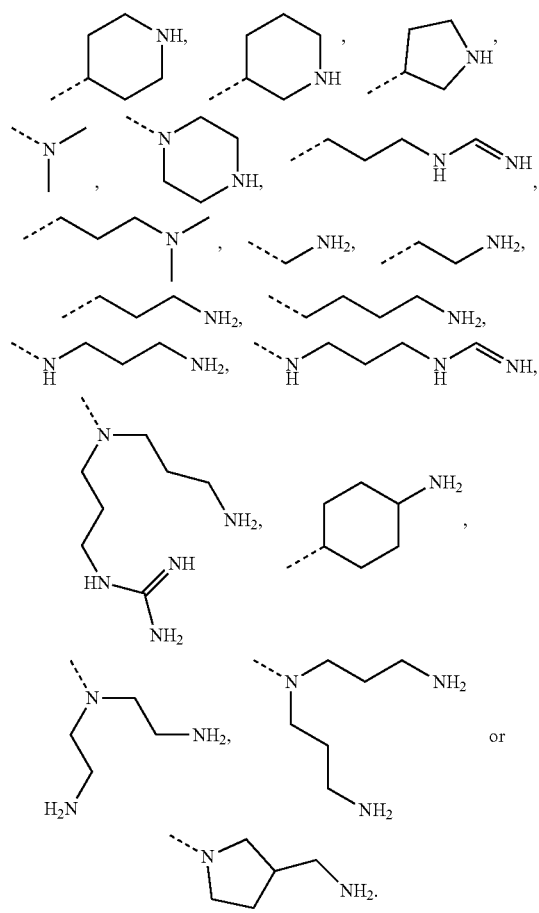

In some embodiments of the present disclosure, $R_6$ is selected from H and piperidinyl optionally substituted by one, two or three R.

In some embodiments of the present disclosure, $R_6$ is selected from H and

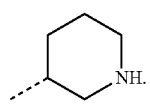

In some embodiments of the present disclosure, the moiety

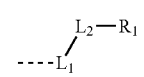

is selected from: H, $CH_3$,

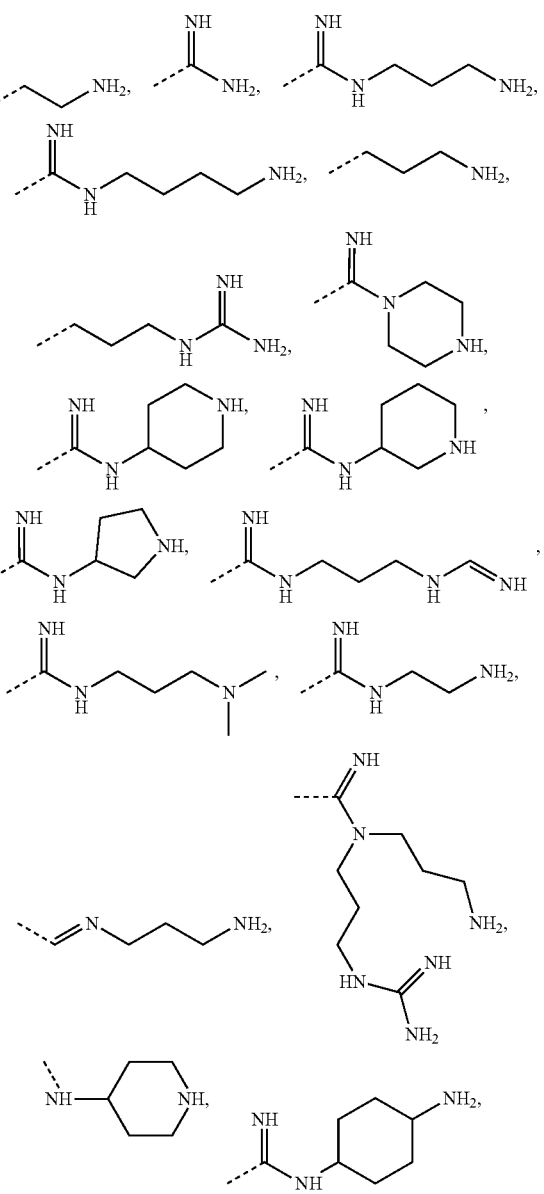

-continued
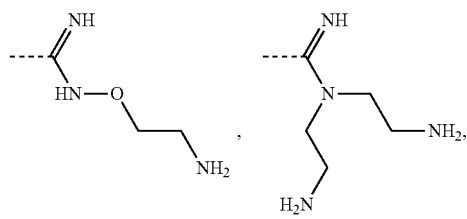
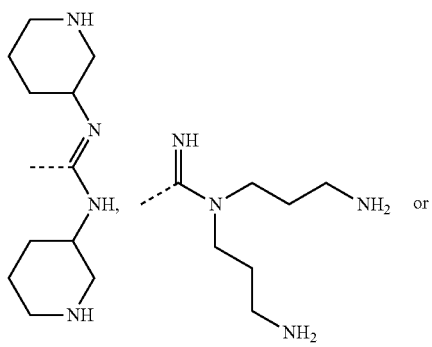
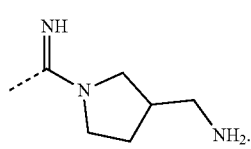
In some embodiments of the present disclosure, R₂ is selected from CH₃.
In some embodiments of the present disclosure, ring A is selected from phenyl.
In some embodiments of the present disclosure, the moiety
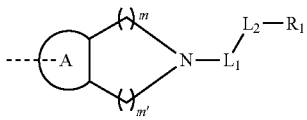
is selected from
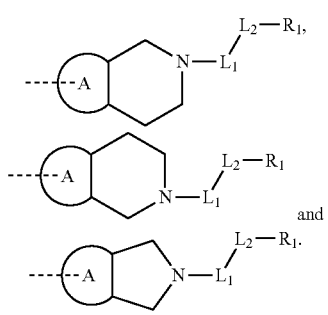
in some embodiments of the present disclosure, the moiety
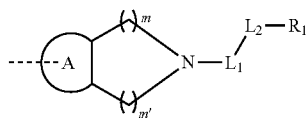
is selected from:
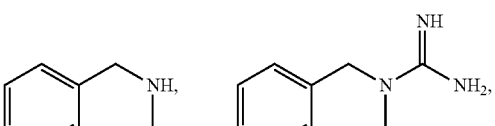
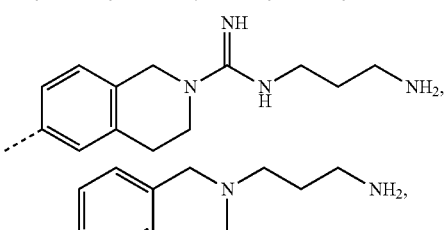
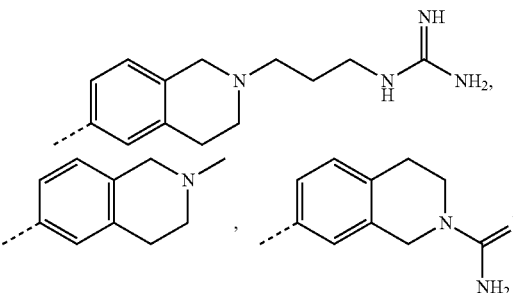
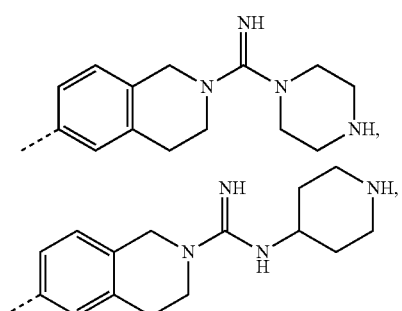
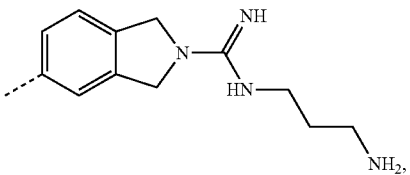
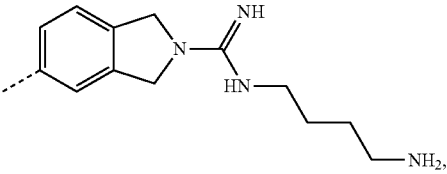

9
-continued
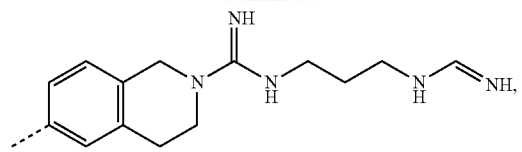
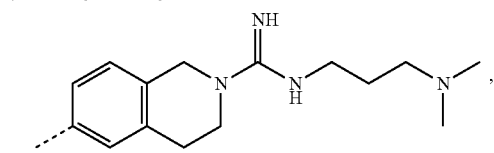
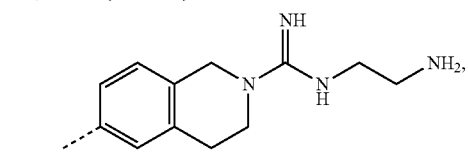
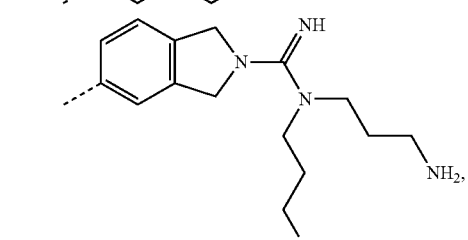
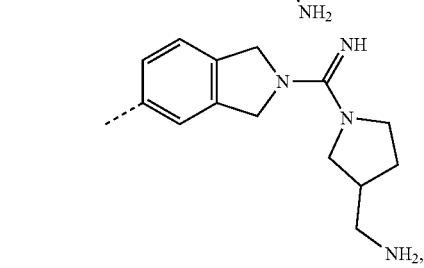
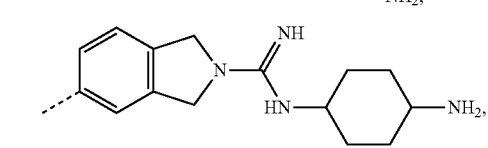
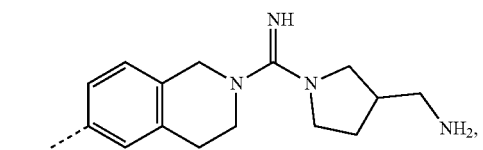
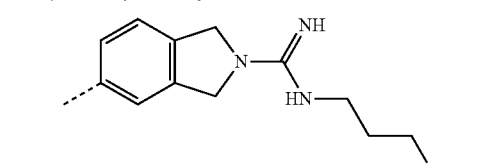
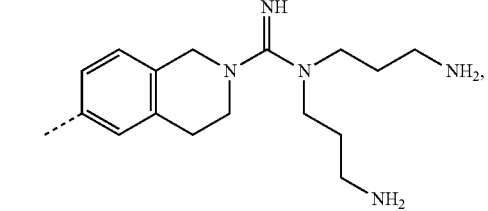
10
-continued
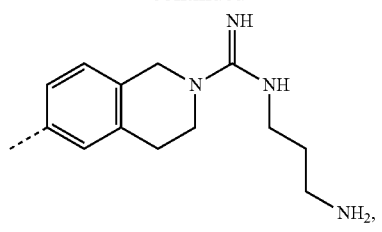
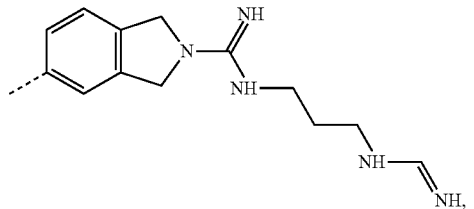
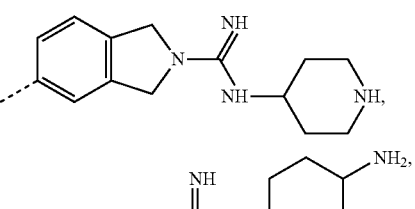
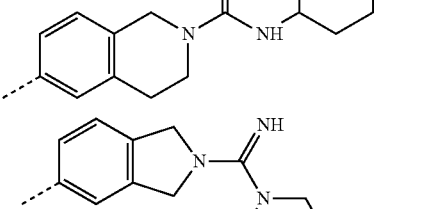
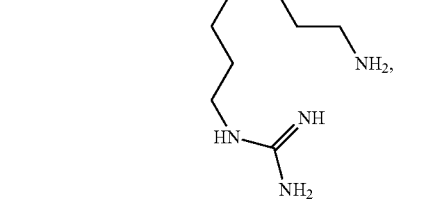
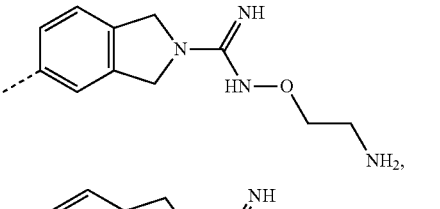
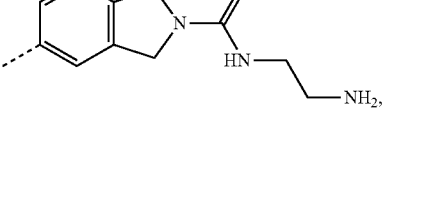
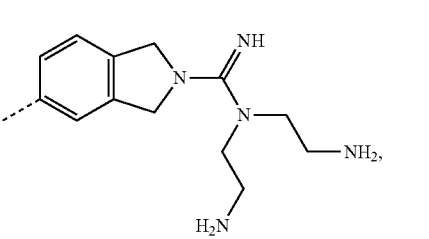

-continued
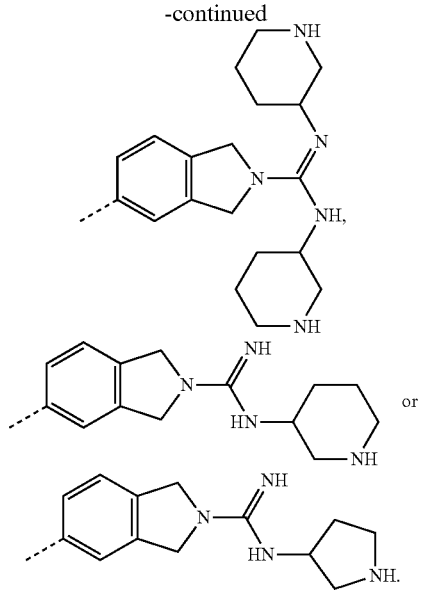
In some embodiments of the present disclosure, the moiety
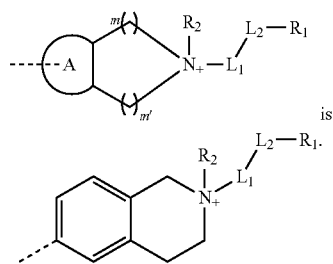
is
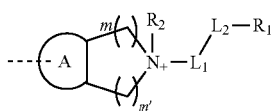
In some embodiments of the present disclosure, the moiety
is selected from
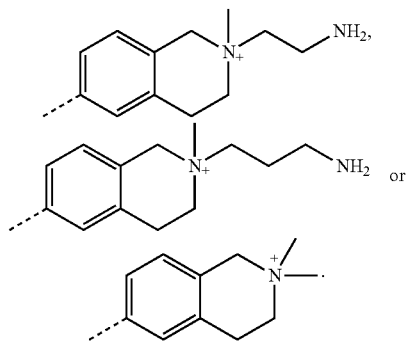
In some embodiments of the present disclosure, the moiety
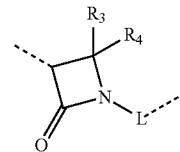
is
selected from:
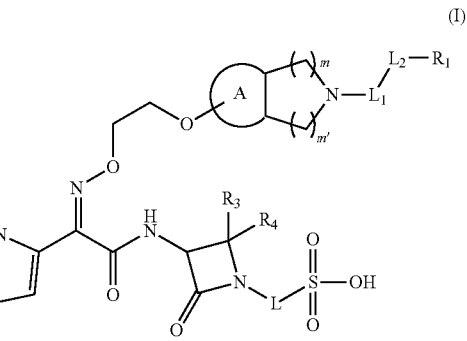
in some embodiments of the present disclosure, the compound is selected from:
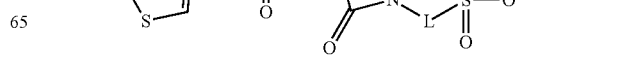
(I)
(II)

-continued
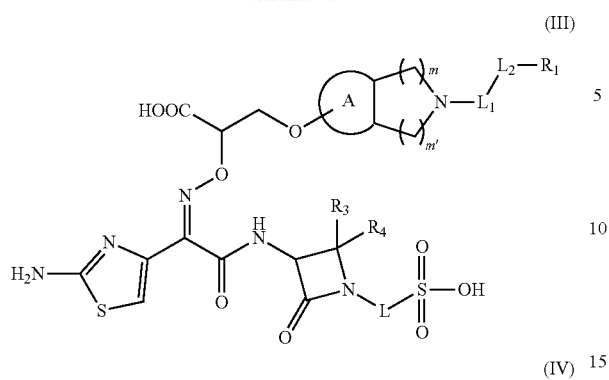
(III)
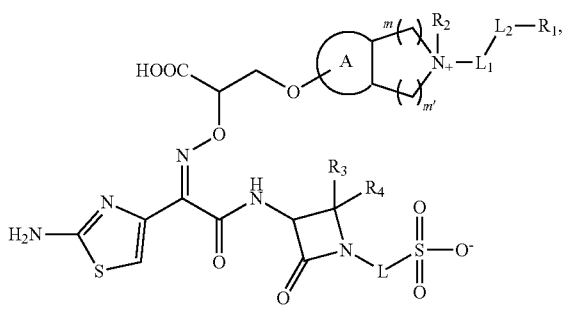
(IV)
wherein, $R_1$, $R_2$, $R_3$, $R_4$, $L_1$, $L_2$, L, m, m' and ring A are as defined in the present disclosure.
In some embodiments of the present disclosure, the compound is selected from:
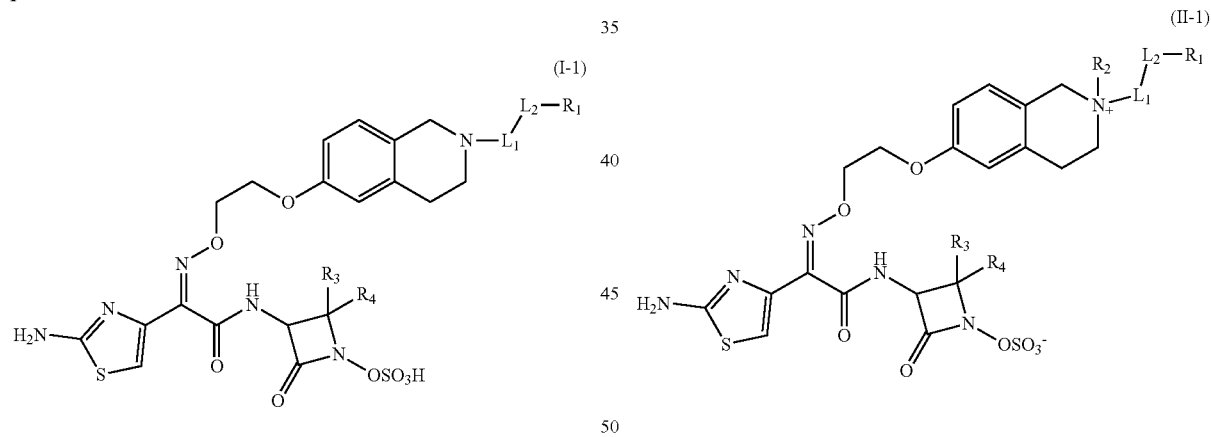
(I-1)
(I-2)
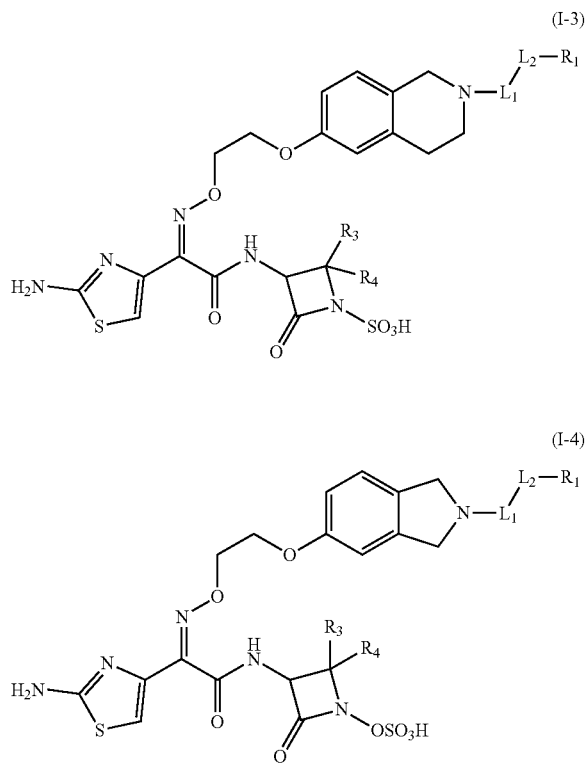
(I-3)
(I-4)
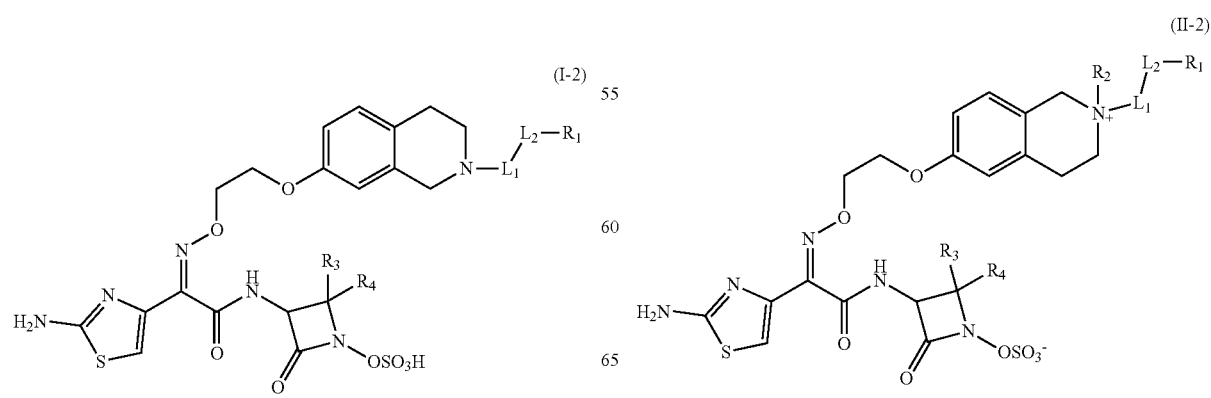
(II-1)
(II-2)

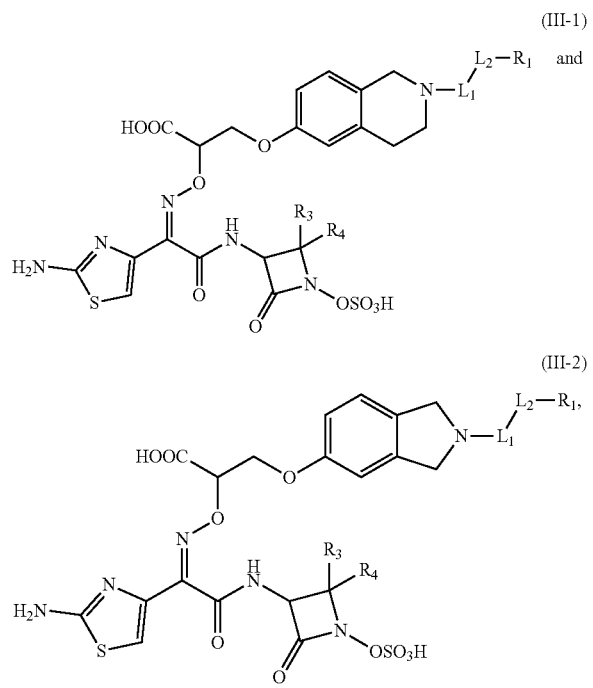
(III-1)
(III-2)
wherein, $R_1$, $R_2$, $R_3$, $R_4$, $L_1$ and $L_2$ are as defined in the present disclosure.
The present disclosure also provides a compound represented by the following formula, an isomer thereof or a pharmaceutically acceptable salt thereof,
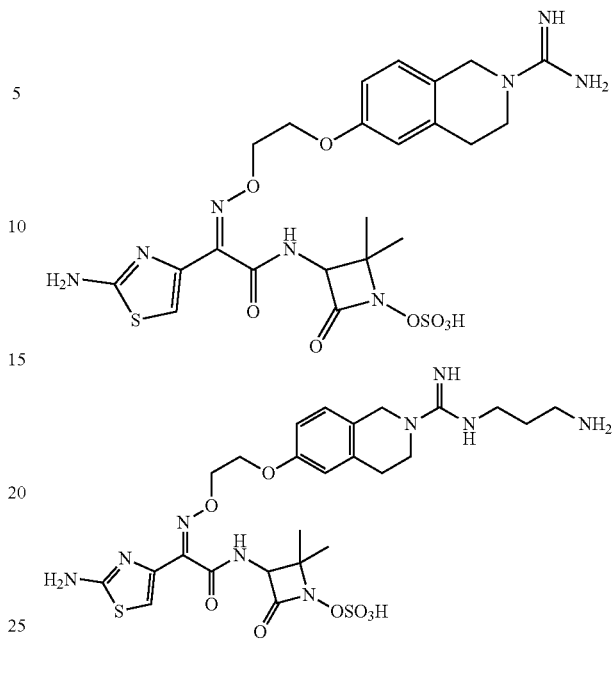

-continued
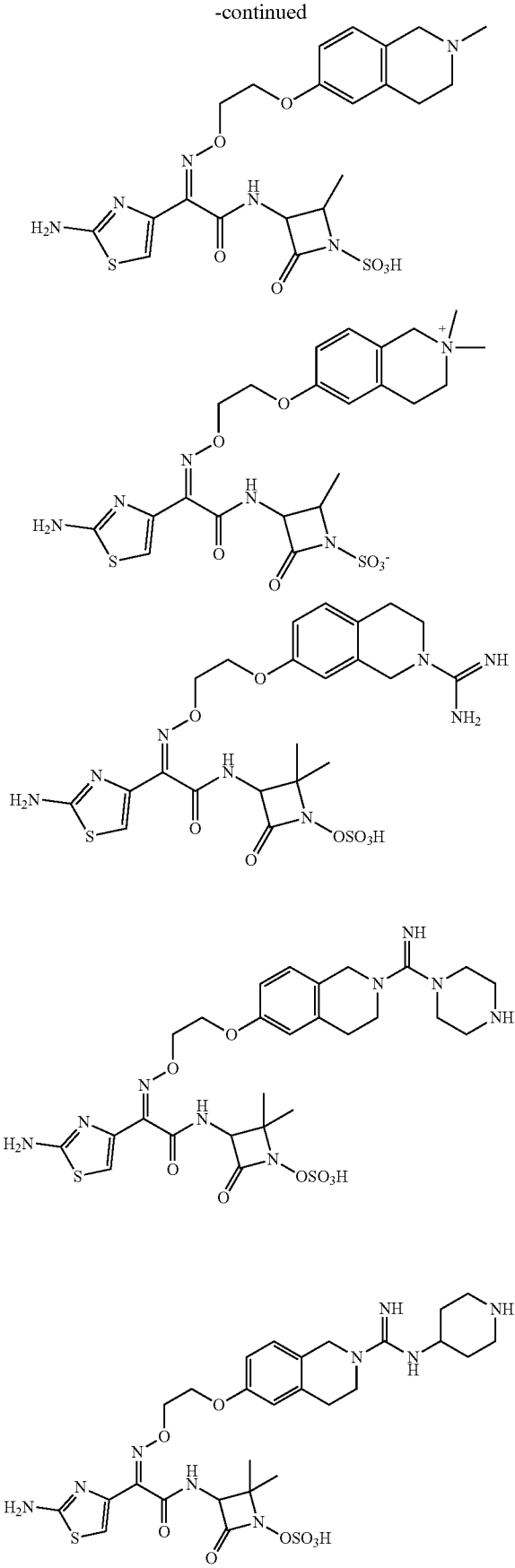
-continued
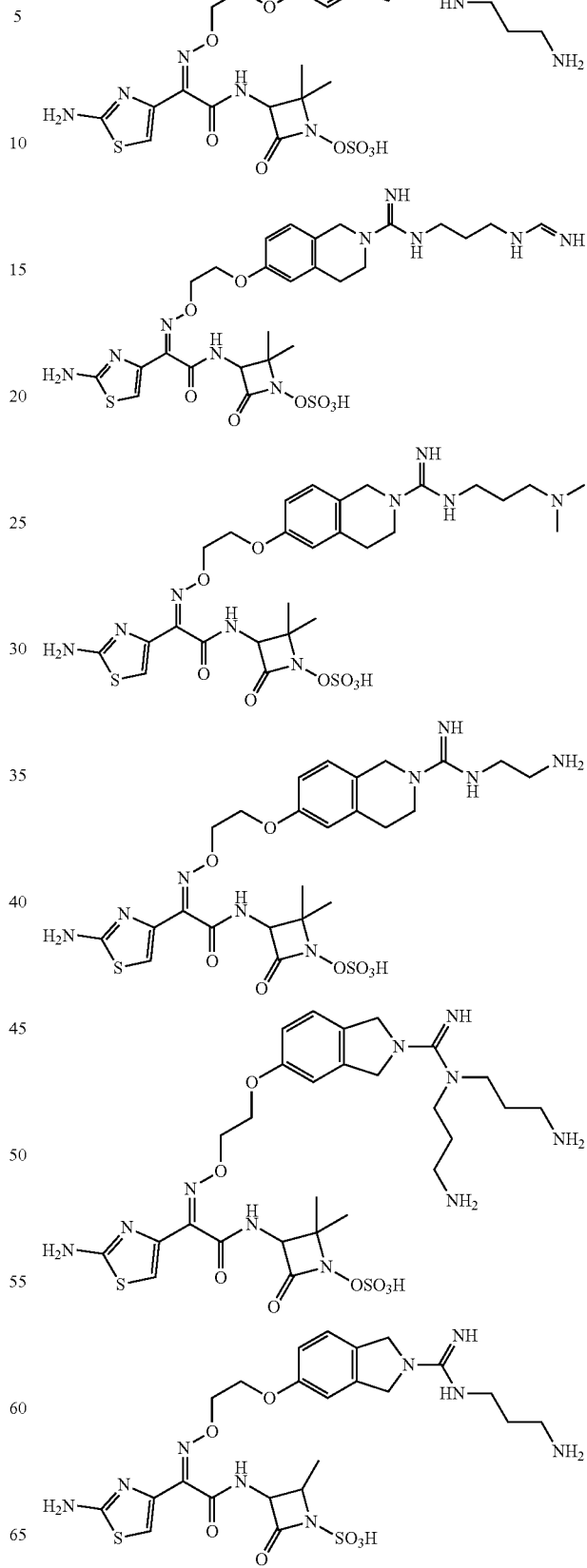

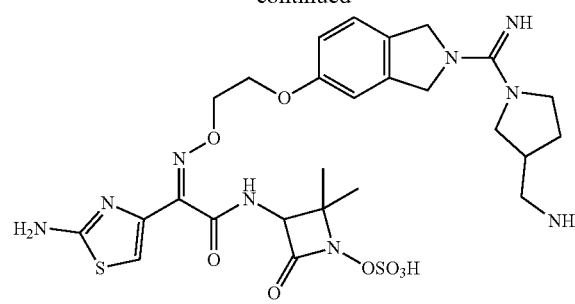
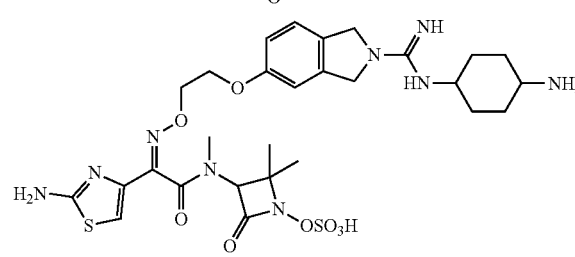
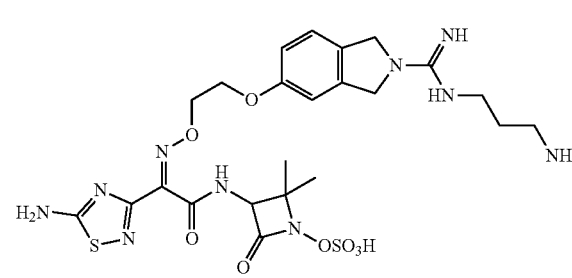
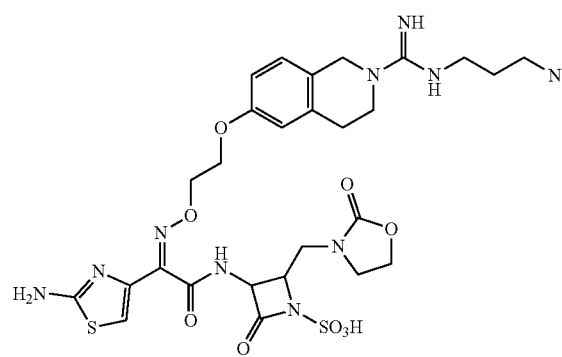
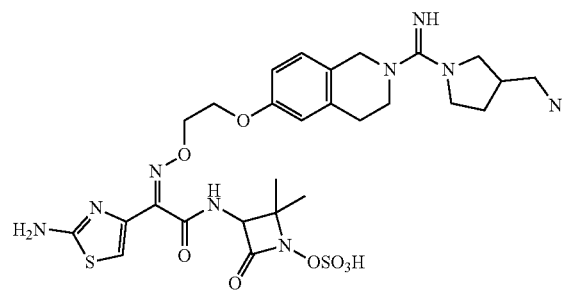
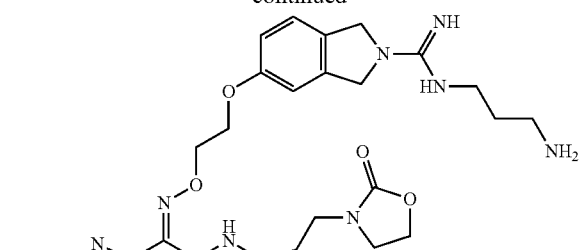
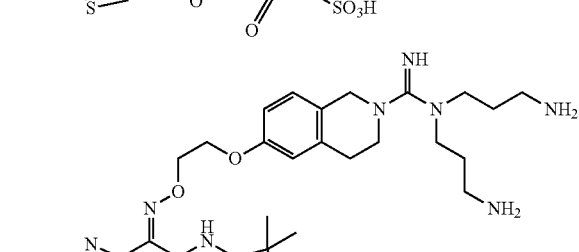
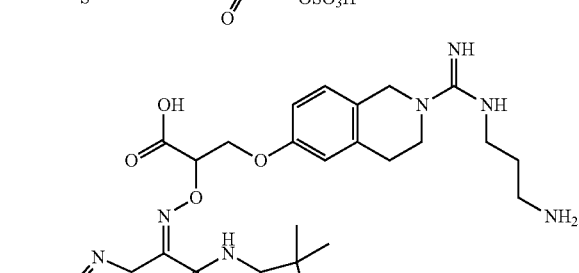
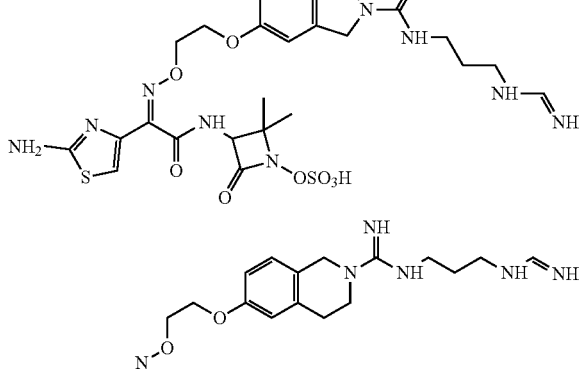
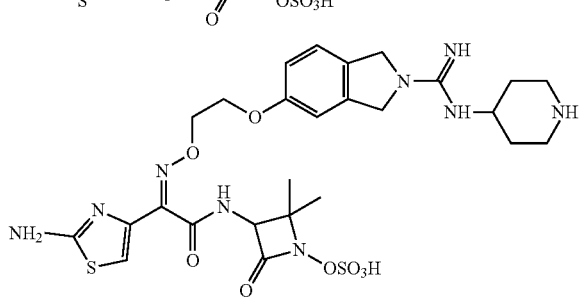

21
-continued
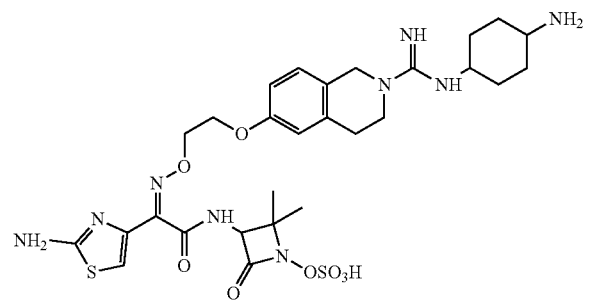
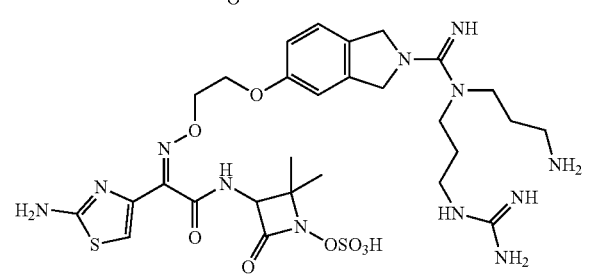
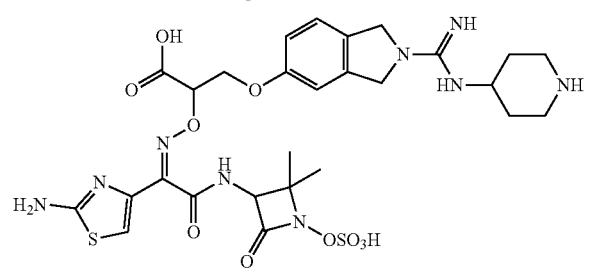
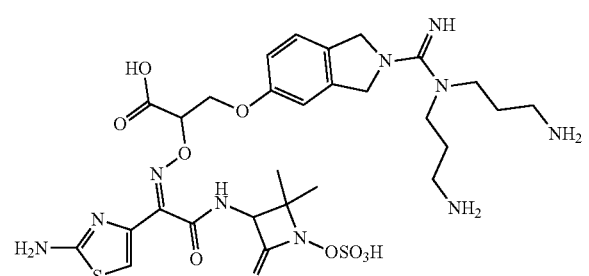
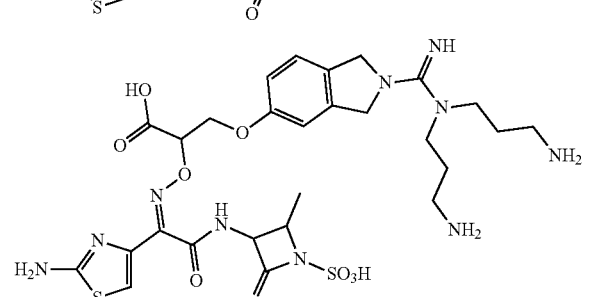
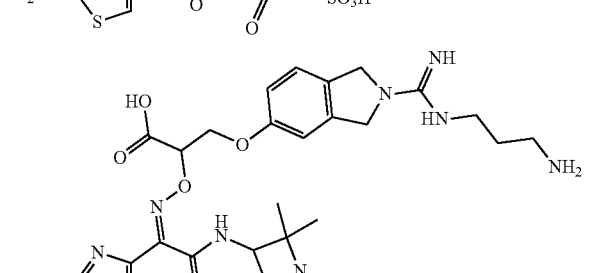
22
-continued
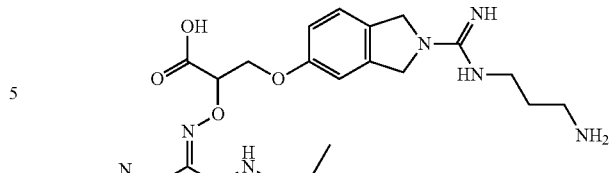
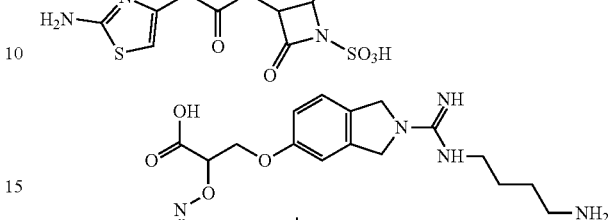
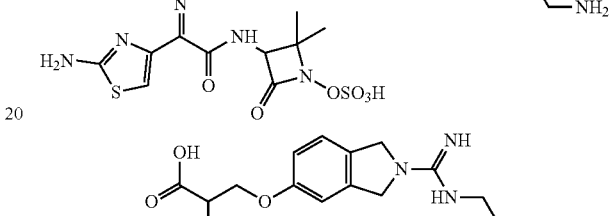
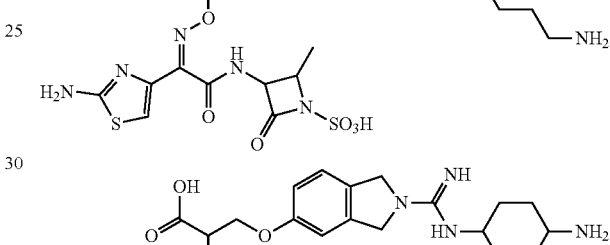
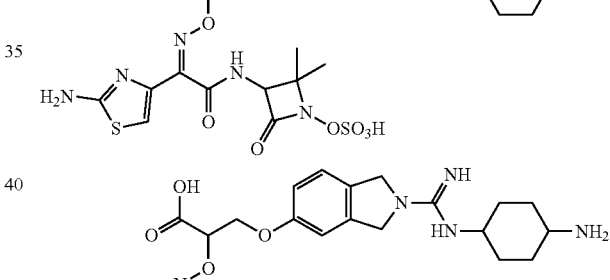
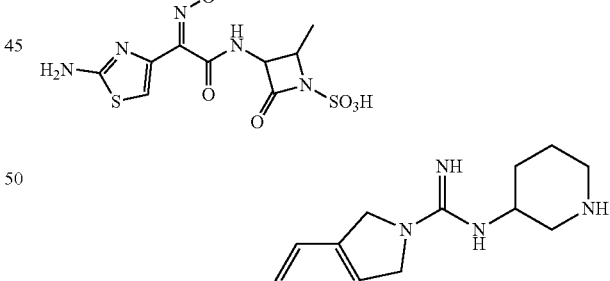
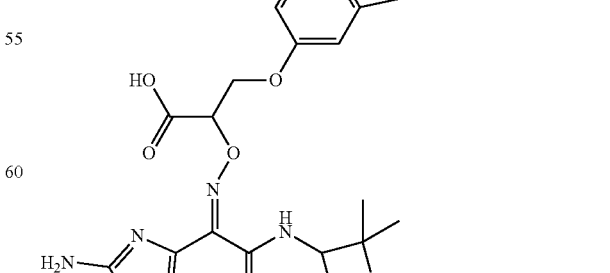

-continued
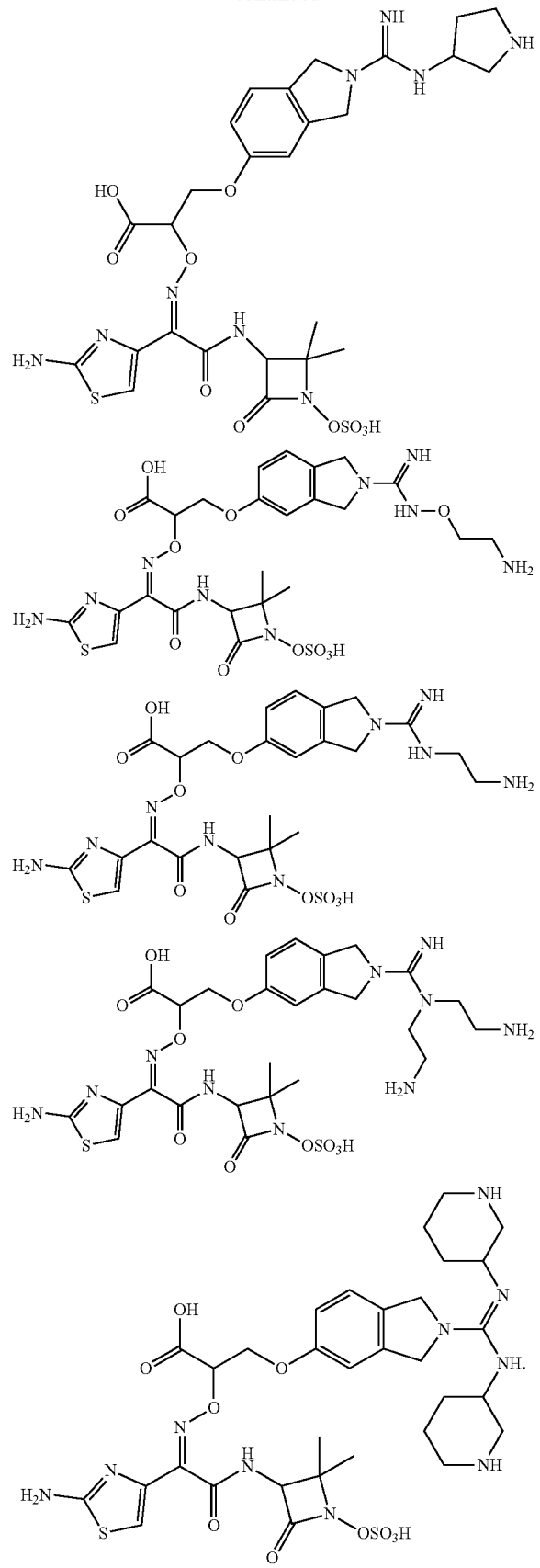
In some embodiments of the present disclosure, the compound is selected from
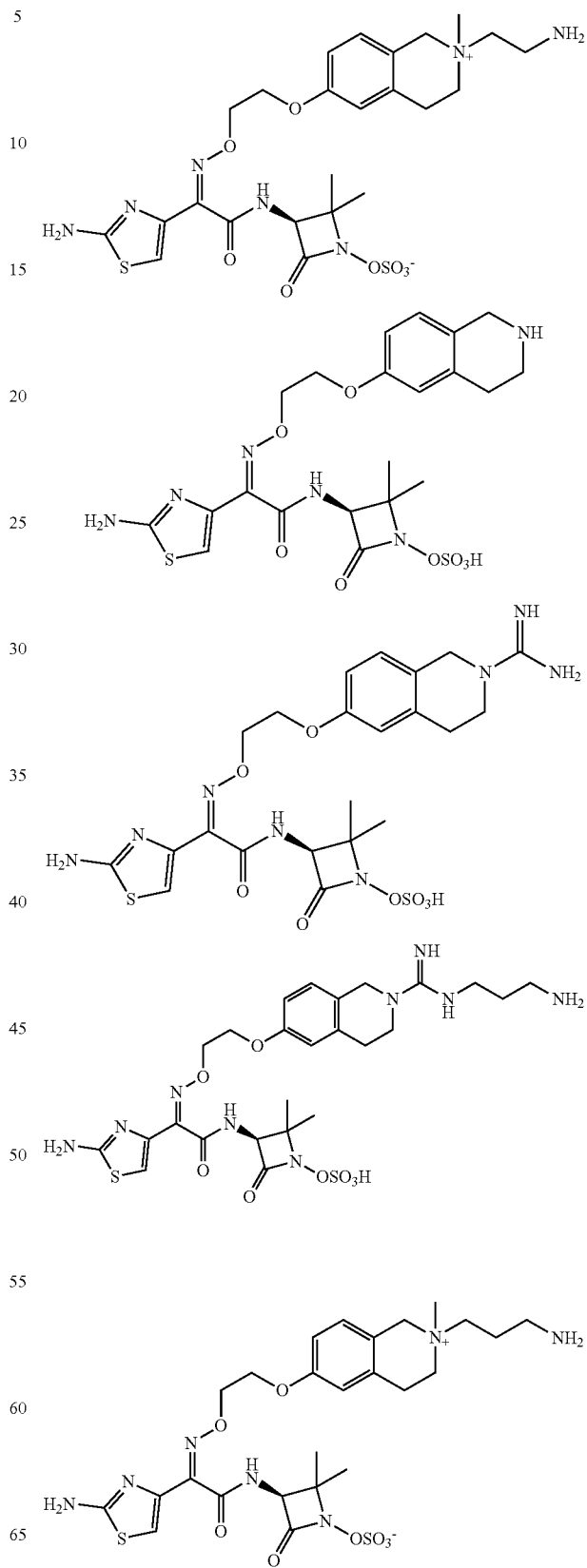

25
-continued
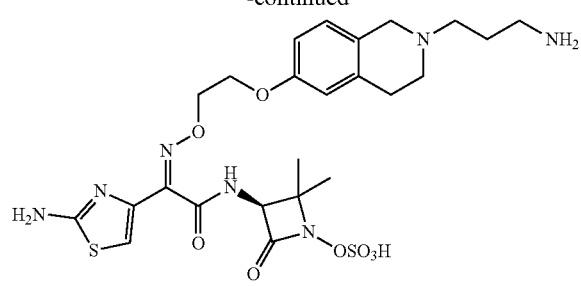
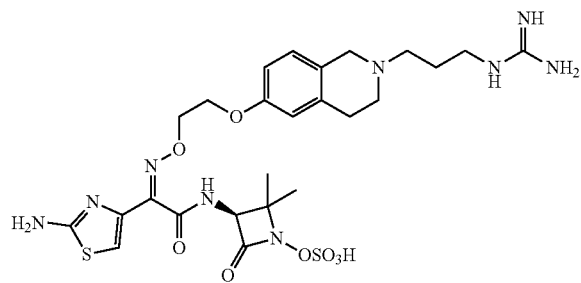
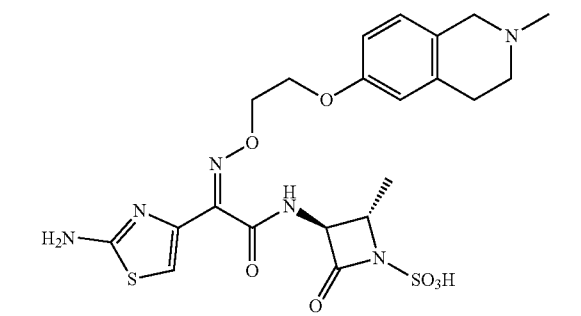
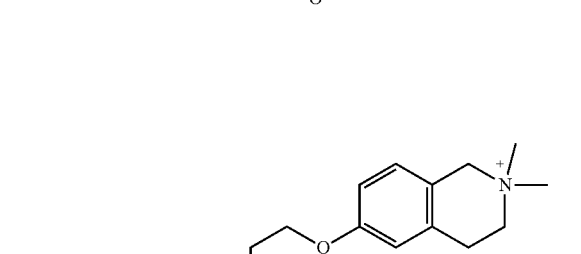
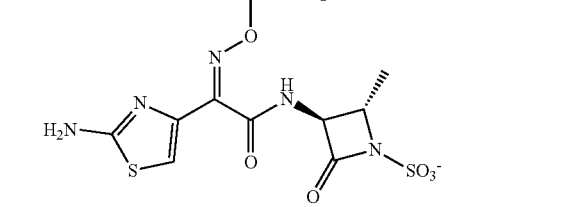
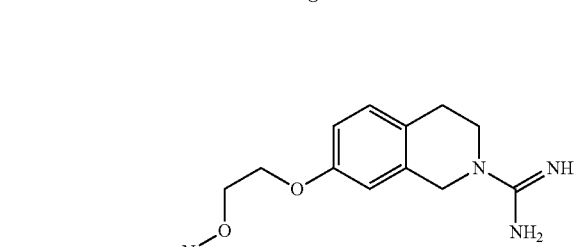
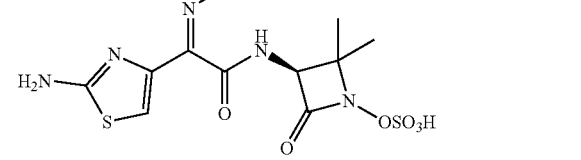
26
-continued
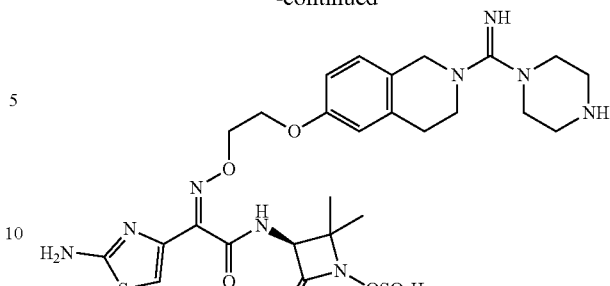
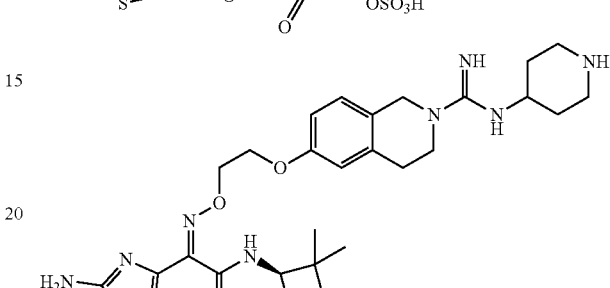
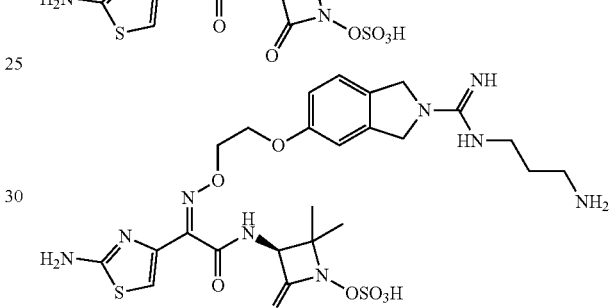
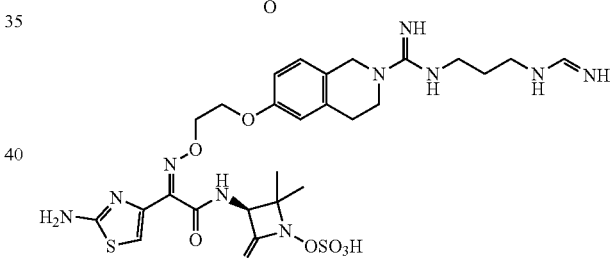
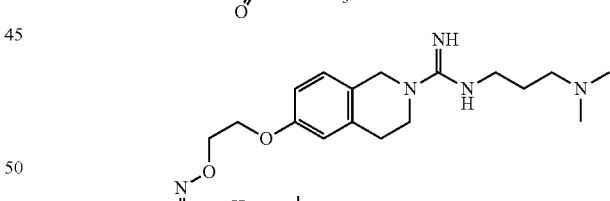
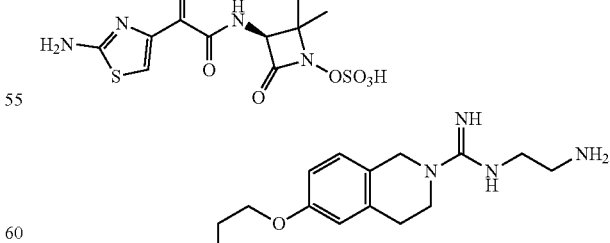
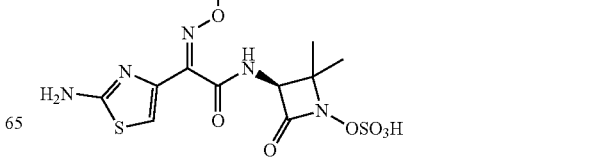

-continued

29
-continued
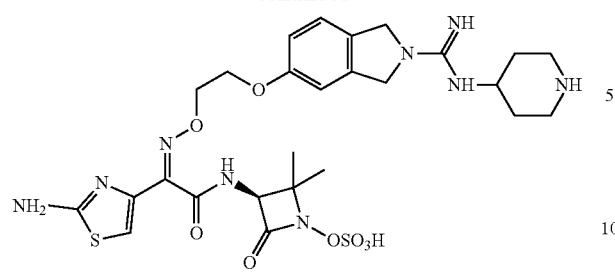
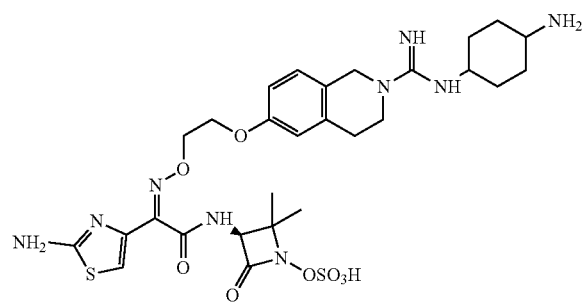
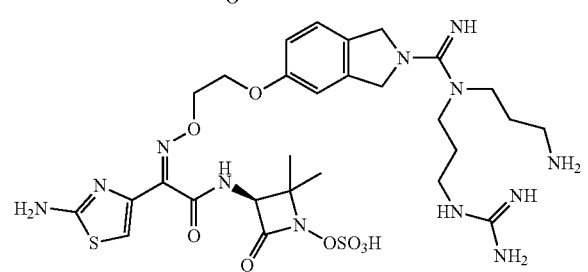
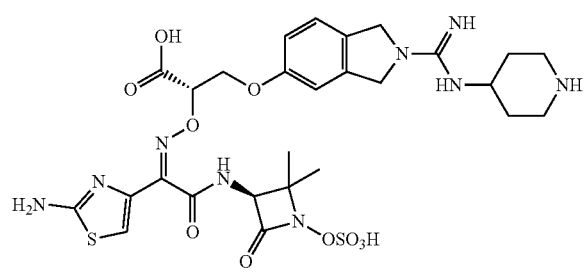
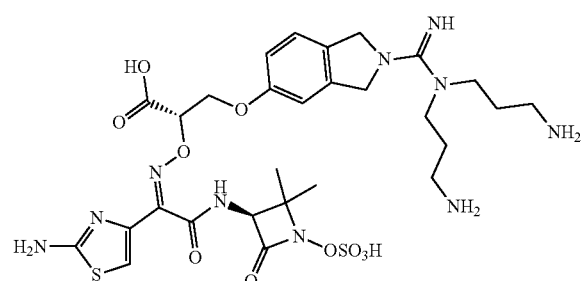
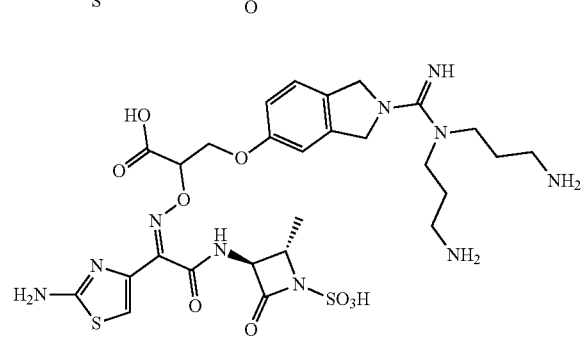
30
-continued
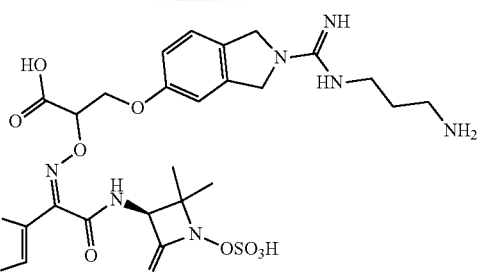
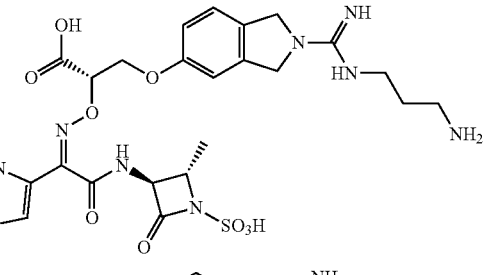
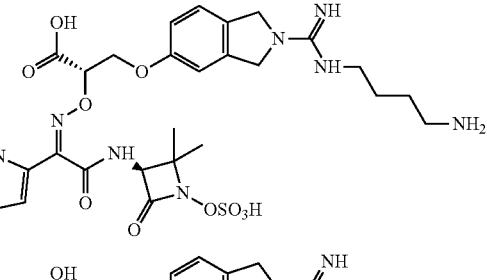
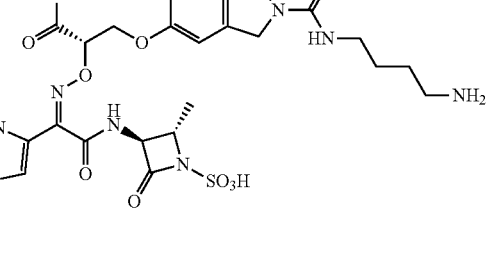
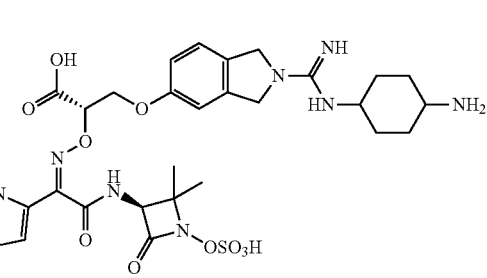
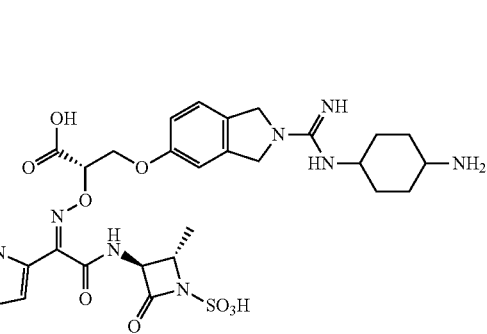

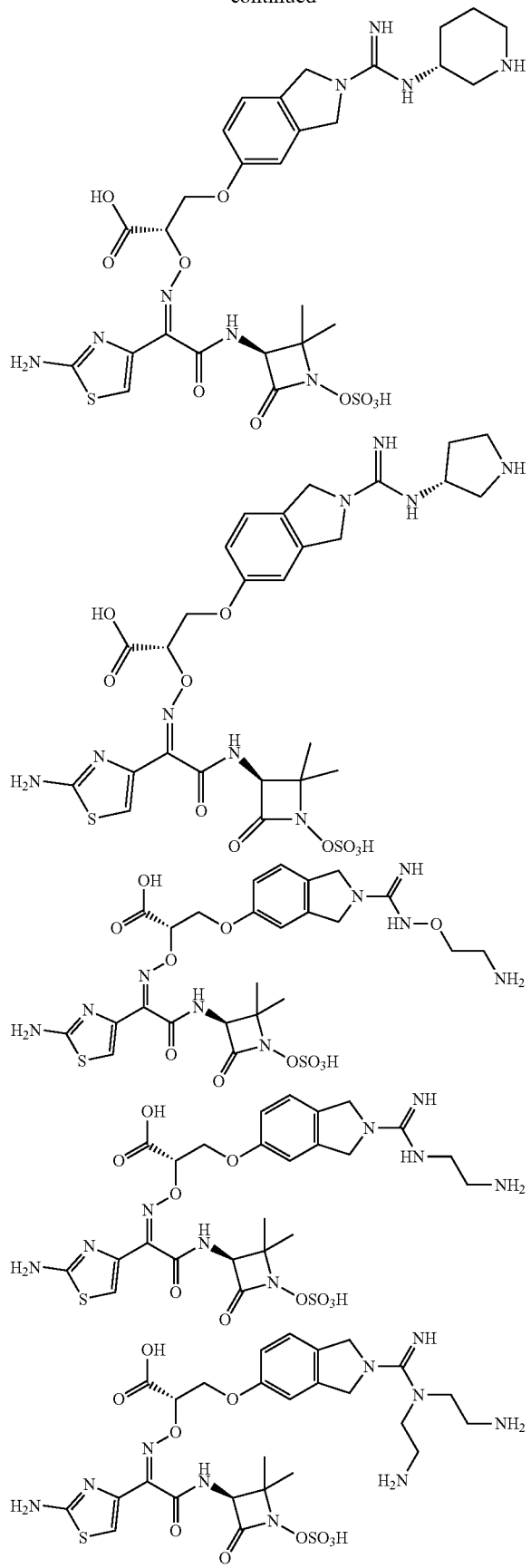

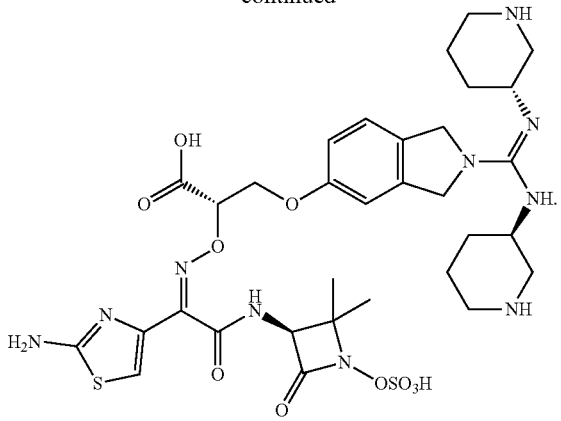

The present disclosure also provides a pharmaceutical composition, comprising a therapeutically effective amount of the compound, the isomer thereof or the pharmaceutically acceptable salt thereof as an active ingredient and a pharmaceutically acceptable carrier.

The present disclosure also provides a use of the compound, the isomer thereof or the pharmaceutically acceptable salt thereof in the manufacture of a medicament for treating a disease related to bacterial infection.

In some embodiments of the present disclosure, the bacteria is Gram-negative bacteria.

Technical Effect:

The compound of the present disclosure has good antibacterial activity against Gram-negative bacteria, especially against *Acinetobacter baumannii, Pseudomonas aeruginosa* and *Klebsiella*. The compound of the present disclosure can be used for treating diseases caused by a variety of Gram-negative resistant bacterial infections, especially diseases caused by drug-resistant bacteria such as B-type metal-containing β-lactamase Gram-negative bacteria (*Acinetobacter baumannii, Pseudomonas aeruginosa* and *Klebsiella*).

Definitions and Description

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (see Berge et al., "Pharmaceutical Salts", Journal of Pharmaceutical Science 66: 1-19 (1977)). Certain specific compounds of the present disclosure that contain both basic and acidic functional groups can be converted to any base or acid addition salt.

Preferably, the neutral form of the compound is regenerated by contacting the salt with a base or an acid in a conventional manner and separating the parent compound. The parent form of the compound differs from its various salt forms in certain physical properties, such as solubility in polar solvents.

The "pharmaceutically acceptable salts" used herein belongs to the derivative of the compounds of the present disclosure, wherein the parent compound is modified by salt formation with acids or bases. Examples of pharmaceutically acceptable salts include, but are not limited to, base such as inorganic acids or organic acid salts amine, acid such as carboxylic or organic salts of alkali metal, and the like. Pharmaceutically acceptable salt includes conventional non-toxic salt or quaternary ammonium salt of the parent compound, such as salts formed from non-toxic inorganic or organic acids. Conventional non-toxic salts include but are not limited to those salt derived from inorganic acids and organic acids selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturaldehyde, propionic acid, salicylic acid, stearic acid, folinatic acid, succinic acid, sulfamic acid, p-aminobenzenesulfonic acid, sulfuric acid, tannin, tartaric acid and p-toluenesulfonic acid.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol, or acetonitrile are preferred.

In addition to the salt form, the compound provided by the present disclosure also exists in prodrug form. The prodrug of the compound described herein is the compound that readily undergoes chemical change under physiological condition to be converted into the compound of the present disclosure. Additionally, the prodrug can be converted to the compound of the present disclosure by a chemical or biochemical method in vivo environment.

Certain compounds of the present disclosure can exist in a nonsolvated form or a solvated form, including hydrated form. Generally, the solvated form is equivalent to the nonsolvated form, and both are encompassed within the scope of the present disclosure.

Certain compounds of the present disclosure can have asymmetric carbon atoms (optical centers) or double bonds. Racemates, diastereomers, geometric isomers and individual isomers are included within the scope of the present disclosure.

Unless otherwise specified, unless otherwise specified, the absolute configuration of a stereogenic center is represented by a wedged solid bond ( ◆ ) and a wedged dashed bond ( ◆ ), a wave line ( ◆ ) represents a wedged solid bond ( ◆ ) or a wedged dashed bond ( ◆ ), and the relative configuration of a stereogenic center is represented by a straight solid bond ( ◆ ) and a straight dashed bond ( ◆ ). When the compound described herein comprises olefinic double bond or other geometrically asymmetric center, unless otherwise specified, they include E, Z geometric isomers. Likewise, all tautomeric forms are included within the scope of the present invention.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the present disclosure, whether radioactive or not, are encompassed within the scope of the present disclosure.

The term "pharmaceutically acceptable carrier" refers to any agent or carrier medium which is capable of delivering an effective amount of the active substance of the present disclosure, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. For other information about the carriers, Remington: Science and Practice of Pharmacy, 21$^{st}$ Edition, Lippincott, Williams & Wilkins (2005) can be referred to, the contents of which are incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present disclosure, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled person in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. For example, the structural unit

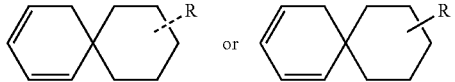

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

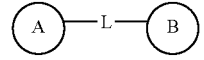

is -MW-, then -MW- can link ring A and ring B to form

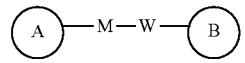

in the direction same as left-to-right reading order, and form

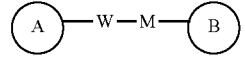

in the direction contrary to left-to-right reading order. A combination of substituents and/or variants thereof is allowed only when such combination can result in a stable compound.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1\text{-}12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3\text{-}12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CHO—$CH_3$, —NH—$CH_2$—NH—H, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

All of the solvents used in the present disclosure are commercially available.

The present disclosure adopts the abbreviating words as followed:

"aq" refers to water; "min" refers to minute(s); "FA" refers to formic acid, "m-CPBA" refers to 3-chloroperoxybenzoic acid; "eq" refers to equivalent; DCC refers to N,N'-dicyclohexylcarbodiimide; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "Cbz" refers to benzyloxycarbonyl, which is an amine protecting group; "Boc" refers to tert-butoxycarbonyl, which is an amine protecting group; "HOAc" refers to acetic acid; ACN refers to acetonitrile; $BH_3$ refers to sodium cyanoborohydride; "r.t." refers to room temperature; "THF" refers to tetrahydrofuran; "$Boc_2O$" refers to di-tert-butyldicarbonate; "TFA" refers to trifluoroacetic acid; "DIPEA" refers to diisopropylethylamine; "$SOCl_2$" refers to thionyl chloride; "$CS_2$" refers to carbon disulfide; "TsOH" refers to p-toluenesulfonic acid; "NFSI" refers to N-fluoro-N-(phenylsulfonyl)benzenesulfonamide; "NCS" refers to 1-chloropyrrolidine-2,5-dione; "n-$Bu_4$NF" refers to tetrabutylammonium fluoride; "iPrOH" refers to 2-propanol; "mp" refers to melting point; "LDA" refers to Lithium diisopropylamide; "TEMPO" refers to 2,2,6,6-tetramethylpiperidine-1-oxyl radical or 2,2,6,6-tetramethylpiperidine oxide; "NaClO" refers to sodium hypochlorite; "$NaClO_2$" refers to sodium chlorite; HOBt refers to 1-hydroxybenzotriazole; "psi" refers to pounds/square inch; "$DMF.SO_3$" refers to N,N-dimethylformamide sulfur trioxide; "$KH_2PO_4$" refers to monopotassium phosphate; "$Bu_4HSO_4$" refers to tetrabutylammonium bisulfate; "$PPh_3$" refers to triphenylphosphine; "$NH_2NH_2.H_2O$" refers to hydrazine hydrate; "DPPF" refers to 1,1'-bis(diphenylphosphino)ferrocene; "$Pd_2(dba)_3$" refers to tris(dibenzylideneacetone) dipalladium (0); "MIC" refers to minimum inhibitory concentration; "DMAP" refers to 4-dimethylaminopyridine; "BnBr" refers to benzyl bromide; "$H_2O_2$" refers to hydrogen peroxide.

DETAILED DESCRIPTION OF THE PREFERRED EMBODIMENT

Figure 1:
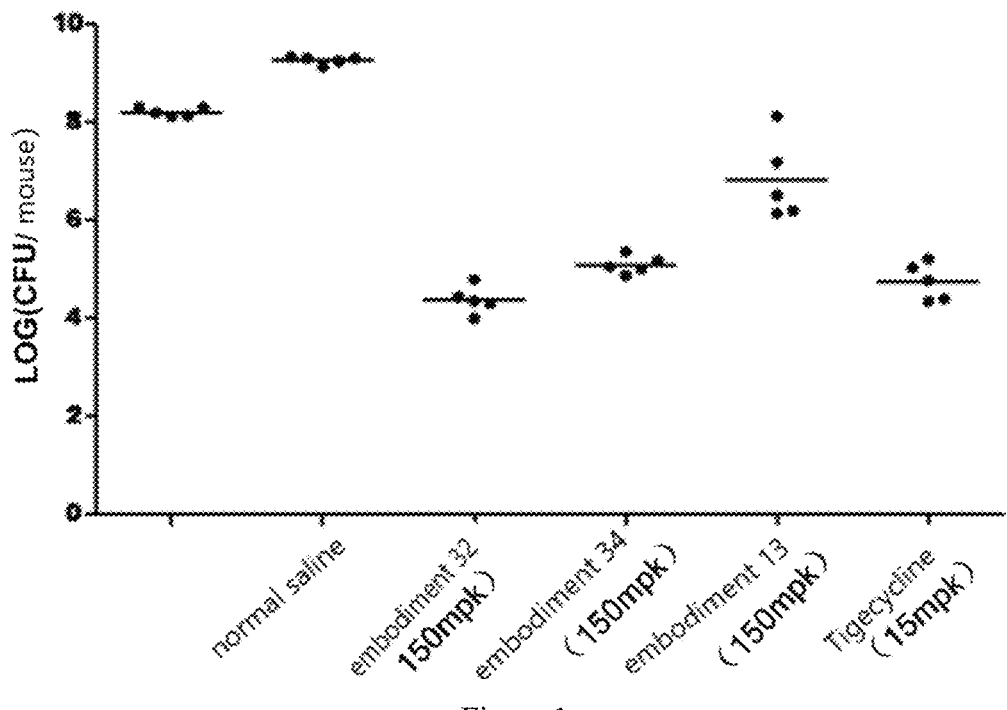
FIG. 1 shows the results of the in vivo efficacy test of the compound on lung infection in mice.

The following examples further illustrate the present disclosure, but the present disclosure is not limited thereto. The present disclosure has been described in detail in the text, and its specific embodiments have also been disclosed, for one skilled person in the art, it is obvious to modify and improve the embodiments of the present disclosure within the spirit and scope of the present invention.

Key Intermediate A1

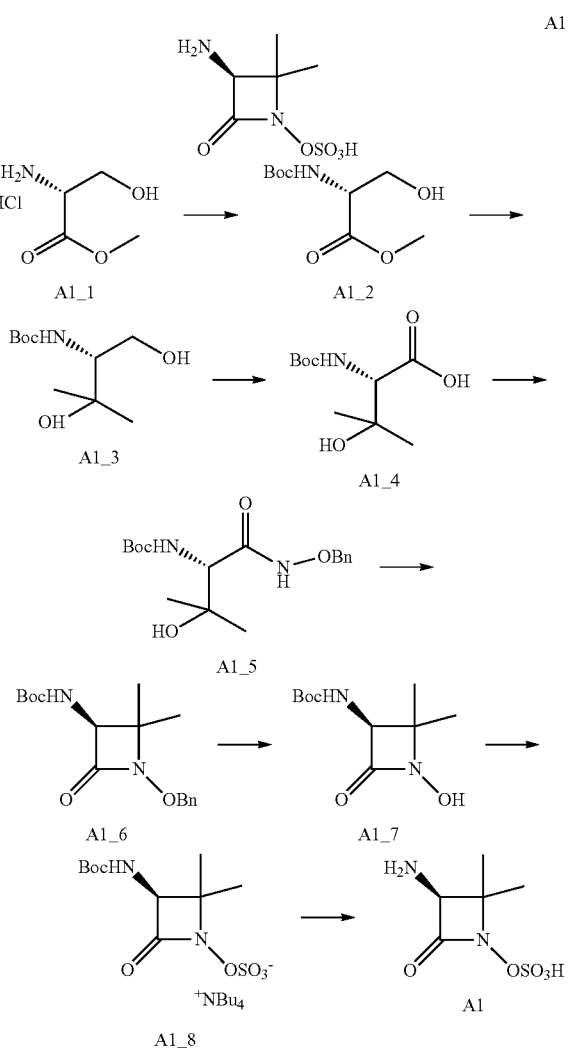

Step 1: compound A1_1 (100.00 g, 642.76 mmol, 1.00 eq) was added to THF (1.50 L), then triethylamine (136.59 g, 1.35 mol, 187.10 mL, 2.10 eq) was added, the obtained mixture was cooled to 0° C., then a solution of $Boc_2O$ (154.31 g, 707.03 mmol, 162.43 mL, 1.10 eq) in TH (500.00 mL) was added dropwise at the same temperature, then the mixture was warmed to 10° C. and stirred for 10 hours, and filtered, the filtrate was concentrated under reduced pressure, saturated sodium bicarbonate solution (300 mL) was then added into the obtained crude product, followed by extraction with ethyl acetate (500 mL*2). The combined organic phase was dried over anhydrous sodium sulfate, filtered and concentrated under reduced pressure to give compound A1_2.

$^1$H NMR (400 MHz, CDCl$_3$) δ (ppm): 5.51 (br s, 1H), 4.46-4.31 (m, 1H), 4.03-3.86 (m, 2H), 3.83-3.72 (m, 3H), 2.64 (br s, 1H), 1.46 (s, 9H).

Step 2: A1_2 was dissolved in THF (2000 mL), the solution was cooled to −50° C. and stirred for 10 min, then MeMgBr (3 M, 638.59 mL, 6.00 eq) was added dropwise at −50° C. for 20 min. The obtained mixture was stirred for 60 mins at 25° C. and then the reaction was quenched by adding dilute hydrochloric acid (2000 mL, 0.5 M) at 0° C., then the obtained mixture was extracted with ethyl acetate (500 mL*2). The combined organic phase was washed with saturated sodium chloride aqueous solution, dried over anhydrous sodium sulfate and filtered, the filtrate was concentrated under reduced pressure, the obtained crude product was washed with petroleum ether/ethyl acetate (70 mL, 10/1) under stirring and then purified by column chromatography (SiO$_2$, petroleum ether/ethyl acetate=10/1 to 1/1 (v/v)) to give compound A1_3.

$^1$H NMR (400 MHz, CDCl$_3$) δ (ppm): 5.41-5.23 (m, 1H), 3.96 (br d, J=11.2 Hz, 1H), 3.79-3.70 (m, 1H), 3.40 (br d, J=8.3 Hz, 1H), 2.53-2.39 (m, 2H), 1.39 (s, 9H), 1.28 (s, 3H), 1.18 (s, 3H).

Step 3: A1_3 (30 g, 136.81 mmol, 1.00 eq) was dissolved in a mixed solution of sodium phosphate buffer (540.00 mL, 0.7 M, 2.76 eq) and acetonitrile (300 mL), followed by adding TEMPO (2.15 g, 13.68 mmol, 0.10 eq), then a solution of NaClO (81.47 g, 5.47 mmol, 67.33 mL, purity: 0.5%, 0.04 eq) and NaClO$_2$ (98.99 g, 1.09 mol, 8.00 eq) in water (300 mL) was added dropwise thereto at 35° C. under stirring. The obtained mixture was stirred at 35° C. for 12 hours, then cooled to room temperature and citric acid (10 g) was added. The obtained mixture was extracted with ethyl acetate (500 mL*4), the combined organic phase was washed with saturated sodium chloride aqueous solution (100 mL), dried over anhydrous sodium sulfate and filtered, the filtrate was concentrated under reduced pressure. Aqueous sodium carbonate solution (300 mL, 2 M) was added to the obtained crude product, and then the solution was washed with ethyl acetate (200 mL*2). The aqueous phase was cooled to 0° C., then the pH value was adjusted to 3.9 with dilute hydrochloric acid (1 M). Then sodium chloride was added into the solution until saturation, and the obtained mixture was washed with ethyl acetate (500 mL*4). The combined organic phase was washed with saturated sodium chloride aqueous solution (50 mL), dried over anhydrous sodium sulfate and filtered and the filtrate was concentrated under reduced pressure to give compound A1_4.

$^1$H NMR (400 MHz, CDCl$_3$) δ (ppm): 5.42 (br d, J=7.8 Hz, 1H), 4.18 (br d, J=8.4 Hz, 1H), 1.39 (s, 9H), 1.30 (s, 3H), 1.22 (s, 3H).

Step 4: A1_4 (48 g, 205.78 mmol, 1.00 eq) was dissolved in DMF (700 mL), then DCC (84.92 g, 411.56 mmol, 83.25 mL, 2.00 eq) and HOBt (55.61 g, 411.56 mmol, 2 eq) were added, the mixture was stirred at 10° C. for 0.5 hour, then O-benzylhydroxylamine hydrochloride (39.41 g, 246.93 mmol, 1.20 eq) and sodium bicarbonate aqueous solution (69.15 g, 823.11 mmol, 32.01 mL, 4 eq) were added thereto. The obtained mixture was stirred at 10° C. for 1.5 hours, then the reaction mixture was filtered and the filtrate was concentrated under reduced pressure. The crude product was diluted with water (400 mL), and extracted with ethyl acetate (500 mL*2). The combined organic phase was washed with saturated sodium chloride aqueous solution, dried over anhydrous sodium sulfate and filtered. The filtrated was concentrated under reduced pressure, the residue was purified by column chromatography (SiO$_2$, petroleum ether/ethyl acetate=6/1 to 3/1 (v/v)) to give compound A1_5.

$^1$H NMR (400 MHz, DMSO-d$_6$) δ (ppm): 11.06 (s, 1H), 7.45-7.32 (m, 5H), 6.45 (br d, J=9.2 Hz, 1H), 4.80 (d, J=2.6 Hz, 2H), 4.65 (s, 1H), 4.04 (d, J=7.0 Hz, 1H), 3.77 (br d, J=9.2 Hz, 1H), 1.40 (s, 9H), 1.11 (s, 3H), 1.08 (s, 3H);

LC-MS (ESI) m/z: 283 (M-56+1).

Step 5: A1_5 (57 g, 168.44 mmol, 1 eq) was dissolved in pyridine (600 mL), the solution was stirred at 55° C. for 12 hours then sulfur trioxide pyridine (187.67 g, 1.18 mol, 7 eq) was added thereto. The reaction mixture was concentrated under reduced pressure, the obtained solid was dissolved in ethyl acetate (800 mL). Potassium carbonate aqueous solution (816.94 mL, 2 M, 9.7 eq) was added dropwise to the solid at 0° C., the obtained mixture was stirred at 100° C. for 2 hours. The reaction was then cooled to room temperature, and extracted with ethyl acetate (400 mL*3). The combined organic phase was dried over anhydrous sodium sulfate and filtered, the filtrate was concentrated under reduced pressure. The obtained crude product was purified by column chromatography (SiO$_2$, petroleum ether/ethyl acetate=12/1 to 9/1 (v/v)) to give compound A1_6.

$^1$H NMR (400 MHz, CDCl$_3$) δ (ppm): 7.41 (br d, J=1.0 Hz, 5H), 5.02-4.97 (m, 2H), 4.32 (d, J=6.7 Hz, 1H), 1.50-1.43 (m, 9H), 1.34 (s, 3H), 1.11 (s, 3H);

LC-MS (ESI) m/z: 321.1 (M+1).

Step 6: A1_6 (31 g, 96.76 mmol, 1.00 eq) was dissolved in methanol (620 mL), then Pd/C (3 g, 10%) was added thereto under nitrogen atmosphere, the reaction bottle was replaced with nitrogen for three times. Then hydrogen was induced at 20° C., the reaction was carried out at 50 psi for 1 hour, the reaction mixture was then filtered and the filtrate was concentrated under reduced pressure to give compound A1_7.

Step 7: DMF.SO$_3$ (17.56 g, 114.65 mmol, 1.2 eq) was added to a solution of A1_7 (22 g, 95.54 mmol, 1.00 eq) in DMF (220 mL). The mixture was stirred at 0° C. for 1 hour, then diluted with saturated KH$_2$PO$_4$ (200 mL). The obtained mixture was extracted with ethyl acetate (100 mL), then Bu$_4$HSO$_4$ (38.93 g, 114.65 mmol, 1.20 eq) was added into the combined aqueous phase at 10° C. for 20 min, the obtained aqueous phase was extracted with EtOAc (350 mL*4). The organic phases were combined and the filtrate was concentrated under reduced pressure to give compound A1_8.

Step 8: A1_8 (68 g, 123.24 mmol, 1.00 eq) was added into trifluoroacetic acid (300 mL), the mixture was stirred at 15° C. for 4 hours under nitrogen atmosphere. The reaction mixture was diluted with dichloromethane (350 mL) and filtered, the filtrate was concentrated under reduced pressure to give compound A1.

$^1$H NMR (400 MHz, DMSO-d$_6$) δ (ppm): 8.79 (br s, 3H), 4.18 (br s, 1H), 1.46-1.38 (m, 6H).

Key Intermediate A2

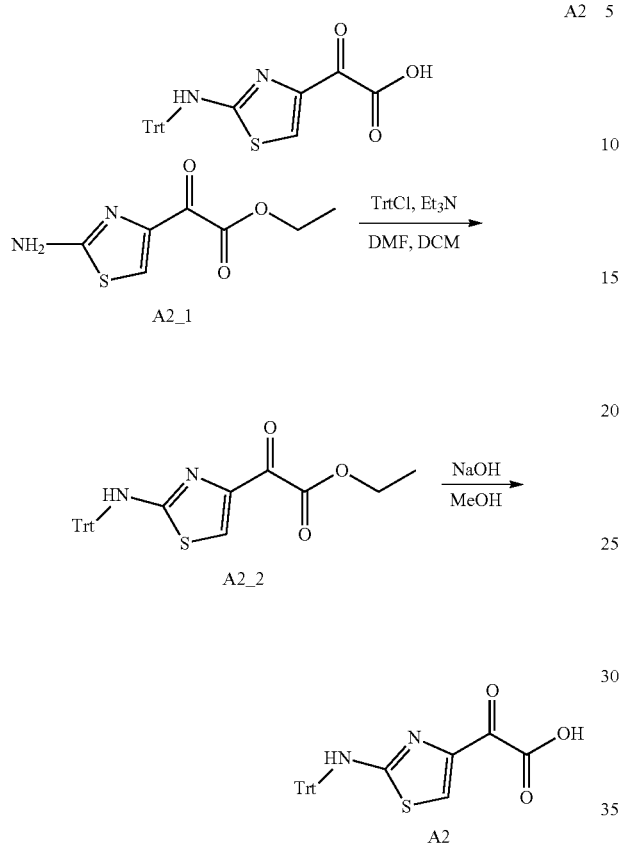

Key Intermediate A3: (Purchased from Shanghai FWD Chemicals Limited.)

Key Intermediate A4

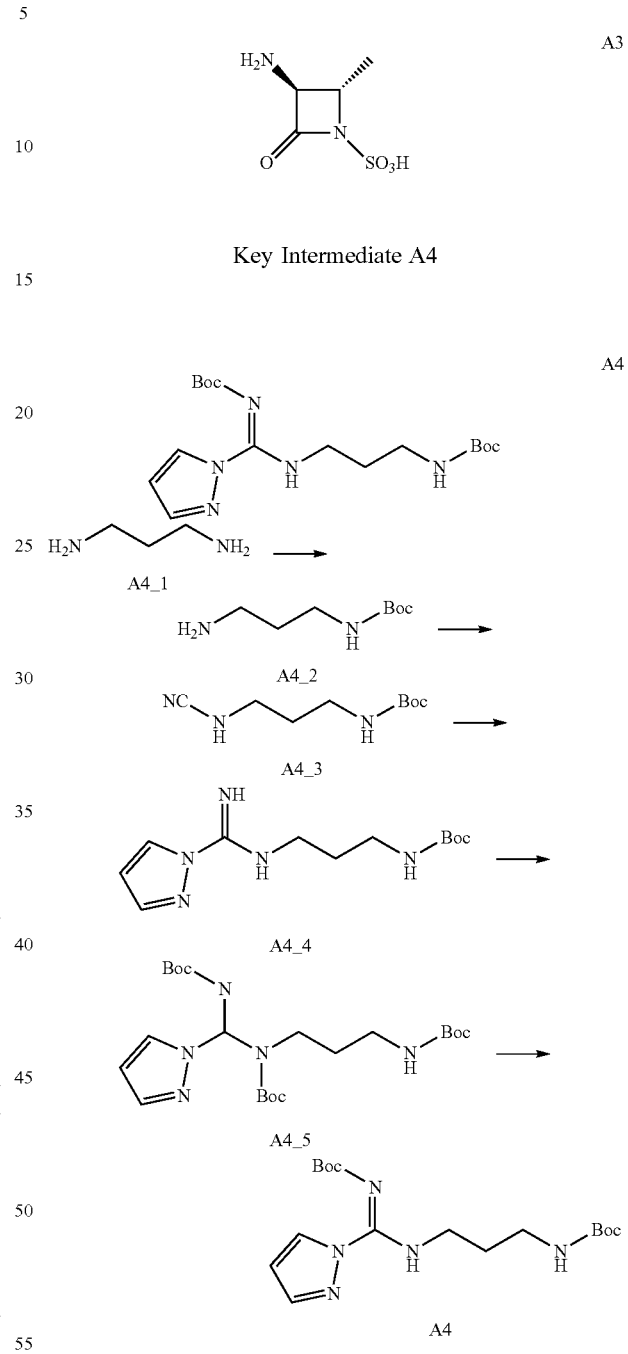

Step 1: A2_1 (97 g, 484.48 mmol, 1 eq) was dissolved in dichloromethane (600 mL) and DMF (400 mL), then triethylamine (49.02 g, 484.48 mmol, 67.43 mL, 1 eq) was added dropwise thereto, the solution was then cooled to −30° C. and triphenylchloromethane (135.06 g, 484.48 mmol, 1 eq) was added under the same temperature. The obtained mixture was stirred at 15° C. for 12 hours, then the reaction mixture was diluted with water (500 mL), and extracted with ethyl acetate (500 mL*2), the combined organic phase was washed with diluted hydrochloric acid (100 mL, 0.1 M), dried over anhydrous sodium sulfate and filtered, the filtrate was concentrated under reduced pressure to give A2_2.

Step 2: sodium hydroxide (24.86 g, 621.43 mmol, 1.1 eq) was added into a solution of A2_2 (250 g, 564.94 mmol, 1 eq) in methanol (750 mL). The obtained mixture was stirred at 60° C. for 10 min, then the reaction mixture was filtered, the obtained solid was dissolved in water (500 mL) and the pH value was adjusted to less than 5 with dilute hydrochloric acid (500 mL, 1 M) accompanied by precipitation. Then the mixture was filtered and the obtained solid was dissolved in dichloromethane (5 L), the obtained solution was dried over anhydrous sodium sulfate and filtered and the filtrate was concentrated under reduced pressure to give intermediate A2.

$^1$H NMR (400 MHz, DMSO-d$_6$) δ (ppm): 9.02 (s, 1H), 7.76 (s, 1H), 7.37-7.21 (m, 15H);

LC-MS (ESI) m/z: 437.2 (M+23).

Step 1: a solution of Boc$_2$O (9.32 g, 42.72 mmol, 9.81 mL, 1.00 eq) in dichloromethane (50 mL) was slowly added dropwise into a solution of A4_1 (19.00 g, 256.34 mmol, 21.35 mL, 6.00 eq) in dichloromethane (150 mL) at 0° C. The mixture was stirred at 20° C. for 1 hour, then the reaction was quenched by adding water (50 mL), the organic phase was separated and washed with water (30 mL), and the aqueous phase was extracted with dichloromethane (30 mL), the organic phases were then combined and dried over anhydrous sodium sulfate and filtered, the filtrate was concentrated under reduced pressure to give compound A4_2.

Step 2: sodium acetate (7.06 g, 86.08 mmol, 2.00 eq) was added into a solution of A4_2 (7.50 g, 43.04 mmol, 7.50 mL, 1.00 eq) in methanol (75.00 mL) at 0° C., then BrCN (6.84 g, 64.56 mmol, 4.75 mL, 1.50 eq) was added thereto. The mixture was stirred at 20° C. for 1 hour, then the reaction was quenched with water (20 mL), and the solution was extracted with ethyl acetate (20 mL). The combined organic phase was washed with saturated sodium chloride (20 mL*2), dried over anhydrous sodium sulfate and filtered, the filtrate was concentrated under reduced pressure to give compound A4_3.

Step 3: compound A4_3 (5.50 g, 27.60 mmol, 1.00 eq) and pyrazole hydrochloride (2.89 g, 27.60 mmol, 1.00 eq) was added into 1,4-dioxane (50.00 mL), the mixture was stirred at 80° C. for 2 hours under nitrogen atmosphere to give a solution of A4_4 in 1,4-dioxane, the solution was directly used in the next step.

Step 4: the crude product of solution of A4_4 (7.38 g, 27.61 mmol, 1.00 eq) in dioxane obtained in the previous step was added into dichloromethane (50.00 mL), followed by adding DMAP (674.53 mg, 5.52 mmol, 0.20 eq) and Boc$_2$O (18.08 g, 82.83 mmol, 19.03 mL, 3.00 eq). The mixture was stirred at 20° C. for 12 hours, then the reaction was quenched by adding water (50 mL), then extracted with ethyl acetate (50 mL*2). The combined organic phase was washed with saturated sodium chloride (30 mL), dried over anhydrous sodium sulfate and filtered, the filtrate was concentrated under reduced pressure, the residue was purified by column chromatography (SiO$_2$, petroleum ether/ethyl acetate=20:1 to 10:1 (v/v)) to give compound A4_5.

$^1$H NMR (400 MHz, CDCl$_3$) δ (ppm): 8.13 (d, J=2.7 Hz, 1H), 7.55 (s, 1H), 6.36-6.28 (m, 1H), 4.89 (br s, 1H), 3.44 (t, J=6.2 Hz, 2H), 3.25-3.14 (m, 2H), 1.87-1.75 (m, 2H), 1.59-1.32 (m, 27H).

Step 5: compound A4_5 (4.00 g, 8.56 mmol, 1.00 eq) was dissolved in a mixed solution of THF (40.00 mL) and water (10.00 mL), then sodium hydroxide (3.42 g, 85.60 mmol, 10.00 eq) was added thereto, the mixture was stirred at 70° C. for 2 hours under nitrogen atmosphere. The reaction mixture was concentrated and extracted with dichloromethane (20 mL), the combined organic phase was washed with saturated sodium chloride (10 mL), dried over anhydrous sodium sulfate and filtered, the filtrate was concentrated under reduced pressure, the residue was purified by column chromatography (SiO$_2$, petroleum ether/ethyl acetate=10/1 to 5/1 (v/v)) to give the intermediate A4.

Key Intermediate A5

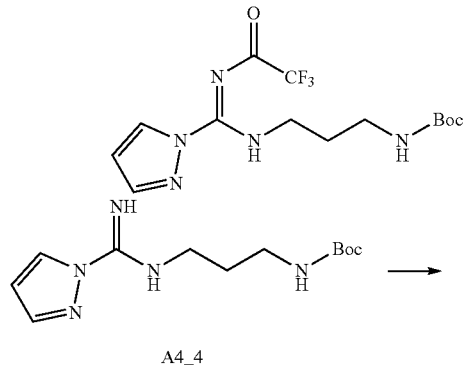

A5

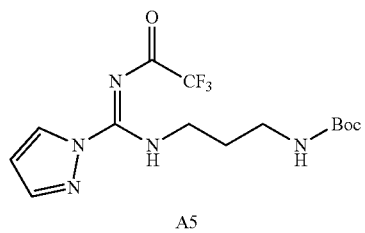

A5

Step 5: trifluoroacetic anhydride (1.66 g, 7.90 mmol, 1.10 mL, 1.2 eq) and triethylamine (1.47 g, 14.48 mmol, 2.02 mL, 2.2 eq) were added to a solution of the hydrochloride of compound A4_4 (2 g, 6.58 mmol, 1 eq) in DCM (20 mL). The mixture was stirred at 10° C. for 1 hour. The reaction mixture was washed with water (20 mL*2) mL, the organic phase was concentrated under reduced pressure to give the intermediate A5.

Key Intermediate A6

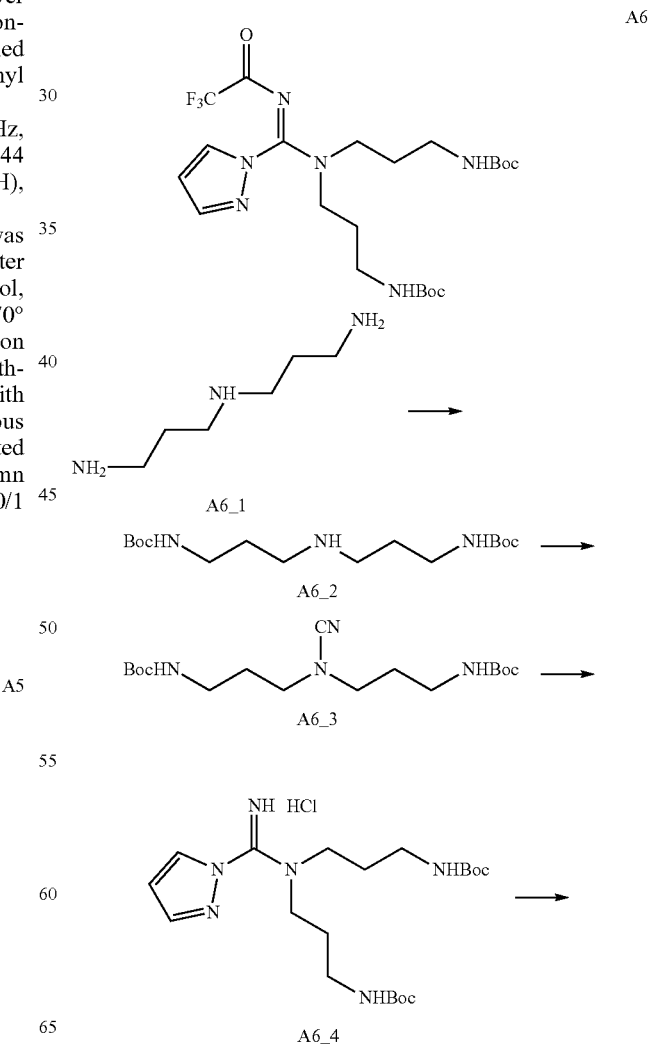

-continued

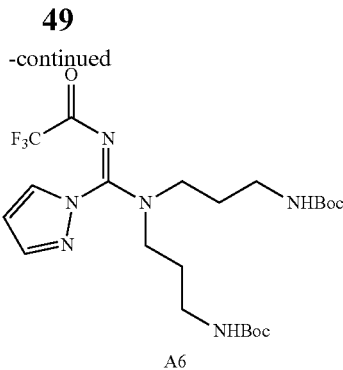

A6

Step 1: a solution of BOC—ONB (29.80 g, 106.69 mmol, 2 eq) and Et₃N (11.34 g, 112.03 mmol, 15.59 mL, 2.1 eq) in THF (330 mL) was added slowly to a solution of A6_1 (7 g, 53.35 mmol, 7.54 mL, 1 eq) in THF (70 mL) at 20° C., the obtained mixture was stirred at 20° C. for 11 hours. The reaction mixture was filtered and the filtrate was concentrated under reduced pressure, the residue was diluted with potassium carbonate solution (100 mL, 2 M), and extracted with ethyl acetate (100 mL*2), the organic phases were combined and concentrated under reduced pressure to give compound A6_2.

Step 2: BrCN (7.86 g, 74.21 mmol, 5.46 mL, 1.64 eq) and sodium acetate (7.43 g, 90.51 mmol, 2 eq) were added into a solution of A6_2 (15 g, 45.26 mmol, 1 eq) in MeOH (150 mL) at 0° C., the mixture was stirred at room temperature for 2 hours, then diluted with saturated sodium carbonate aqueous solution (300 mL) and extracted with ethyl acetate (100 mL). The organic phase was concentrated under reduced pressure, the residue was purified by column chromatography (SiO₂, petroleum ether/ethyl acetate=5/1 to 1/1) to give compound A6_3.

Step 3: compound A6_3 (4.2 g, 11.78 mmol, 1 eq) and pyrazole hydrochloride (1.23 g, 11.78 mmol, 1 eq) were separately added into THF (40 mL) and replaced with nitrogen gas for three times, the mixture was stirred to react at 75° C. for 12 hours. The reaction mixture was cooled to room temperature and diluted with ethyl acetate (100 mL), and filtered, the filter cake was collected, and dried to give compound A6_4.

LCMS (ESI) m/z: 425.4 (M+1).

Step 4: TFAA (765.41 mg, 3.64 mmol, 506.89 μL, 0.8 eq) and triethylamine (1.01 g, 10.02 mmol, 1.39 mL, 2.2 eq) were added into a solution of the compound A6_4 (2.1 g, 4.56 mmol, 1 eq) in DCM (20 mL) at 0° C., the mixture was stirred at 0° C. for 20 min, and diluted with water (20 mL), the obtained mixture was extracted with DCM (50 mL*2), the organic phases were combined and concentrated under reduced pressure to give compound A6.

Key Intermediate A7

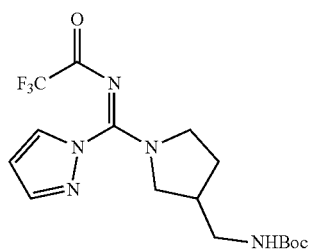

A7

-continued

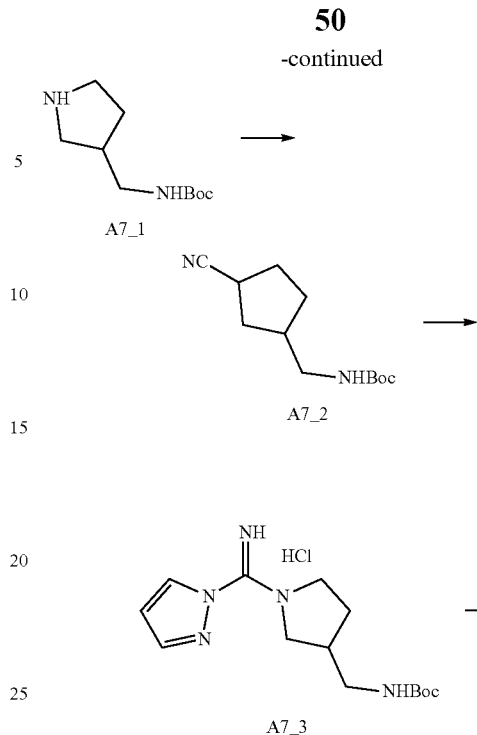

Step 1: BrCN (4.46 g, 42.11 mmol, 1.69 eq) and AcONa (4.10 g, 49.93 mmol, 2 eq) were added into a solution of A7_1 (5 g, 24.97 mmol, 1 eq) in MeOH (50 mL) at 0° C. The mixture was stirred at 20° C. for 12 hours, then diluted with saturated sodium carbonate solution (100 mL), and extracted with ethyl acetate (50 mL). The organic phases were combined and concentrated under reduced pressure, the obtained residue was purified by column chromatography (SiO₂, petroleum ether/ethyl acetate=5/1 to 1/1) to give compound A7_2.

Step 2: A7_2 (4.3 g, 19.09 mmol, 1 eq) was added to a solution of pyrazole hydrochloride (2.00 g, 19.09 mmol, 1 eq) in THF (40 mL) at room temperature. The mixture was stirred at 80° C. for 12 hours, and concentrated under reduced pressure to give compound A7_3.

Step 3: TFAA (5.12 g, 24.37 mmol, 3.39 mL, 1.1 eq) and TEA (6.73 g, 66.47 mmol, 9.25 mL, 3 eq) were added to a solution of A7_3 (6.5 g, 22.16 mmol, 1 eq) in DCM (60 mL) at 0° C. The mixture was stirred at 25° C. for 2 hours, then diluted with water (50 mL) and extracted with DCM (50 mL*2). The organic phases were combined and concentrated under reduced pressure to give compound A7.

Key Intermediate A8
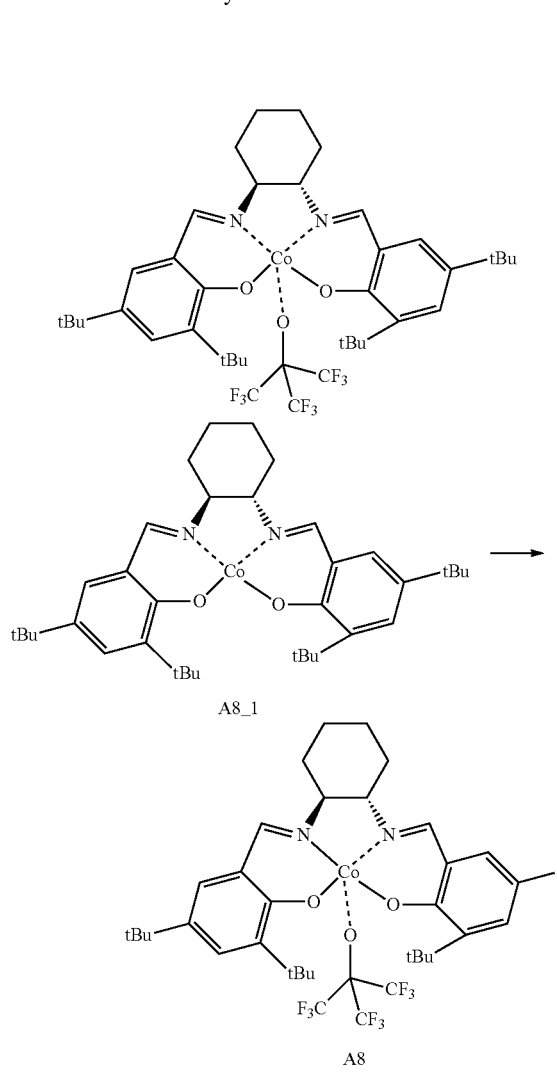
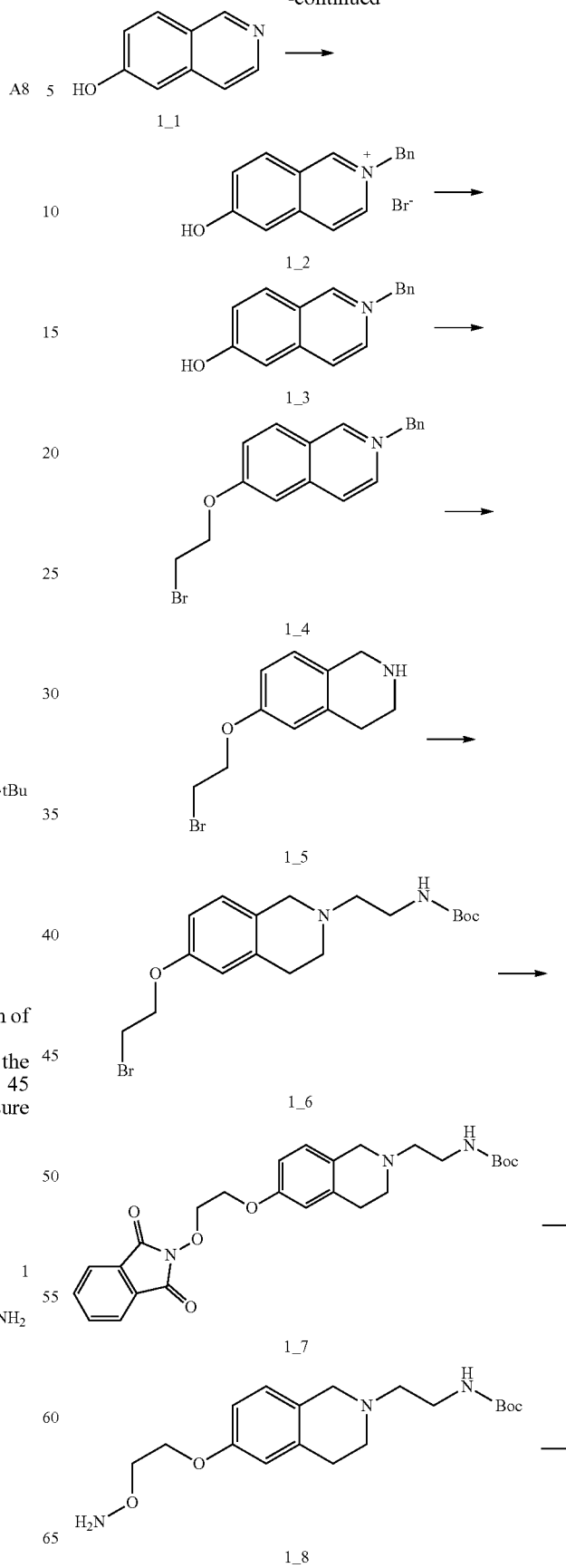
Step 1: compound A8_1 was added to a mixed solution of 1,1,1,3,3,3-hexafluoro-2-(trifluoromethyl)propan-2-ol (10.16 g, 43.06 mmol, 10 eq) and DCM (20 mL), the reaction solution was stirred at room temperature for 45 mins (20-25° C.), then concentrated under reduced pressure to give compound A8.
Embodiment 1
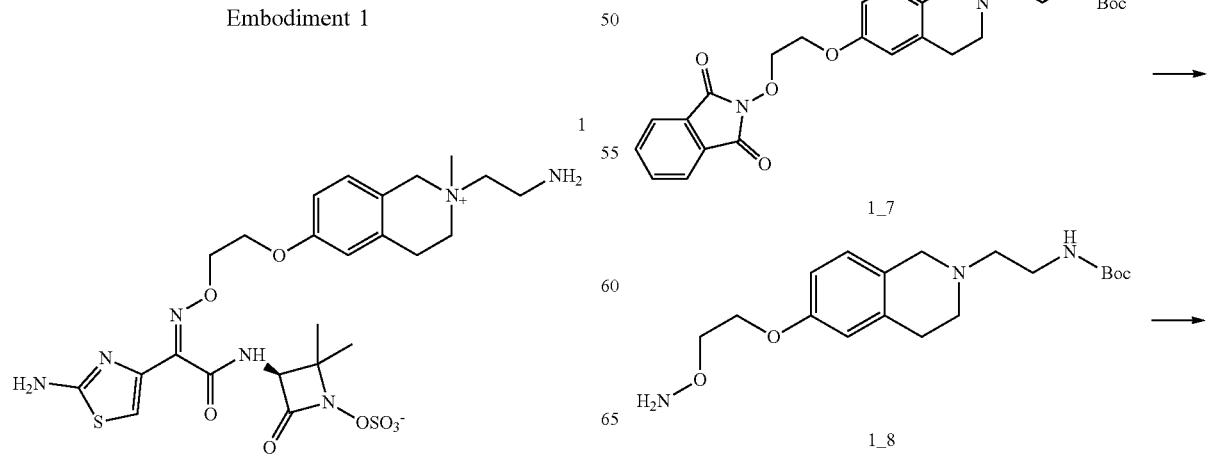

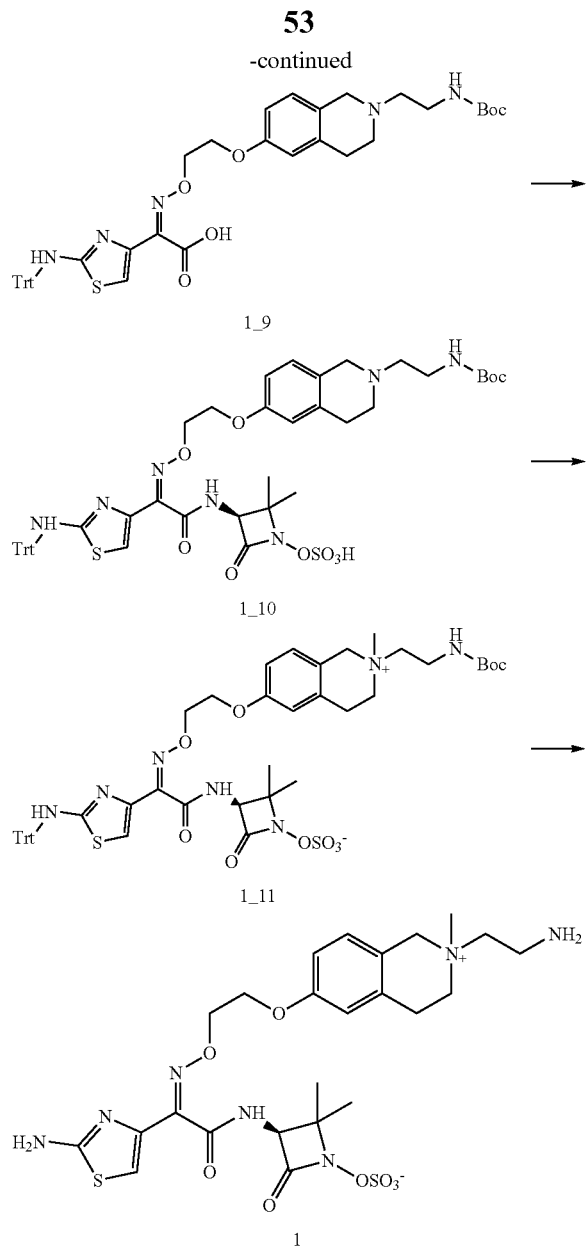

Step 1: BnBr (7.66 g, 44.77 mmol, 5.32 mL, 1.30 eq) was added into a solution of compound 1_1 (5.00 g, 34.44 mmol, 1.00 eq) in ethanol (60.00 mL) at 15° C. The mixture was stirred at 60° C. for 14 hours, then cooled to room temperature, the mixture was then concentrated under reduced pressure. The crude product was washed with ethyl acetate (30 mL) to give compound 1_2.

Step 2: NaBH₄ (3.00 g, 79.30 mmol, 2.39 eq) was added to a solution of compound 1_2 (10.50 g, 33.21 mmol, 1.00 eq) in methanol (110.00 mL) at 0° C., the mixture was stirred at 15° C. for 2 hours, then water (10 mL) was added thereto and the mixture was stirred for another 5 min. The aqueous phase was extracted with dichloromethane (100 mL). The combined organic phase was washed with saturated sodium chloride (20 mL), dried over anhydrous sodium sulfate and filtered, the filtrate was concentrated under reduced pressure to give compound 1_3.

LC-MS (ESI) m/z=240.3 (M+1).

Step 3: compound 1_3 (2.50 g, 10.45 mmol, 1.00 eq), sodium hydroxide aqueous solution (50.00 mL, 1 M) and 1,2-dibromoethane (62.25 g, 331.37 mmol, 25.00 mL, 31.72 eq) were mixed and stirred at 90° C. for 2 hours, then the mixture was poured into water (10 mL) and stirred for 5 min. The aqueous phase was extracted with ethyl acetate (100 mL), the combined organic phase was washed with saturated sodium chloride aqueous solution (30 mL), dried over anhydrous sodium sulfate and filtered, the filtrate was concentrated under reduced pressure, the residue was purified by column chromatography (SiO₂, petroleum ether/ethyl acetate=1/0 to 3/1 (v/v)) to give compound 1_4.

Step 4: chloro-1-chloroethyl carbonate (2.39 g, 16.75 mmol, 2.00 eq) was added to a solution of compound 1_4 (2.90 g, 8.38 mmol, 1.00 eq) in 1,2-dichloroethane (30.00 mL) at 0° C., the mixture was stirred at 100° C. for 2 hours. The mixture was concentrated under reduced pressure and methanol (30.00 mL) was added thereto, the mixture was then stirred at 100° C. for 3 hours, concentrated under reduced pressure and washed with ethyl acetate (20 mL), the hydrochloride of compound 1_5 was obtained after drying.

Step 5: potassium carbonate (944.70 mg, 6.84 mmol, 2.00 eq) and tert-butyl N-(2-bromoethyl) carbamate (919.07 mg, 4.10 mmol, 1.20 eq) were added to a solution of the hydrochloride of compound 1_5 (1.00 g, 3.42 mmol, 1.00 eq) in DMF (10.00 mL). The mixture was stirred at 60° C. for 14 hours, concentrated under reduced pressure, and then the residue was purified by column chromatography (SiO₂, petroleum ether/ethyl acetate=10/1 to 1/1 (v/v)) to give compound 1_6.

Step 6: triethylamine (203.90 mg, 2.01 mmol, 279.31 μl, 1.30 eq) and 2-hydroxyisoindoline-1,3-dione (252.85 mg, 1.55 mmol, 1.00 eq) were added to a solution of compound 1_6 (620.00 mg, 1.55 mmol, 1.00 eq) in DMF (2.00 mL). The mixture was stirred at 45° C. for 12 hours, concentrated under reduced pressure, then saturated sodium carbonate aqueous solution (20 mL) was added to the residue, followed by extracting with ethyl acetate (50 mL*2), the combined organic phase was washed with saturated sodium chloride aqueous solution (20 mL), dried over anhydrous sodium sulfate and filtered, the filtrate was concentrated under reduced pressure, the obtained residue was purified by preparative TLC (SiO₂, petroleum ether/ethyl acetate=1/1 (v/v)) to give compound 1_7.

LC-MS (ESI) m/z: 482.4 (M+1).

Step 7: NH₂NH₂.H₂O (14.71 mg, 249.72 μmol, 14.28 μL, purity 85%, 1 eq) was added to a solution of compound 1_7 (130 mg, 249.72 μmol, 1 eq) in ethanol (2 mL). The mixture was stirred at 50° C. for 2 hours and filtered, the filtrate was concentrated under reduced pressure to give compound 1_8.

Step 8: intermediate A2 (84.91 mg, 204.87 μmol, 0.9 eq) was added to a mixed solution of compound 1_8 (80 mg, 227.64 mol, 1 eq) in methanol (3 mL) and dichloromethane (1 mL). The mixture was stirred at 15° C. for 0.5 hour, concentrated under reduced pressure, then dilute hydrochloric acid (10 mL, 0.5 M) was added to the residue, the aqueous phase was extracted with ethyl acetate (50 mL*2). The combined organic phase was washed with saturated sodium chloride aqueous solution (30 mL), dried over anhydrous sodium sulfate and filtered, the filtrate was concentrated under reduced pressure to give compound 1_9.

LC-MS (ESI) m/z: 748.6 (M+1).

Step 9: DCC (64.55 mg, 312.88 μmol, 63.29 μL, 2 eq) and HOBt (42.28 mg, 312.88 μmol, 2 eq) were added to a solution of compound 1_9 (150 mg, 156.44 μmol, 1 eq) in DMF (2 mL). The mixture was stirred at 15° C. for 1 hour, then intermediate A1 (36.17 mg, 172.08 μmol, 1.1 eq) and sodium bicarbonate (52.57 mg, 625.75 μmol, 24.34 μL, 4 eq) were added thereto, the mixture was stirred at 15° C. for 4 hours, then concentrated under reduced pressure, the obtained residue was poured into water (20 mL) and the mixture was stirred for 5 min, extracted with ethyl acetate (100 mL), the combined organic phase was washed with saturated sodium chloride aqueous solution (20 mL), dried over anhydrous sodium sulfate, then filtered and concentrated under reduced pressure, the residue was purified by preparative TLC (SiO$_2$, dichloromethane/methanol=10/1 (v/v)) to give compound 110.

LC-MS (ESI) m/z: 940.7 (M+1).

Step 10: iodomethane (1.84 g, 12.96 mmol, 807.02 μL, 137.64 eq) was added to a solution of compound 1_10 (90 mg, 94.18 μmol, 1 eq) in THF (1 mL). The mixture was stirred at 15° C. for 14 hours and concentrated under reduced pressure, the obtained residue was dissolved in DMF (2 mL), then iodomethane (1.74 g, 12.26 mmol, 763.16 μL, 130.16 eq) and potassium carbonate (13.02 mg, 94.18 μmol, 1 eq) were added thereto, the solution was stirred at 15° C. for another 1 hour, then concentrated under reduced pressure to give compound 1_11.

Step 11: TFA (3.08 g, 27.01 mmol, 2 mL, 286.67 eq) was added to a solution of compound 1_11 (90 mg, 94.23 μmol, 1 eq) in dichloromethane (1 mL), the obtained mixture was stirred at 15° C. for 0.5 hour and concentrated under reduced pressure, the residue was purified by preparative HPLC (column: Boston Green ODS 150*30 5μ; mobile phase: [water (0.225% formic acid)-acetonitrile]; acetonitrile %: 3%-30%, 10 min) to give compound 1.

$^1$H NMR (400 MHz, DMSO-d$_6$) δ (ppm): 9.42 (br d, J=7.5 Hz, 1H), 8.22 (s, 1H), 7.20 (br s, 2H), 7.11 (br d, J=9.0 Hz, 1H), 6.89 (br s, 1H), 6.76 (s, 1H), 4.69-4.46 (m, 3H), 4.37 (br s, 2H), 4.19 (br s, 2H), 3.58-3.53 (m, 4H), 3.13 (br s, 2H), 3.10 (s, 3H), 3.03 (br s, 2H), 1.39-1.29 (m, 3H), 1.28-1.15 (m, 3H);

LC-MS (ESI) m/z: 612.7 (M+1).

Embodiment 2

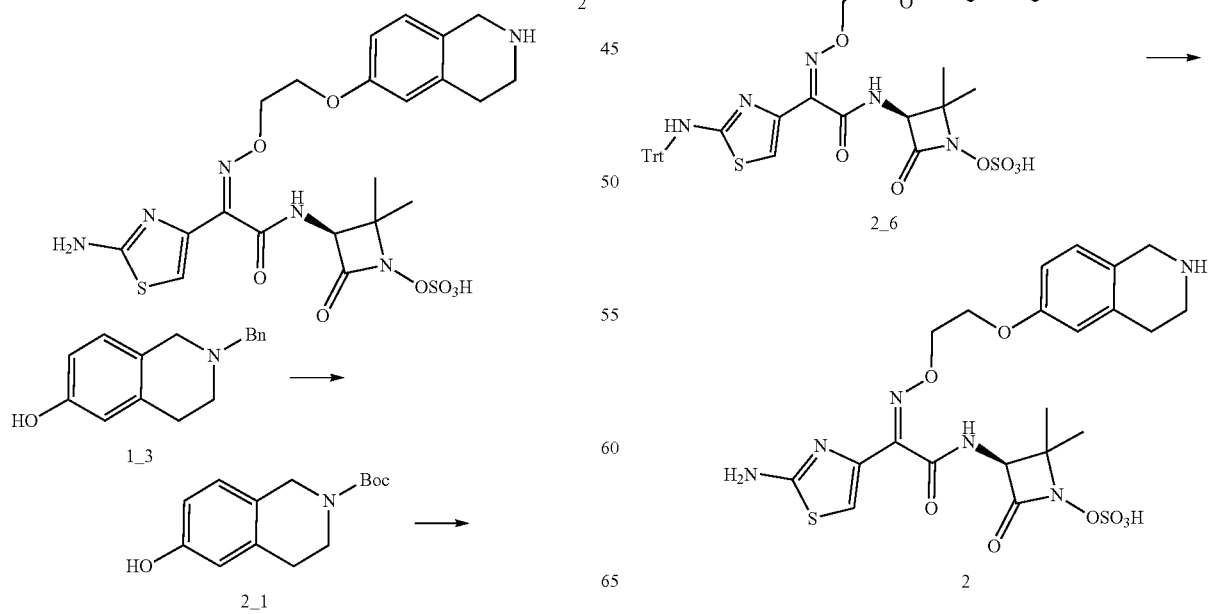

Step 1: Pd(OH)$_2$/C (200 mg, 10%) and Boc$_2$O (3.83 g, 17.55 mmol, 1.5 eq) were added to a solution of compound 1_3 (2.80 g, 11.70 mmol, 1.00 eq) in methanol (30.00 mL) under nitrogen atmosphere, the mixture was ventilated with hydrogen for 3 times at 30° C. and stirred for 2 hours under hydrogen (50 psi), after filtering, the filtrate was concentrated under reduced pressure, the residue was purified by silicon chromatography (SiO$_2$, petroleum ether/ethyl acetate=1/0 to 1/1 (v/v)) to give compound 2_1.

Step 2: compound 2_1 (3.90 g, 15.64 mmol, 1.00 eq) was added to sodium hydroxide (40.00 mL, 1 M) solution, then 1,2-dibromoethane (49.80 g, 265.09 mmol, 20.00 mL, 16.95 eq) and tetrabutylammonium bromide (100.84 mg, 312.80 μmol, 0.02 eq) were added thereto. The mixture was stirred at 90° C. for 2 hours, then poured into water (10 mL) and stirred for another 5 min, the aqueous phase was extracted with ethyl acetate (100 mL), the organic phases were combined and washed with saturated sodium chloride aqueous solution (30 mL), dried over anhydrous sodium sulfate, the obtained mixture was filtered, then concentrated under reduced pressure, the residue was purified by silica gel chromatography (SiO$_2$, petroleum ether/ethyl acetate=1/0 to 50/1 (v/v)) to give compound 2_2.

Step 3: triethylamine (1.11 g, 10.95 mmol, 1.52 mL, 1.30 eq) and 2-hydroxyisoindoline-1,3-dione (1.37 g, 8.42 mmol, 1.00 eq) were added to a solution of compound 2_2 (3.00 g, 8.42 mmol, 1.00 eq) in DMF (20.00 mL). The mixture was stirred at 50° C. for 12 hours, then concentrated under reduced pressure, the residue was purified by silica gel chromatography (SiO$_2$, petroleum ether/ethyl acetate=10/1 to 3/1 (v/v)) to give compound 2_3.

LC-MS (ESI) m/z: 339.3 (M-99).

Step 4: NH$_2$NH$_2$.H$_2$O (120.89 mg, 2.05 mmol, 117.36 μL, purity: 85%, 1.00 eq) was added to a solution of compound 2_3 (900.00 mg, 2.05 mmol, 1.00 eq) in ethanol (15.00 mL). The mixture was stirred at 45° C. for 2 hours and filtered, the filtrate was concentrated under reduced pressure to give compound 2_4.

Step 5: intermediate A2 (650.00 mg, 1.57 mmol, 1.00 eq) was added to a solution of compound 2_4 (580.31 mg, 1.88 mmol, 1.20 eq) in dichloromethane (3.00 mL) and methanol (9.00 mL). The mixture was stirred at 15° C. for 1 hour, and concentrated under reduced pressure, then dilute hydrochloric acid (40 mL, 0.5 M) was added to the residue, the aqueous phase was extracted with ethyl acetate (50 mL). The combined organic phase was washed with saturated sodium chloride aqueous solution (20 mL), dried over anhydrous sulfuric acid, filtered, and the filtrate was concentrated under reduced pressure to give compound 2_5.

Step 6: DCC (548.84 mg, 2.66 mmol, 538.08 μL, 2.00 eq) and HOBt (359.42 mg, 2.66 mmol, 2.00 eq) were added to a solution of compound 2_5 (940.00 mg, 1.33 mmol, 1.00 eq) in DMF (10.00 mL). The mixture was stirred at 15° C. for 1 hour, then sodium bicarbonate (446.93 mg, 5.32 mmol, 206.91 μL, 4.00 eq) and intermediate A1 (307.54 mg, 1.46 mmol, 1.10 eq) were added thereto. The mixture was stirred at 15° C. for 11 hours, then concentrated under reduced pressure and the residue was poured into water (10 mL) and stirred for 5 min, then extracted with ethyl acetate (100 mL). The combined organic phase was washed with saturated sodium chloride aqueous solution (20 mL), dried over anhydrous sodium sulfate and filtered, the filtrate was concentrated under reduced pressure, the residue was purified by silica gel chromatography (SiO$_2$, dichloromethane/methanol=30/1 to 10/1 (v/v)) to give compound 2_6.

Step 7: the mixture of compound 2_6 (50.00 mg, 55.74 μmol, 1.00 eq) and formic acid (1 mL) was stirred at 40° C. for 40 min, then ethyl acetate (20 mL) and water (1 mL) were added to the residue and then stirred and washed, the aqueous phase was separated, which was purified by preparative HPLC (column: Boston Green ODS 150*30 5 u; mobile phase: [water (0.225% formic acid)-acetonitrile]; acetonitrile %: 1%-30%, 10 min) to give compound 2.

$^1$H NMR (400 MHz, D$_2$O) δ (ppm): 8.34 (s, 1H), 7.08 (d, J=8.6 Hz, 1H), 6.90 (s, 1H), 6.84 (dd, J=2.6, 8.6 Hz, 1H), 6.80 (s, 1H), 4.80-4.76 (m, 2H), 4.47 (br d, J=2.3 Hz, 2H), 4.28-4.25 (m, 1H), 4.23 (s, 2H), 3.47-3.31 (m, 2H), 3.00 (t, J=6.4 Hz, 2H), 1.44 (s, 3H), 1.15 (s, 3H);

LC-MS (ESI) m/z: 555.3 (M+1).

Embodiment 3

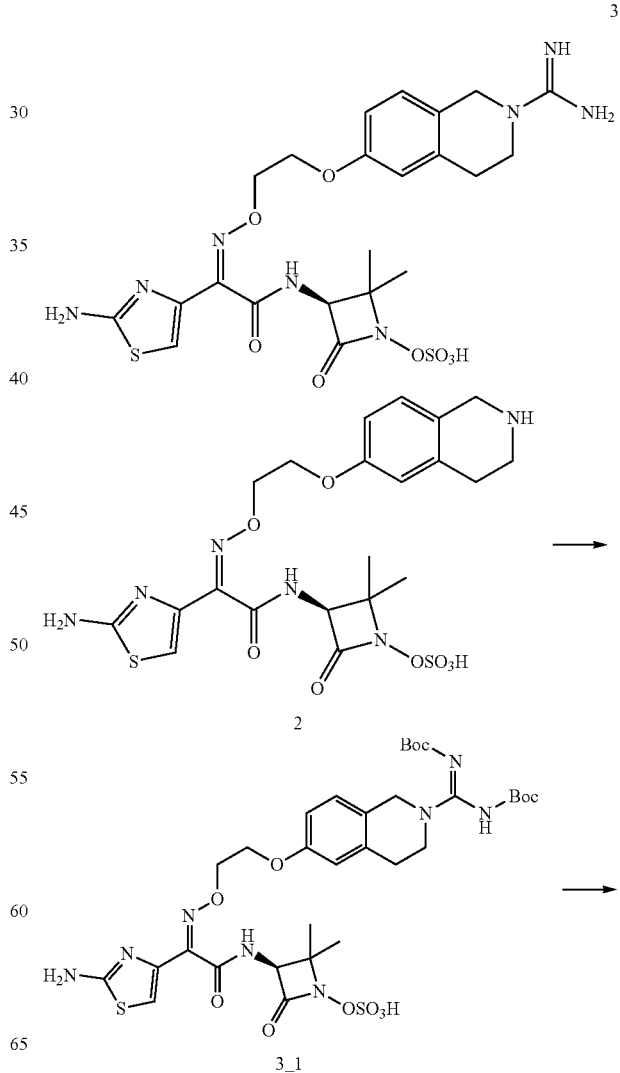

-continued

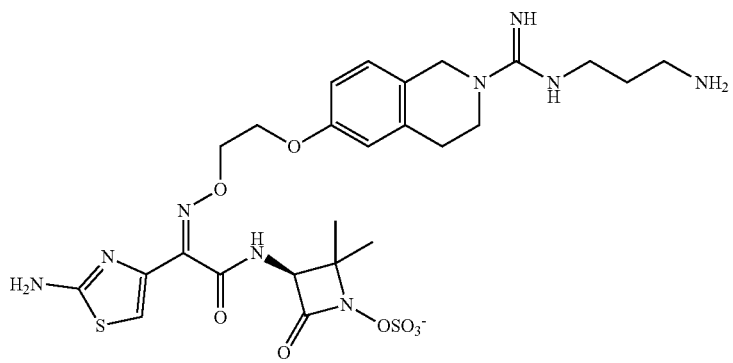

3

Step 1: DIPEA (154.63 mg, 1.20 mmol, 208.96 μL, 4.0 eq) and tert-butyl (((tert-butoxycarbonyl)amino)(1H-pyrazol-1-yl)methylene)carbamate (Z)-tert-butyl ester (102.12 mg, 329.03 μmol, 1.10 eq) were added to a solution of a trifluoroacetate of compound 2 (200.00 mg, 299.12 μmol, 1.00 eq) in DMF (2.00 mL). The mixture was stirred at 40° C. for 2 hours and concentrated under reduced pressure, the residue was purified by preparative TLC (SiO₂, dichloromethane/methanol=6/1 (v/v)) to give compound 3_1.

Step 2: TFA (4.62 g, 40.52 mmol, 3 mL, 358.77 eq) was added to a solution of compound 3_1 (90.00 mg, 112.94 μmol, 1.00 eq) in dichloromethane (1.00 mL). The mixture was stirred at 15° C. for 0.5 hour and concentrated under reduced pressure, the residue was purified by preparative HPLC (column: Boston Green ODS 150*30 5 u; mobile phase: [water (0.22 5% formic acid)-acetonitrile]; acetonitrile %: 5%-35%, 10 min) to give compound 3.

¹H NMR (400 MHz, DMSO-d₆) δ (ppm): 9.43 (br d, J=7.9 Hz, 1H), 7.45 (br s, 4H), 7.21 (br s, 2H), 7.08 (br d, J=8.2 Hz, 1H), 6.90-6.80 (m, 2H), 6.76 (s, 1H), 4.59 (br d, J=7.9 Hz, 1H), 4.49 (s, 2H), 4.37 (br s, 2H), 4.18 (br s, 2H), 3.56 (br t, J=5.4 Hz, 2H), 2.89 (br s, 2H), 1.40 (s, 3H), 1.23 (s, 3H);

LC-MS (ESI) m/z: 597.2 (M+1).

Embodiment 4

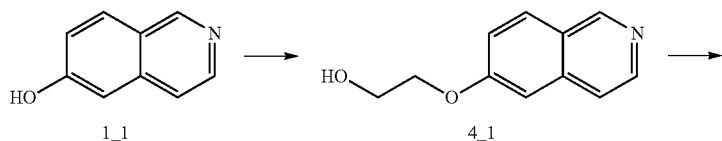

4

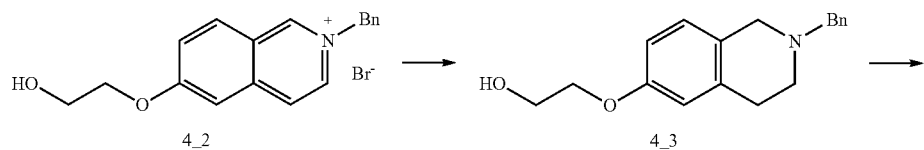

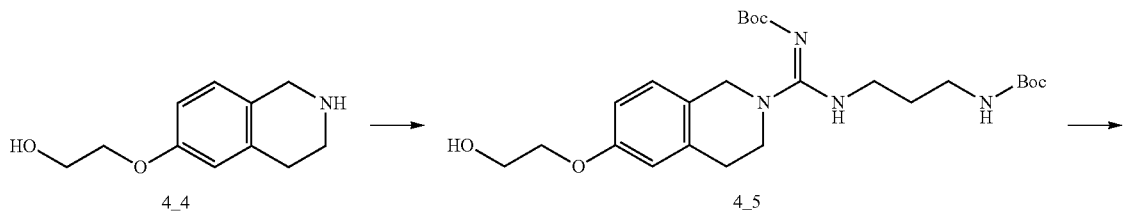

-continued
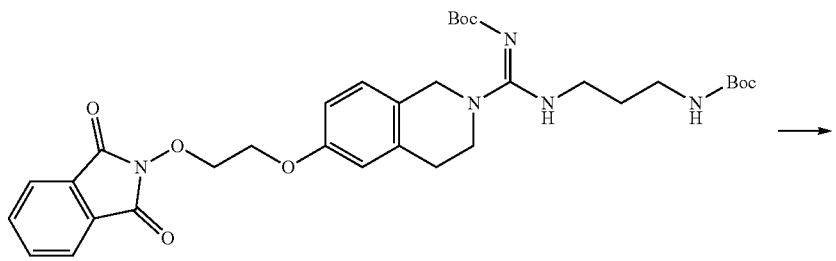
4_6
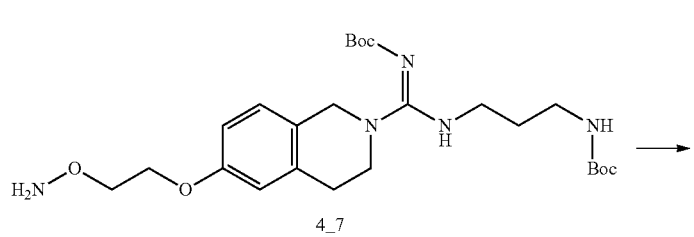
4_7
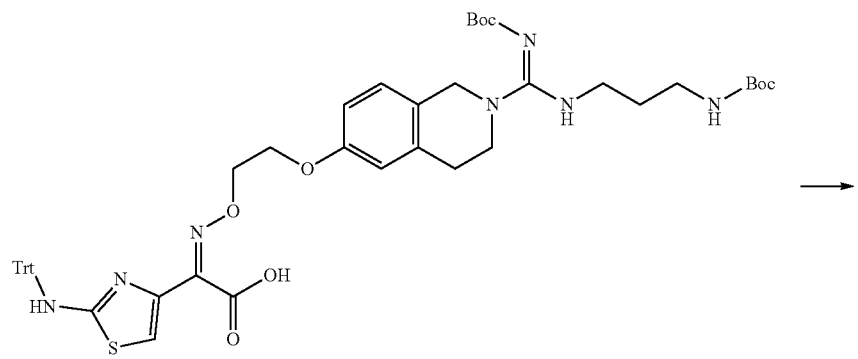
4_8
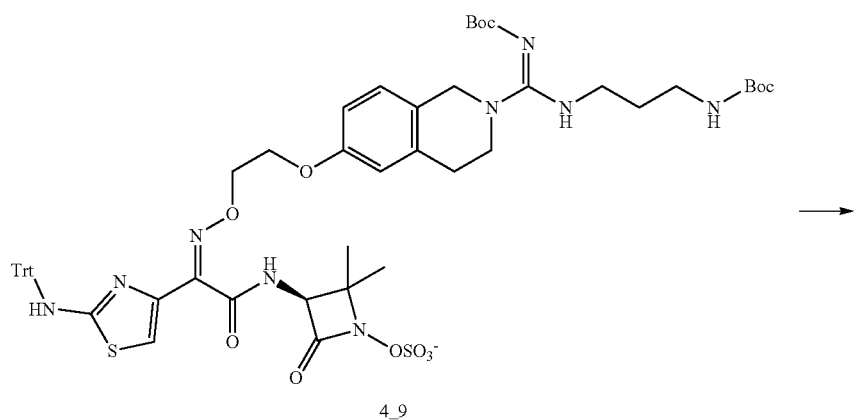
4_9

-continued

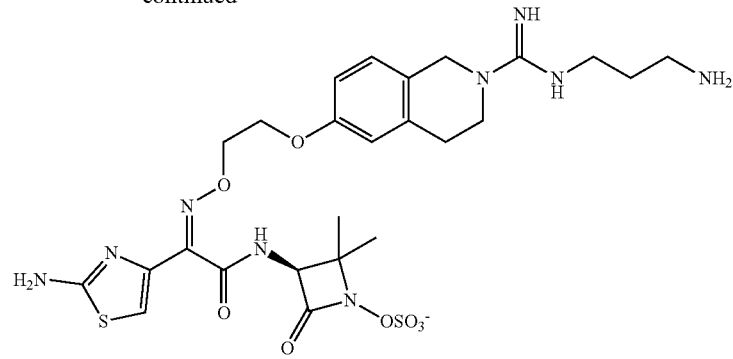

4

Step 1: potassium carbonate (6.28 g, 45.47 mmol, 1.1 eq) was added to a solution of compound 1_1 (6 g, 41.33 mmol, 1 eq) and 1,3-dioxolane-2-one (4.37 g, 49.60 mmol, 3.31 mL, 1.2 eq) in DMF (80 mL). The mixture was stirred at 150° C. for 1 hour under nitrogen atmosphere, then concentrated under reduced pressure to removed DMF, the residue was diluted with water (30 mL), then extracted with ethyl acetate (100 mL*5). The combined organic phase was concentrated under reduced pressure to give compound 4_1.

$^1$H NMR (400 MHz, DMSO-$d_6$) δ (ppm): 9.15 (s, 1H), 8.52-8.29 (m, 1H), 8.18-7.90 (m, 1H), 7.84-7.57 (m, 1H), 7.50-7.09 (m, 2H), 5.16-4.81 (m, 1H), 4.16 (br s, 2H), 3.95-3.66 (m, 2H).

Step 2: BnBr (2.35 g, 13.74 mmol, 1.63 mL, 1.3 eq) was added to a solution of compound 4_1 (2 g, 10.57 mmol, 1 eq) in methanol (30 mL). The mixture was stirred at 60° C. for 12 hours, then concentrated under reduced pressure, the residue was diluted with ethyl acetate (50 mL) and stirred for 20 min, then the solid was collected after filtering to give compound 4_2.

$^1$H NMR (400 MHz, DMSO-$d_6$) δ (ppm): 10.04 (s, 1H), 8.75-8.67 (m, 1H), 8.44-8.40 (m, 1H), 8.36-8.32 (m, 1H), 7.79-7.76 (m, 1H), 7.71-7.66 (m, 1H), 7.55 (s, 2H), 7.44 (s, 3H), 5.89 (s, 2H), 4.36-4.24 (m, 2H), 3.89-3.78 (m, 2H).

Step 3: NaBH$_4$ (998.64 mg, 26.40 mmol, 2.5 eq) was added to a solution of compound 4_2 (3.17 g, 10.56 mmol, 1 eq) in methanol (40 mL) at 0° C. The mixture was stirred at 15° C. for 2 hours, then the reaction was quenched by adding water (10 mL), the solvent was removed by concentration under reduced pressure, the residue was diluted with water (30 mL), and extracted with ethyl acetate (30 mL), the organic phases were combined and concentrated under reduced pressure, the residue was purified by column chromatography (SiO$_2$, petroleum ether/ethyl acetate=1/1 to 1/2 (v/v)) to give compound 4_3.

$^1$H NMR (400 MHz, CDCl$_3$) δ (ppm): 7.48-7.26 (m, 5H), 6.96-6.89 (m, 1H), 6.75-6.70 (m, 1H), 6.69-6.67 (m, 1H), 4.08-4.01 (m, 2H), 3.96-3.90 (m, 2H), 3.72 (s, 2H), 3.61 (s, 2H), 2.93-2.87 (m, 2H), 2.80-2.72 (m, 2H).

Step 4: NH$_3$.H$_2$O (1.82 g, 51.93 mmol, 2 mL, purity: 36%, 7.36 eq) was added to a solution of compound 4_3 (2 g, 7.06 mmol, 1 eq) in methanol (20 mL), Pd(OH)$_2$/C (100 mg, 10%) was added under nitrogen atmosphere, the obtained mixture was ventilated with hydrogen for 3 times, then stirred at 50° C. for 12 hours under hydrogen (50 psi), the mixture was then filtered, the filtrate was concentrated under reduced pressure to give compound 4_4.

Step 5: DIPEA (802.58 mg, 6.21 mmol, 1.08 mL, 2 eq) and intermediate A4 (1.14 g, 3.10 mmol, 1 eq) were added to a solution of compound 4_4 (600 mg, 3.10 mmol, 1 eq) in DMF (15 mL). The mixture was stirred at 90° C. for 12 hours and concentrated under reduced pressure, the residue was purified by column chromatography (SiO$_2$, petroleum ether/ethyl acetate=1/1 to 0/1 (v/v)) to give compound 4_5.

Step 6: compound 4_5 (740 mg, 1.38 mmol, 1 eq), 2-hydroxyisoindoline-1,3-dione (225.07 mg, 1.38 mmol, 1 eq) and PPh$_3$ (434.25 mg, 1.66 mmol, 1.2 eq) were dissolved in THF (20 mL), then DIAD (334.78 mg, 1.66 mmol, 321.90 μL, 1.2 eq) was added thereto. The mixture was stirred at 15° C. for 12 hours under nitrogen atmosphere, and concentrated under reduced pressure, the residue was purified by column chromatography (SiO$_2$, dichloromethane/methanol=100/1 to 10/1 (v/v)) to give compound 4_6.

Step 7: NH$_2$NH$_2$.H$_2$O (39.25 mg, 784.04 μmol, 38.11 μL) was added to a solution of compound 46 (500 mg, 784.04 μmol, 1 eq) in ethanol (10 mL). The mixture was stirred at 15° C. for 1 hour then filtered, the filtrate was concentrated under reduced pressure, the residue was diluted with hydrochloric acid (10 mL, 0.5 M) and extracted with dichloromethane (10 mL), the pH value of the aqueous phase was adjusted to 8-9 by using saturated sodium bicarbonate, then extracted with dichloromethane (10 mL). The organic phases were combined and concentrated under reduced pressure to give compound 4_7.

Step 8: compound 4_7 (130 mg, 160.54 μmol, 1 eq) was dissolved in a mixed solution of ethanol (3 mL) and dichloromethane (1 mL), then intermediate A2 (66.54 mg, 160.54 μmol, 1 eq) was added thereto. The mixture was stirred at 15° C. for 1 hour and concentrated under reduced pressure, the residue was purified by preparative TLC (SiO$_2$, dichloromethane/methanol=10/1 (v/v)) to give compound 4_8.

Step 9: DCC (36.51 mg, 176.97 μmol, 35.80 μL, 2 eq) and HOBt (23.91 mg, 176.97 μmol, 2 eq) were added to a solution of compound 4_8 (80 mg, 88.49 μmol, 1 eq) in DMF (3 mL). The mixture was stirred at 35° C. for 1 hour, then A1 (22.32 mg, 106.18 μmol, 1.2 eq) and sodium bicarbonate (29.73 mg, 353.95 μmol, 13.77 μL, 4 eq) were added thereto, the mixture was stirred at 35° C. for 12 hours and concentrated under reduced pressure, the residue was purified by preparative TLC (SiO$_2$, dichloromethane/methanol=8/1 (v/v)) to give compound 4_9.

Step 10: compound 4_9 (90 mg, 71.32 mL, 1 eq) was dissolved in HCOOH (2 mL), the mixture was stirred at 40° C. for 1 hour and concentrated under reduced pressure. The obtained residue was purified by preparative HPLC (formic acid, column: Boston Green ODS 150*30 5u; mobile phase: [water (0.225% formic acid)-acetonitrile]; acetonitrile %: 1%-27%, 10 min) to give compound 4.
$^1$H NMR (400 MHz, DMSO-d$_6$) δ (ppm): 8.39 (s, 2H), 7.15-7.05 (m, 1H), 6.86-6.78 (m, 2H), 6.76 (s, 1H), 4.59 (s, 1H), 4.48-4.42 (m, 2H), 4.40-4.32 (m, 2H), 4.19-4.12 (m, 2H), 3.58-3.49 (m, 2H), 3.59-3.47 (m, 2H), 3.31-3.22 (m, 2H), 2.93-2.76 (m, 4H), 1.86-1.72 (m, 2H), 1.38 (s, 3H), 1.19 (s, 3H);
LC-MS (ESI) m/z: 654 (M+1).
Embodiment 5

-continued

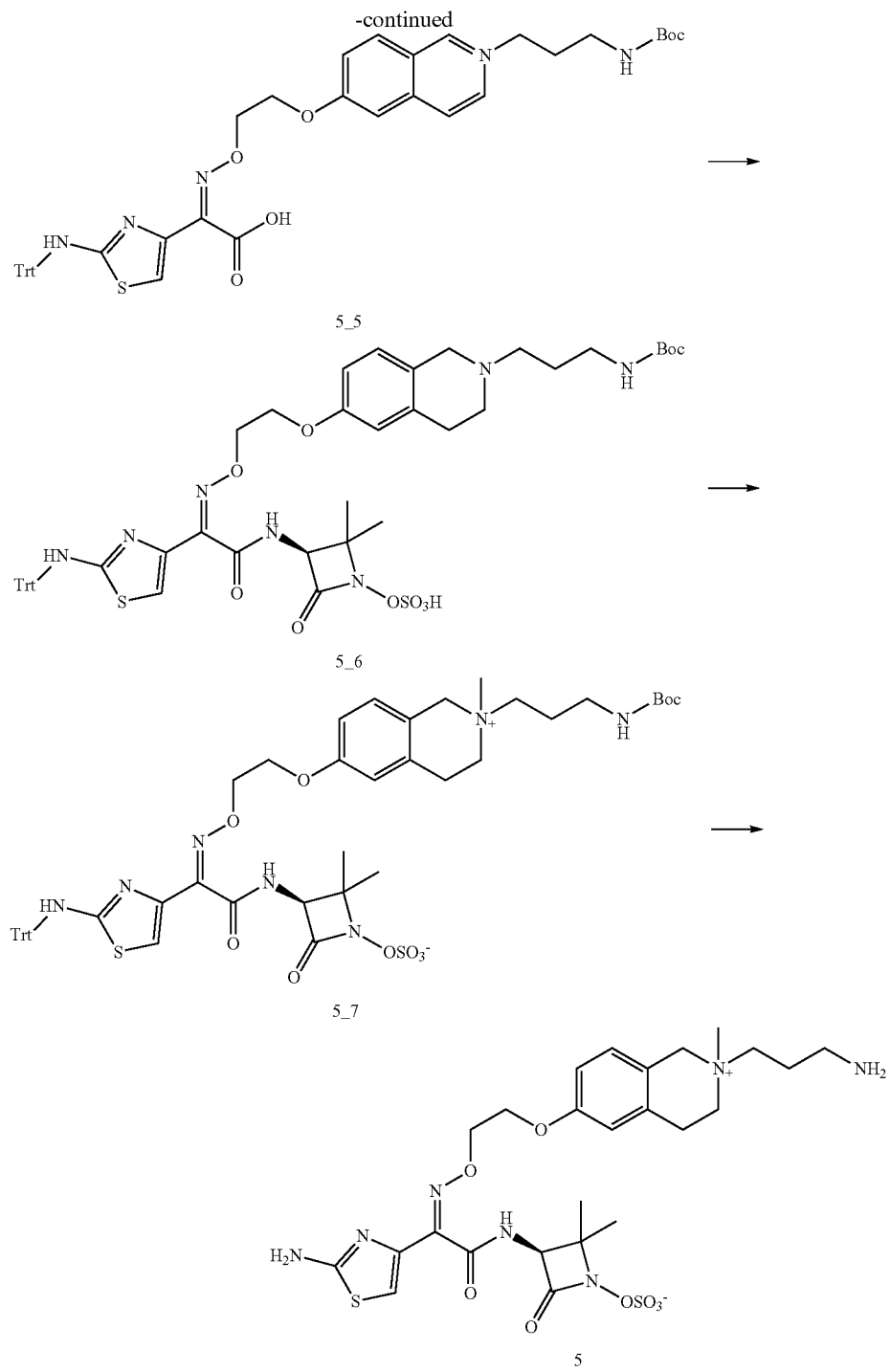

Step 1: tert-butyl N-(3-bromopropyl)carbamate (3.02 g, 12.68 mmol, 1.5 eq) and potassium iodide (2.81 g, 16.91 mmol, 2 eq) were added to a mixed solution of compound 4_1 (1.6 g, 8.46 mmol, 1 eq in acetone (16 mL) and methanol (16 mL)). The mixture was stirred at 70° C. for 12 hours and concentrated under reduced pressure, the residue was purified by silica gel chromatography (SiO₂, dichloromethane/methanol=50/1 to 20/1 (v/v)) to give compound 5_1.

Step 2: compound 5_1 (2.1 g, 4.91 mmol, 1 eq), 2-hydroxyisoindoline-1,3-dione (961.99 mg, 5.90 mmol, 1.2 eq), and PPh₃ (1.55 g, 5.90 mmol, 1.2 eq) were added to DMF (20 mL), then DIAD (1.19 g, 5.90 mmol, 1.15 mL, 1.2 eq) was added thereto at 0° C. The mixture was stirred at 15° C. for 18 hours and concentrated under reduced pressure, the residue was stirred and washed with ethyl acetate (20 mL*2) to give compound 5_2.

Step 3: NH₂NH₂.H₂O (286.97 mg, 4.87 mmol, 278.62 µL, purity: 85%, 1 eq) was added to a solution of compound 5_2 (2.4 g, 4.87 mmol, 1 eq) in ethanol (25 mL). The mixture was stirred at 15° C. for 1 hour, then poured into water (20 mL), the aqueous phase was washed with dichloromethane (50 mL), then concentrated under reduced pressure to give compound 5_3.

Step 4: NaBH$_4$ (313.15 mg, 8.28 mmol, 3 eq) was added to a solution of compound 5_3 (1 g, 2.76 mmol, 1 eq) in methanol (20 mL). The mixture was stirred at 15° C. for 0.5 hour, the reaction was quenched by adding water (10 mL), the obtained mixture was concentrated under reduced pressure to remove methanol, the residue aqueous phase was extracted with ethyl acetate (50 mL*2), the organic phases were combined and washed with saturated sodium chloride aqueous solution (20 mL), dried over anhydrous sodium sulfate, filtered and concentrated under reduced pressure to give compound 5_4.

Step 5: intermediate A2 (737.77 mg, 1.78 mmol, 1 eq) was added to a solution of compound 5_4 (650 mg, 1.78 mmol, 1 eq) in dichloromethane (1 mL) and methanol (3 mL). The mixture was stirred at 15° C. for 1 hour and concentrated under reduced pressure, the residue was washed with ethyl acetate (20 mL*2) to give compound 5_5.

Step 6: HOBt (212.81 mg, 1.57 mmol, 2 equivalent) and DCC (324.96 mg, 1.57 mmol, 318.58 μL, 2 eq) were added to a solution of compound 5_5 (600 mg, 787.48 μmol, 1 eq) in DMF (6 mL). The mixture was stirred at 15° C. for 1 hour, sodium bicarbonate (264.61 mg, 3.15 mmol, 122.51 μL, 4 eq) and intermediate A1 (248.30 mg, 1.18 mmol, 1.5 eq) were added thereto, the mixture was then stirred at 15° C. for 16 hours, and further stirred at 25° C. for another 1 hour. The mixture was filtered, the filtrate was concentrated under reduced pressure, the residue was purified by silica gel chromatography (dichloromethane/methanol=50/1 to 10/1 (v/v)) to give compound 5_6.

LC-MS (ESI) m/z: 954.8 (M+1).

Step 7: iodomethane (1.19 g, 8.38 mmol, 521.93 μL, 29.08 eq) and potassium carbonate (39.84 mg, 288.30 μmol, 1 eq) were added to a solution of compound 5_6 (300 mg, 288.30 μmol, 1 eq) in DMF (1 mL). The mixture was stirred at 15° C. for 0.5 hour and concentrated under reduced pressure to give compound 5_7.

Step 8: TFA (3.08 g, 27.01 mmol, 2.00 mL, 87.26 eq) was added to a solution of compound 5_7 (300 mg, 309.55 μmol, 1 eq) in dichloromethane (1 mL). The mixture was stirred at 15° C. for 1 hour and concentrated under reduced pressure, the residue was purified by preparative HPLC (column: Phenomenex Synergi C18 150*25*10 μm; mobile phase: [water (0.225% formic acid)-acetonitrile]; acetonitrile %: 1%-18%, 10 min) to give compound 5.

$^1$H NMR (400 MHz, DMSO-d$_6$) δ (ppm): 9.44 (br d, J=7.8 Hz, 1H), 8.35 (br s, 1H), 7.22 (s, 2H), 7.12 (br d, J=8.3 Hz, 1H), 6.95-6.87 (m, 2H), 6.76 (s, 1H), 4.58 (s, 1H), 4.52 (br s, 2H), 4.38 (br s, 2H), 4.19 (br s, 2H), 3.62-3.58 (m, 4H), 3.14 (br s, 3H), 3.06 (br s, 2H), 2.72 (br s, 2H), 1.95 (br s, 2H), 1.40 (s, 3H), 1.20 (s, 3H);

LC-MS (ESI) m/z: 626.5 (M+1).

Embodiment 6

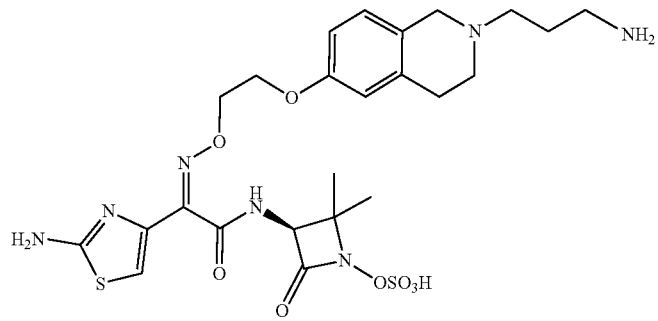

6

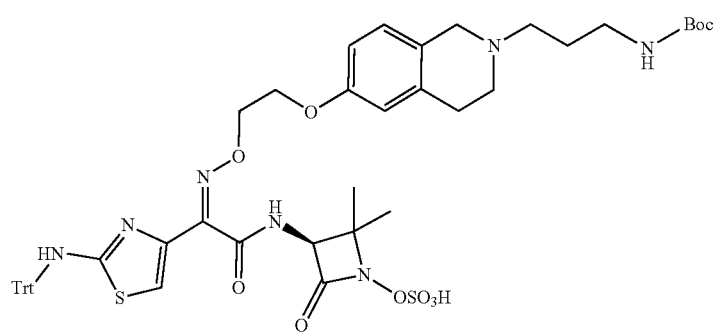

5_6

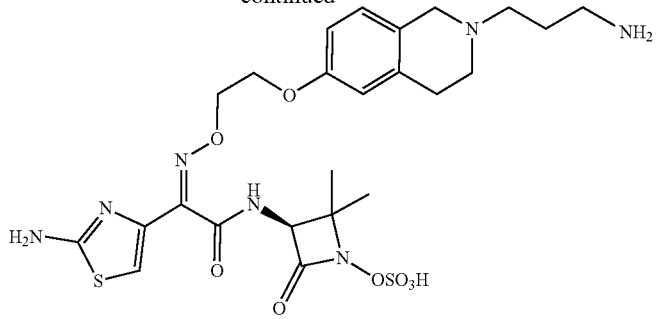

6

Step 1: TFA (2.57 g, 22.52 mmol, 1.67 mL) was added to a solution of compound 5_6 (100 mg, 96.10 μmol, 1 eq) in dichloromethane (1 mL), the mixture was stirred at 15° C. for 1 hour and concentrated under reduced pressure, the residue was purified by preparative HPLC (column: Phenomenex Synergi C18 150*25*10 m; mobile phase: [water (0.225% formic acid)-acetonitrile]; acetonitrile %: 1%-25%, 10 min) to give compound 6.

$^1$H NMR (400 MHz, DMSO-$d_6$) δ (ppm): 9.44 (d, J=8.1 Hz, 1H), 8.23 (s, 1H), 7.22 (s, 2H), 6.96 (d, J=8.4 Hz, 1H), 6.76 (s, 1H), 6.72 (d, J=2.6 Hz, 1H), 6.70 (s, 1H), 6.69 (s, 1H), 4.60 (d, J=7.9 Hz, 1H), 4.35 (br t, J=4.5 Hz, 2H), 4.15-4.11 (m, 2H), 3.49 (br s, 4H), 2.88 (br t, J=7.0 Hz, 2H), 2.82-2.76 (m, 2H), 2.62 (br t, J=5.8 Hz, 2H), 1.78 (br t, J=6.7 Hz, 2H), 1.40 (s, 3H), 1.22 (s, 3H);

LC-MS (ESI) m/z: 612.5 (M+1).

Embodiment 7

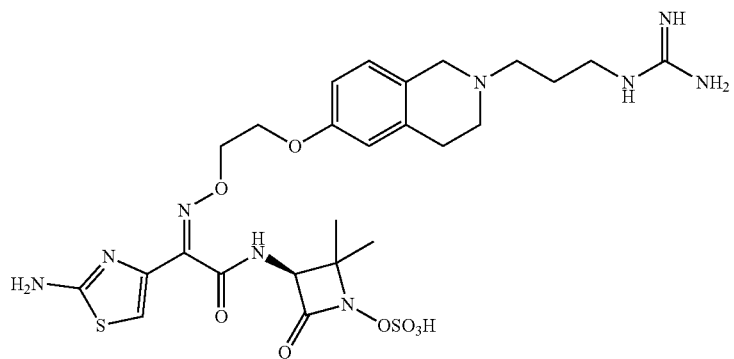

7

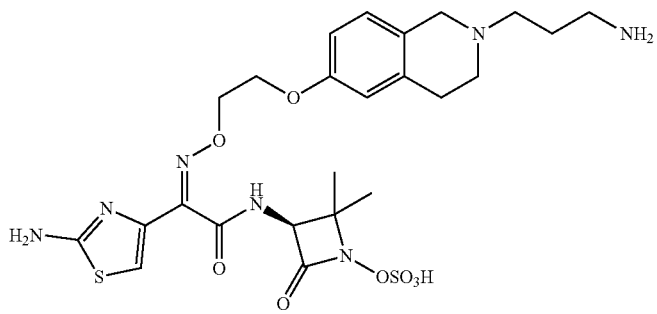

6

-continued

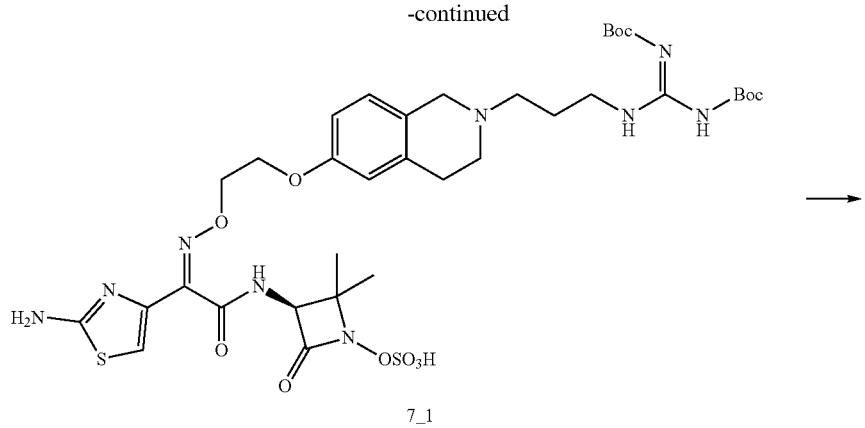

7_1

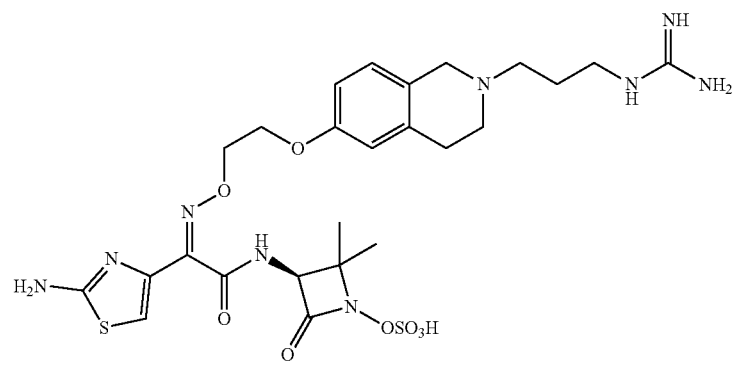

7

Step 1: triethylamine (27.69 mg, 273.67 μmol, 38.09 μL, 3 eq) and tert-butyl N-[(tert-butoxycarbonylamino)-pyrazol-1-yl-methylene] carbamate (28.31 mg, 91.22 μmol, 1 eq) were added to a solution of a formate of compound 6 (60 mg, 91.22 μmol, 1 eq) in DMF (1 mL). The mixture was stirred at 40° C. for 12 hours and concentrated under reduced pressure, the residue was purified by preparative TLC (SiO₂, dichloromethane/methanol=10/1 (v/v)) to give compound 7_1.

Step 2: compound 7_1 (78 mg, 91.34 μmol, 1 eq) was added to formic acid (1.83 g, 39.76 mmol, 1.5 mL, 435.31 eq), the mixture was stirred at 40° C. for 40 mins and concentrated under reduced pressure, the residue was purified by preparative HPLC (column: Phenomenex Synergi C18 150*25*10 μm; mobile phase: [water (0.225% formic acid)-acetonitrile]; acetonitrile %: 1%-25%, 10 min) to give compound 7.

¹H NMR (400 MHz, DMSO-d₆) δ (ppm): 9.43 (d, J=8.0 Hz, 1H), 8.21 (s, 1H), 7.51 (br s, 1H), 7.20 (s, 2H), 6.97 (d, J=8.4 Hz, 1H), 6.76 (s, 1H), 6.73-6.67 (m, 2H), 4.60 (d, J=7.9 Hz, 1H), 4.34 (br d, J=4.8 Hz, 2H), 4.13 (br d, J=3.6 Hz, 2H), 3.21-3.04 (m, 2H), 2.83-2.77 (m, 2H), 2.71-2.66 (m, 2H), 2.47-2.44 (m, 2H), 2.35-2.30 (m, 2H), 1.73 (br t, J=6.5 Hz, 2H), 1.40 (s, 3H), 1.23 (s, 3H);

LC-MS (ESI) m/z: 654.5 (M+1).

Embodiment 8

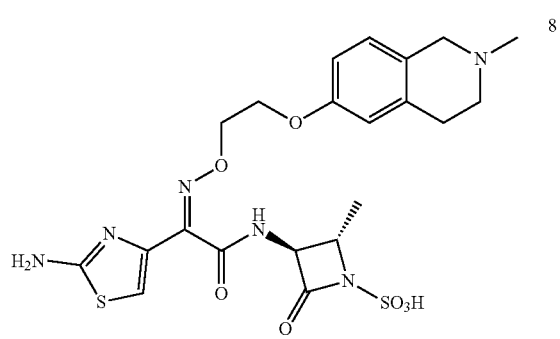
8

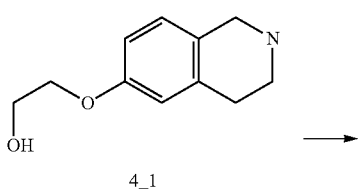
4_1

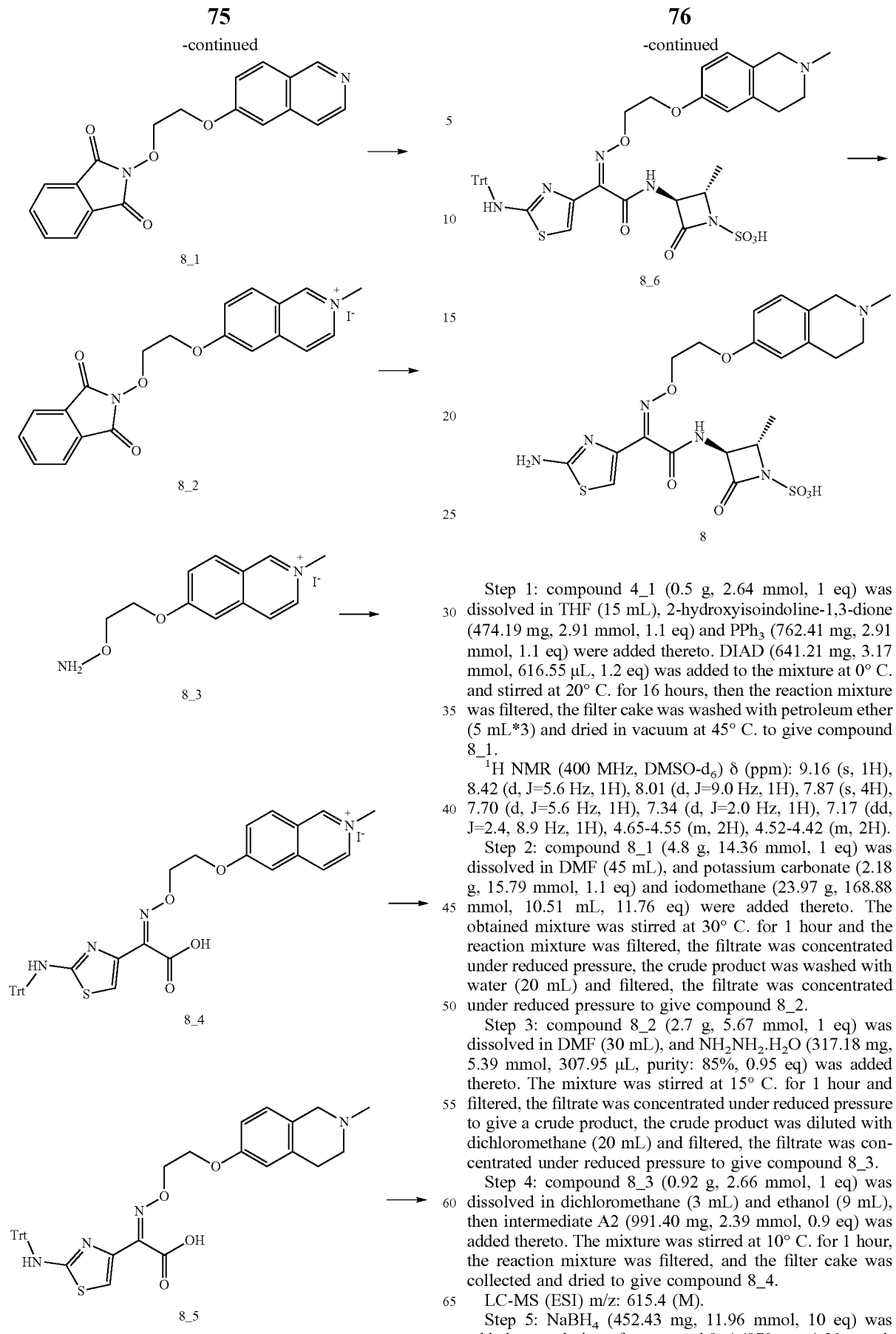

Step 1: compound 4_1 (0.5 g, 2.64 mmol, 1 eq) was dissolved in THF (15 mL), 2-hydroxyisoindoline-1,3-dione (474.19 mg, 2.91 mmol, 1.1 eq) and PPh$_3$ (762.41 mg, 2.91 mmol, 1.1 eq) were added thereto. DIAD (641.21 mg, 3.17 mmol, 616.55 μL, 1.2 eq) was added to the mixture at 0° C. and stirred at 20° C. for 16 hours, then the reaction mixture was filtered, the filter cake was washed with petroleum ether (5 mL*3) and dried in vacuum at 45° C. to give compound 8_1.

$^1$H NMR (400 MHz, DMSO-d$_6$) δ (ppm): 9.16 (s, 1H), 8.42 (d, J=5.6 Hz, 1H), 8.01 (d, J=9.0 Hz, 1H), 7.87 (s, 4H), 7.70 (d, J=5.6 Hz, 1H), 7.34 (d, J=2.0 Hz, 1H), 7.17 (dd, J=2.4, 8.9 Hz, 1H), 4.65-4.55 (m, 2H), 4.52-4.42 (m, 2H).

Step 2: compound 8_1 (4.8 g, 14.36 mmol, 1 eq) was dissolved in DMF (45 mL), and potassium carbonate (2.18 g, 15.79 mmol, 1.1 eq) and iodomethane (23.97 g, 168.88 mmol, 10.51 mL, 11.76 eq) were added thereto. The obtained mixture was stirred at 30° C. for 1 hour and the reaction mixture was filtered, the filtrate was concentrated under reduced pressure, the crude product was washed with water (20 mL) and filtered, the filtrate was concentrated under reduced pressure to give compound 8_2.

Step 3: compound 8_2 (2.7 g, 5.67 mmol, 1 eq) was dissolved in DMF (30 mL), and NH$_2$NH$_2$.H$_2$O (317.18 mg, 5.39 mmol, 307.95 μL, purity: 85%, 0.95 eq) was added thereto. The mixture was stirred at 15° C. for 1 hour and filtered, the filtrate was concentrated under reduced pressure to give a crude product, the crude product was diluted with dichloromethane (20 mL) and filtered, the filtrate was concentrated under reduced pressure to give compound 8_3.

Step 4: compound 8_3 (0.92 g, 2.66 mmol, 1 eq) was dissolved in dichloromethane (3 mL) and ethanol (9 mL), then intermediate A2 (991.40 mg, 2.39 mmol, 0.9 eq) was added thereto. The mixture was stirred at 10° C. for 1 hour, the reaction mixture was filtered, and the filter cake was collected and dried to give compound 8_4.

LC-MS (ESI) m/z: 615.4 (M).

Step 5: NaBH$_4$ (452.43 mg, 11.96 mmol, 10 eq) was added to a solution of compound 8_4 (870 mg, 1.20 mmol, 1 eq) in methanol (10 mL). The mixture was stirred at 15° C. for 0.5 hour and concentrated under reduced pressure, the obtained residue was purified by column chromatography (SiO$_2$, dichloromethane/methanol=20/1 to 10/1 (v/v)) to give compound 8_5.

Step 6: DCC (197.39 mg, 956.68 μmol, 193.52 μL, 2 eq) and HOBt (129.27 mg, 956.68 μmol, 2 eq) were added to a solution of compound 8_5 (400 mg, 478.34 μmol, 1 eq) in DMF (10 mL). The mixture was stirred at 40° C. for 1 hour, then intermediate A3 (103.43 mg, 574.01 μmol, 1.2 eq) and sodium bicarbonate (160.74 mg, 1.91 mmol, 74.41 μL, 4 eq) were added to the reaction, the mixture was stirred at 40° C. for 12 hours, then concentrated under reduced pressure, the residue was diluted with water (10 mL) and extracted with dichloromethane (10 mL*2). The organic phases were combined and concentrated under reduced pressure, the obtained residue was purified by column chromatography (SiO$_2$, dichloromethane/methanol=20/1 to 1/1 (v/v)) to give compound 8_6.

Step 7: compound 8_6 (50 mg, 64.03 μmol, 1 eq) was dissolved in formic acid (1 mL), the mixture was stirred at 40° C. for 40 mins and concentrated under reduced pressure, the residue was purified by preparative HPLC (FA condition) (column: Boston Green ODS 150*30 5 u; mobile phase: [water (0.225% formic acid)-acetonitrile]), B %: 1%-30%, 10 min) to give compound 8.

$^1$H NMR (400 MHz, DMSO-d$_6$) δ (ppm): 7.08-7.02 (m, 1H), 6.86-6.79 (m, 2H), 6.75 (s, 1H), 4.41 (d, J=2.6 Hz, 1H), 4.43-4.40 (m, 2H), 4.39-4.32 (m, 2H), 4.21-4.15 (m, 2H), 4.01 (s, 2H), 3.68-3.66 (m, 1H), 3.22-3.14 (m, 2H), 3.02-2.94 (m, 2H), 2.72 (s, 3H), 1.33 (d, J=6.1 Hz, 3H);

LC-MS (ESI) m/z: 539 (M+1).

Embodiment 9

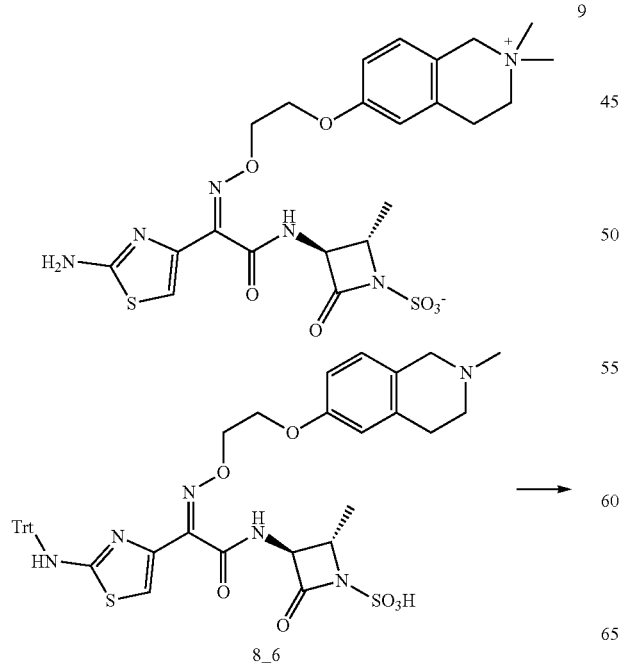

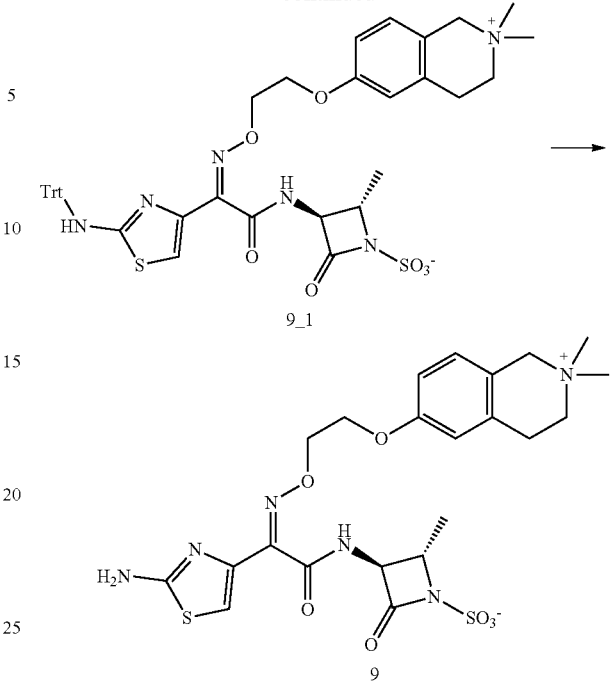

Step 1: sodium carbonate (21.72 mg, 204.89 μmol, 2 eq) and iodomethane (1.19 g, 8.38 mmol, 521.93 μL, 81.84 eq) was added to a solution of compound 8_6 (80 mg, 102.44 μmol, 1 eq) in DMF (2 mL). The mixture was stirred at 40° C. for 2 hours and filtered, the filtrate was concentrated under reduced pressure to give compound 9_1.

Step 2: compound 9_1 (100 mg, 110.29 mmol, 1 eq) was added to formic acid (2 mL), the mixture was stirred at 40° C. for 40 mins and diluted with water (10 mL), then washed with dichloromethane (10 mL*2), the aqueous phase was concentrated under reduced pressure, the residue was purified by preparative HPLC (FA condition) (column: Boston Green ODS 150*30 5 u; mobile phase: [water (0.225% formic acid)-acetonitrile]; acetonitrile %: 1%-27%, 10 min) to give compound 9.

$^1$H NMR (400 MHz, DMSO-d$_6$) δ (ppm): 7.12-7.07 (m, 1H), 6.94-6.89 (m, 2H), 6.75 (s, 1H), 4.48 (s, 2H), 4.41 (d, J=2.6 Hz, 1H), 4.39-4.35 (m, 2H), 4.25-4.17 (m, 2H), 3.66-3.65 (m, 1H), 3.21-3.05 (m, 10H), 1.31 (d, J=6.2 Hz, 3H).

LC-MS (ESI) m/z: 553.3 (M+1).

Embodiment 10

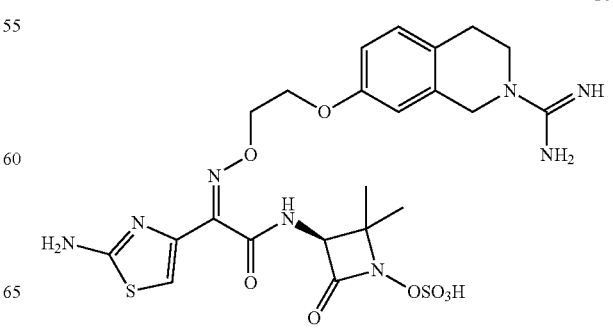

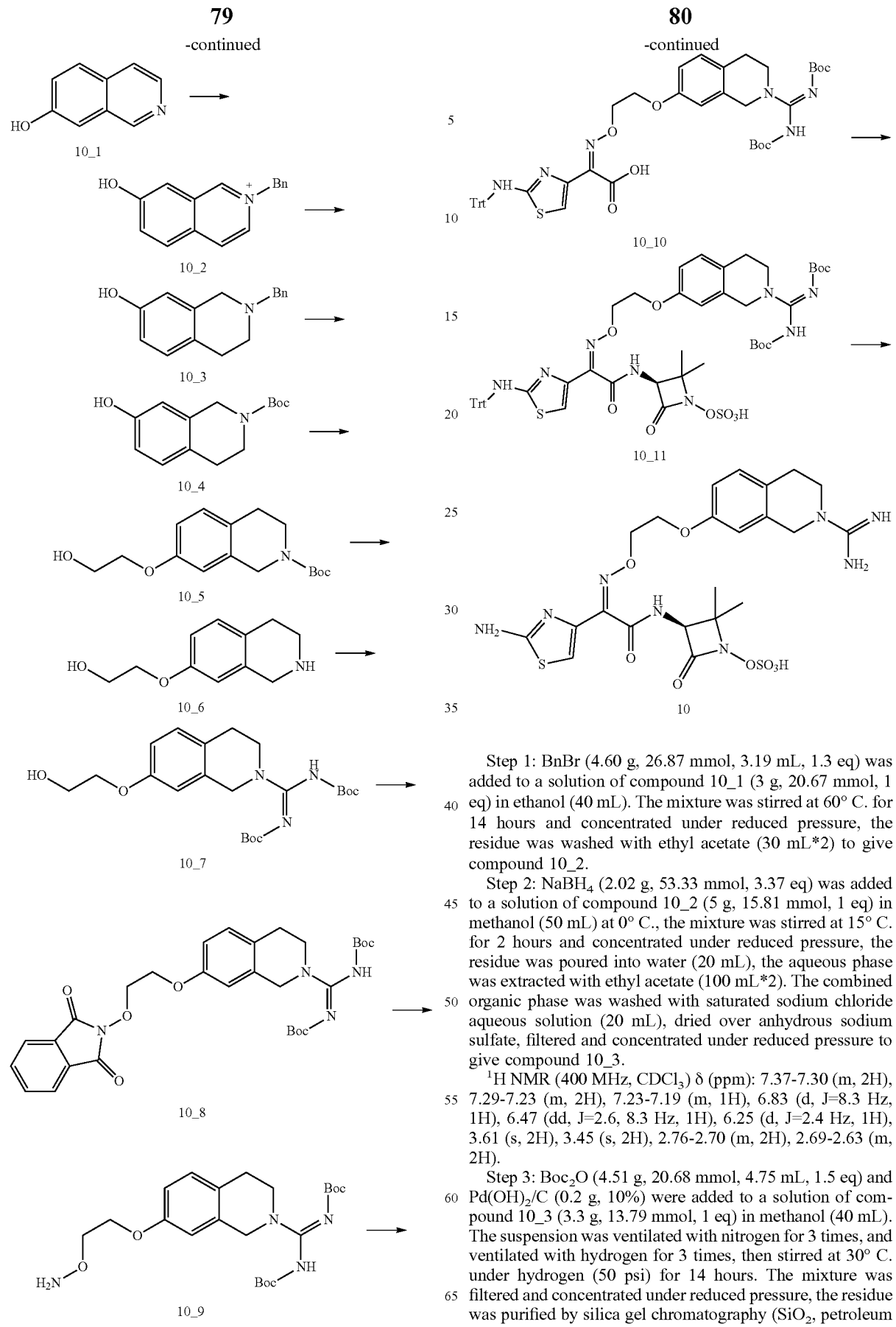

Step 1: BnBr (4.60 g, 26.87 mmol, 3.19 mL, 1.3 eq) was added to a solution of compound 10_1 (3 g, 20.67 mmol, 1 eq) in ethanol (40 mL). The mixture was stirred at 60° C. for 14 hours and concentrated under reduced pressure, the residue was washed with ethyl acetate (30 mL*2) to give compound 10_2.

Step 2: NaBH$_4$ (2.02 g, 53.33 mmol, 3.37 eq) was added to a solution of compound 10_2 (5 g, 15.81 mmol, 1 eq) in methanol (50 mL) at 0° C., the mixture was stirred at 15° C. for 2 hours and concentrated under reduced pressure, the residue was poured into water (20 mL), the aqueous phase was extracted with ethyl acetate (100 mL*2). The combined organic phase was washed with saturated sodium chloride aqueous solution (20 mL), dried over anhydrous sodium sulfate, filtered and concentrated under reduced pressure to give compound 10_3.

$^1$H NMR (400 MHz, CDCl$_3$) δ (ppm): 7.37-7.30 (m, 2H), 7.29-7.23 (m, 2H), 7.23-7.19 (m, 1H), 6.83 (d, J=8.3 Hz, 1H), 6.47 (dd, J=2.6, 8.3 Hz, 1H), 6.25 (d, J=2.4 Hz, 1H), 3.61 (s, 2H), 3.45 (s, 2H), 2.76-2.70 (m, 2H), 2.69-2.63 (m, 2H).

Step 3: Boc$_2$O (4.51 g, 20.68 mmol, 4.75 mL, 1.5 eq) and Pd(OH)$_2$/C (0.2 g, 10%) were added to a solution of compound 10_3 (3.3 g, 13.79 mmol, 1 eq) in methanol (40 mL). The suspension was ventilated with nitrogen for 3 times, and ventilated with hydrogen for 3 times, then stirred at 30° C. under hydrogen (50 psi) for 14 hours. The mixture was filtered and concentrated under reduced pressure, the residue was purified by silica gel chromatography (SiO$_2$, petroleum ether/ethyl acetate=1/0 to 5/1 (v/v)) to give compound 10_4.

¹H NMR (400 MHz, CDCl₃) δ (ppm): 6.92 (d, J=8.4 Hz, 1H), 6.61 (br d, J=6.9 Hz, 2H), 4.46 (br s, 2H), 3.55 (br t, J=5.8 Hz, 2H), 2.68 (t, J=5.8 Hz, 2H), 1.42 (s, 9H).

Step 4: potassium carbonate (1.42 g, 10.28 mmol, 1.1 eq) and 1,3-dioxolane-2-one (987.29 mg, 11.21 mmol, 747.95 µL, 1.2 eq) were added to a solution of compound 10_4 (2.4 g, 9.34 mmol, 1 eq) in DMF (30 mL). The mixture was stirred at 135° C. for 4 hours, then filtered and concentrated under reduced pressure, the residue was poured into water (20 mL). The aqueous phase was extracted with ethyl acetate (100 mL*2), the organic phases were combined and washed with saturated sodium chloride aqueous solution (30 mL), dried over anhydrous sodium sulfate, filtered and concentrated under reduced pressure to give compound 10_5.

Step 5: compound 10_5 (3 g, 10.23 mmol, 1 eq) was added to a hydrogen chloride ethyl acetate solution (10.23 mmol, 30 mL, 4 M), the mixture was stirred at 10° C. for 20 mins and concentrated under reduced pressure to give a hydrochloride of compound 10_6.

Step 6: DIPEA (5.29 g, 40.92 mmol, 7.13 mL, 4 eq) and tert-butyl N-[(tert-butoxycarbonylamino)-pyrazol-1-yl-methylene] carbamate (3.18 g, 10.23 mmol, 1 eq) were added to a solution of the hydrochloride of compound 10_6 (2.35 g, 10.23 mmol, 1 eq) in DMF (25 mL). The mixture was stirred at 40° C. for 3 hours and concentrated under reduced pressure, the residue was poured into water (30 mL) and extracted with ethyl acetate (100 mL). The organic phases were combined and washed with saturated sodium chloride aqueous solution (30 mL), dried over anhydrous sodium sulfate, filtered and concentrated under reduced pressure, the residue was purified by silica gel chromatography (SiO₂, petroleum ether/ethyl acetate=10/1 to 1/1 (v/v)) to give compound 10_7.

Step 7: 2-hydroxyisoindoline-1,3-dione (886.92 mg, 5.44 mmol, 1.2 eq) and PPh₃ (1.43 g, 5.44 mmol, 1.2 eq) were added to a solution of compound 10_7 (2 g, 4.53 mmol, 1 eq) in THF (20 mL), then DIAD (1.10 g, 5.44 mmol, 1.06 mL, 1.2 eq) was added dropwise at 0° C. The mixture was stirred at 15° C. for 5 hours and concentrated under reduced pressure, the residue was purified by silica gel chromatography (petroleum ether/ethyl acetate=10/1 to 1/1 (v/v)) to give compound 10_8.

LC-MS (ESI) m/z: 581.5 (M+1).

Step 8: NH₂NH₂·H₂O (138.21 mg, 2.35 mmol, 134.19 µL, purity: 85%, 1 eq) was added to a solution of compound 10_8 (1.8 g, 2.35 mmol, 40.95 µL, 1 eq) in ethanol (20 mL). The mixture was stirred at 45° C. for 0.5 hour and filtered, the filtrate was concentrated under reduced pressure, water (10 mL) was added into the residue, the mixture was extracted with ethyl acetate (50 mL). The organic phases were combined and washed with saturated sodium chloride aqueous solution (20 mL), dried over anhydrous sodium sulfate then filtered, and the filtrate was concentrated under reduced pressure to give compound 10_9.

Step 9: intermediate A2 (735.98 mg, 1.78 mmol, 1 eq) was added to a mixed solution of compound 10_9 (0.8 g, 1.78 mmol, 1 eq) in methanol (9 mL) and dichloromethane (3 mL). The mixture was stirred at 15° C. for 10 mins and concentrated under reduced pressure, the residue was washed with ethyl acetate (30 mL) to give compound 10_10.

Step 10: HOBt (127.62 mg, 944.52 µmol, 2 eq) and DCC (194.88 mg, 944.52 µmol, 2 eq) were added to a solution of compound 10_10 (400 mg, 472.26 µmol, 1 eq) in DMF (5 mL). The mixture was stirred at 15° C. for 1 hour, then sodium bicarbonate (158.70 mg, 1.89 mmol, 73.47 µL, 4 eq) and intermediate A1 (129.06 mg, 613.94 µmol, 1.3 eq) were added thereto. The mixture was stirred at 15° C. for another 12 hours and concentrated under reduced pressure, the residue was purified by silica gel chromatography (SiO₂, dichloromethane/methanol=20/1 to 10/1 (v/v)) followed by preparative TLC (SiO₂, dichloromethane/methanol=10/1 (v/v)) to give compound 10_11.

Step 11: TFA (2.10 g, 18.39 mmol, 1.36 mL, 1403.52 eq) was added to a dichloromethane (1 mL) solution of compound 10_11 (20 mg, 13.10 µmol, 1 eq). The mixture was stirred at 15° C. for 0.5 hour and concentrated under reduced pressure, the residue was purified by preparative HPLC (column: Phenomenex Synergi C18 150*25*10 µm; mobile phase: [water (0.225% formic acid)-acetonitrile]; acetonitrile %: 5%-35%, 10 min) to give compound 10.

¹H NMR (400 MHz, DMSO-d₆) δ (ppm): 8.43 (s, 1H), 7.15 (br d, J=8.4 Hz, 1H), 6.84 (br d, J=7.7 Hz, 1H), 6.78-6.69 (m, 2H), 4.59 (s, 1H), 4.51 (s, 2H), 4.36 (br s, 2H), 4.16 (br s, 2H), 3.69-3.62 (m, 4H), 2.83 (br s, 2H), 1.39 (s, 3H), 1.22 (s, 3H);

LC-MS (ESI) m/z: 597.4 (M+1).

Embodiment 11

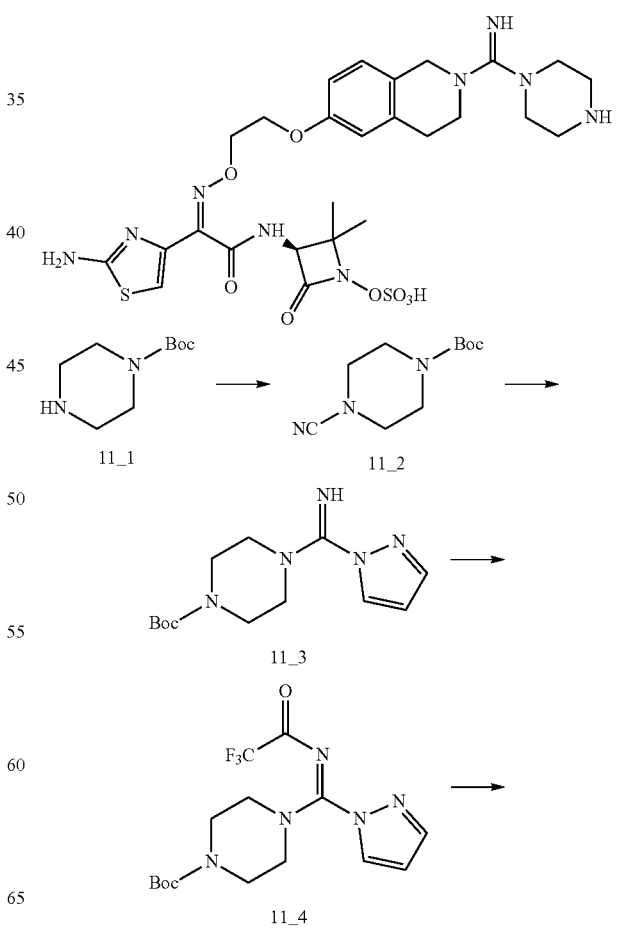

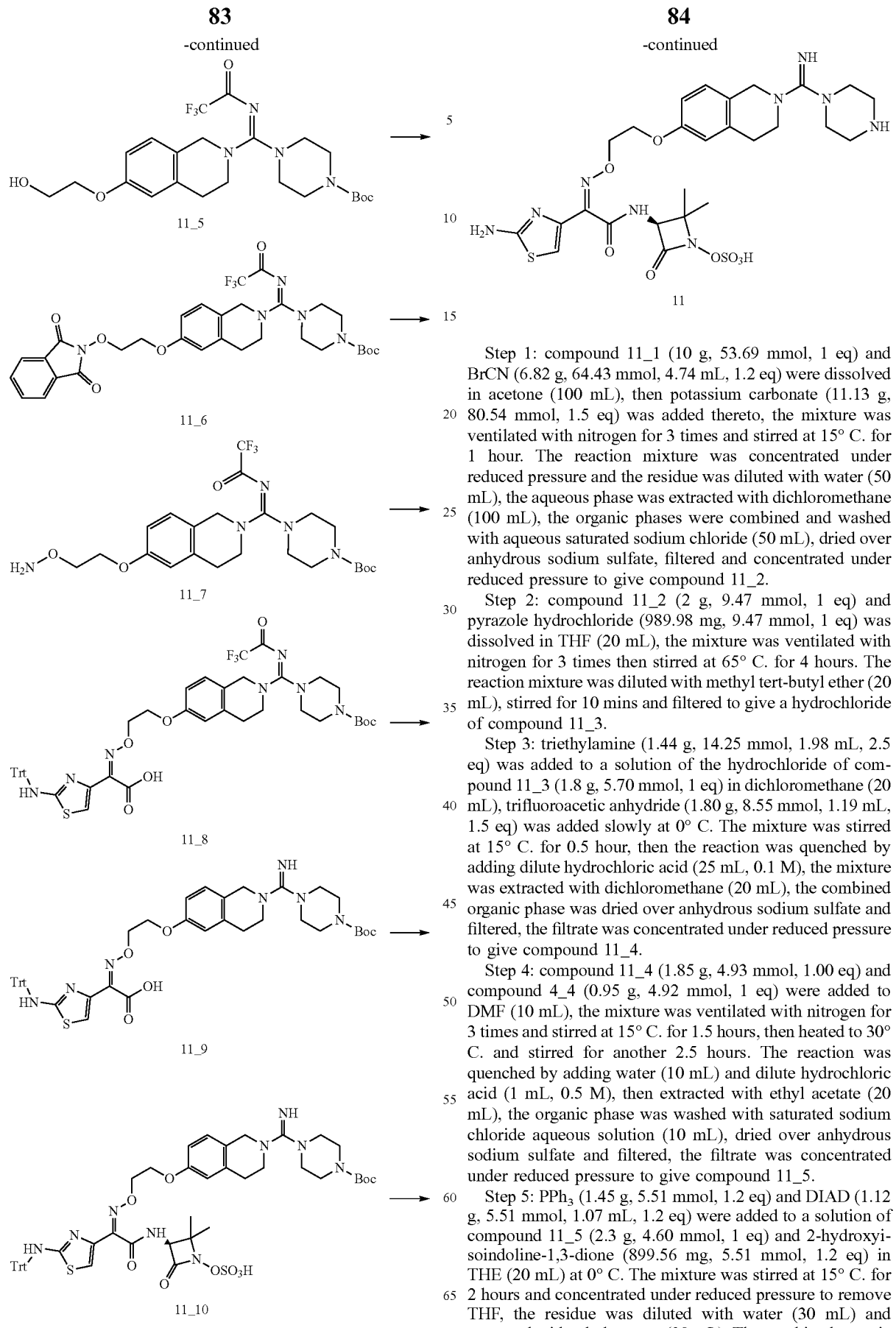

Step 1: compound 11_1 (10 g, 53.69 mmol, 1 eq) and BrCN (6.82 g, 64.43 mmol, 4.74 mL, 1.2 eq) were dissolved in acetone (100 mL), then potassium carbonate (11.13 g, 80.54 mmol, 1.5 eq) was added thereto, the mixture was ventilated with nitrogen for 3 times and stirred at 15° C. for 1 hour. The reaction mixture was concentrated under reduced pressure and the residue was diluted with water (50 mL), the aqueous phase was extracted with dichloromethane (100 mL), the organic phases were combined and washed with aqueous saturated sodium chloride (50 mL), dried over anhydrous sodium sulfate, filtered and concentrated under reduced pressure to give compound 11_2.

Step 2: compound 11_2 (2 g, 9.47 mmol, 1 eq) and pyrazole hydrochloride (989.98 mg, 9.47 mmol, 1 eq) was dissolved in THF (20 mL), the mixture was ventilated with nitrogen for 3 times then stirred at 65° C. for 4 hours. The reaction mixture was diluted with methyl tert-butyl ether (20 mL), stirred for 10 mins and filtered to give a hydrochloride of compound 11_3.

Step 3: triethylamine (1.44 g, 14.25 mmol, 1.98 mL, 2.5 eq) was added to a solution of the hydrochloride of compound 11_3 (1.8 g, 5.70 mmol, 1 eq) in dichloromethane (20 mL), trifluoroacetic anhydride (1.80 g, 8.55 mmol, 1.19 mL, 1.5 eq) was added slowly at 0° C. The mixture was stirred at 15° C. for 0.5 hour, then the reaction was quenched by adding dilute hydrochloric acid (25 mL, 0.1 M), the mixture was extracted with dichloromethane (20 mL), the combined organic phase was dried over anhydrous sodium sulfate and filtered, the filtrate was concentrated under reduced pressure to give compound 11_4.

Step 4: compound 11_4 (1.85 g, 4.93 mmol, 1.00 eq) and compound 4_4 (0.95 g, 4.92 mmol, 1 eq) were added to DMF (10 mL), the mixture was ventilated with nitrogen for 3 times and stirred at 15° C. for 1.5 hours, then heated to 30° C. and stirred for another 2.5 hours. The reaction was quenched by adding water (10 mL) and dilute hydrochloric acid (1 mL, 0.5 M), then extracted with ethyl acetate (20 mL), the organic phase was washed with saturated sodium chloride aqueous solution (10 mL), dried over anhydrous sodium sulfate and filtered, the filtrate was concentrated under reduced pressure to give compound 11_5.

Step 5: PPh$_3$ (1.45 g, 5.51 mmol, 1.2 eq) and DIAD (1.12 g, 5.51 mmol, 1.07 mL, 1.2 eq) were added to a solution of compound 11_5 (2.3 g, 4.60 mmol, 1 eq) and 2-hydroxyisoindoline-1,3-dione (899.56 mg, 5.51 mmol, 1.2 eq) in THF (20 mL) at 0° C. The mixture was stirred at 15° C. for 2 hours and concentrated under reduced pressure to remove THF, the residue was diluted with water (30 mL) and extracted with ethyl acetate (30 mL). The combined organic phase was dried over anhydrous sodium sulfate and filtered, the filtrate was concentrated under reduced pressure to give compound 11_6.

Step 6: compound 11_6 (1.5 g, 2.32 mmol, 1 eq) was dissolved in ethanol (10 mL) and dichloromethane (5 mL), $NH_2NH_2 \cdot H_2O$ (136.83 mg, 2.32 mmol, 132.85 L, 85% purity, 1 eq) was added thereto. The mixture was stirred at 15° C. for 0.5 hour and filtered, the filtrate was concentrated under reduced pressure, the residue was diluted with water (10 mL) and extracted with dichloromethane (10 mL). The combined organic phase was dried over anhydrous sodium sulfate, filtered and concentrated under reduced pressure to give compound 11_7.

Step 7: compound 11_7 (400 mg, 775.91 μmol, 1.61 eq) and intermediate A2 (200 mg, 482.54 μmol, 1 eq) were added to a mixed solution of dichloromethane (5 mL) and ethanol (5 mL), and stirred at 15° C. for 0.5 hour. The reaction mixture was concentrated under reduced pressure, the residue was slurried with petroleum ether/ethyl acetate (12 mL, 5/1), the filter cake was collected after filtering to give compound 11_8.

Step 8: compound 11_8 (500 mg, 548.25 μmol, 1 eq) and potassium carbonate (151.54 mg, 1.10 mmol, 2 eq) were added to a mixed solution of methanol (5 mL) and water (0.1 mL), and stirred at 15° C. under nitrogen atmosphere for 2 hours and concentrated under reduced pressure, the residue were diluted with saturated sodium chloride aqueous solution (10 mL), and extracted with dichloromethane (20 mL). The combined organic phase was dried over anhydrous sodium sulfate, filtered and concentrated under reduced pressure, the residue was washed with petroleum ether/ethyl acetate (15 mL, 2/1) under stirring, the filter cake was collected after filtering to give compound 11_9.

Step 9: compound 11_9 (200 mg, 245.10 μmol, 1 eq) was dissolved in DMF (2 mL), then DCC (101.14 mg, 490.21 μmol, 99.16 μL, 2 eq) and HOBt (66.24 mg, 490.21 μmol, 2 eq) were added thereto. The mixture was stirred at 15° C. and under nitrogen atmosphere for 1 hour, then intermediate A1 (66.98 mg, 318.64 μmol, 1.3 eq) and sodium bicarbonate (82.36 mg, 980.42 mmol, 38.13 μL, 4 eq) were added thereto, the mixture was stirred for 11 hours then filtered, and the filtrate was concentrated under reduced pressure, the residue was purified by preparative TLC ($SiO_2$, dichloromethane/methanol=10/1 (v/v)) to give compound 11_10.

Step 10: TFA (1 mL) was added to a solution of compound 11_10 (100 mg, 99.19 μmol, 1 eq) in dichloromethane (1 mL) at 0° C. The mixture was stirred at 0° C. for 40 min, then the reaction mixture was diluted with petroleum ether/ethyl acetate (5 mL, 1/4) and precipitation appeared, the mixture was filtered and solid was collected, which was purified by preparative HPLC (FA, column: Boston Green ODS 150*30 5 u; mobile phase: [water (0.225% formic acid)-acetonitrile]; acetonitrile %: 1%-27%, 10 min) to give compound 11.

$^1$H NMR (400 MHz, DMSO-$d_6$) δ (ppm): 9.43 (d, J=7.8 Hz, 1H), 8.19 (s, 1H), 8.02 (br s, 1H), 7.22 (s, 2H), 7.11 (d, J=9.0 Hz, 1H), 6.86-6.79 (m, 2H), 6.76 (s, 1H), 4.59 (d, J=7.9 Hz, 1H), 4.47 (s, 2H), 4.36 (br d, J=4.9 Hz, 2H), 4.17 (br d, J=2.6 Hz, 2H), 3.64-3.54 (m, 2H), 3.28 (br s, 4H), 2.99-2.91 (m, 2H), 2.80 (br s, 4H), 1.40 (s, 3H), 1.21 (s, 3H).

LC-MS (ESI) m/z: 666.4 (M+1).

Embodiment 12

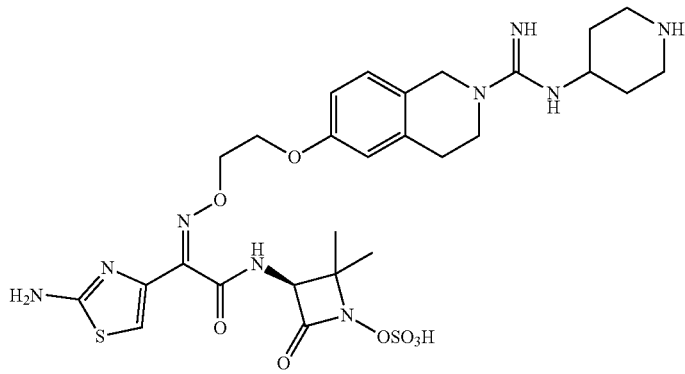

12

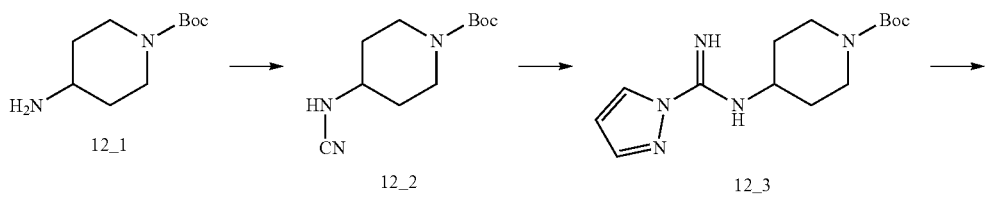

-continued
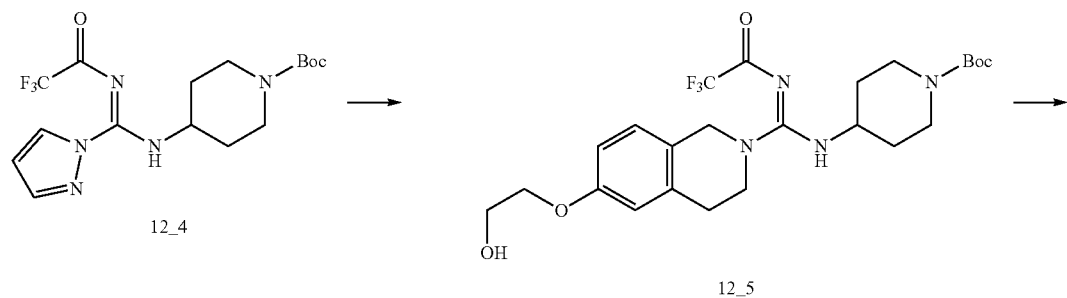
12_4
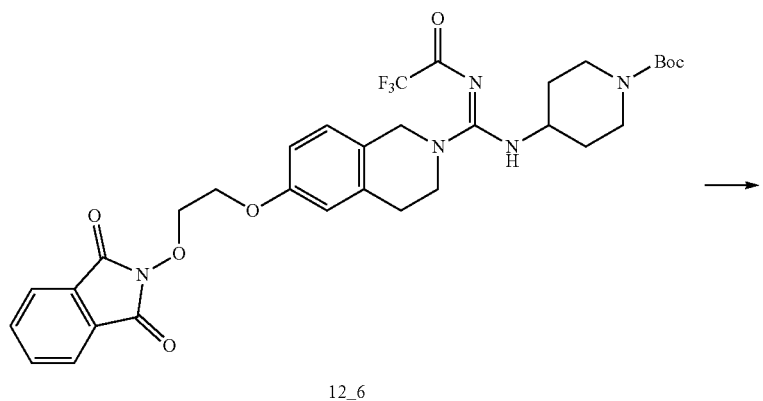
12_5
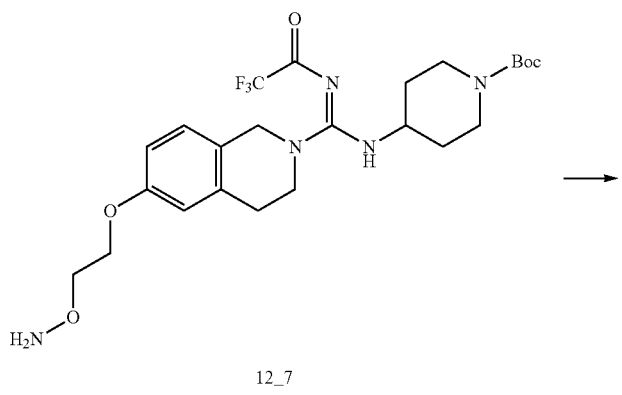
12_6
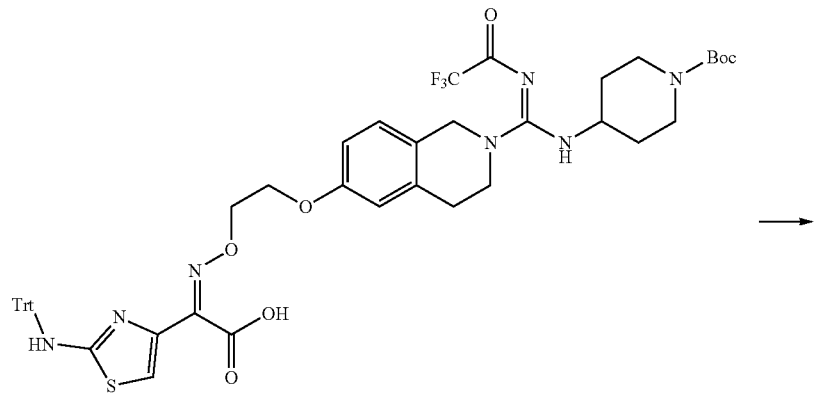
12_7
12_8

-continued

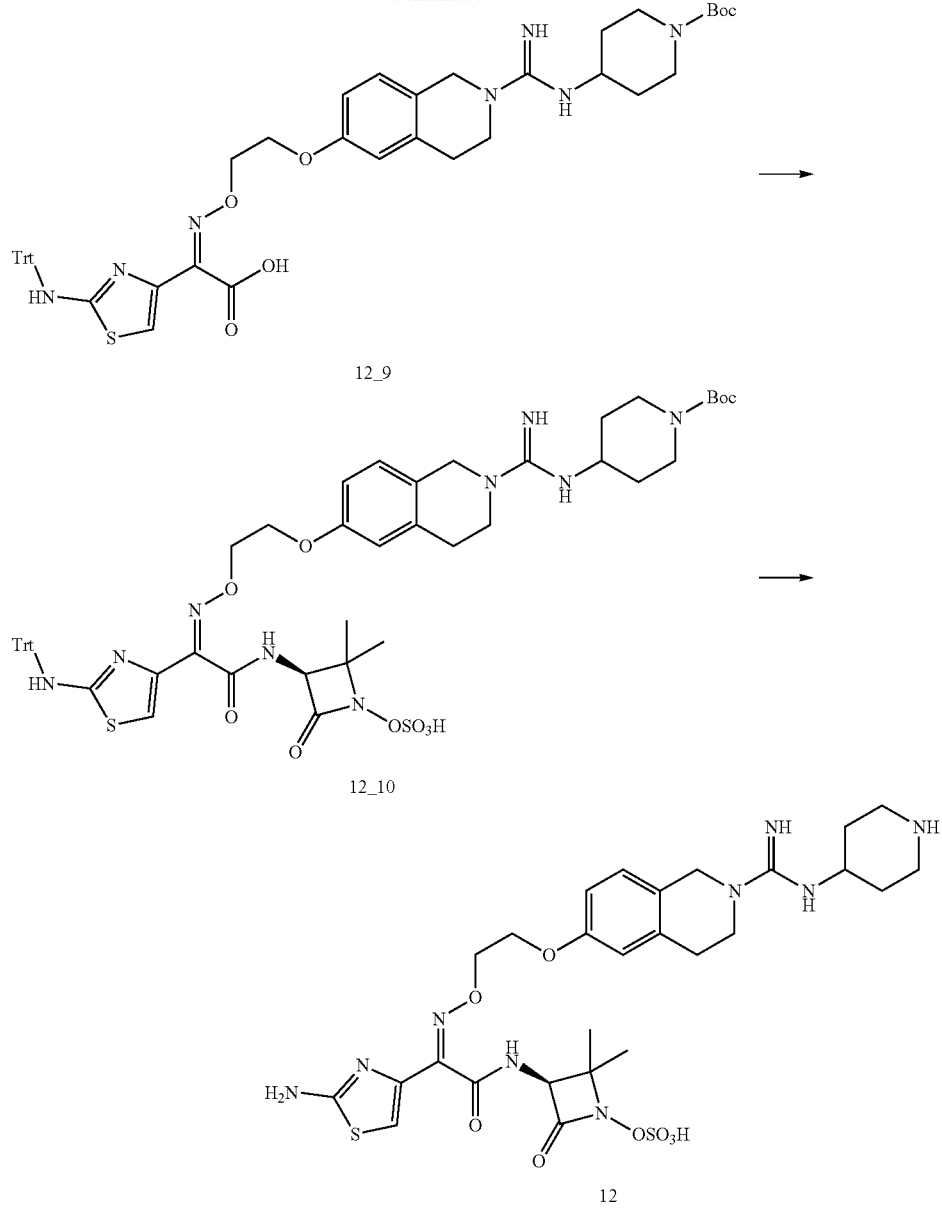

12_9

12_10

12

Step 1: compound 12_1 (2 g, 9.99 mmol, 1 eq), BrCN (1.59 g, 14.98 mmol, 1.10 mL, 1.5 eq) and sodium acetate (4.10 g, 49.93 mmol, 5 eq) were added to ethanol (20 mL), the mixture was stirred at room temperature (10-15° C.) for 2 hours and concentrated under reduced pressure to remove the solvent, water (20 mL) was then added to the reaction mixture. The obtained mixture was extracted with ethyl acetate (15 mL*2), the combined organic phase was washed with saturated sodium chloride aqueous solution (10 mL), dried over sodium sulfate, the mixture was concentrated under reduced pressure to remove the solvent and to give compound 12_2.

Step 2: compound 12_2 (2.3 g, 10.21 mmol, 1 eq), 1H-pyrazole hydrochloride (764.52 mg, 11.23 mmol, 1.1 eq) were added to THF (30 mL), the mixture was ventilated with nitrogen for 3 times, and stirred at 70° C. for 1.5 hours under nitrogen protection. The mixture was cooled to room temperature and methyl tert-butyl ether (30 mL) was added. The mixture was filtered, the filter cake was washed with methyl tert-butyl ether (20 mL) to give hydrochloride of compound 12_3.

LC-MS (ESI) m/z: 294.2 (M+1).

Step 3: the hydrochloride of compound 12_3 (1.8 g, 5.46 mmol, 1 eq) and triethylamine (1.38 g, 13.64 mmol, 1.90 mL, 2.5 eq) were added to dichloromethane (20 mL), then trifluoroacetic anhydride (1.72 g, 8.19 mmol, 1.14 mL, 1.5 eq) was added thereto at 0° C. The reaction mixture was stirred at room temperature (10-15° C.) for 2 hours and dichloromethane (20 mL) was added, the obtained mixture was diluted with hydrochloric acid (5 mL, 0.5 M) and washed with water (10 mL), dried over anhydrous sodium sulfate, then filtered and the mixture was concentrated under reduced pressure to remove the solvent and to give compound 12_4.

Step 4: compound 12_4 (2.1 g, 5.39 mmol, 1 eq) was dissolved in DMF (20 mL), compound 4_4 (1.35 g, 7.01 mmol, 1.3 eq) was added thereto and ventilated with nitrogen for 3 times, the mixture was stirred at room temperature for 1 hour under nitrogen protection, then stirred at 30° C. for another 24 hours. Saturated sodium chloride (50 ml) was added the reaction mixture, the mixture was extracted with ethyl acetate (30 mL*2). The combined organic phase was washed with saturated sodium chloride, dried over anhydrous sodium sulfate and filtered, the mixture was concentrated under reduced pressure to remove the solvent, and the residue was purified by column chromatography ($SiO_2$, petroleum ether/ethyl acetate/methanol=3/1/0 to 0/10/1 (v/v)) to give compound 12_5.

LC-MS (ESI) m/z: 515.4 (M+1).

Step 5: DIAD (1.06 g, 5.25 mmol, 1.02 mL, 1.5 eq) was added to a solution of compound 12_5 (2.05 g, 3.50 mmol, 1 eq), 2-hydroxyisoindoline-1,3-dione (684.81 mg, 4.20 mmol, 1.2 eq) and $PPh_3$ (1.84 g, 7.00 mmol, 2 eq) in THF (20 mL). The reaction mixture was stirred at room temperature (10-15° C.) for 12 hours, then concentrated under reduced pressure to remove the solvent, then water (20 mL) was added to the mixture. The obtained mixture was ethyl acetate (20 mL*2), the combined organic phase was washed with saturated sodium chloride, dried over anhydrous sodium sulfate and filtered, the mixture was concentrated under reduced pressure to remove the solvent, the residue was purified by column chromatography ($SiO_2$, petroleum ether/ethyl acetate=3/1 to 1/0 (v/v)) to give compound 12_6.

LC-MS (ESI) m/z: 660.4 (M+1).

Step 6: compound 12_6 (4 g, 2.85 mmol, 1 eq) was dissolved in dichloromethane (10 mL) and ethanol (10 mL), then $NH_2NH_2 \cdot H_2O$ (167.85 mg, 2.85 mmol, 162.96 μL, purity: 85%, 1 eq) was added thereto. The reaction mixture was stirred at room temperature for 2 hours (10-15° C.) and filtered, the filtrate was concentrated under reduced pressure, then dichloromethane (10 mL) was added to the obtained residue, and filtered for another time. The filtrate was washed with water (10 mL) and dried over anhydrous sodium sulfate, filtered and concentrated under reduced pressure to give compound 12_7.

Step 7: compound 12_7 (1 g, 1.89 mmol, 1 eq) was dissolved in dichloromethane (5 mL) and ethanol (15 mL), then intermediate A2 (391.35 mg, 944.19 μmol, 0.5 eq) was added thereto, the mixture was stirred at room temperature (15-20° C.) for 3 hours and concentrated under reduced pressure, the residue was washed with petroleum ether/ethyl acetate (30 ml, 2:1) for two times under stirring to give compound 12_8.

LC-MS (ESI) m/z: 926.5 (M+1).

Step 8: potassium carbonate (202.02 mg, 1.46 mmol, 3 eq) was added to a solution of compound 12_8 (640 mg, 487.25 μmol, 1 eq) in methanol (10 mL), the mixture was stirred at 30° C. for 15 hours and concentrated under reduced pressure, the residue was dissolved in dichloromethane (20 mL), the organic phase was washed with saturated sodium chloride aqueous solution (10 mL), dried over anhydrous sodium sulfate, and concentrated under reduced pressure to give compound 12_9.

LC-MS (ESI) m/z: 830.5 (M+1).

Step 9: DCC (83.52 mg, 404.82 μmol, 81.89 μL, 2 eq) and HOBt (54.70 mg, 404.82 μmol, 2 eq) were added to a solution of compound 12_9 (210 mg, 202.41 μmol, 1 eq) in DMF (1 mL). The reaction mixture was stirred at room temperature (10-15° C.) for 1 hour, then intermediate A1 (63.82 mg, 303.61 μmol, 1.5 eq) and sodium bicarbonate (68.01 mg, 809.64 μmol, 31.49 μL, 4 eq) were added. The reaction mixture was stirred at 30° C. for 12 hours and filtered, then concentrated under reduced pressure to remove the solvent, the residue was purified by preparative TLC ($SiO_2$, dichloromethane/methanol=10/1 (v/v)) to give compound 12_10.

LC-MS (ESI) m/z: 1022.6 (M+1).

Step 10: trifluoroacetic acid (1 mL) was added to a solution of compound 1210 (64 mg, 62.61 μmol, 1 eq) in dichloromethane (1 mL), the mixture was stirred at −15° C. for 0.5 hour, then stirred at 0° C. for another 0.5 hour. Ethyl acetate/petroleum ether (10 mL, 4:1) was added to the reaction mixture to form a white solid, which was filtered out and purified by preparative HPLC (column: Boston Green ODS 150*30 5 u; mobile phase: [water (0.225% formic acid)-acetonitrile]; acetonitrile %: 1%-28%, 10 min) to give compound 12.

LC-MS (ESI) m/z: 680.3 (M+1);

1H NMR (400 MHz, DMSO-$d_6$+$D_2O$) δ (ppm): 8.35 (br s, 1H), 7.09 (br d, J=8.3 Hz, 1H), 6.85-6.78 (m, 2H), 6.75 (s, 1H), 4.57 (s, 1H), 4.46 (br s, 2H), 4.36 (br s, 2H), 4.16 (br s, 2H), 3.23 (br s, 2H), 2.87 (br s, 2H), 2.76 (br s, 2H), 2.67 (br d, J=1.8 Hz, 2H), 1.91 (br s, 2H), 1.67 (br s, 2H), 1.37 (s, 3H), 1.18 (s, 3H).

Embodiment 13

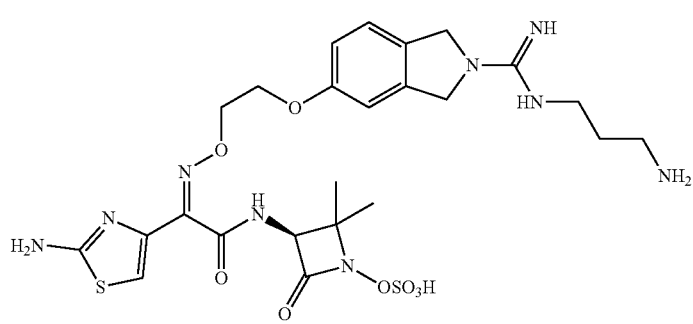

-continued
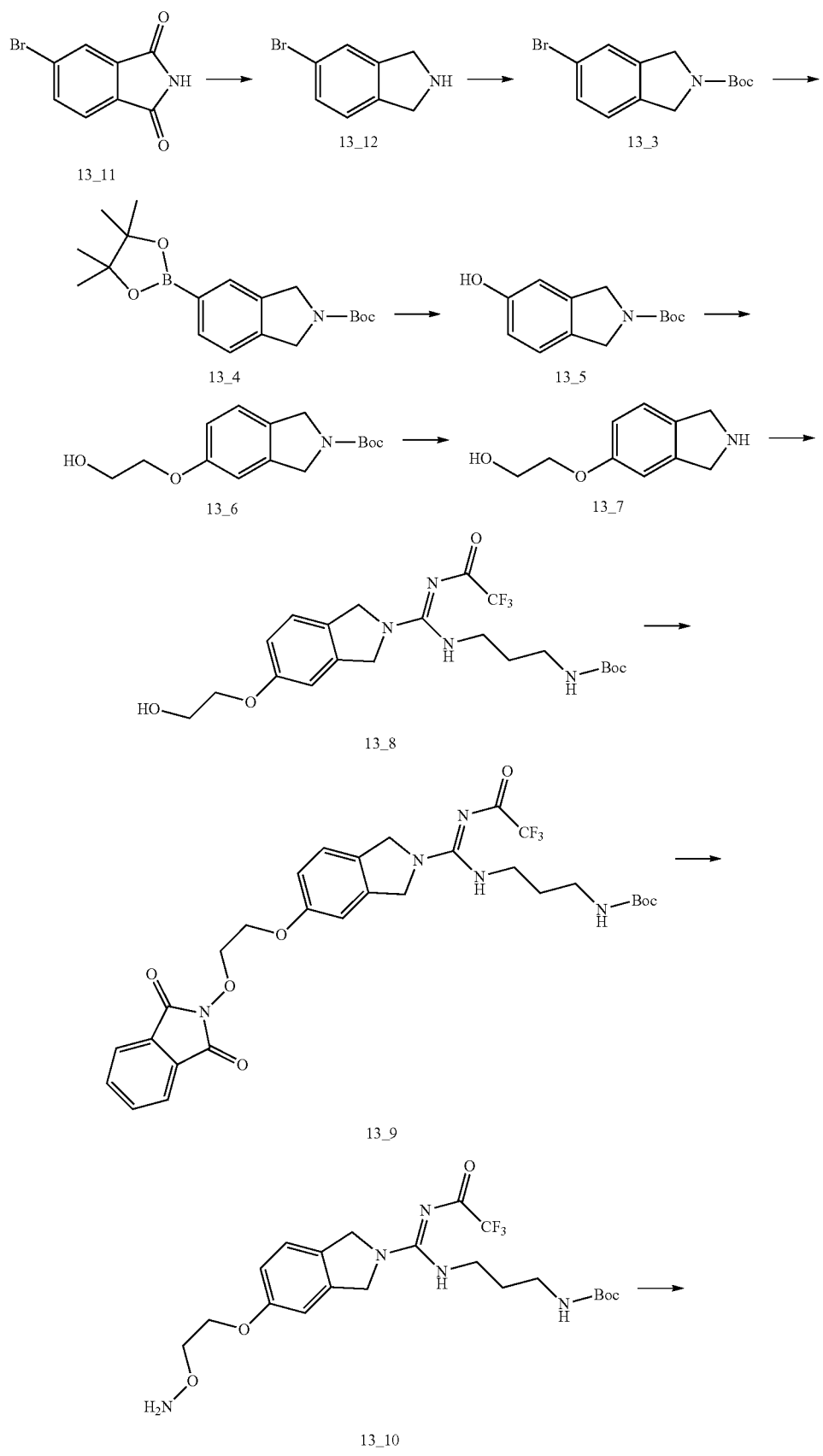

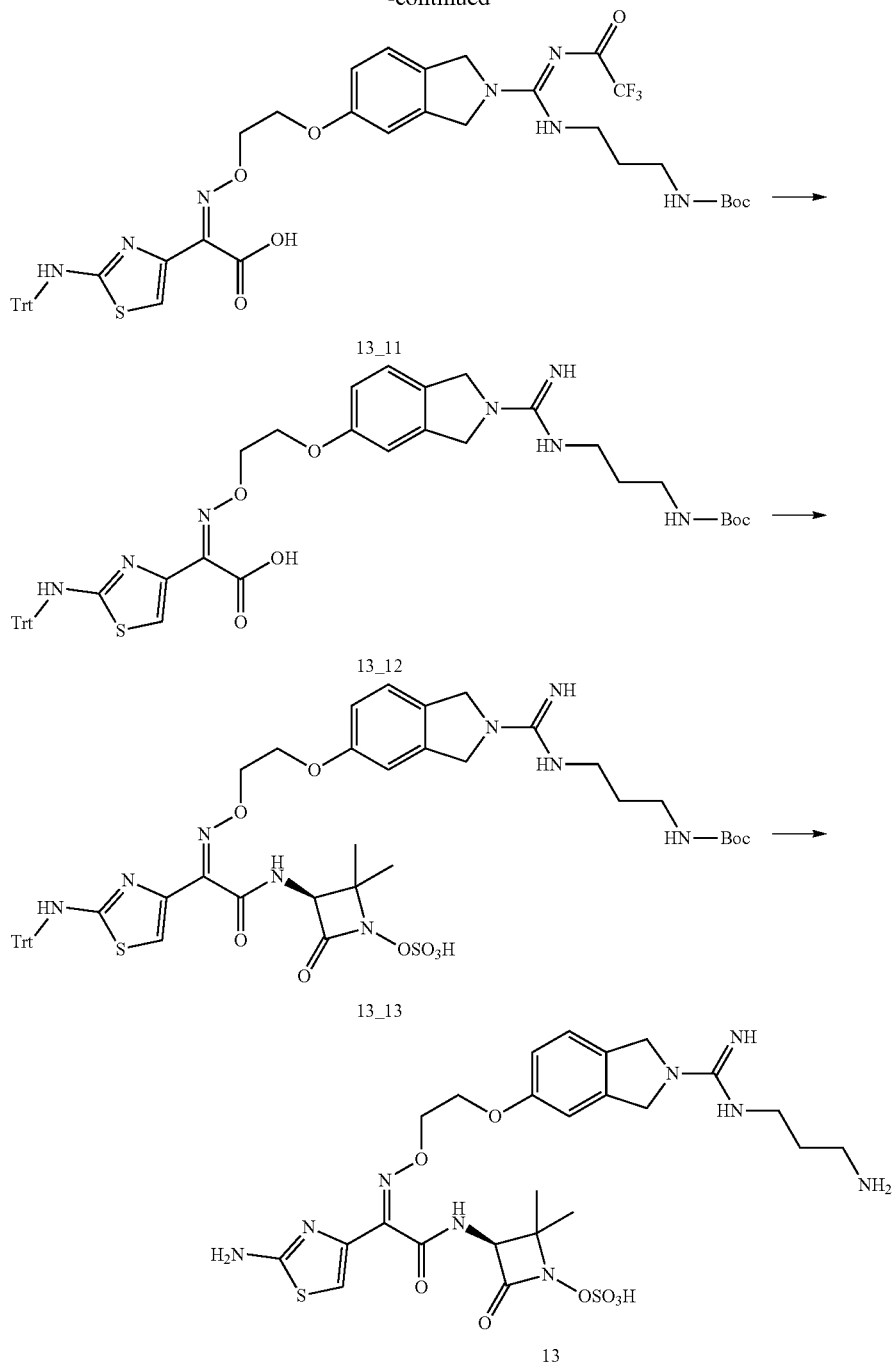

Step 1: BH₃.SMe₂ (10 M, 38.49 mL, 3 eq) was added to a solution of compound 13_1 (29 g, 128.30 mmol, 1 eq) in THF (300 mL). The mixture was reacted at 80° C. for 12 hours, then cooled to 0° C. and quenched by adding methanol (100 mL). Then, dilute hydrochloric acid (90 mL, 1M) was added to the mixture, and the mixture was stirred at 80° C. for 1 hour, concentrated under reduced pressure to remove the solvent. The residue was diluted with water (100 mL), extracted with ethyl acetate (150 mL*2). The pH value of the aqueous phase was adjusted to 10-11 by sodium hydroxide aqueous solution (1 M), the obtained aqueous phase was then extracted with ethyl acetate (150 mL*2). The organic phases were combined and dried over anhydrous sodium sulfate, filtered and concentrated under reduced pressure to give compound 13_2.

Step 2: Boc₂ (6.61 g, 30.29 mmol, 6.96 mL, 1 eq) and triethylamine (6.13 g, 60.59 mmol, 8.43 mL, 2 eq) was added to a solution of compound 132 (6 g, 30.29 mmol, 1 eq) in dichloromethane (50 mL). The mixture was stirred at 20° C. for 12 hours, then concentrated under reduced pressure to remove the solvent. The residue was diluted with water (100 mL) and extracted with ethyl acetate (50 mL*3). The organic phases were combined and concentrated under reduced pressure, the obtained residue was purified by column chromatography (SiO$_2$, petroleum ether/ethyl acetate=1/0 to 10/1 (v/v)) to give compound 13_3.

Step 3: Pd (dppf) Cl$_2$.CH$_2$Cl$_2$ (2.46 g, 3.02 mmol, 0.1 eq) and potassium acetate (11.85 g, 120.73 mmol, 4 eq) were added to a solution of compound 13_3 (9 g, 30.18 mmol, 1 eq) and 4,4,4',4',5,5,5',5'-octamethyl-2,2'-di (1,3,2-dioxaborolane) (15.33 g, 60.37 mmol, 2 eq) in DMSO (150 mL). The mixture was ventilated with nitrogen for 3 times and then stirred at 90° C. for 12 hours. The reaction mixture was diluted with water (200 mL) and extracted with ethyl acetate (150 mL*3). The combined organic phase was filtered, and the filtrate was concentrated under reduced pressure, the residue was purified by column chromatography (SiO$_2$, petroleum ether/ethyl acetate=100/1 to 20/1 (v/v)) to give compound 13_4.

Step 4: H$_2$O$_2$ (86.69 g, 764.69 mmol, 73.47 mL, 30% purity: 24 eq) and acetic acid (9.95 g, 165.68 mmol, 9.48 mL, 5.2 eq) were added to a solution of compound 13_4 (11 g, 31.86 mmol, 1 eq) in THF (100 mL). The mixture was stirred at 20° C. for 12 hours, then the reaction was quenched with saturated sodium carbonate (30 mL), the obtained mixture was diluted with water (10 mL) and extracted with ethyl acetate (20 mL*2). The organic phase was combined and concentrated under reduced pressure, the residue was purified by column chromatography (SiO$_2$, petroleum ether/ethyl acetate=15/1 to 7/1 (v/v)) to give compound 13_5. LC-MS (ESI) m/z: 180 (M-56+1). $^1$H NMR (400 MHz, DMSO-d$_6$) δ (ppm): 7.09 (t, J=6.3 Hz, 1H), 6.72-6.65 (m, 2H), 4.47 (br t, J=12.7 Hz, 4H), 1.45 (s, 9H).

Step 5: potassium carbonate (2.58 g, 18.70 mmol, 1.1 eq) and 1,3-dioxolane-2-one (4 g, 17.00 mmol, 1 eq) were added to a solution of compound 13_5 (2.25 g, 25.50 mmol, 1.70 mL, 1.5 eq) in DMF (30 mL). The mixture was stirred at 150° C. for 1 hour and concentrated under reduced pressure, the residue was diluted with water (50 mL) and extracted with ethyl acetate (50 mL*2). The organic phases were combined and concentrated under reduced pressure, the residue was purified by column chromatography (SiO$_2$, petroleum ether/ethyl acetate=7/1 to 3/1 (v/v)) to give compound 13_6. $^1$H NMR (400 MHz, DMSO-d$_6$) δ (ppm): 7.21 (dd, J=5.9, 8.0 Hz, 1H), 6.91 (d, J=5.5 Hz, 1H), 6.85 (d, J=8.6 Hz, 1H), 4.87 (t, J=5.5 Hz, 1H), 4.56-4.46 (m, 5H), 3.99-3.93 (m, 2H), 3.70 (q, J=5.3 Hz, 2H), 1.45 (s, 9H).

Step 6: TFA (6.16 g, 54.02 mmol, 4 mL, 12.58 eq) was added to a solution of compound 13_6 (1.2 g, 4.30 mmol, 1 eq) in dichloromethane (5 mL). The mixture was stirred at 10° C. for 1 hour and concentrated under reduced pressure, the residue was diluted with methanol (5 mL) and was added dropwise to a hydrogen chloride ethyl acetate solution (4 M, 15 mL) at −10° C. during 10 min, the mixture was filtered and the filter cake was collected and dried, which was then diluted in a mixed solution of methanol (10 mL) and potassium carbonate (1.19 g, 8.59 mmol, 2 eq), the mixture was then stirred at 15° C. for 2 hours and filtered, the filtrate was concentrated under reduced pressure to give compound 13_7.

Step 7: compound 13_7 (0.3 g, 1.67 mmol, 1 eq) and intermediate A5 (608.21 mg, 1.67 mmol, 1 eq) was dissolved in DMF (10 mL), the mixture was stirred at 10° C. for 0.5 hour and diluted with water (50 mL), then extracted with ethyl acetate (50 mL*2). The organic phases were combined and washed with saturated sodium chloride (20 mL*2), dried over anhydrous sodium sulfate, filtered and concentrated under reduced pressure, the residue was purified by column chromatography (SiO$_2$, DCM/MeOH=50/1 to 20/1 (v/v)) to give compound 13_8. LC-MS (ESI) m/z: 475.3 (M+1).

Step 8: 2-hydroxyisoindoline-1,3-dione (104.52 mg, 640.71 μmol, 0.95 eq) and compound 13_8 (320 mg, 674.43 mmol, 1 eq) were dissolved in THF (5 mL), then PPh$_3$ (212.27 mg, 809.32 μmol, 1.2 eq) and DIAD (163.65 mg, 809.32 μmol, 157.36 μL, 1.2 eq) were added thereto. The mixture was stirred at 20° C. for 0.5 hour and concentrated under reduced pressure to remove the solvent, the residue was diluted with water (50 mL) and extracted with ethyl acetate (50 mL*2). The organic phases were combined and concentrated under reduced pressure to remove the solvent, the residue was purified by column chromatography (SiO$_2$, petroleum ether/ethyl acetate=2/1 to 1/3 (v/v)) to give compound 13_9. LC-MS (ESI) m/z: 620.3 (M+1).

Step 9: NH$_2$NH$_2$.H$_2$O (41.82 mg, 710.15 μmol, 40.61 μl, 85% purity, 1.1 eq) was added to a solution of compound 13_9 (0.4 g, 645.59 μmol, 1 eq) in ethanol (5 mL) and dichloromethane (1 mL). The mixture was stirred at 15° C. for 10 mins and diluted with water (20 mL), then extracted with ethyl acetate (20 mL*3). The organic phases were combined and filtered, then concentrated under reduced pressure to give compound 13_10. LC-MS (ESI) m/z: 490.3 (M+1).

Step 10: compound 13_10 (0.3 g, 612.89 μmol, 1 eq) was added to a solution of intermediate A2 (203.22 mg, 490.31 μmol, 0.8 eq) in dichloromethane (2 mL) and ethanol (5 mL). The mixture was stirred at 15° C. for 10 mins and concentrated under reduced pressure to give compound 13_11. LC-MS (ESI) m/z: 886.4 (M+1).

Step 11: potassium carbonate (156.00 mg, 1.13 mmol, 2 eq) was added to a solution of compound 13_11 (0.5 g, 564.37 μmol, 1 eq) in methanol (5 mL) and water (0.1 mL), the mixture was stirred at 15° C. for 24 hours and diluted with dilute hydrochloric acid (20 mL, 0.1 M), then extracted with dichloromethane (50 mL*2). The organic phases were combined and washed with saturated sodium chloride (10 mL*2), dried over anhydrous sodium sulfate, filtered and concentrated under reduced pressure, the residue was purified by column chromatography (SiO$_2$, DCM/MeOH=10/1 to 0/1 (v/v)) to give compound 13_12. LC-MS (ESI) m/z: 790.4 (M+1).

Step 12: HOBt (102.63 mg, 759.55 μmol, 2 eq) and DCC (156.72 mg, 759.55 μmol, 153.64 μL, 2 eq) was added to a solution of compound 13_12 (0.3 g, 379.77 μmol, 1 eq) in DMF (4 mL). The mixture was stirred at room temperature for 0.5 hour, then intermediate A1 (103.78 mg, 493.71 μmol, 1.3 eq) and sodium bicarbonate (127.62 mg, 1.52 mmol, 59.08 μL, 4 eq) were added thereto. The obtained mixture was stirred at 15° C. for 11.5 hours and filtered, then concentrated under reduced pressure, the residue was purified by preparative TLC (SiO$_2$, DCM/MeOH=8/1 (v/v)) to give compound 13_13. LC-MS (ESI) m/z: 983.6 (M+1)

Step 13: TFA (1.54 g, 13.51 mmol, 1 mL, 73.69 eq) was added to a solution of compound 13_13 (180 mg, 183.27 μmol, 1 eq) in dichloromethane (1 mL). The mixture was stirred at 0° C. for 10 mins and then diluted with petroleum ether/ethyl acetate (10 mL, 1/1), the mixture was filtered under reduced pressure and the filter cake was dried, which was purified by preparative HPLC (column: Boston Green ODS 150*30 5 u; mobile phase: [water (0.225% formic acid)-acetonitrile]; acetonitrile %: 2%-32%, 10 min) to give compound 13. $^1$H NMR (400 MHz, DMSO-d$_6$+D$_2$O) δ (ppm): 8.34 (s, 1H), 7.33-7.24 (m, 1H), 7.06-6.89 (m, 2H), 6.76 (s, 1H), 4.76-4.57 (m, 5H), 4.38 (br s, 2H), 4.20-4.15 (m, 1H), 3.36-3.23 (m, 2H), 2.85 (br t, J=7.5 Hz, 2H), 1.80 (br s, 2H), 1.37 (s, 3H), 1.17 (s, 3H); LC-MS (ESI) m/z: 640.4 (M+1).

Embodiment 14

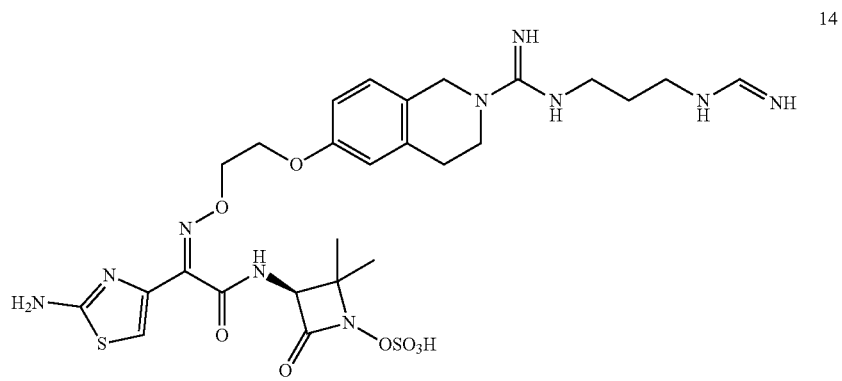

14

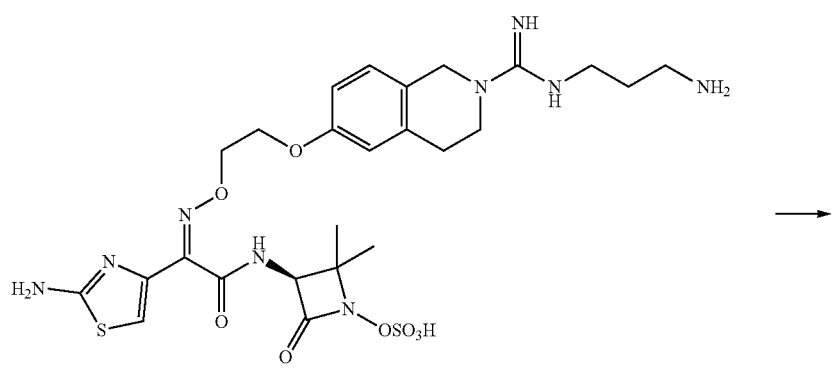

6

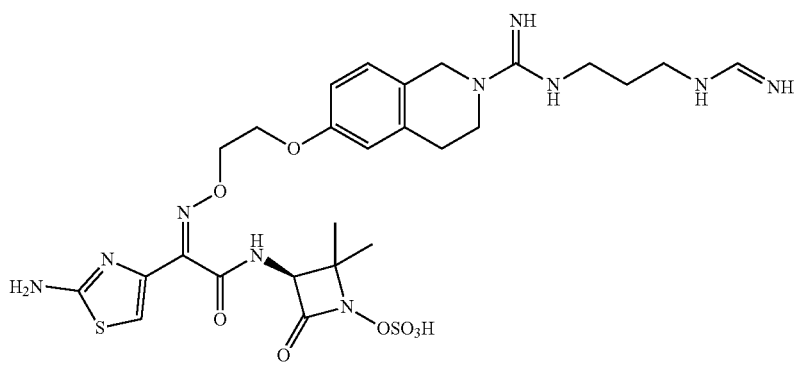

14

Step 1: the trifluoroacetate of compound 6 (100 mg, 113.41 μmol, 1 eq), ethyl formimidate hydrochloride (12.42 mg, 113.41 μmol, 1 eq, HCl) and triethylamine (34.43 mg, 340.22 μmol, 47.36 μL, 3 eq) were dissolved in DMF (1 mL), the mixture was stirred at 15° C. for 24 hours. The mixture was then filtered, and the filtrate was purified by preparative HPLC (FA, column: Boston Green ODS 150*30 5 u; mobile phase: [water (0.225% formic acid)-acetonitrile]; acetonitrile %: 3%-33%, 10 min) to give compound 14. $^1$H NMR (400 MHz, DMSO-$d_6$) δ (ppm): 9.44 (br d, J=7.6 Hz, 1H), 8.46 (s, 1H), 7.90 (br s, 1H), 7.23 (s, 2H), 7.08 (br d, J=8.3 Hz, 1H), 6.88-6.80 (m, 2H), 6.76 (s, 1H), 4.59 (d, J=7.3 Hz, 1H), 4.50 (br s, 2H), 4.36 (br d, J=4.4 Hz, 2H), 4.17 (br d, J=3.1 Hz, 2H), 3.58 (br s, 2H), 3.30 (br d, J=6.4 Hz, 2H), 2.89 (br s, 2H), 1.79 (br d, J=5.4 Hz, 2H), 1.39 (s, 3H), 1.22 (s, 3H);

LC-MS (ESI) m/z: 681.4 (M+1).

Embodiment 15

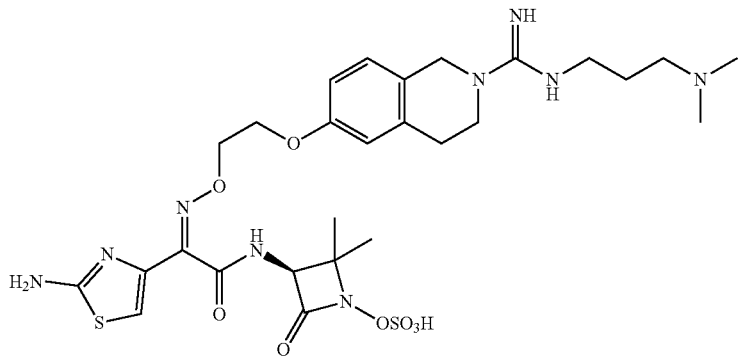

15

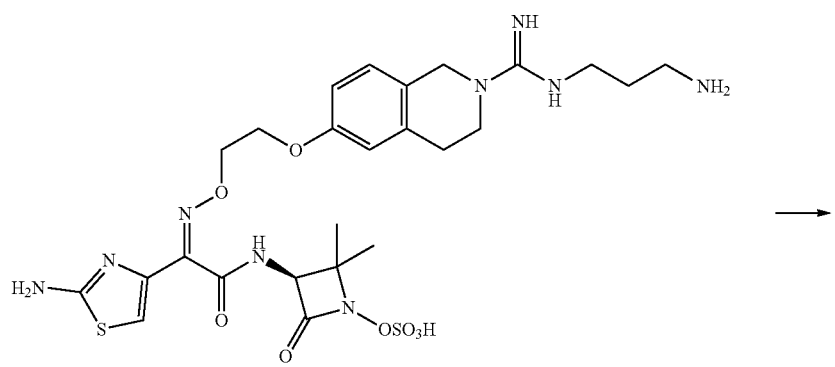

6

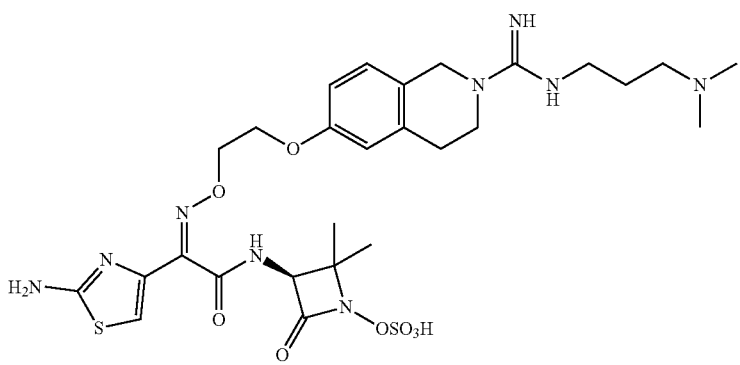

15

Step 1: compound 6 (100 mg, 113.41 μmol, 1 eq, 2TFA), formaldehyde solution (9.20 mg, 113.41 μmol, 8.44 μL, 1 eq) and anhydrous sodium sulfate (80.54 mg, 567.04 μmol, 57.53 μL, 5 eq) were added to MeOH (1 mL), the mixture was stirred at 15° C. for 1 hour then NaBH$_3$(CN) (14.25 mg, 226.82 μmol, 2 eq) was added thereto. The mixture was stirred at 15° C. for another 11 hour and filtered, the filtrate was purified by preparative HPLC (FA, column: Boston Green ODS 150*30 5 u; mobile phase: [water (0.225% formic acid)-acetonitrile]; acetonitrile %: 2%-32%, 10 min) to give compound 15.

$^1$H NMR (400 MHz, DMSO-d$_6$) δ (ppm): 9.42 (d, J=7.8 Hz, 1H), 8.18 (s, 1H), 7.83 (br s, 3H), 7.20 (s, 2H), 7.09 (br d, J=8.3 Hz, 1H), 6.93-6.82 (m, 2H), 6.76 (s, 1H), 4.58 (d, J=7.8 Hz, 1H), 4.47 (s, 2H), 4.37 (brs, 2H), 4.18 (br s, 2H), 3.55 (br d, J=5.9 Hz, 2H), 3.26 (br d, J=7.0 Hz, 2H), 2.90 (br d, J=5.9 Hz, 2H), 2.37-2.32 (m, 3H), 2.20 (s, 6H), 1.75-1.65 (m, 2H), 1.40 (s, 3H), 1.22 (s, 3H);

LC-MS (ESI) m/z: 682.4 (M+1).

Embodiment 16
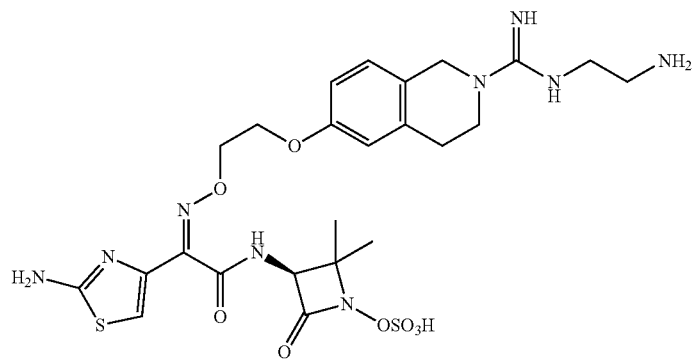
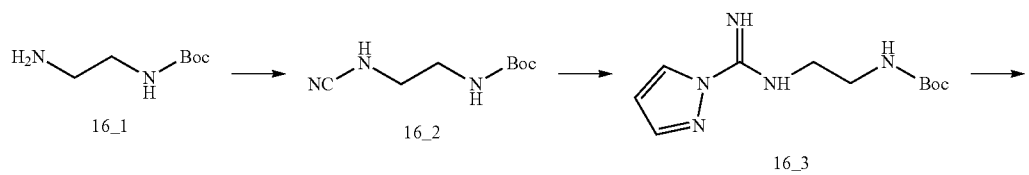
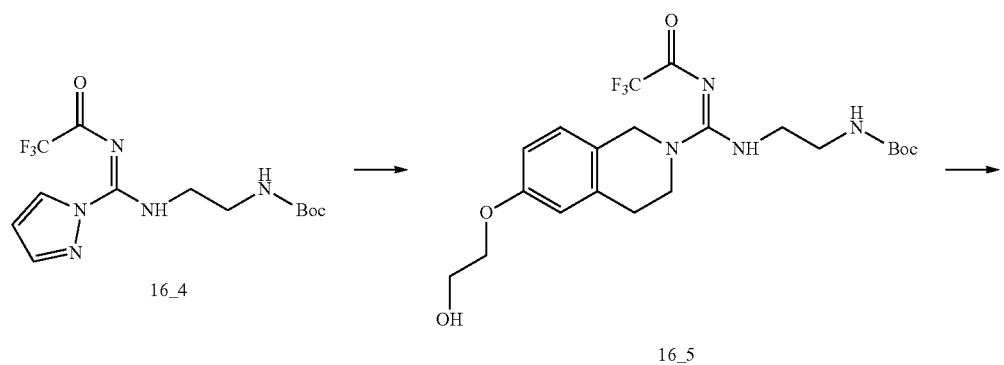
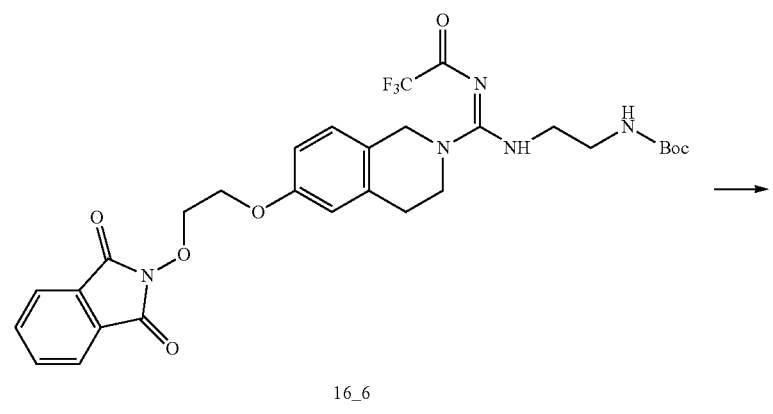

-continued
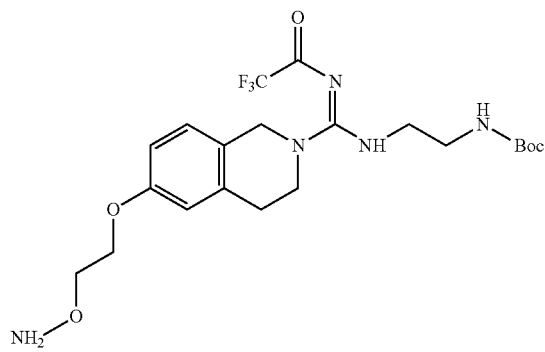 
16_7
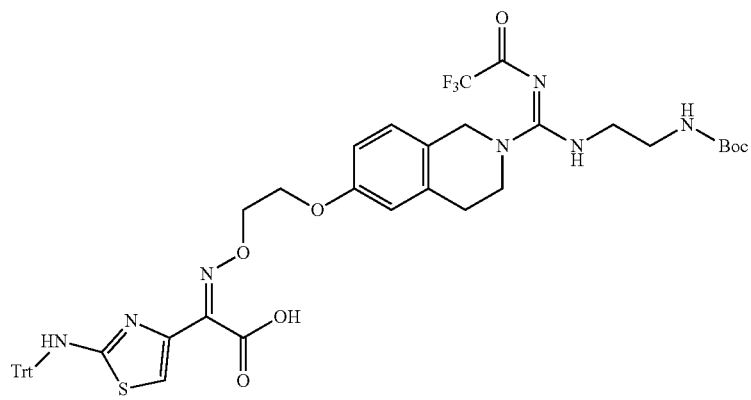 
16_8
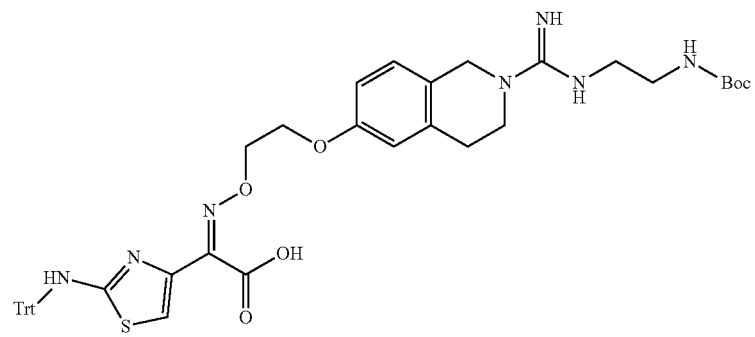 
16_9
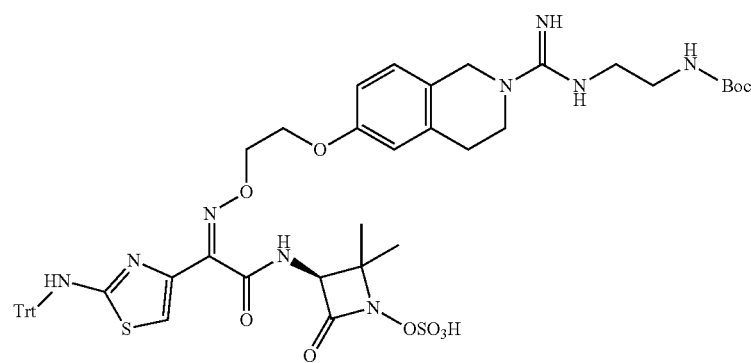 
16_10

-continued

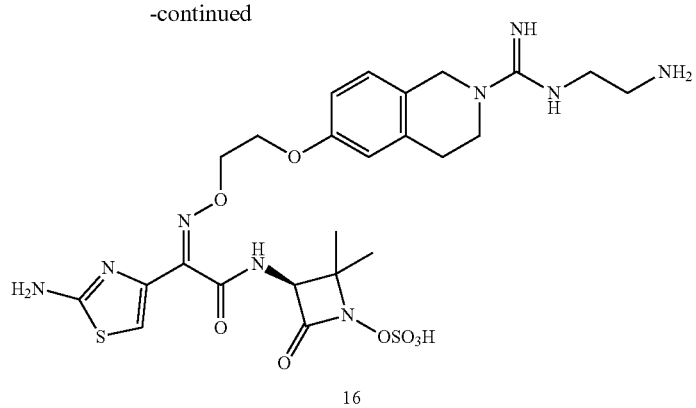

16

Step 1: 16_1 (2 g, 12.48 mmol, 1.96 mL, 1 eq), BrCN (1.98 g, 18.72 mmol, 1.38 mL, 1.5 eq) and NaOAc (5.12 g, 62.42 mmol, 5 eq) were added to ethanol (20 mL), the mixture was ventilated with nitrogen for 3 times, and the mixture was stirred at 10-15° C. for 2 hours, then concentrated under reduced pressure to remove the solvent, water (30 mL) was added to the reaction mixture, and extracted with ethyl acetate (20 mL*2). The organic phases were combined and washed with saline, dried over anhydrous sodium sulfate. The mixture was filtered and the filtrate was concentrated under reduced pressure to give compound 16_2.

Step 2: pyrazole hydrochloride (1.30 g, 12.42 mmol, 1 eq) was added to a solution of compound 162 (2.3 g, 12.42 mmol, 1 eq) in THF (40 mL). The mixture was stirred at 70° C. for 12 hours and then concentrated under reduced pressure to give a hydrochloride of compound 16_3.

Step 3: trifluoroacetic anhydride (829.18 mg, 3.95 mmol, 549.12 µL, 1 eq) and triethylamine (798.97 mg, 7.90 mmol, 1.10 mL, 2 eq) were added to a solution of the hydrochloride of compound 16_3 (1 g, 3.95 mmol, 1 eq) in dichloromethane (10 mL). The mixture was stirred at 0° C. for 1 hour, then the reaction was quenched by adding dilute hydrochloric acid (10 mL, 1 M), the obtained mixture was extracted with dichloromethane (50 mL). The combined organic phase was washed with saturated sodium chloride (20 mL), dried over anhydrous sodium sulfate, filtered and concentrated under reduced pressure to give compound 16_4.

Step 4: compound 16_4 (500 mg, 306.89 µmol, 1 eq) and compound 4_4 (59.30 mg, 306.89 µmol, 1 eq) were dissolved in DMF (5 mL), the reaction mixture was stirred at 30° C. for 2 hours. The reaction mixture was poured into water (10 mL) and stirred for 5 min, the aqueous phase was extracted with ethyl acetate (50 mL). The combined organic phase was washed with saturated sodium chloride (20 mL) and dried over anhydrous sodium sulfate, then filtered and concentrated under reduced pressure to give compound 16_5.

Step 5: compound 16_5 (0.4 g, 843.04 µmol, 1 eq), 2-hydroxyisoindoline-1,3-dione (165.03 mg, 1.01 mmol, 1.2 eq), and PPh₃ (265.34 mg, 1.01 mmol, 1.2 eq) were added to THF (4 mL), DIAD (204.56 mg, 1.01 mmol, 196.70 µL, 1.2 eq) was added thereto at 0° C. The mixture was stirred at 15° C. for 3 hours and concentrated under reduced pressure, the residue was poured into water (20 mL) and stirred for 5 min, the aqueous phase was extracted with ethyl acetate (50 mL). The organic phases were combined and washed with saturated sodium chloride aqueous solution (20 mL), dried over anhydrous sodium sulfate, filtered and concentrated under reduced pressure, the residue was purified by column chromatography (SiO₂, petroleum ether/ethyl acetate=5/1 to 0/1 (v/v)) to give compound 16_6.

LC-MS (ESI) m/z: 620.3 (M+1).

Step 6: NH₂NH₂·H₂O (19.01 mg, 322.80 µmol, 18.46 µL, 85% purity, 1 eq) was added to a solution of compound 16_6 (200 mg, 322.80 µmol, 1 eq) in ethanol (2 mL). The mixture was stirred at 20° C. for 1 hour and filtered, the filtrate was concentrated under reduced pressure, the residue was diluted with water (20 mL), the aqueous phase was extracted with ethyl acetate (50 mL×2). The combined organic phase was washed with saturated sodium chloride aqueous solution (20 mL), dried over anhydrous sodium sulfate, filtered and concentrated under reduced pressure to give compound 16_7.

Step 7: intermediate A2 (101.61 mg, 245.15 µmol, 1 eq) was added to a solution of compound 16_7 (120 mg, 245.15 µmol, 1 eq) in methanol (3 mL) and dichloromethane (1 mL). The mixture was stirred at 15° C. for 1 hour and concentrated under reduced pressure to give compound 16_8.

Step 8: potassium carbonate (78.00 mg, 564.37 µmol, 2.5 eq) was added to a solution of compound 16_8 (200 mg, 225.75 µmol, 1 eq) in methanol (1 mL). The mixture was stirred at 15° C. for 14 hours and the residue was poured into water (10 mL) and stirred for 5 min, then the mixture was extracted with dichloromethane (50 mL*2). The combined organic phase was washed with saturated sodium chloride solution (30 mL), dried over anhydrous sodium sulfate and filtered, the filtrate was concentrated under reduced pressure, the residue was washed (20 mL*3, petroleum ether/ethyl acetate=1/1), the filter cake was collected after filtering to give compound 16_9. LC-MS (ESI) m/z: 790.5 (M+1).

Step 9: DCC (41.79 mg, 202.55 µmol, 40.97 µL, 2 eq) and HOBt (27.37 mg, 202.55 µmol, 2 eq) were added to a solution of compound 16_9 (80 mg, 101.27 µmol, 1 eq) in DMF (2 mL). The mixture was stirred at 15° C. for 30 min, then sodium bicarbonate (34.03 mg, 405.09 µmol, 15.75 µL, 4 eq) and intermediate A1 (31.93 mg, 151.91 µmol, 1.5 eq) were added thereto. The mixture was stirred at 15° C. for 11.5 hours and filtered, the filtrate was concentrated under reduced pressure, the residue was purified by preparative TLC (SiO₂, dichloromethane/methanol=10/1) to give compound 16_10. LC-MS (ESI) m/z: 982.6 (M+1).

Step 10: TFA (1.54 g, 13.51 mmol, 1 mL, 442.16 eq) was added to a solution of compound 16_10 (30 mg, 30.55 µmol, 1 eq) in dichloromethane (1 mL) at −15° C. The mixture was stirred at 0° C. for 30 mins and concentrated under reduced pressure, the residue was purified by preparative HPLC (column: Boston Green ODS 150*30 5 u; mobile phase: [water (0.225% formic acid)-ACN]; B %: 8%-38%, 10 min) to give compound 16. ¹H NMR (400 MHz, DMSO-d₆) δ (ppm): 8.36 (s, 3H), 7.10 (br d, J=8.9 Hz, 1H), 6.88 (s, 1H), 6.82 (br s, 2H), 4.88-4.87 (m, 2H), 4.46 (s, 4H), 3.59-3.48 (m, 4H), 3.18 (t, J=6.4 Hz, 2H), 2.86 (br d, J=6.1 Hz, 2H), 1.98-1.96 (m, 1H), 1.39 (S, 3H), 1.05 (s, 3H));
LC-MS (ESI) m/z: 640.4 (M+1).
Embodiment 17
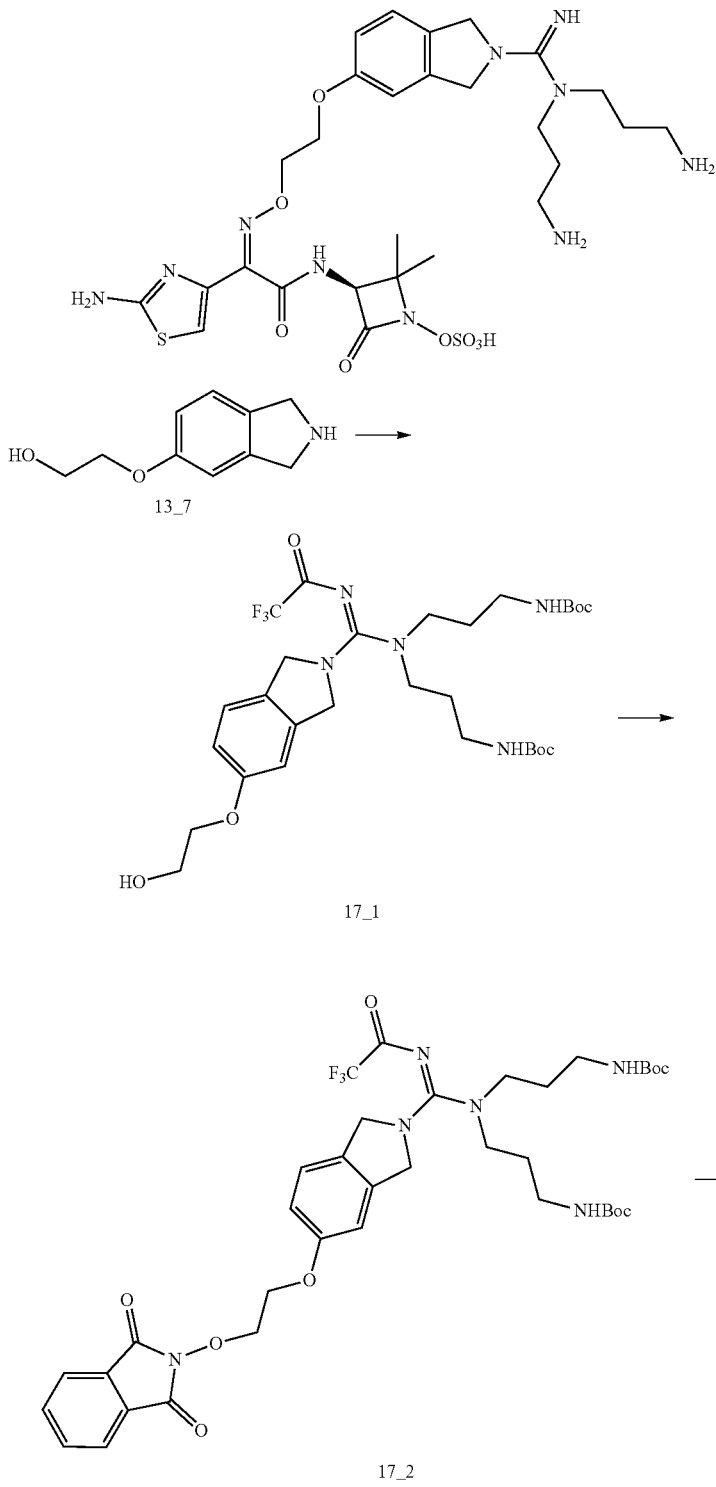

-continued
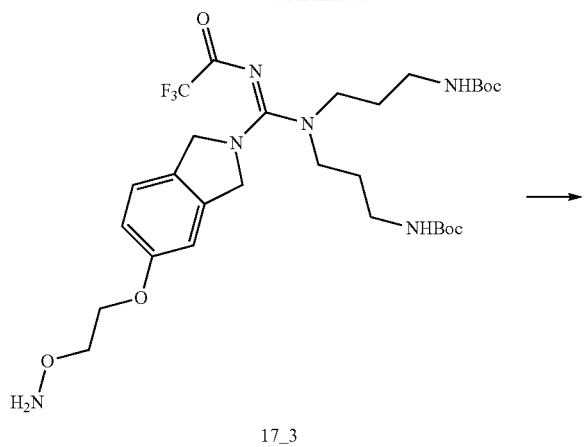
17_3
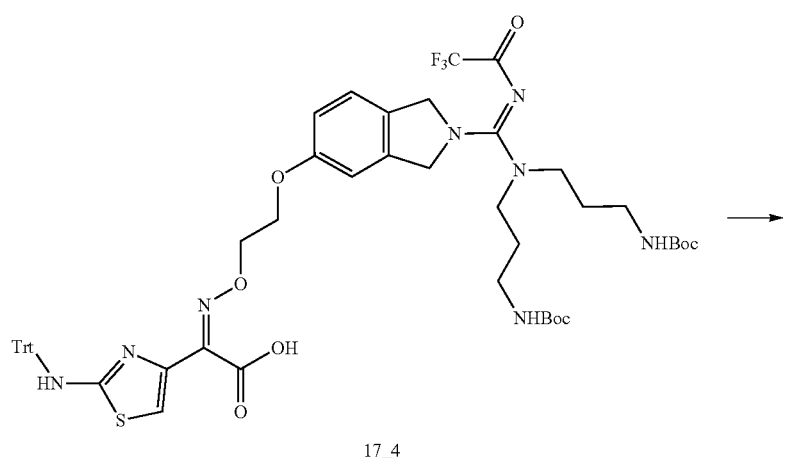
17_4
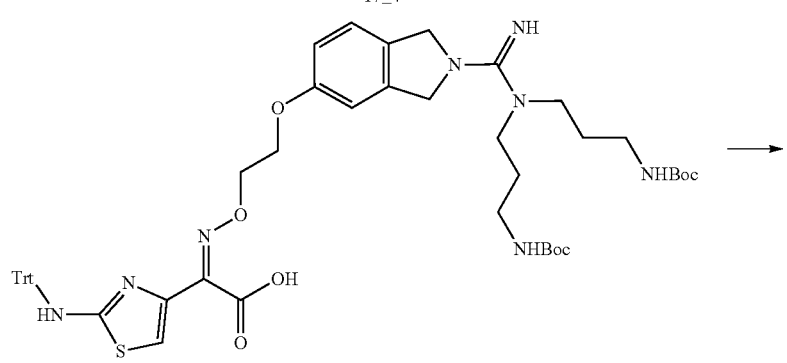
17_5
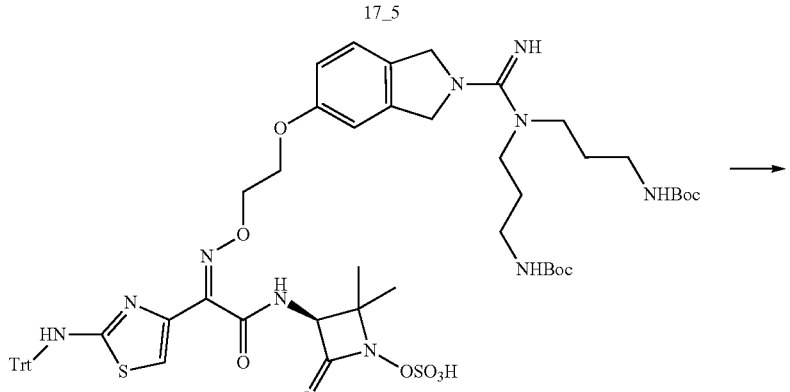
17_6

-continued

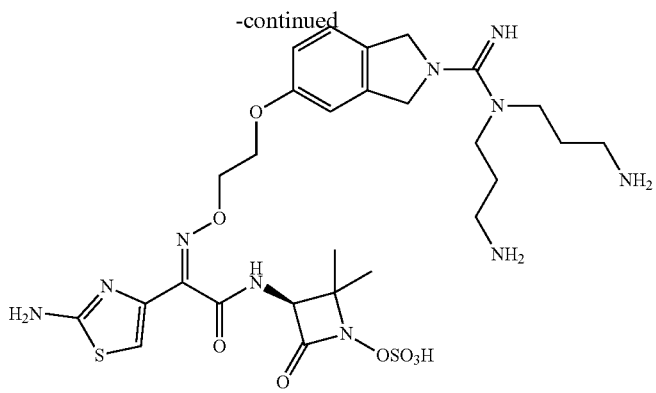

17

Step 1: triethylamine (1.24 g, 12.29 mmol, 1.71 mL, 4 eq) and the trifluoroacetate of 13_7 (901.33 mg, 3.07 mmol, 1 eq) were added to a solution of compound A6 (1.6 g, 3.07 mmol, 1 eq) in DMF (20 mL), the obtained mixture was stirred at 45° C. for 12 hours. The reaction mixture was cooled to room temperature and diluted with water (40 mL), then extracted with ethyl acetate (50 mL*2), the combined organic phase was concentrated under reduced pressure, the obtained residue was purified by column chromatography ($SiO_2$, petroleum ether/ethyl acetate=2/1 to 0/1) to give compound 17_1.

LCMS (ESI) m/z: 632.4 (M+1).

Step 2: $PPh_3$ (199.72 mg, 761.46 μmol, 1.3 eq) was added to a solution of compound 17_1 (370 mg, 585.74 mol, 1 eq) and 2-hydroxyisoindoline-1,3-dione (95.55 mg, 585.74 μmol, 1 eq) in THF (8 mL), then DIAD (153.97 mg, 761.46 μmol, 148.05 μL, 1.3 eq) was added dropwise at 0° C. The obtained mixture was stirred at 25° C. for 1 hour and concentrated under reduced pressure to remove the solvent, the residue was purified by column chromatography ($SiO_2$, petroleum ether/ethyl acetate=5/1 to 2/1) to give compound 17_2.

Step 3: $NH_2NH_2.H_2O$ (58.38 mg, 991.25 μmol, 56.68 μL, 85% purity, 1.1 eq) was added to a solution of compound 17_2 (700 mg, 901.14 mol, 1 eq) in EtOH (10 mL) at 25° C. and stirred for 1 hour. The reaction mixture was concentrated under reduced pressure to remove the solvent, the residue was diluted with water (40 mL) and washed with DCM (40 mL*2). The organic phases were combined and concentrated under reduced pressure to give compound 17_3.

Step 4: intermediate A2 (256.36 mg, 618.53 μmol, 1 eq) was added to a mixed solution of compound 17_3 (400 mg, 618.53 mol, 1 eq) in MeOH (3 mL) and DCM (3 mL). The mixture was stirred at 25° C. for 0.5 hour and concentrated under reduced pressure, the residue was purified by column chromatography ($SiO_2$, MeOH/DCM=0/1 to 10/1) to give compound 17_4.

Step 5: potassium carbonate (231.85 mg, 1.68 mmol, 5 eq) was added to a solution of compound 17_4 (350 mg, 335.52 μmol, 1 eq) in MeOH (5 mL). The mixture was stirred at 40° C. for 14 hours and concentrated under reduced pressure, the residue was poured into water (20 mL) and stirred for 5 min. The aqueous phase was extracted with DCM (100 mL). The combined organic phase was washed with saturated sodium chloride aqueous solution (20 mL), dried over anhydrous sodium sulfate, filtered and concentrated under reduced pressure to give compound 17_5.

Step 6: N,N'-diisopropylcarbodiimide (79.95 mg, 633.48 μmol, 98.09 μL, 2 eq) and HOBt (85.60 mg, 633.48 μmol, 2 eq) were added to a solution of compound 17_5 (300 mg, 316.74 μmol, 1 eq) in DMF (3 mL). The mixture was stirred at 25° C. for 30 min, then intermediate A1 (86.56 mg, 411.76 μmol, 1.3 eq) and $NaHCO_3$ (106.43 mg, 1.27 mmol, 4 eq) were added thereto. The mixture was stirred at 25° C. for 12 hours then poured into water (10 mL) and stirred for another 5 min, the mixture was filtered and the filter cake was collected, which was purified by preparative TLC ($SiO_2$, dichloromethane/methanol=10/1) to give compound 17_6.

LCMS (ESI) m/z: 1139.7 (M+1).

Step 7: TFA (1.54 g, 13.51 mmol, 1 mL, 208.28 eq) was added to a solution of compound 17_6 (80 mg, 64.84 μmol, 1 eq) in DCM (1 mL) at 0° C., then stirred for 30 min, then a mixed solution of petroleum ether/ethyl acetate (10 mL, 1/2) was added to the reaction mixture and stirred for 5 min, the mixture was filtered and the filter cake was collected, which was purified by preparative HPLC column (Boston Green ODS 150*30*5 μm; mobile phase: [water (0.225% FA)-acetonitrile]; acetonitrile %: 1%-27%, 10 min) to give compound 17. $^1H$ NMR (400 MHz, DMSO-$d_6$) δ (ppm): 7.25 (d, J=8.4 Hz, 1H), 7.03-6.99 (m, 1H), 6.97-6.90 (m, 2H), 4.86 (br s, 4H), 4.56 (br d, J=2.9 Hz, 1H), 3.45 (t, J=7.2 Hz, 4H), 3.05-2.86 (m, 4H), 2.08-1.91 (m, 4H), 1.45 (s, 3H), 1.05 (s, 3H); LCMS (ESI) m/z: 697.4 (M+1).

Embodiment 18

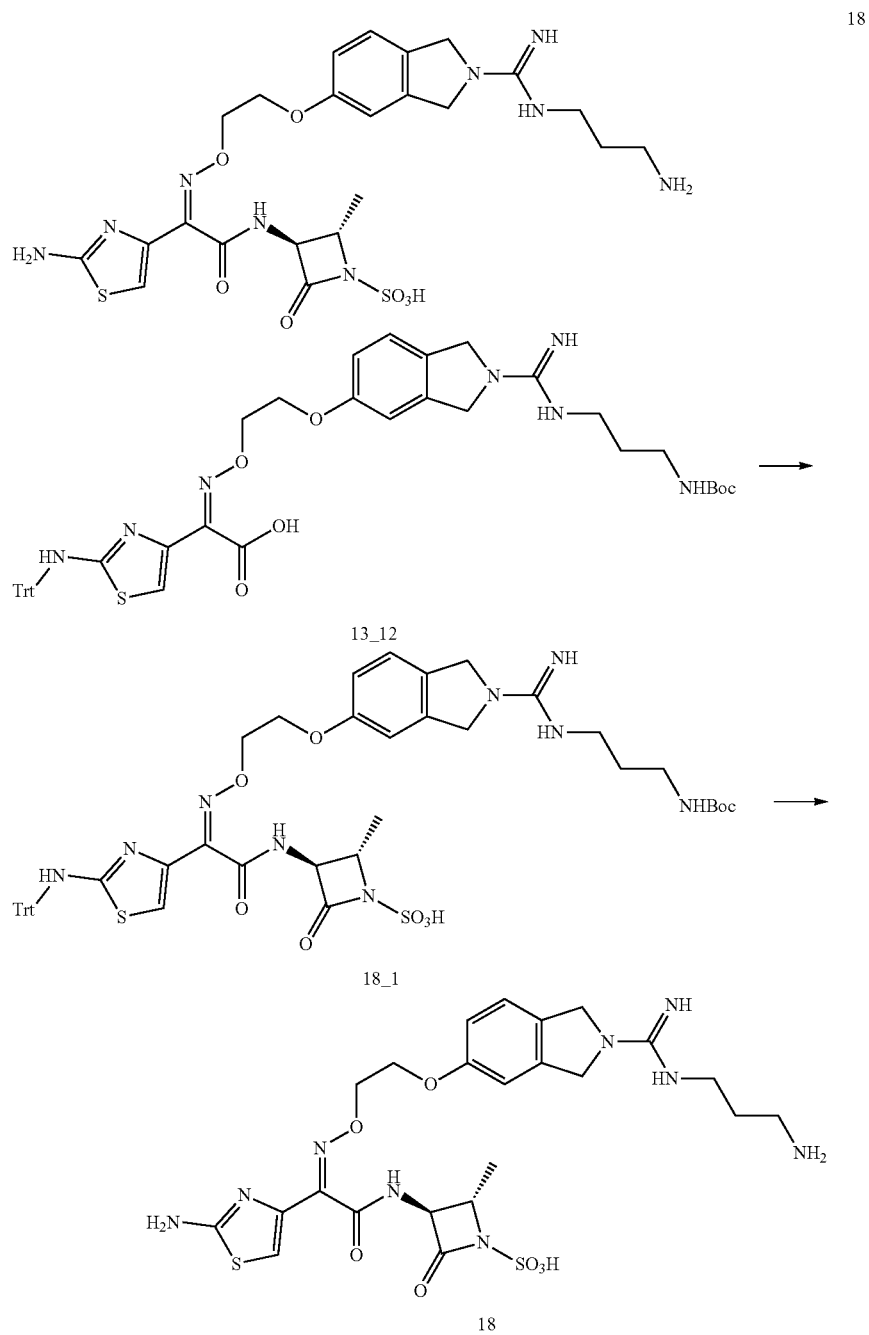

Step 1: HOBt (171.05 mg, 1.27 mmol, 2 eq) and DIC (159.76 mg, 1.27 mmol, 196.02 μL, 2 eq) were added to a solution of compound 13_12 (500 mg, 632.96 μmol, 1 eq) in DMF (5 mL) at room temperature, the mixture was stirred at room temperature for 60 min, then intermediate A3 (148.26 mg, 822.85 μmol, 1.3 eq) and NaHCO$_3$ (212.70 mg, 2.53 mmol, 4 eq) were added thereto. The obtained mixture was stirred at room temperature for 11 hours and diluted with water (50 mL), the mixture was filtered under reduced pressure and the filter cake was collected, then dried to give compound 18_1. LCMS (ESI) m/z: 952.4 (M+1).

Step 2: TFA (4 mL) was added to a DCM (5 mL) of compound 18_1 (450 mg, 472.64 μmol, 1 eq) at 0° C., the obtained mixture was stirred at 0° C. for 2 hours, the mixture was concentrated under reduced pressure to remove the solvent, the residue was purified by preparative HPLC (column: Boston pH-lex 150*25*10 μm; mobile phase: [water (0.1% TFA)-ACN]; acetonitrile %: 15%-29%, 8 min) to give compound 18.

$^1$H NMR (400 MHz, DMSO-d$_6$+D$_2$O) δ (ppm): 7.26 (d, J=8.3 Hz, 1H), 7.00-6.90 (m, 2H), 6.86 (s, 1H), 4.69 (br s, 2H), 4.63 (br s, 2H), 4.40 (br dd, J=3.2, 13.2 Hz, 3H), 4.23

(br d, J=3.9 Hz, 2H), 3.74 (br dd, J=2.7, 6.2 Hz, 1H), 3.28 (br t, J=6.6 Hz, 2H), 2.86 (br t, J=7.6 Hz, 2H), 1.86-1.76 (m, 2H), 1.32 (d, J=6.1 Hz, 3H); LCMS (ESI) m/z: 610.4 (M).

Embodiment 19

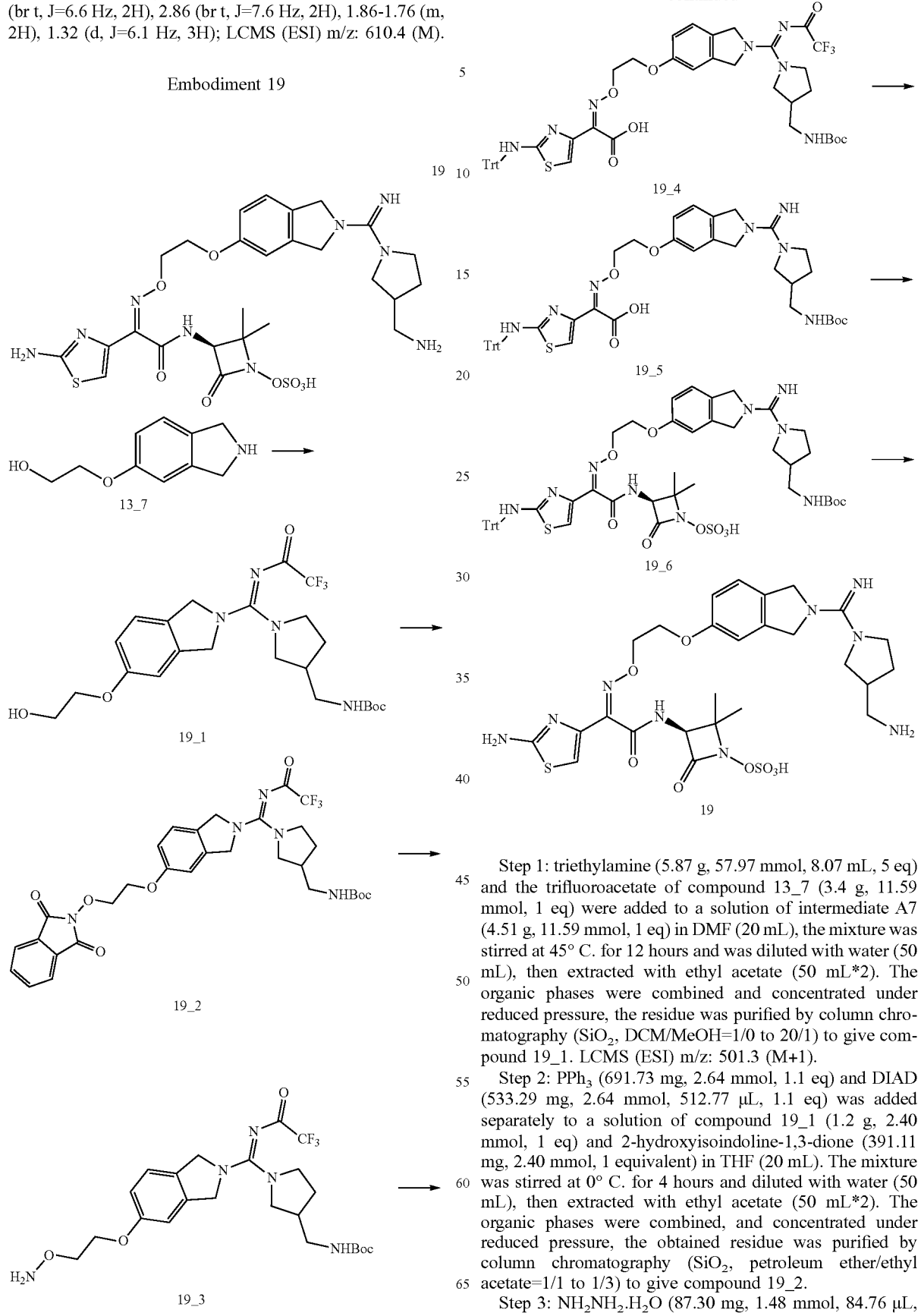

Step 1: triethylamine (5.87 g, 57.97 mmol, 8.07 mL, 5 eq) and the trifluoroacetate of compound 13_7 (3.4 g, 11.59 mmol, 1 eq) were added to a solution of intermediate A7 (4.51 g, 11.59 mmol, 1 eq) in DMF (20 mL), the mixture was stirred at 45° C. for 12 hours and was diluted with water (50 mL), then extracted with ethyl acetate (50 mL*2). The organic phases were combined and concentrated under reduced pressure, the residue was purified by column chromatography (SiO₂, DCM/MeOH=1/0 to 20/1) to give compound 19_1. LCMS (ESI) m/z: 501.3 (M+1).

Step 2: PPh₃ (691.73 mg, 2.64 mmol, 1.1 eq) and DIAD (533.29 mg, 2.64 mmol, 512.77 μL, 1.1 eq) was added separately to a solution of compound 19_1 (1.2 g, 2.40 mmol, 1 eq) and 2-hydroxyisoindoline-1,3-dione (391.11 mg, 2.40 mmol, 1 equivalent) in THF (20 mL). The mixture was stirred at 0° C. for 4 hours and diluted with water (50 mL), then extracted with ethyl acetate (50 mL*2). The organic phases were combined, and concentrated under reduced pressure, the obtained residue was purified by column chromatography (SiO₂, petroleum ether/ethyl acetate=1/1 to 1/3) to give compound 19_2.

Step 3: NH₂NH₂.H₂O (87.30 mg, 1.48 mmol, 84.76 μL, 85% purity, 1.1 eq) was added to a solution of compound 19_2 (870 mg, 1.35 mmol, 1 eq) in EtOH (10 mL). The mixture was stirred at 25° C. for 10 mins and concentrated under reduced pressure, the residue was diluted with water (30 mL) and extracted with DCM (50 mL*2). The organic phases were combined, and concentrated under reduced pressure to give compound 19_3.

Step 4: intermediate A2 (401.99 mg, 969.89 µmol, 1 eq) was added to a mixed solution of compound 19_3 (500 mg, 969.89 µmol, 1 eq) in EtOH (5 mL) and DCM (5 mL). The mixture was stirred at 25° C. for 0.5 hour and concentrated under reduced pressure, the residue was washed with petroleum ether/ethyl acetate (50 mL, 1/5) under stirring, and filtered. The filter cake was collected and dried to give compound 19_4. LCMS (ESI) m/z: 912.2 (M+1).

Step 5: potassium carbonate (985.04 mg, 7.13 mmol, 10 eq) was added to a solution of compound 19_4 (650 mg, 712.73 µmol, 1 eq) in MeOH (5 mL). The reaction mixture was stirred at 50° C. for 12 hours and concentrated under reduced pressure, the residue was diluted with water (10 mL) and the pH value was adjusted to 5 by using dilute hydrochloric acid (10%), the aqueous phase was extracted with DCM (20 mL*2). The combined organic phase was washed with saturated sodium chloride, dried over anhydrous sodium sulfate and filtered, the filtrate was concentrated under reduced pressure. The residue was washed with ethyl acetate/petroleum ether (30 mL, 3/1) under stirring to give compound 19_5.

Step 6: DIC (123.73 mg, 980.42 µmol, 151.81 µL, 2 eq) and HOBt (132.48 mg, 980.42 mmol, 2 eq) were added to a solution of compound 19_5 (400 mg, 490.21 µmol, 1 eq) in DMF (3 mL). The mixture was stirred at room temperature (20-30° C.) for 30 min, then intermediate A1 (123.66 mg, 588.25 µmol, 1.2 eq) and NaHCO$_3$ (164.72 mg, 1.96 mmol, 4 eq) were added thereto and stirred at room temperature (20-30° C.) for 5 hours. Water (10 mL) was added to the reaction mixture and stirred for 5 min. After precipitation of a while solid, the mixture was filtered under vacuum, the filter cake was collected and dried, and was washed with ethyl acetate/petroleum ether (10 mL, 2/1) under stirring to give compound 19_6.

Step 7: TFA (1 mL) was added to a solution of compound 19_6 (130 mg, 128.951 mmol) in DCM (2 mL) at 0° C. The reaction mixture was stirred at room temperature (20-30° C.) for 30 min, then EtOAc (10 mL) was added, a white solid was precipitated. The reaction mixture was filtered and the filter cake was collected, which was purified by preparative HPLC (column: Phenomenex Synergi C18 150*25*10 µm; mobile phase: [water (0.225% formic acid)-ACN]; acetonitrile %: 1%-17%, 8 min) to give compound 19. $^1$H NMR (400 MHz, D$_2$O) δ (ppm): 8.37 (s, 1H), 7.23 (d, J=8.2 Hz, 1H), 6.96-6.86 (m, 3H), 4.99-4.80 (m, 4H), 4.50-4.23 (m, 5H), 3.76 (br t, J=8.3 Hz, 1H), 3.69-3.57 (m, 2H), 3.37 (br t, J=8.9 Hz, 1H), 3.20-3.02 (m, 2H), 2.63 (br d, J=6.5 Hz, 1H), 2.32-2.13 (m, 1H), 1.81 (br d, J=8.9 Hz, 1H), 1.44 (d, J=2.5 Hz, 3H), 1.09 (br d, J=9.9 Hz, 3H); LCMS (ESI) m/z: 666.5 (M+1).

Embodiment 20

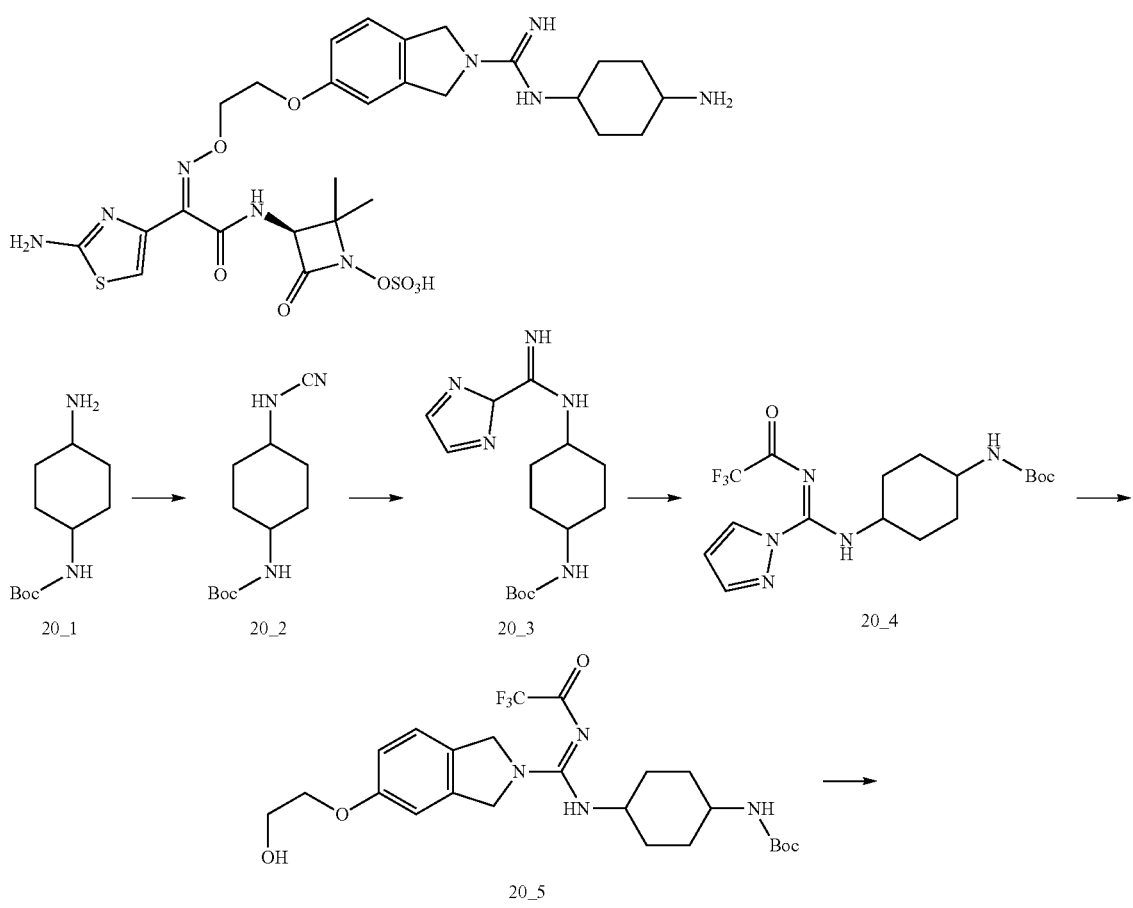

-continued
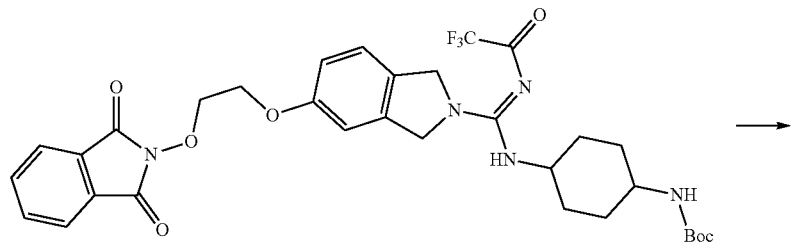
20_6
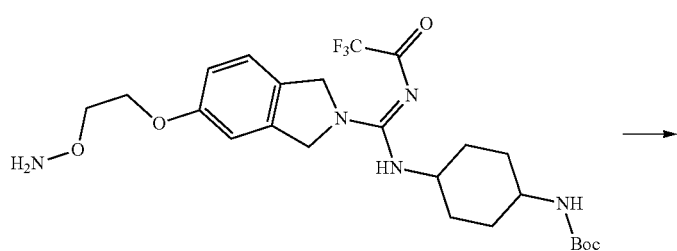
20_7
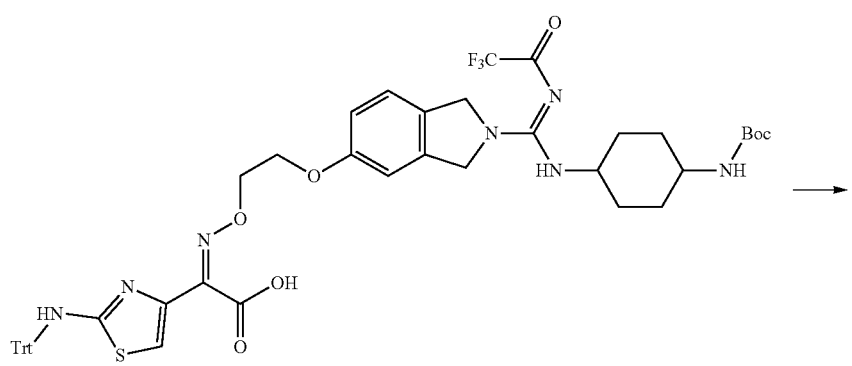
20_8
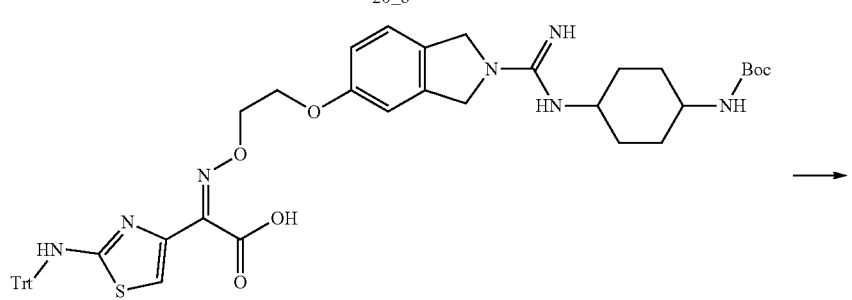
20_9
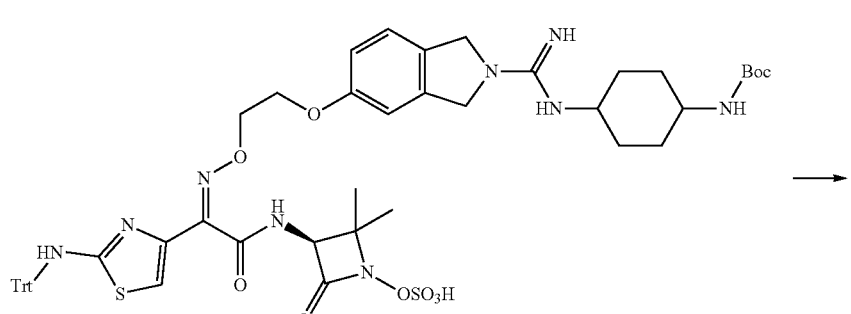
20_10

-continued

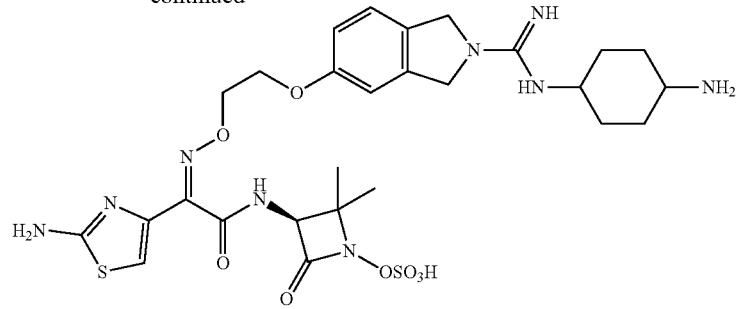

20

Step 1: BrCN (2.97 g, 28.00 mmol, 2.06 mL, 1.2 eq) and AcONa (3.83 g, 46.66 mmol, 2 eq) were added to a solution of compound 20_1 (5 g, 23.33 mmol, 1 eq) in MeOH (50 mL). The reaction mixture was stirred at room temperature (20-25° C.) for 2 hours and water (200 mL) was added thereto, the obtained mixture was extracted with EtOAc (100 mL*2), the organic phases were combined and dried over anhydrous sodium sulfate and filtered, then concentrated under reduced pressure, the residue was purified by column chromatography (SiO$_2$, petroleum ether/ethyl acetate=5/1 to 1/1) to give compound 20_2.

Step 2: pyrazole hydrochloride (1.83 g, 17.55 mmol, 1 eq) was added to a solution of compound 20_2 (4.2 g, 17.55 mmol, 1 eq) in THF (100 mL). The mixture was stirred at 70° C. for 12 hours and a white solid formed. The reaction mixture was filtered to give compound 20_3.

Step 3: triethylamine (1.41 g, 13.96 mmol, 1.94 mL, 1.5 eq) was added to a solution of compound 20_3 (3.2 g, 9.31 mmol, 1 eq) in DCM (30 mL), then trifluoroacetic anhydride (1.76 g, 8.38 mmol, 1.17 mL, 0.9 eq) was added thereto. The reaction mixture was stirred at room temperature (20-25° C.) for 2 hours and then poured into water (50 mL), the obtained mixture was extracted with DCM (30 mL), the combined organic phase was washed with saturated sodium chloride, and dried over anhydrous sodium sulfate, the mixture was concentrated under reduced pressure to remove the solvent and to give compound 20_4.

Step 4: triethylamine (3.68 g, 36.38 mmol, 5.06 mL, 5 eq) was added to a solution of the trifluoroacetate of compound 13_7 (3.2 g, 10.91 mmol, 1.5 eq) and compound 20_4 (2.93 g, 7.28 mmol, 1 equivalent) in DMF (20 mL). The reaction mixture was stirred at 45° C. for 12 hours and was poured into water (200 mL), after vacuum filtration, the filter cake was collected, which was purified by column chromatography (SiO$_2$, petroleum ether/ethyl acetate=4/1 to 0/1) to give compound 20_5.

Step 5: DIAD (539.50 mg, 2.67 mmol, 518.75 μL, 2 eq) was added dropwise to a solution of compound 20_5 (0.780 g, 1.33 mmol, 1 eq), 2-hydroxyisoindoline-1,3-dione (217.62 mg, 1.33 mmol, 1 eq) and PPh$_3$ (419.87 mg, 1.60 mmol, 1.2 eq) in THF (5 mL) at 0° C. The mixture was stirred at room temperature (20-30° C.) for 12 hours and concentrated under reduced pressure, the residue was diluted with EtOAc (20 mL) and washed with saturated sodium chloride, dried over anhydrous sodium sulfate and filtered, then the filtrate was concentrated under reduced pressure, the residue was purified by column chromatography (SiO$_2$, petroleum ether/ethyl acetate=10/1 to 0/1) to give compound 20_6.

Step 6: NH$_2$NH$_2$.H$_2$O (59.31 mg, 1.01 mmol, 57.58 μL, 85% purity, 1 eq) was added to a mixed solution of compound 20_6 (730 mg, 1.01 mmol, 1 eq) in MeOH (5 mL) and DCM (5 mL). The mixture was stirred at room temperature (20-30° C.) for 1 hour and concentrated under reduced pressure, the solid obtained was dissolved in DCM (10 mL) and filtered. The organic phase was washed with saturated sodium chloride, dried over anhydrous sodium sulfate and filtered, then concentrated under reduced pressure to give compound 20_7.

Step 7: 20_7 (600 mg, 1.13 mmol, 1.13 eq) was added to a mixed solution of compound intermediate A2 (414 mg, 998.85 μmol, 1 eq) in DCM (5 mL) and MeOH (5 mL). The mixture was stirred at room temperature (20-30° C.) for 2 hours and concentrated under reduced pressure, the residue was washed with ethyl acetate/petroleum ether (20 mL, 1/1) under stirring to give compound 20_8.

Step 8: potassium carbonate (272.01 mg, 1.97 mmol, 2.5 eq) was added to a solution of compound 20_8 (729 mg, 787.25 mol, 1 eq) in MeOH (10 mL). The reaction mixture was stirred at 45° C. for 12 hours and concentrated under reduced pressure. The residue was dissolved in DCM (20 mL) and washed with water and dilute hydrochloric acid (10 mL, 1M), dried over anhydrous sodium sulfate and filtered, then concentrated under reduced pressure. The residue was washed with ethyl acetate/petroleum ether (20 mL, 1/1) to give compound 20_9.

Step 9: HOBt (227.92 mg, 1.69 mmol, 2 equivalent) and DIC (212.86 mg, 1.69 mmol, 261.18 μL, 2 eq) were added to a solution of compound 20_9 (700 mg, 843.37 μmol, 1 eq) in DMF (10 mL), the mixture was stirred at room temperature (20-30° C.) for 30 min, then intermediate A1 (248.20 mg, 1.18 mmol, 1.4 eq) and NaHCO$_3$ (283.39 mg, 3.37 mmol, 131.20 μL, 4 eq) were added to the reaction mixture and stirred at room temperature (20-30° C.) for 12 hours. Then, water (10 mL) was added to the reaction mixture and a while solid precipitated, the mixture was filtered and the filter cake was collected, which was purified by preparative TLC (SiO$_2$, DCM/MeOH=10/1) to give compound 20_10.

Step 10: TFA (1 mL) was added to a solution of compound 20_10 (230 mg, 225.01 μmol, 1 eq) in DCM (2 mL) at 0° C. The mixture was stirred at 0° C. for 30 mins then ethyl acetate (10 mL) was added thereto, a white solid precipitated. The solid was filtered out and purified by preparative HPLC (equipment: ASCWH-GX-C, column: Boston Green ODS 150*30*5 μm, condition: water (0.225% formic acid)-acetonitrile) to give compound 20. $^1$H NMR (400 MHz, DMSO-d$_6$+D$_2$O) δ (ppm): 8.33 (s, 1H), 7.23-7.01 (m, 1H), 6.98-6.64 (m, 3H), 4.49-4.08 (m, 8H), 3.37 (br s, 1H), 3.14 (br s, 1H), 2.04 (br s, 4H), 1.54-1.35 (m, 7H), 1.22-1.01 (m, 3H). LCMS (ESI) m/z: 680.3 (M+1).

Embodiment 21
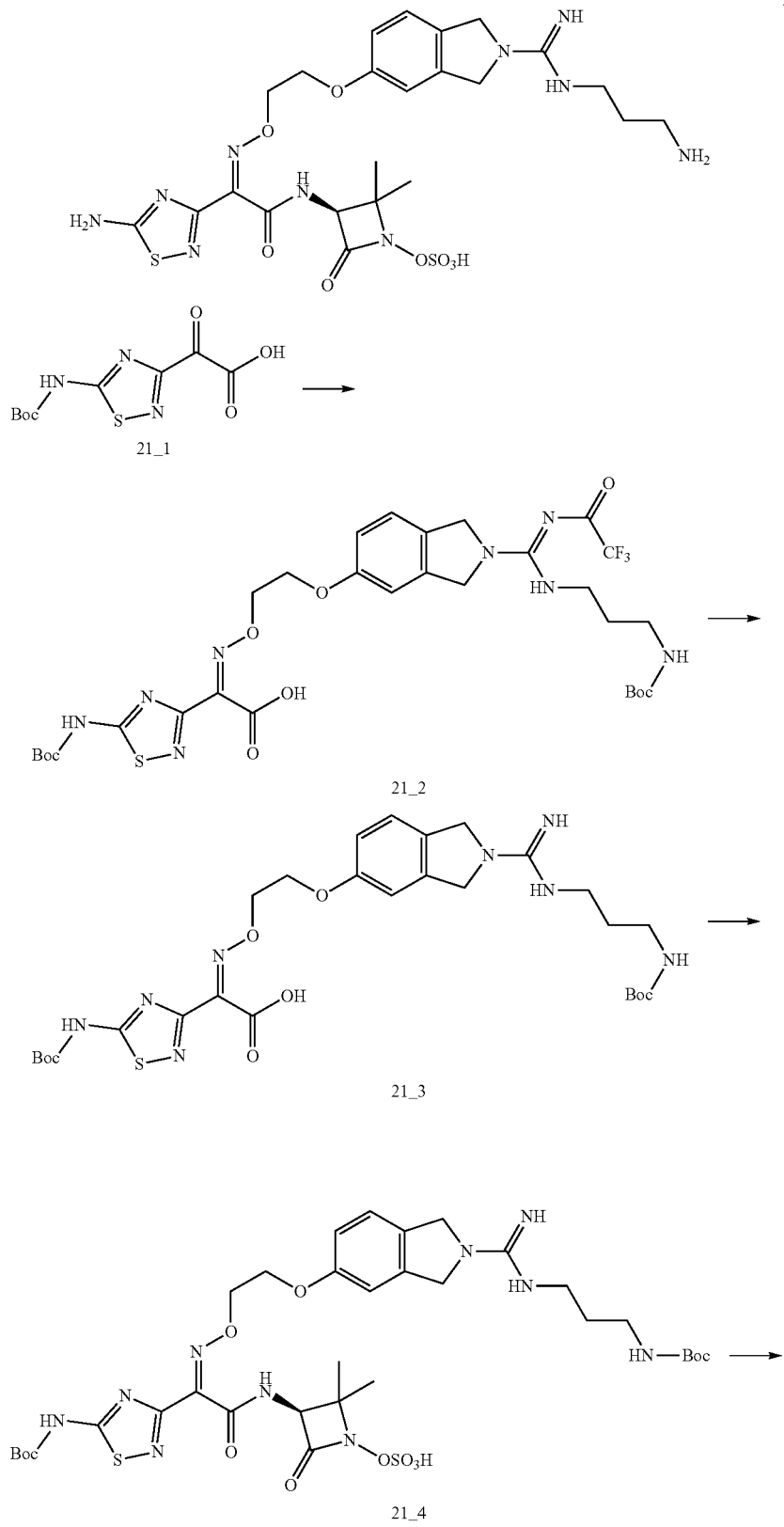

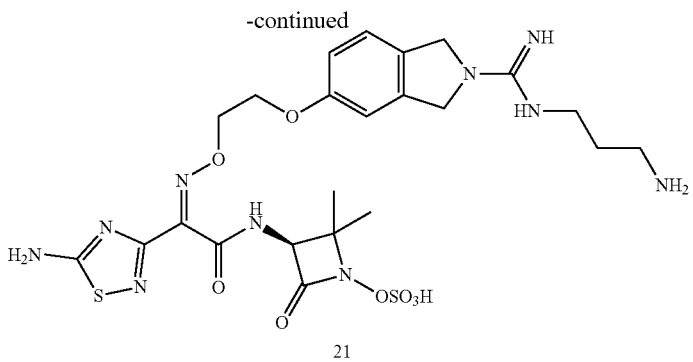

21

Step 1: compound 13_10 (240 mg, 405.93 μmol, 9.62 e-1 eq) was added to a mixed solution of compound 21_1 (150 mg, 422.12 μmol, 1 eq) (see WO2017106064) in MeOH (5 mL) and DCM (5 mL), the mixture was stirred at 20° C. for 0.5 hour. The reaction mixture was concentrated under reduced pressure to give compound 21_2.

Step 2: compound 21_2 (350 mg, 373.76 μmol, 1 eq) and potassium carbonate (154.97 mg, 1.12 mmol, 3 eq) were added to MeOH (5 mL), the reaction flask was ventilated with nitrogen for 3 times, then the mixture was stirred at 45° C. for 24 hours under nitrogen atmosphere, the reaction mixture was concentrated under reduced pressure to remove MeOH, the residue was diluted with DCM (30 mL), the pH value was adjusted to less than 6 by using dilute hydrochloric acid (0.5 M), then extracted with DCM/MeOH (20 mL, 10/1), the organic phase was dried over anhydrous sodium sulfate, filtered and concentrated under reduced pressure, the residue was washed with ethyl acetate (5 mL) under stirring, the solid was filtered out and collected to give compound 21_3.

Step 3: HOBt (50.01 mg, 370.09 μmol, 2 eq) and DIC (46.71 mg, 370.09 μmol, 57.31 μL, 2 eq) were added to a solution of compound 21_3 (150 mg, 185.05 μmol, 1 eq) in DMF (2 mL), the mixture was stirred at 25° C. for 1 hour, then intermediate A1 (50.57 mg, 240.56 μmol, 1.3 eq) and NaHCO$_3$ (62.18 mg, 740.19 μmol, 28.79 μL, 4 eq) were added thereto, the mixture was stirred at 25° C. for 11 h and the reaction was quenched by adding water (20 mL), then extracted with ethyl acetate (15 mL*2). The combined organic phase was washed with saturated sodium chloride (10 mL), dried over anhydrous sodium sulfate, filtered and concentrated under reduced pressure, the obtained residue was purified by preparative TLC (SiO$_2$, DCM/MeOH=10/1) to give compound 21_4.

Step 4: TFA (542.37 mg, 4.76 mmol, 352.19 μL, 52.61 eq) was added to a solution of compound 21_4 (80 mg, 90.42 μmol, 1 eq) in DCM (1 mL) at 0° C. The mixture was stirred at 20° C. for 1 hour and concentrated under reduced pressure, the obtained residue was purified by preparative HPLC (FA, column: Boston Green ODS 150*30 5 μm; mobile phase: [water (0.225% formic acid)-ACN]; acetonitrile %: 2%-32%, 10 min) to give compound 21. $^1$H NMR (400 MHz, DMSO-d$_6$+D$_2$O) δ (ppm): 8.45-8.33 (m, 1H), 7.29 (br d, J=8.9 Hz, 1H), 7.00-6.90 (m, 2H), 4.68 (br d, J=18.3 Hz, 4H), 4.56 (s, 1H), 4.47 (br s, 2H), 4.21 (br s, 2H), 3.29 (br s, 2H), 2.83 (br s, 2H), 1.77 (br s, 2H), 1.37 (s, 3H), 1.18 (s, 3H); LCMS (ESI) m/z: 641.1 (M+1).

Embodiment 22

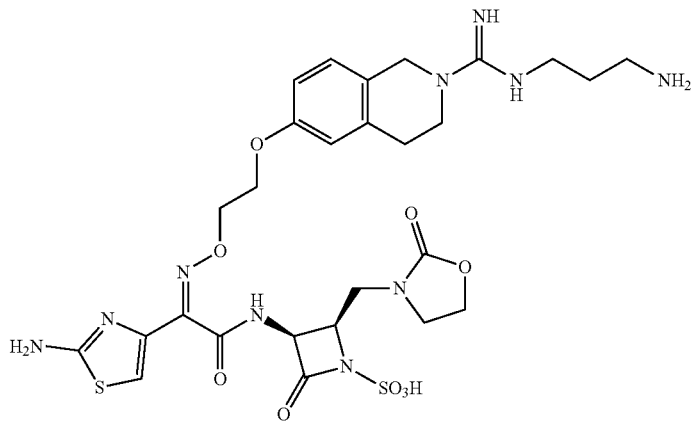

22

-continued

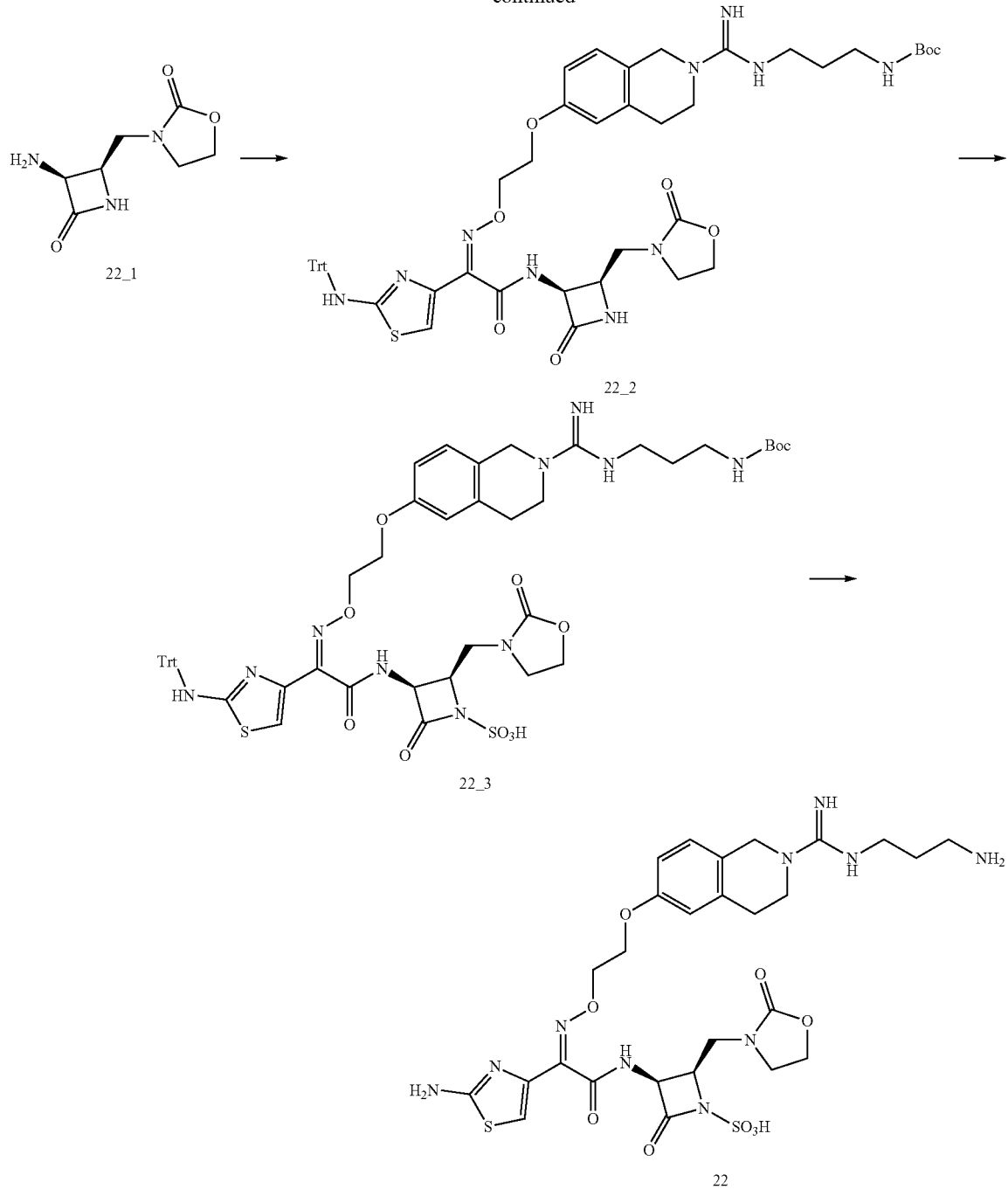

Step 1: DIC (62.79 mg, 497.53 μmol, 77.04 μL, 2 eq) and HOBt (67.23 mg, 497.53 μmol, 2 eq) were added to a solution of compound 16_9 (200 mg, 248.77 μmol, 1 eq) in DMF (2 mL). The mixture was stirred at 25° C. for 1 hour, then compound 22_1 (69.10 mg, 373.15 μmol, 1.5 eq) (see US2015266867A1) and NaHCO$_3$ (83.59 mg, 995.07 μmol, 38.70 μL, 4 eq) were added thereto, the mixture was stirred at 25° C. for 11 hours, then the reaction was quenched by adding water (10 mL), after diluted with ethyl acetate (10 mL), some dissolvable oil formed in the mixture, which was filtered and the oily product was extracted with DCM (20 mL). The combined organic phase was washed with saturated sodium chloride (10 mL), dried over anhydrous sodium sulfate, filtered and concentrated under reduced pressure to give compound 22_2.

Step 2: N,N-dimethylformamide sulfur trioxide (31.54 mg, 205.95 μmol, 2 eq) was added to a solution of compound 22_2 (100 mg, 102.97 μmol, 1 eq) in DMF (1 mL) at 0° C., the mixture was stirred at 0° C. for 1 hour and N,N-dimethylformamide sulfur trioxide (31.54 mg, 205.95 μmol, 2 eq) was added for another time, then the mixture was stirred at 0° C. for another 1 hour. The reaction was quenched at 0° C. by adding water (10 mL), then extracted with DCM (10 mL*2). The combined organic phase was washed with saturated sodium chloride, dried over anhydrous sodium sulfate, filtered and concentrated under reduced pressure, to give compound 22_3.

Step 3: TFA (770.00 mg, 6.75 mmol, 0.5 mL, 70.99 eq) was added to a solution of compound 22_3 (100 mg, 95.13 mmol, 1 eq) in DCM (0.5 mL). The mixture was stirred at 0° C. for 1 hour, then ethyl acetate/petroleum ether (5 mL, 4/1) was added and a solid precipitated, the mixture was filtered and the filter cake was collected, which was purified by preparative HPLC (TFA, column: Phenomenex Synergi C18 150*25*10 μm; mobile phase: [water (0.1% TFA)-ACN]; acetonitrile %: 1%-30%, 6 min) to give compound 22. $^{1}$H NMR (400 MHz, DMSO-d$_{6}$+D$_{2}$O) δ (ppm): 7.08 (d, J=9.2 Hz, 1H), 6.83-6.75 (m, 3H), 5.18 (d, J=5.8 Hz, 1H), 4.45 (s, 2H), 4.39 (br s, 2H), 4.18 (br s, 2H), 4.15-4.09 (m, 1H), 4.06-3.94 (m, 2H), 3.59-3.49 (m, 3H), 3.48-3.34 (m, 2H), 3.30-3.16 (m, 3H), 2.89-2.78 (m, 4H), 1.83-1.72 (m, 2H); LCMS (ESI) m/z: 709.1 (M+1).

Embodiment 23

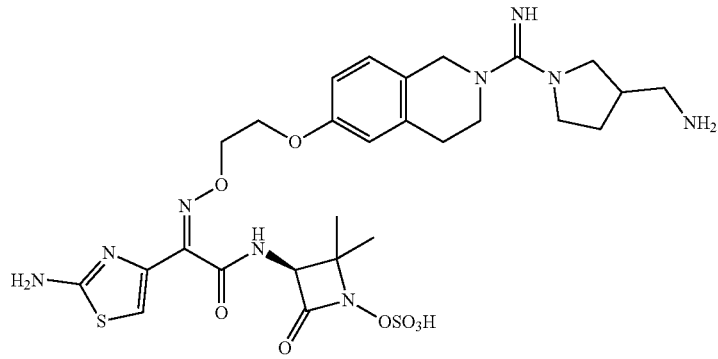

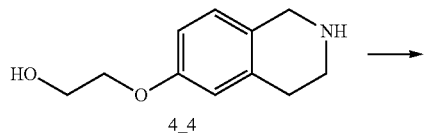

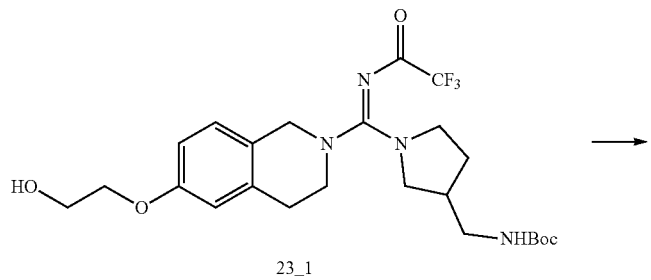

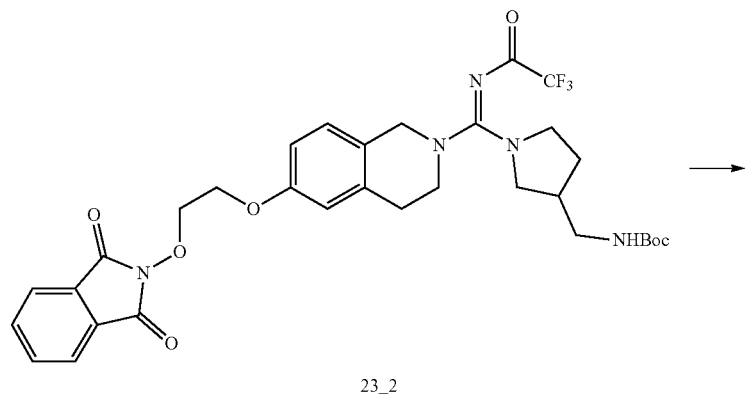

-continued
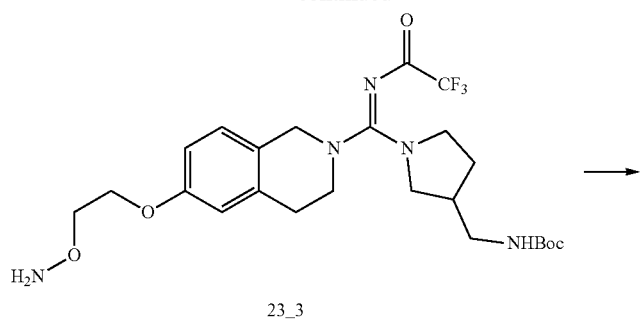
23_3
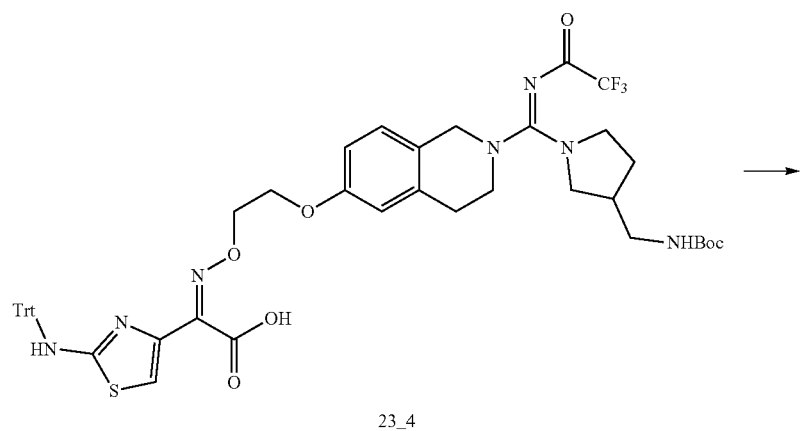
23_4
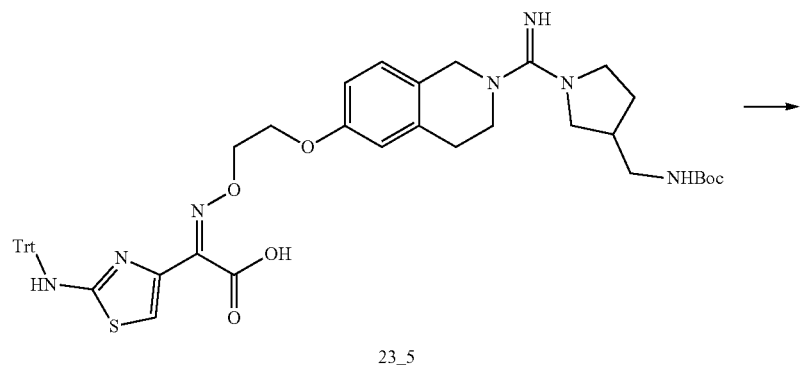
23_5
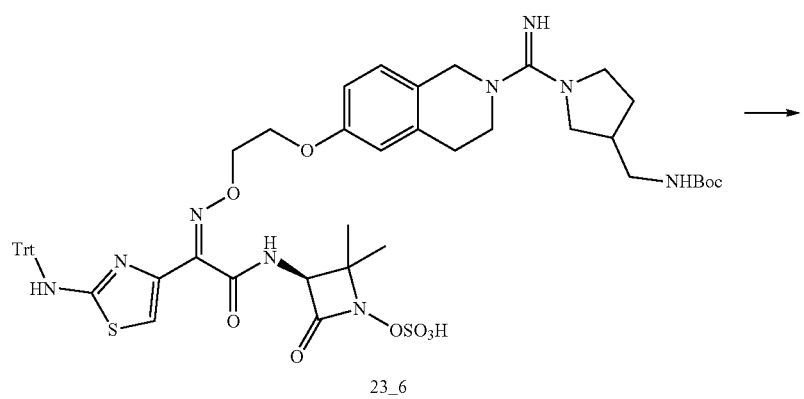
23_6

-continued

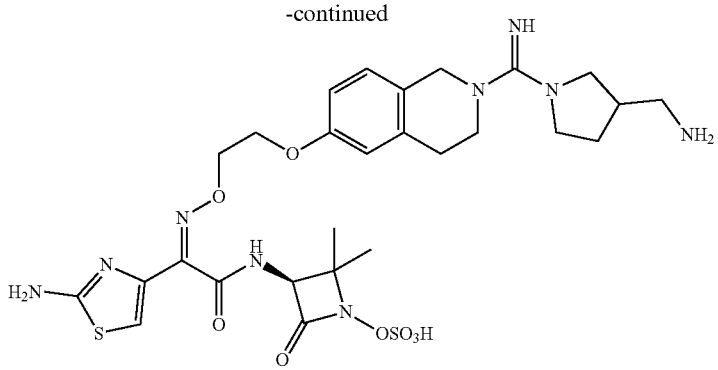

23

Step 1: intermediate A7 (2.7 g, 6.93 mmol, 1 eq), compound 4_4 (1.34 g, 6.93 mmol, 1 eq) and triethylamine (701.68 mg, 6.93 mmol, 965.17 µL, 1 eq) were dissolved in DMF (20 mL), the mixture was ventilated with nitrogen for 3 times and stirred at 45° C. for 12 hours, then concentrated under reduced pressure to remove DMF, the residue was diluted with water (20 mL) and extracted with ethyl acetate (20 mL*2). The combined organic phase was washed with saturated sodium chloride (10 mL), dried over anhydrous sodium sulfate, filtered and concentrated under reduced pressure, the residue was purified by column chromatography ($SiO_2$, petroleum ether/ethyl acetate=2/1 to 0/1) to give compound 23_1.

Step 2: DIAD (896.03 mg, 4.43 mmol, 861.56 µL, 1.2 eq) was added to a solution of compound 231 (1.9 g, 3.69 mmol, 1 eq), 2-hydroxyisoindoline-1,3-dione (722.86 mg, 4.43 mmol, 1.2 eq) and $PPh_3$ (1.16 g, 4.43 mmol, 1.2 eq) in THF (20 mL). The mixture was stirred at 20° C. for 1 hour and concentrated under reduced pressure to remove THF, the residue was purified by column chromatography ($SiO_2$, petroleum ether/ethyl acetate=1/1 to 0/1) to give compound 23_2.

Step 3: $NH_2NH_2 \cdot H_2O$ (211.27 mg, 3.59 mmol, 205.11 µL, 85% purity, 2 eq) was added to a solution of compound 23_2 (2.2 g, 1.79 mmol, 1 eq) in EtOH (22 mL). The mixture was stirred at 25° C. for 0.5 hour and concentrated under reduced pressure to remove the solvent, the residue was diluted with DCM (20 mL) and filtered. The organic phase was washed with saturated sodium chloride (10 mL), dried over anhydrous sodium sulfate, filtered and concentrated under reduced pressure to give compound 23_3.

Step 4: compound 23_3 (1.4 g, 1.89 mmol, 1 eq) and intermediate A2 (782.69 mg, 1.89 mmol, 1 eq) were added to a mixed solution of DCM (10 mL) and MeOH (10 mL), then the mixture was stirred at 25° C. for 1 hour under nitrogen atmosphere, the reaction mixture was concentrated under reduced pressure to remove the solvent to give compound 23_4.

Step 5: compound 23_4 (1.8 g, 1.94 mmol, 1 eq) was dissolved in MeOH (20 mL), then potassium carbonate (1.34 g, 9.72 mmol, 5 eq) was added thereto and ventilated with nitrogen for 3 times, the mixture was stirred at 45° C. for 12 hours. The reaction mixture was concentrated under reduced pressure to remove MeOH, the residue was diluted with water (50 mL) and DCM (100 mL), and the pH value was adjusted to 5 with dilute hydrochloric acid (1 M), the organic phase was separated and washed with saturated sodium chloride solution (50 mL), dried over anhydrous sodium sulfate, then filtered and concentrated under reduced pressure, the residue was washed with ethyl acetate (20 mL) under stirring, the mixture was then filtered and the filter cake was collected and washed with ethyl acetate/dichloromethane (20 mL, 1/1) under stirring, then filtered for another time to give compound 23_5.

Step 6: DIC (76.02 mg, 602.41 µmol, 93.28 µL, 2 eq) and HOBt (81.40 mg, 602.41 µmol, 2 eq) were added to a solution of compound 23_5 (250 mg, 301.20 µmol, 1 eq) in DMF (3 mL). The mixture was stirred at 25° C. for 1 hour, then intermediate A1 (82.31 mg, 391.56 µmol, 1.3 eq) and $NaHCO_3$ (101.21 mg, 1.20 mmol, 46.86 µL, 4 eq) were added thereto. The mixture was stirred at 25° C. for 11 hours, then concentrated under reduced pressure to remove DMF, the residue was diluted with DCM (5 mL), the organic phase washed with saturated sodium chloride, dried over anhydrous sodium sulfate, filtered and concentrated under reduced pressure, the residue was purified by preparative TLC ($SiO_2$, DCM/MeOH=8/1) to give compound 23_6.

Step 7: TFA (991.61 mg, 8.70 mmol, 643.90 µL, 86.29 eq) and water (0.05 mL) were added to a solution of compound 23_6 (160 mg, 100.79 µmol, 1 eq) in DCM (1 mL), the mixture was stirred at 0° C. for 1 hour, then the reaction mixture diluted with petroleum ether/ethyl acetate (10 mL, 1/4), and filtered to give a solid, which was purified by preparative HPLC (TFA, column: Boston, pH-lex 150*25 10 µm; mobile phase: [water (0.1% TFA)-ACN]; acetonitrile %: 10%-34%, 8 min) to give compound 23. $^1H$ NMR (400 MHz, $D_2O$) δ (ppm): 7.06 (br d, J=8.3 Hz, 1H), 7.02 (d, J=1.7 Hz, 1H), 6.78 (br s, 2H), 4.54 (br s, 2H), 4.42 (br s, 2H), 4.30 (br s, 2H), 3.71-3.42 (m, 5H), 3.28 (t, J=9.2 Hz, 1H), 3.07 (dq, J=7.3, 12.9 Hz, 2H), 2.98-2.77 (m, 2H), 2.68-2.52 (m, 1H), 2.19 (br dd, J=5.8, 11.7 Hz, 1H), 1.82-1.68 (m, 1H), 1.39 (br d, J=3.9 Hz, 3H), 1.04 (br d, J=9.8 Hz, 3H); LCMS (ESI) m/z: 680.3 (M+1).

Embodiment 24
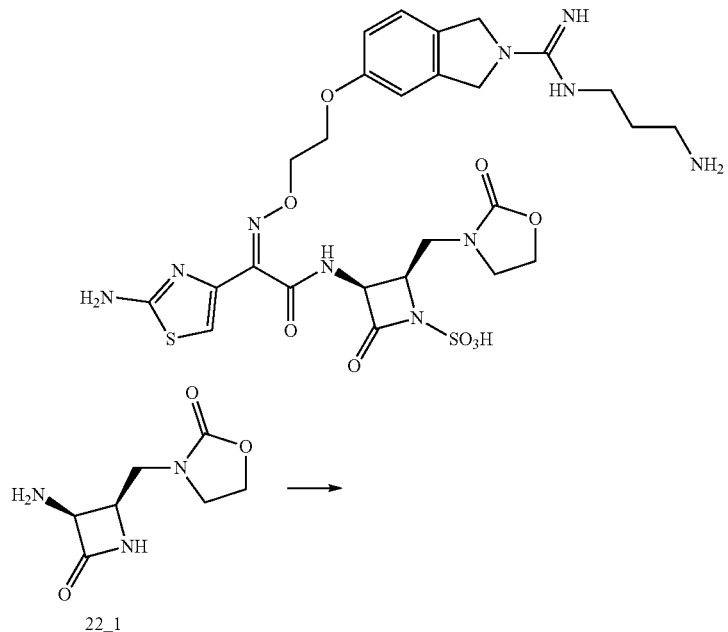
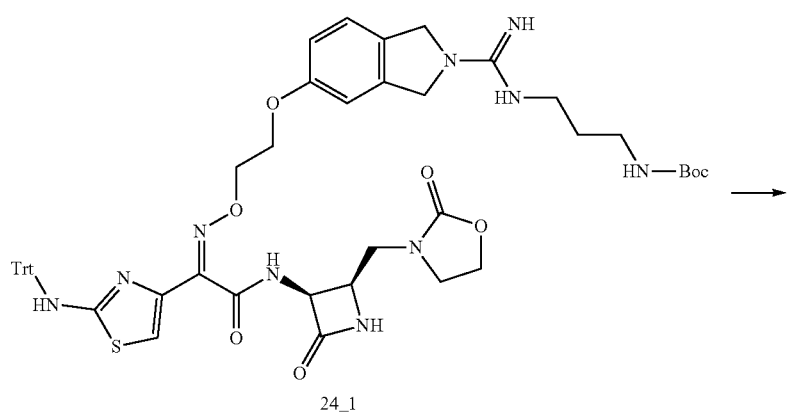
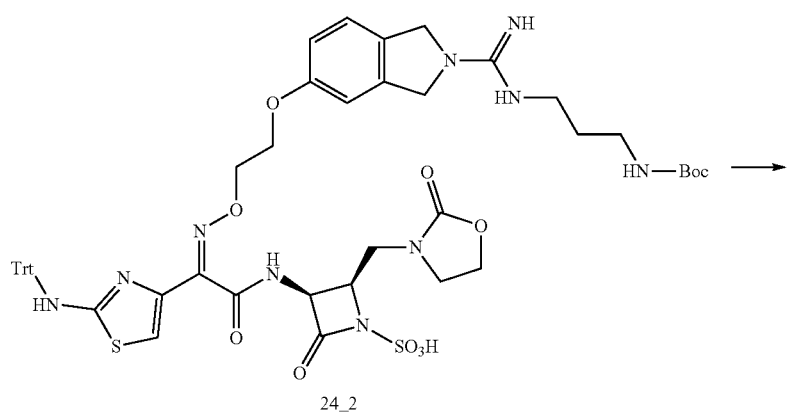

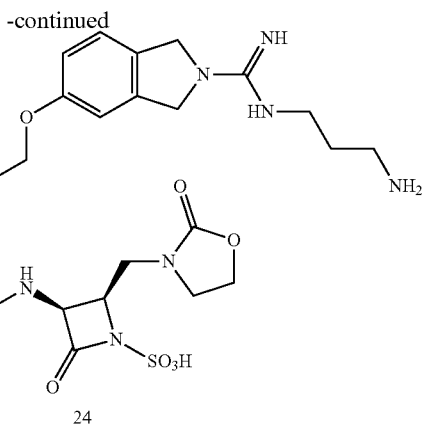

24

Step 1: DIC (63.90 mg, 506.37 μmol, 78.41 μl, 2 eq) and HOBt (68.42 mg, 506.37 μmol, 2 eq) were added to a solution of compound 13_12 (200 mg, 253.18 μmol, 1 eq) in DMF (2 mL). The mixture was stirred at 20° C. for 1 hour, then compound 22_1 (70.33 mg, 379.78 μmol, 1.5 eq) and NaHCO$_3$ (85.08 mg, 1.01 mmol, 39.39 μL, 4 eq) were added thereto. The mixture was stirred at 20° C. for 11 hours, then concentrated under reduced pressure to remove DMF, the residue was diluted with water (5 mL) and ethyl acetate (5 mL), and stirred for 10 min, then the mixture was filtered to give a filter cake, which was then dissolved in DCM (10 mL), the organic phase was dried over anhydrous sodium sulfate, then filtered and concentrated under reduced pressure to give compound 24_1.

Step 2: N,N-dimethylformamide sulfur trioxide (57.61 mg, 376.13 μmol, 2 eq) was added to a solution of compound 24_1 (180 mg, 188.07 μmol, 1 eq) in DMF (2 mL) at 0° C. The mixture was stirred at 0° C. for 1 hour, N,N-dimethylformamide sulfur trioxide (86.41 mg, 564.20 μmol, 3 eq) was added for another time, then stirred at 0° C. for 1 hour. The reaction was quenched by adding water (10 mL) at 0° C., then extracted with DCM (10 mL*2), the combined organic phase was dried over anhydrous sodium sulfate, filtered and concentrated under reduced pressure to give compound 24_2.

Step 3: TFA (1 mL) and water (0.05 mL) was added to a solution of compound 24_2 (150 mg, 83.48 mol, 1 eq) in DCM (1 mL). The mixture was stirred at 0° C. for 1 hour and concentrated under reduced pressure to remove DCM, the residue was diluted with water (2 mL) and ethyl acetate (5 mL), the aqueous phase was separated and purified by preparative HPLC (TFA, column: Boston, pH-lex 150*25× 10 μm; mobile phase: [water (0.1% TFA)-ACN]); acetonitrile %: 5%-29%, 8 min) to give compound 24. $^1$H NMR (400 MHz, D$_2$O) δ (ppm): 7.28 (d, J=8.7 Hz, 1H), 7.04 (br s, 1H), 6.96-6.86 (m, 2H), 5.27 (d, J=5.9 Hz, 1H), 4.65-4.50 (m, 4H), 4.46-4.39 (m, 1H), 4.28 (br d, J=3.8 Hz, 2H), 4.06-3.95 (m, 1H), 3.90-3.80 (m, 1H), 3.50-3.30 (m, 4H), 3.12-2.98 (m, 4H), 2.01-1.90 (m, 2H). LCMS (ESI) m/z: 695.2 (M+1).

Embodiment 25

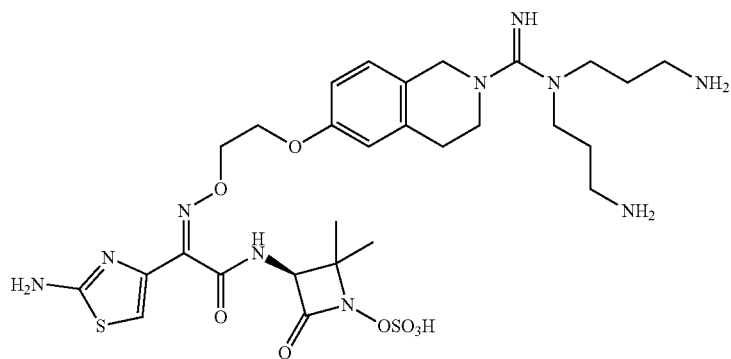

25

-continued
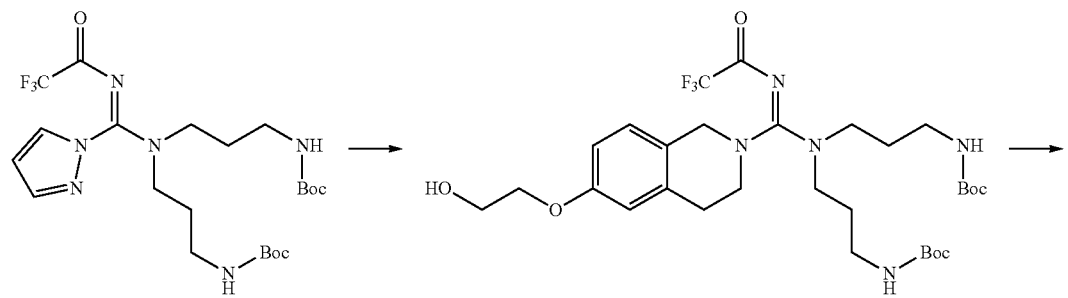
A6
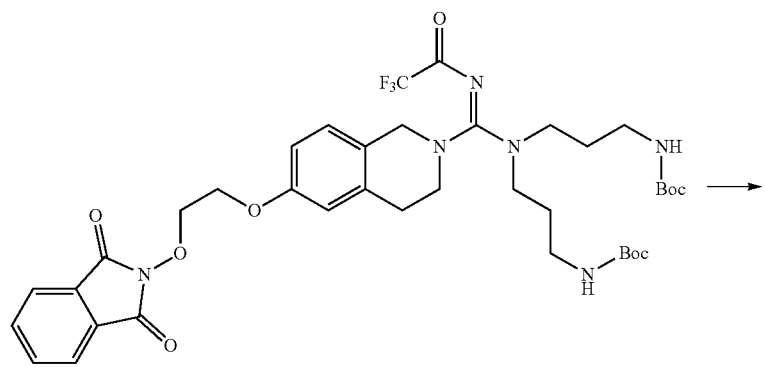
25_1
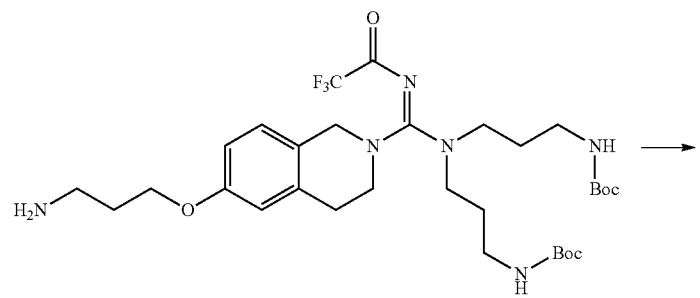
25_2
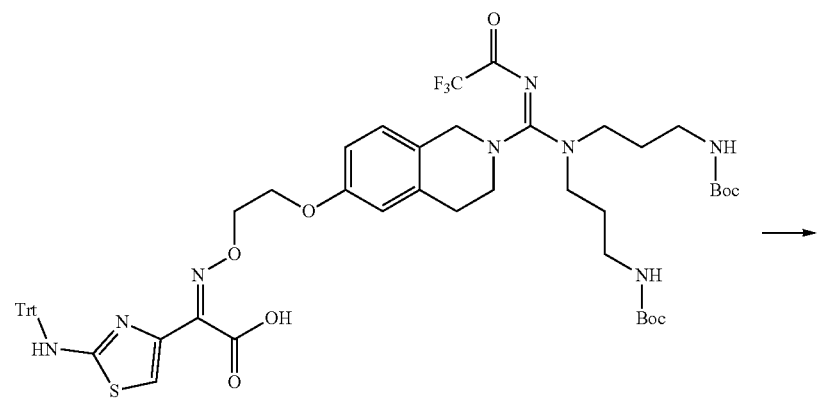
25_3
25_4

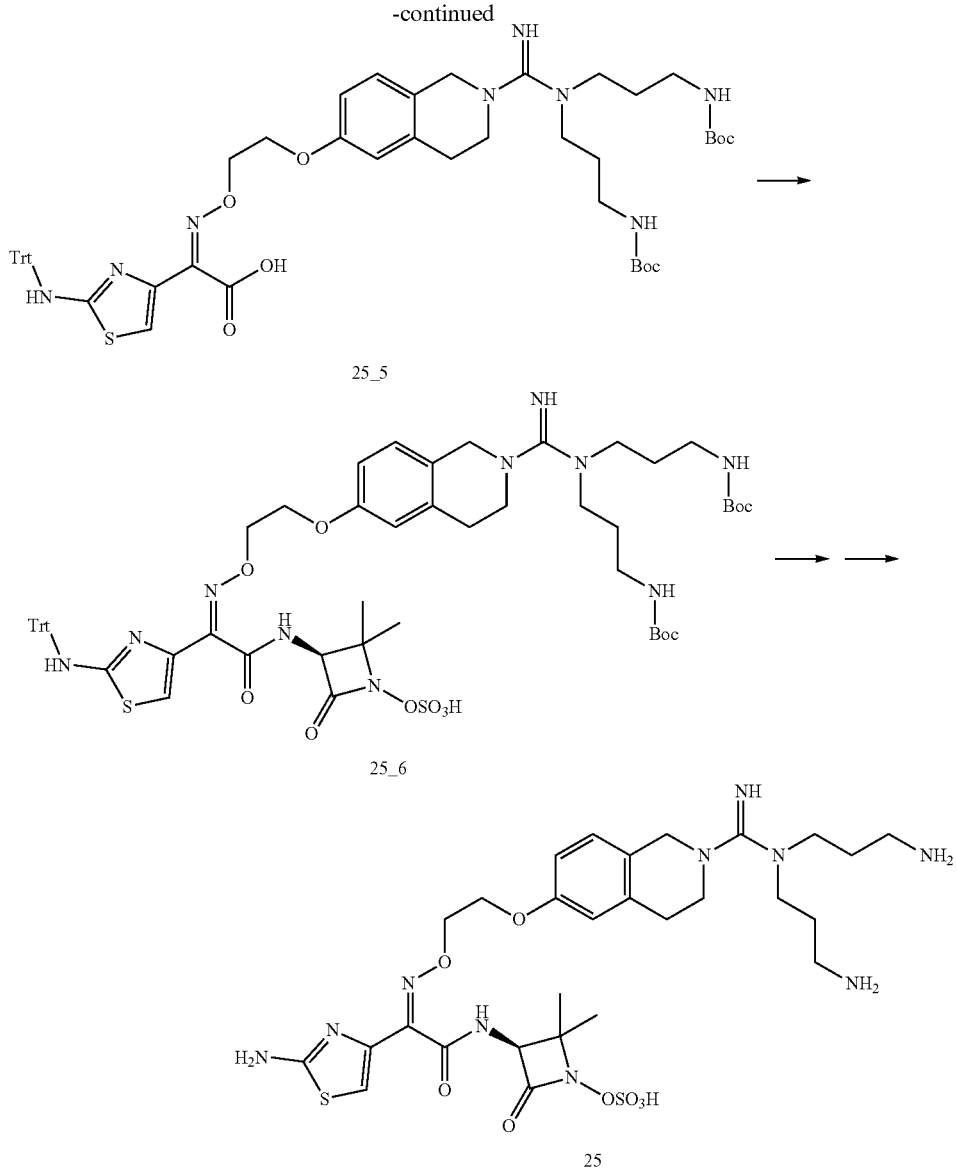

Step 1: compound 4_4 (705.34 mg, 3.65 mmol, 1 eq), intermediate A6 (1.9 g, 3.65 mmol, 1 eq) and TEA (369.35 mg, 3.65 mmol, 1 eq) were added to DMF (20 mL), then the mixture was stirred at 40° C. for 12 hours. The reaction mixture was concentrated under reduced pressure to remove DMF, the residue was diluted with water (20 mL), extracted with ethyl acetate (30 mL), and the organic phases were combined and washed with saturated sodium chloride (10 mL), dried over anhydrous sodium sulfate, filtered and concentrated under reduced pressure to give compound 25_1.

Step 2: DIAD (676.42 mg, 3.35 mmol, 650.40 µL, 1.2 eq) was added to a solution of compound 251 (1.8 g, 2.79 mmol, 1 eq), 2-hydroxyisoindoline-1,3-dione (545.70 mg, 3.35 mmol, 1.2 eq) and PPh$_3$ (877.40 mg, 3.35 mmol, 1.2 eq) in THF (20 mL) at 0° C. The mixture was stirred at 25° C. for 1 hour and concentrated under reduced pressure to remove THF, the obtained residue was purified by column chromatography (SiO$_2$, petroleum ether/ethyl acetate=1/1 to 0/1) to give compound 25_2.

Step 3: NH$_2$NH$_2$.H$_2$O (139.45 mg, 2.37 mmol, 135.39 µL, purity: 85%, 2 eq) was added to a solution of compound 25_2 (1.2 g, 1.18 mmol, 1 eq) in EtOH (12 mL). The mixture was stirred at 25° C. for 0.5 hour and filtered, then concentrated to remove the solvent, the residue was diluted with DCM (20 mL). The organic phase was washed with saturated saline (10 mL), then dried over anhydrous sodium sulfate, filtered and concentrated under reduced pressure to give compound 253.

Step 4: compound 25_3 (900 mg, 1.36 mmol, 1 eq) and intermediate A2 (564.58 mg, 1.36 mmol, 1 eq) were dissolved in DCM (5 mL) and MeOH (5 mL), then the mixture was stirred at 25° C. for 1 hour, the reaction mixture was concentrated under reduced pressure to give compound 25_4.

Step 5: compound 25_4 (1.4 g, 907.92 µmol, 1 eq) and potassium carbonate (627.40 mg, 4.54 mmol, 5 eq) were added to MeOH (14 mL), then the mixture was ventilated with nitrogen for 3 times, the mixture was stirred at 40° C. for 12 hours. The reaction mixture was concentrated under reduced pressure to remove MeOH, the residue was diluted with DCM (200 mL) and water (50 mL), and the pH was adjusted to less than 5 by using dilute hydrochloric acid (1 M), the organic phase was separated and washed with saturated sodium chloride (50 mL), dried over anhydrous sodium sulfate, filtered and concentrated under reduced pressure, the residue was washed with ethyl acetate (20 mL) under stirring, the mixture was filtered and the filter cake was collected to give compound 25_5.

Step 6: DIC (46.90 mg, 371.67 μmol, 57.55 μL, 2 eq) and HOBt (50.22 mg, 371.67 μmol, 2 eq) were added to a solution of compound 25_5 (200 mg, 185.83 mol, 1 eq) in DMF (2 mL), the mixture was stirred at 25° C. for 1 hour, then intermediate A1 (58.60 mg, 278.75 μmol, 1.5 eq) and NaHCO₃ (62.45 mg, 743.34 μmol, 28.91 μL, 4 eq) were added thereto. The mixture was stirred at 25° C. for 11 hours and concentrated under reduced pressure to remove DMF, the residue was diluted with water (5 mL), then extracted with DCM (10 mL), the organic phase was dried over anhydrous sodium sulfate, filtered and concentrated under reduced pressure, the residue was purified by preparative TLC (SiO₂, DCM/MeOH=10/1) to give compound 25_6.

Step 7: TFA (770.00 mg, 6.75 mmol, 0.5 mL, 55.63 eq) and water (0.05 mL) were added to a DCM (0.5 mL) solution of compound 25_6 (140 mg, 121.38 μmol, 1 eq). The mixture was stirred at 0° C. for 1 hour, then diluted with ethyl acetate/petroleum ether (5 mL, 4:1), the mixture was filtered to give a yellow solid, which was purified by preparative HPLC (TFA, column: Phenomenex Synergi C18 150*25*10 μm; mobile phase: [water (0.1% TFA)-ACN]; acetonitrile %: 1%-30%, 9 min) to give compound 25. ¹H NMR (400 MHz, D₂O) δ (ppm): 7.11-6.94 (m, 2H), 6.85-6.72 (m, 2H), 4.45 (br s, 5H), 4.27 (br s, 2H), 3.59 (br s, 2H), 3.38 (br s, 4H), 2.90 (br d, J=7.4 Hz, 6H), 1.92 (br s, 4H), 1.39 (s, 3H), 1.02 (s, 3H); LCMS (ESI) m/z: 711.2 (M+1).

Embodiment 26

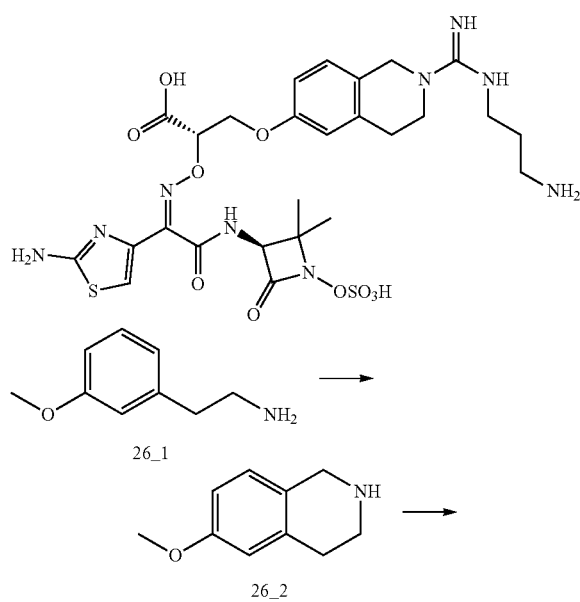

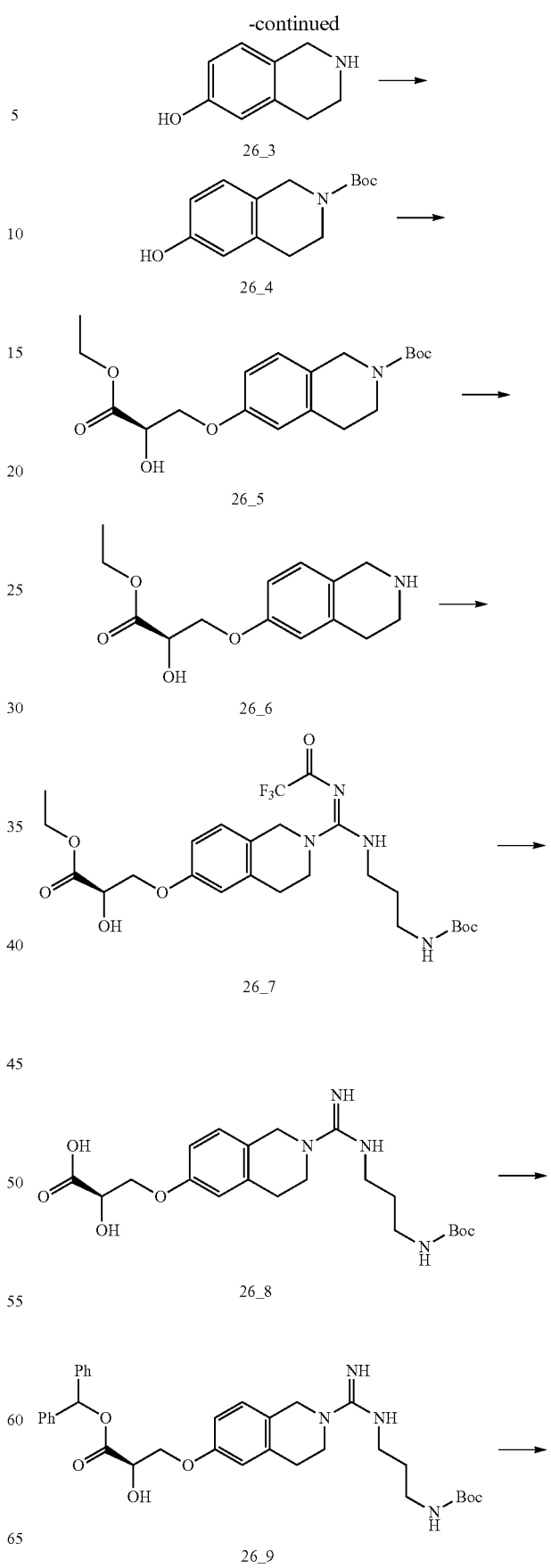

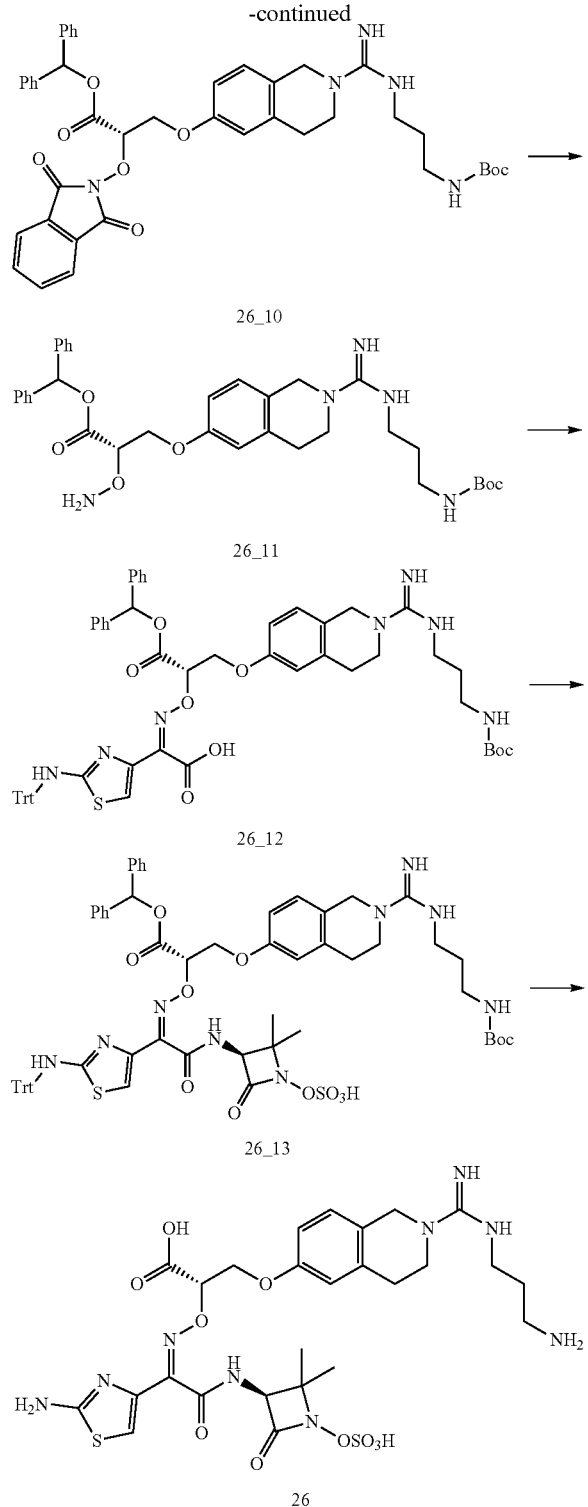

ethyl acetate (450 mL*2). The combined organic phase was dried over anhydrous sodium sulfate, filtered and concentrated to give compound 26_2.

Step 2: compound 26_2 (140 g, 857.76 mmol, 1 eq) was added to a mixed solution of AcOH (300 mL) and HBr/AcOH (300 mL), the mixture was ventilated with nitrogen for 3 times and stirred at 90° C. for 36 hours. The reaction mixture was cooled to room temperature, then diluted with ethyl acetate (400 mL) and stirred for 30 min, the solid was filtered and collected to give a hydrobromide of compound 26_3.

Step 3: TEA (127.97 g, 1.26 mol, 176.03 mL, 3 eq) and Boc$_2$O (101.20 g, 463.71 mmol, 106.53 mL, 1.1 eq) were added to a solution of the hydrobromide of compound 26_3 (97 g, 421.55 mmol, 1 eq) in DCM (1000 mL). The mixture was stirred at 15° C. for 12 hours, then water (500 mL) was added thereto, the organic phase was separated and washed with dilute hydrochloric acid (500 mL, 0.5 M), dried over anhydrous sodium sulfate, then filtered and concentrated under reduced pressure, the residue was washed with petroleum ether/ethyl acetate (330 mL, 10/1) under stirring, then filtered, and a solid after filtering was collected to give compound 26_4. $^1$H NMR (400 MHz, CDCl$_3$) δ=6.89 (d, J=8.3 Hz, 1H), 6.60 (br d, J=8.3 Hz, 1H), 6.55 (d, J=2.4 Hz, 1H), 4.88 (s, 1H), 4.42 (s, 2H), 3.54 (br s, 2H), 2.70 (t, J=5.9 Hz, 2H), 1.42 (s, 9H).

Step 4: ethyl oxirane-2-carboxylate (6.99 g, 60.17 mmol, 3 eq), intermediate A8 (841.11 mg, 1.00 mmol, 0.05 eq) and molecular sieve 4 Å (7 g) were added to a solution of compound 26_4 (5 g, 20.06 mmol, 1 eq) in methyl tert-butyl ether (5 mL). The mixture was stirred at room temperature (20-30° C.) for 12 hours, then pyridinium p-toluenesulfonate (120 mg) was added thereto, the mixture was diluted with methyl tert-butyl ether (5 mL) and filtered with a small section of silica gel, then washed with petroleum ether/ethyl acetate (100 mL, 1/1), the organic phases were combined and concentrated under reduced pressure, the residue was purified by column chromatography (SiO$_2$, petroleum ether/ethyl acetate=4/1) to give compound 26_5.

Step 5: TFA (5 mL) was added to a solution of compound 26_5 (3 g, 8.21 mmol, 1 eq) in DCM (10 mL), the mixture was stirred at room temperature (20-30° C.) for 30 mins and concentrated under reduced pressure to give a trifluoroacetate of compound 26_6.

Step 6: triethylamine (2.56 g, 25.31 mmol, 3.52 mL, 3 eq) and intermediate A5 (3.68 g, 10.12 mmol, 1.2 eq) (20-30° C.) were added to a solution of the trifluoroacetate of compound 26_6 (3.2 g, 8.44 mmol, 1 eq) in DMF (20 mL). The reaction mixture was stirred at 45° C. for 12 hours and cooled to room temperature, then water (10 mL) was added thereto, the mixture was extracted with ethyl acetate (10 mL*2), the organic phases were combined and washed with water, hydrochloric acid (10 mL, 0.5 M) and saturated sodium chloride, dried over anhydrous sodium sulfate and filtered, then concentrated under reduced pressure, the residue was purified by column chromatography (SiO$_2$, petroleum ether/ethyl acetate=10/1 to 1/1) to give compound 26_7.

Step 7: NaOH (149.85 mg, 3.75 mmol, 2.1 eq) was added to a solution of compound 26_7 (1 g, 1.78 mmol, 1 eq) in MeOH (5 mL). The mixture was stirred at room temperature (20-30° C.) for 12 hours, then the mixture was concentrated under reduced pressure to remove the solvent and to give compound 26_8.

Step 8: [diazo(phenyl)methyl]benzene (1.07 g, 5.50 mmol, 3 eq) was added to a solution of compound 26_8 (0.8 g, 1.83 mmol, 1 eq) in MeOH (5 mL). The reaction mixture Step 1: formaldehyde (26.81 g, 892.83 mmol, 24.59 mL, 1 eq) was added to a solution of 2-(3-methoxyphenyl) ethylamine (26_1, 135 g, 892.83 mmol, 131.07 mL, 1 eq) in HCOOH (900 mL) at 15° C., the mixture was stirred at 45° C. for 12 hours and concentrated under reduced pressure, the obtained residue was diluted with water (500 mL), the pH value was adjusted to more than 9 by using sodium hydroxide solution (4 M), the obtained mixture was extracted with was stirred at room temperature for 12 hours and the mixture was concentrated under reduced pressure to remove the solvent, the residue was purified by column chromatography (SiO$_2$, DCM/MeOH=5/1) to give compound 26_9.

Step 9: DIAD (603.89 mg, 2.99 mmol, 580.66 μL, 2 eq) was added to a solution of compound 26_9 (0.9 g, 1.49 mmol, 1 eq), 2-hydroxyisoindoline-1,3-dione (292.31 mg, 1.79 mmol, 1.2 eq) and PPh$_3$ (587.48 mg, 2.24 mmol, 1.5 eq) in THF (10 mL). The mixture was stirred at room temperature (20-30° C.) for 1 hour, then concentrated under reduced pressure, the residue was diluted with DCM (20 mL), and washed with water and saturated sodium chloride, then the mixture was concentrated under reduced pressure to remove the solvent, the residue was purified by column chromatography (SiO$_2$, DCM/MeOH=10/1) to give compound 26_10.

Step 10: NH$_2$NH$_2$.H$_2$O (26.79 mg, 668.60 μmol, purity: 85%, 1 eq) was added to a mixed solution of compound 26_10 (0.5 g, 668.60 mol, 1 eq) in methanol (5 mL) and DCM (5 mL). The mixture was stirred at room temperature (20-30° C.) for 0.5 hour and concentrated under reduced pressure, then DCM (10 mL) was added thereto, the residue was filtered, concentrated under reduced pressure to give compound 26_11.

Step 11: intermediate A2 (216.05 mg, 521.26 μmol, 0.7 eq) was added to a mixed solution of compound 26_11 (460 mg, 744.66 mol, 1 eq) in DCM (5 mL) and MeOH (2 mL). The mixture was stirred at room temperature (20-30° C.) for 1 hour, and the mixture was concentrated under reduced pressure to remove the solvent, the residue was grinded with ethyl acetate (30 mL) for 12 hours to give compound 26_12.

Step 12: HOBt (47.96 mg, 354.96 μmol, 1.2 eq) and DIC (44.80 mg, 354.96 μmol, 54.96 μL, 1.2 eq) were added to a solution of compound 26_12 (300 mg, 295.80 μmol, 1 eq) in DMF (3 mL). The reaction mixture was stirred at room temperature (20-25° C.) for 1 hour, then intermediate A1 (80.83 mg, 384.54 μmol, 1.3 eq) and NaHCO$_3$ (99.40 mg, 1.18 mmol, 46.02 μL, 4 eq) were added thereto, the obtained mixture was stirred at room temperature (20-30° C.) for 12 hours, and the reaction was quenched by adding water (10 mL), a yellow solid formed, after filtration, the yellow solid was dissolved in DCM (10 mL), and was washed with saturated sodium chloride, the mixture was concentrated under reduced pressure to remove the solvent, and the residue was purified by preparative TLC (SiO$_2$, DCM/MeOH=10/1) to give compound 26_13.

Step 13: TFA (1 mL) was added to a solution of compound 26_13 (240 mg, 198.94 μmol, 1 eq) in DCM (2 mL) at 0° C. The reaction mixture was stirred for 0.5 hour at this temperature and ethyl acetate (10 mL) was added, a yellow solid precipitated, and then filtered, the filter cake was purified by preparative HPLC (column: Boston pH-lex 150×25×10 μm; mobile phase: [water (0.1% TFA)-ACN]; acetonitrile %: 3%-30%, 9 min) to give compound 26. $^1$H NMR (400 MHz, D$_2$O) δ (ppm): 7.13-7.04 (m, 2H), 6.85-6.76 (m, 2H), 5.15 (dd, J=2.4, 5.0 Hz, 1H), 4.61 (s, 1H), 4.52-4.42 (m, 4H), 3.52 (br t, J=5.9 Hz, 2H), 3.34 (t, J=7.0 Hz, 2H), 3.03 (br t, J=7.8 Hz, 2H), 2.87 (br t, J=5.7 Hz, 2H), 1.96 (quin, J=7.4 Hz, 2H), 1.38 (s, 3H), 1.01 (s, 3H); LCMS m/z: 698.3 (M+1).

Embodiment 27

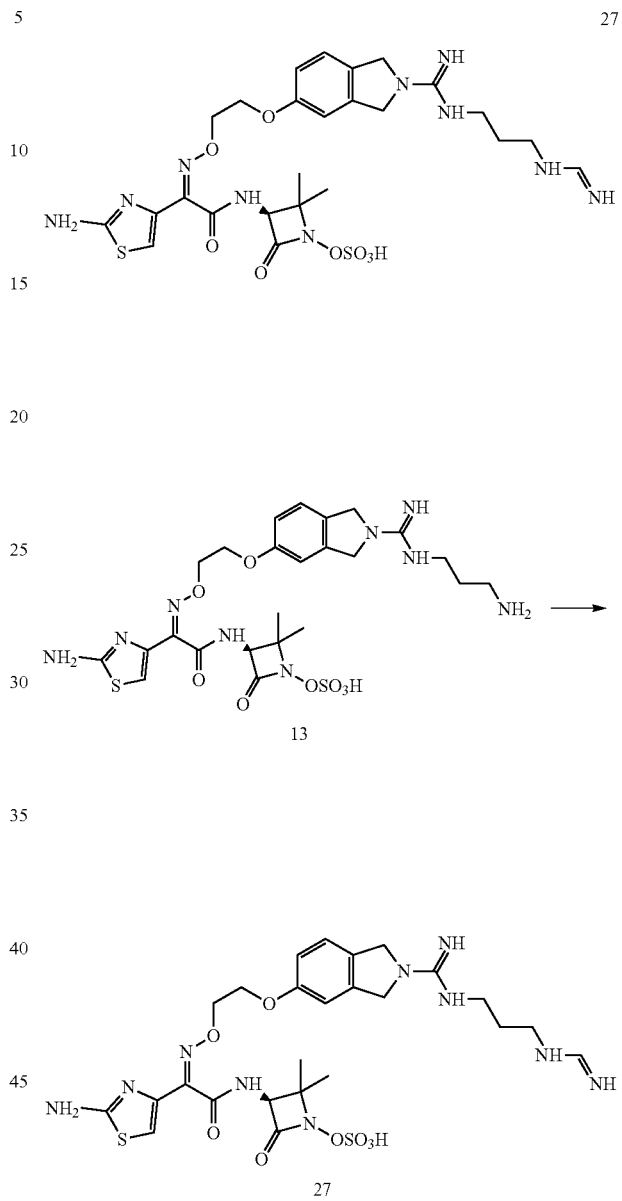

Step 1: DIPEA (28.51 mg, 220.57 μmol, 38.42 μL, 4 eq) and ethyl formimidate hydrochloride (7.85 mg, 71.69 μmol, 1.3 eq) were added to a solution of the trifluoroacetate of compound 13 in DMF (0.5 mL). The mixture was stirred at 25° C. for 2 hours and concentrated under reduced pressure, the residue was purified by preparative HPLC (column: Phenomenex Synergi C18 150*25*10 μm; mobile phase: [water (0.1% TFA)-ACN]; acetonitrile %: 1%-30%, 13 min) to give compound 27. $^1$H NMR (400 MHz, D$_2$O) δ (ppm): 7.73-7.67 (m, 1H), 7.18 (br d, J=8.9 Hz, 1H), 6.95 (s, 1H), 6.90-6.83 (m, 2H), 4.62 (br s, 2H), 4.58 (br s, 2H), 4.29 (br s, 2H), 4.25 (br s, 2H), 3.44-3.34 (m, 2H), 3.30 (br d, J=4.1 Hz, 3H), 1.94-1.77 (m, 2H), 1.37 (s, 3H), 0.98 (s, 3H); LCMS (ESI) m/z: 667.1 (M+1).

Embodiment 28

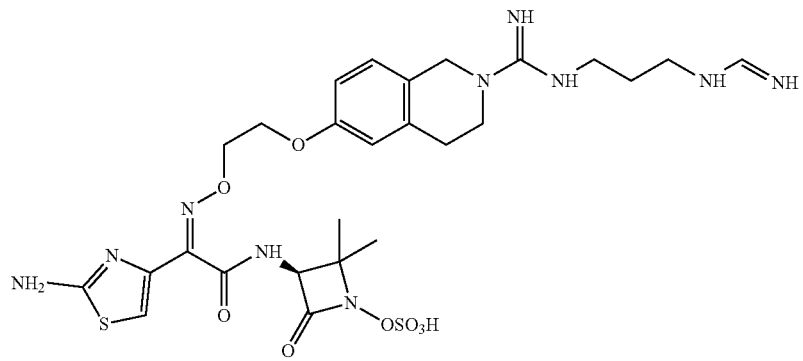

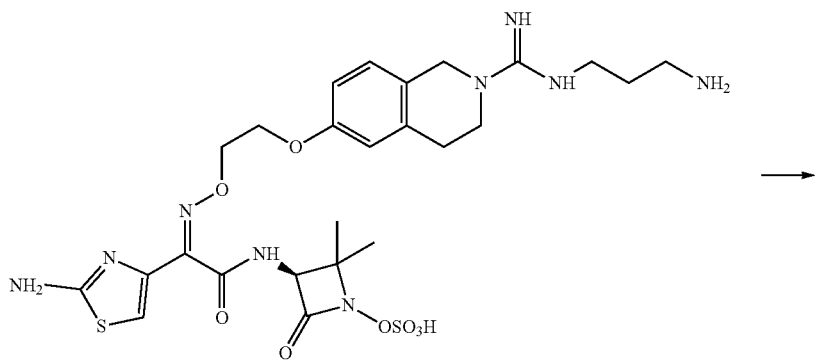

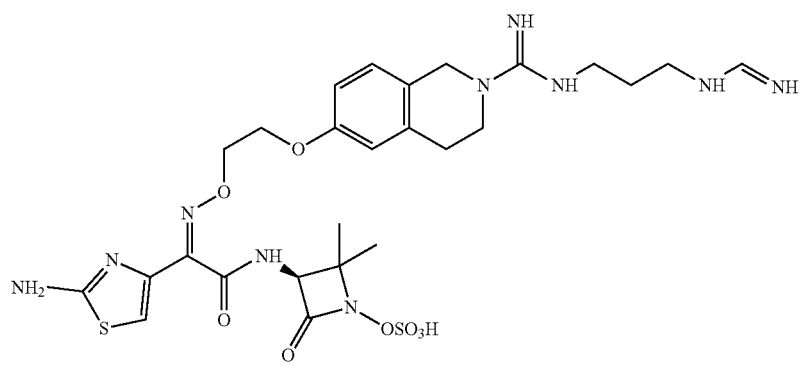

Step 1: ethyl formimidate hydrochloride (16.15 mg, 147.43 μmol, 1.3 eq) and DIPEA (58.63 mg, 453.63 μmol, 79.01 μL, 4 eq) were added to a solution of the trifluoroacetate of compound 4 (100 mg, 113.41 μmol, 1 eq) in DMF (1 mL). The mixture was stirred at 25° C. for 2 hours and concentrated under reduced pressure, the residue was purified by preparative HPLC (column: Boston pH-lex 150*25 10 μm; mobile phase: [water (0.1% TFA)-ACN]; acetonitrile %: 10%-40%, 10 min) to give compound 28. $^1$H NMR (400 MHz, D$_2$O) δ (ppm): 7.73-7.64 (m, 1H), 7.05 (br d, J=9.0 Hz, 1H), 6.95 (s, 1H), 6.78 (br s, 2H), 4.63 (s, 2H), 4.49 (br s, 2H), 4.39 (s, 2H), 4.27 (br d, J=4.0 Hz, 2H), 3.55-3.43 (m, 2H), 3.27 (br d, J=6.1 Hz, 3H), 2.82 (br s, 2H), 1.93-1.76 (m, 2H), 1.35 (s, 3H), 0.99 (s, 3H); LCMS (ESI) m/z: 681.3 (M+1).

Embodiment 29
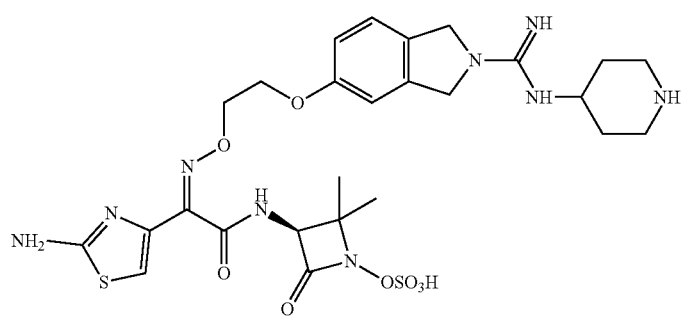
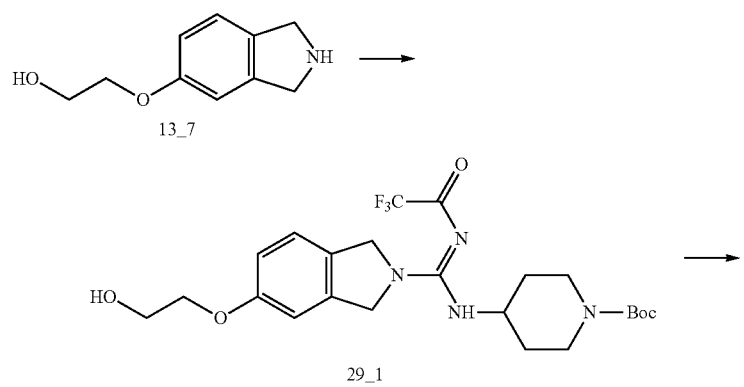
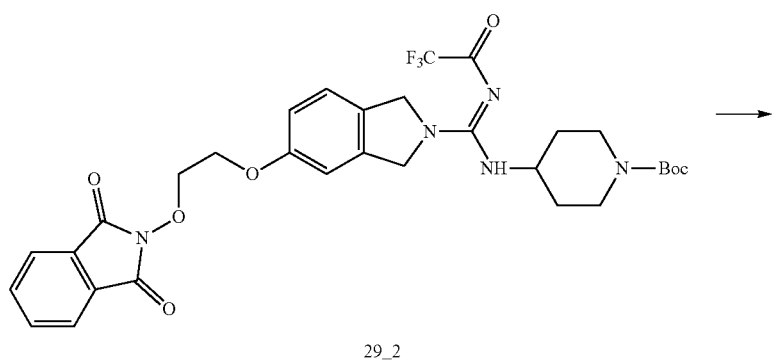
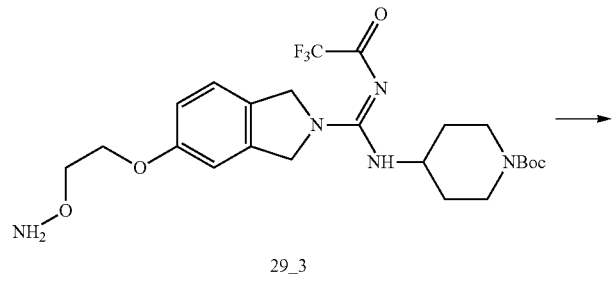

-continued

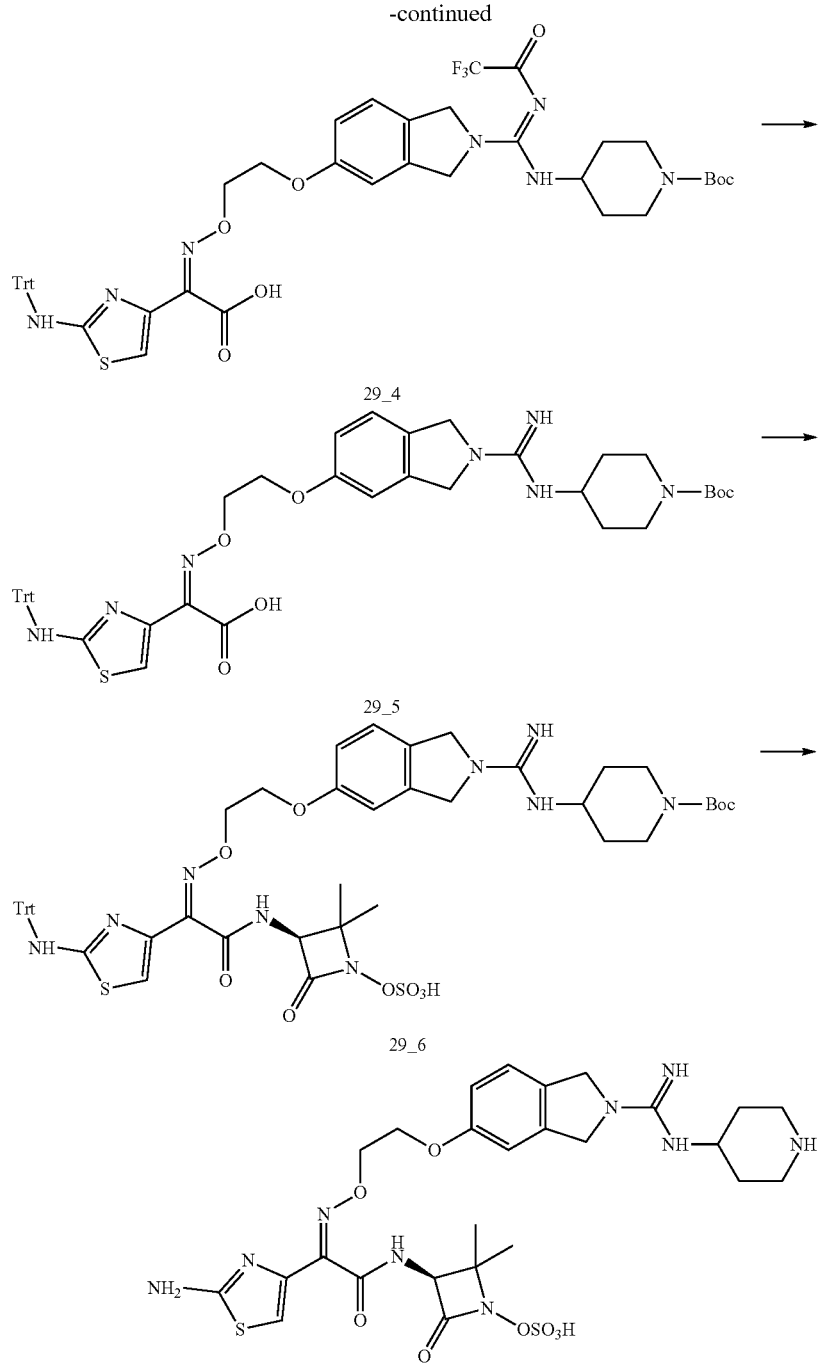

Step 1: TEA (2.60 g, 25.68 mmol, 3.57 mL, 5 eq) was added to a solution of compound 12_4 (2 g, 5.14 mmol, 1 eq) and the trifluoroacetate of 13_7 (1.5 g, 5.12 mmol, 1 eq) in DMF (20 mL). The mixture was stirred at 40° C. for 15 hours then poured into water (40 mL), the mixture was then extracted with ethyl acetate (100 mL*2), the organic phases were combined and washed with saturated sodium chloride (2 mL), dried over anhydrous sodium sulfate, filtered and concentrated under reduced pressure, the residue was purified by silica gel chromatography (SiO$_2$, ethyl acetate/methanol=1/0 to 10/1) to give compound 29_1.

Step 2: DIAD (339.36 mg, 1.68 mmol, 326.31 μL, 1.2 eq) was added to a solution of compound 29_1 (700 mg, 1.40 mmol, 1 eq), 2-hydroxyisoindoline-1,3-dione (273.78 mg, 1.68 mmol, 1.2 eq), PPh$_3$ (440.19 mg, 1.68 mmol, 1.2 eq) in THF (8 mL) at 0° C. The mixture was stirred at room temperature for 2 hours and concentrated under reduced pressure, the residue was purified by silica gel chromatography (petroleum ether/ethyl acetate=3/1 to 0/1) to give compound 29_2.

Step 3: NH$_2$NH$_2$.H$_2$O (17.57 mg, 298.38 μmol, 17.06 μL, purity: 85%) was added to a solution of compound 29_2 (400 mg, 298.38 mmol, 1 eq) in EtOH (5 mL). The mixture was stirred at room temperature for 1 hour and concentrated under reduced pressure, and the residue was dissolved in ethyl acetate (20 mL) and filtered, the filtrate was concentrated under reduced pressure to give compound 29_3.

Step 4: intermediate A2 (238.78 mg, 576.11 μmol, 0.9 eq) was added to a mixed solution of compound 29_3 (330 mg, 640.12 μmol, 1 eq) in MeOH (3 mL) and DCM (1 mL). The mixture was stirred at room temperature for 30 mins and concentrated under reduced pressure, the residue was washed with petroleum ether/ethyl acetate (20 mL, 1/1) under stirring, then filtered and the filter cake was collected to give compound 29_4.

Step 5: potassium carbonate (132.60 mg, 959.45 μmol, 2.5 eq) was added to a solution of compound 29_4 (350 mg, 383.78 μmol, 1 eq) in MeOH (5 mL). The mixture was stirred at 40° C. for 12 hours and concentrated under reduced pressure. The residue was poured into water (10 mL) and extracted with DCM (50 mL). The combined organic phase was washed with dilute hydrochloric acid (10 mL*3, 0.1 M), dried over anhydrous sodium sulfate and filtered, then concentrated under reduced pressure, the residue was washed with ethyl acetate (30 mL), filtered and the obtained filter cake was compound 29_5.

Step 6: DIC (92.80 mg, 735.31 μmol, 113.86 μL, 2 eq) and HOBt (99.36 mg, 735.31 μmol, 2 eq) were added to a solution of compound 29_5 (300 mg, 367.66 mol, 1 eq) in DMF (3 mL). The mixture was stirred at room temperature for 1 hour then intermediate A1 (100.47 mg, 477.95 μmol, 1.3 eq) and NaHCO$_3$ (123.55 mg, 1.47 mmol, 57.20 μL, 4 eq) were added. The mixture was stirred at room temperature for another 13 hours then poured into water (10 mL), a yellow precipitation was formed, which was filtered and the filter cake was collected, which was purified by preparative TLC (SiO$_2$, DCM/MeOH=10/1) to give compound 29_6.

Step 7: TFA (1.54 g, 13.51 mmol, 1 mL) was added to a solution of compound 29_6 (100 mg, 79.12 μmol, 1 eq) in DCM (1 mL) at 0° C. The mixture was stirred for 30 mins then petroleum ether/ethyl acetate (10 mL, 1/2) was added thereto and stirred for another 5 min, the mixture was then filtered and the filter cake was collected, then purified by preparative HPLC (column: Boston Green ODS 150*30 5 u; mobile phase: [water (0.225% formic acid)-ACN]; acetonitrile %: 3%-33%, 10 min) to give compound 29. $^1$H NMR (400 MHz, D$_2$O) δ (ppm): 8.34 (s, 1H), 7.21 (br d, J=9.3 Hz, 1H), 6.92-6.88 (m, 2H), 6.86 (s, 1H), 4.60 (br s, 4H), 4.46 (br s, 2H), 4.36-4.19 (m, 3H), 3.73 (br s, 1H), 3.45 (br d, J=14.3 Hz, 2H), 3.07-2.98 (m, 2H), 2.19 (d, J=17.5 Hz, 2H), 1.80 (br d, J=10.0 Hz, 2H), 1.40 (s, 3H), 1.03 (s, 3H); LCMS (ESI) m/z: 666.3 (M+1).

Embodiment 30

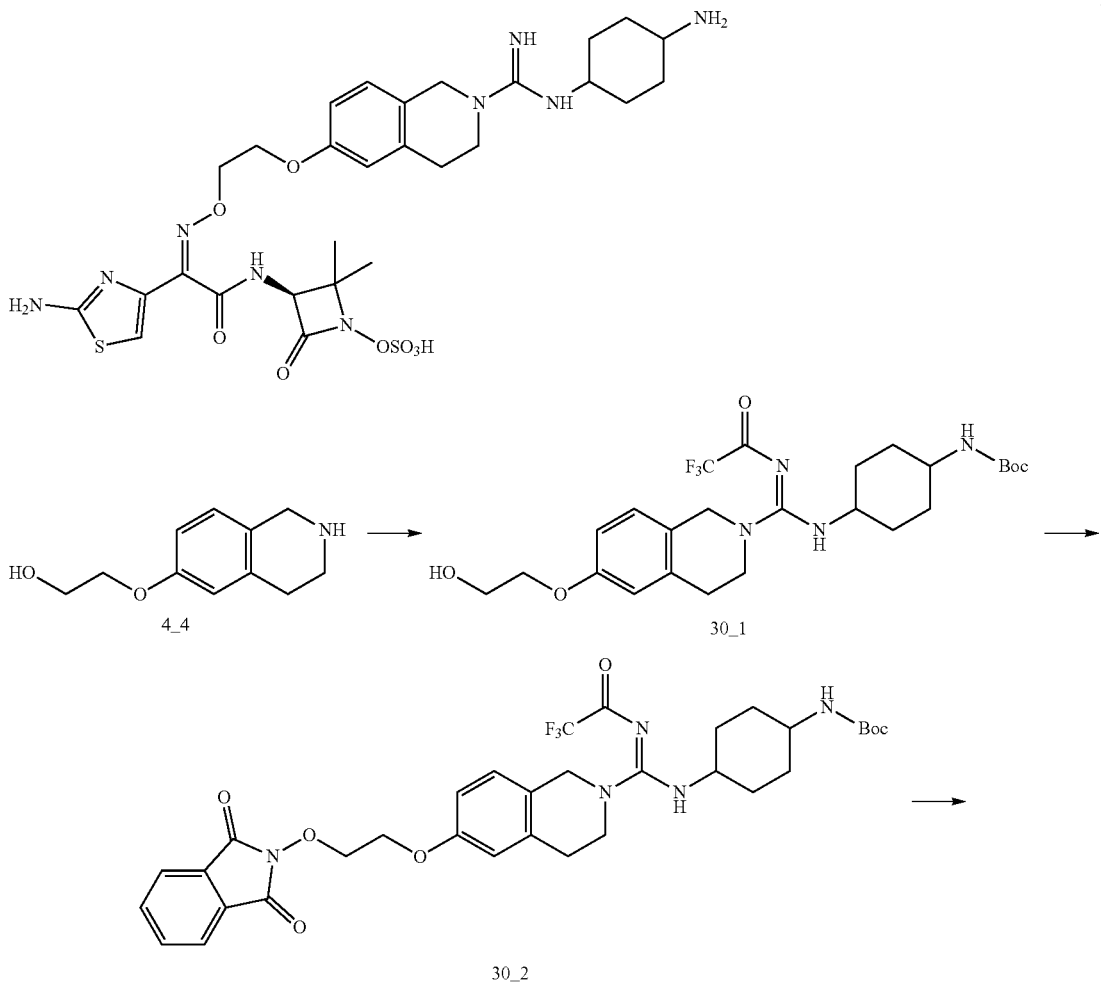

-continued
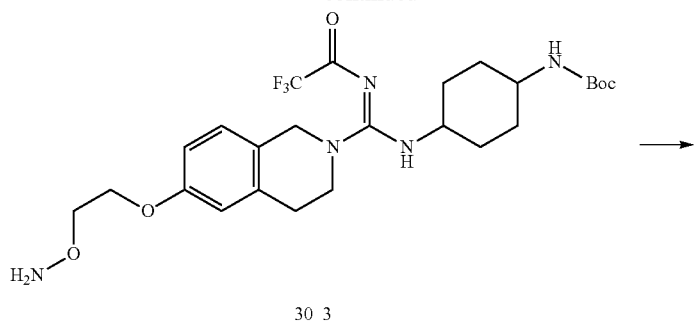
30_3
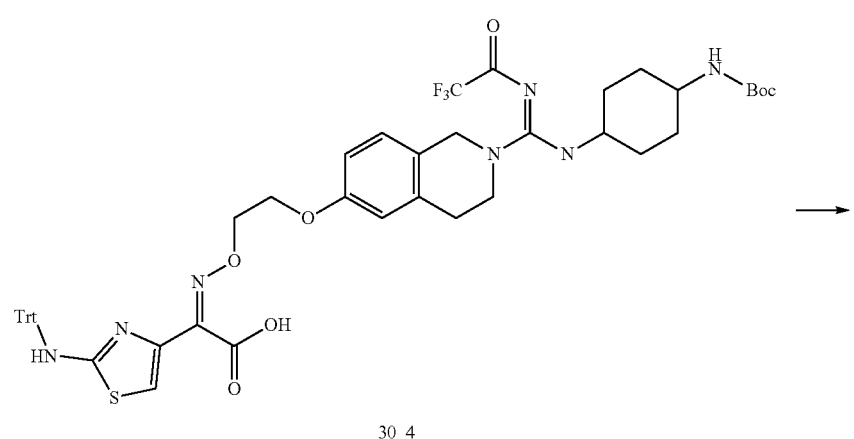
30_4
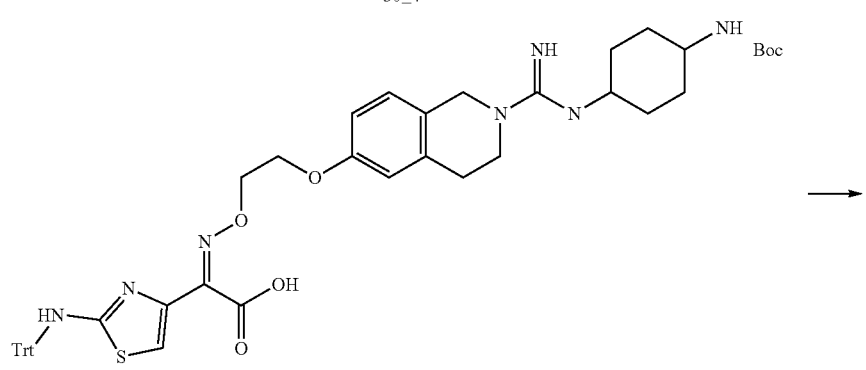
30_5
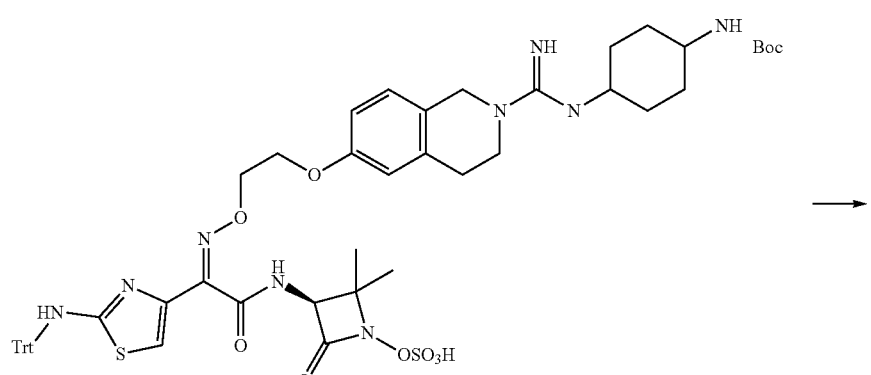
30_6

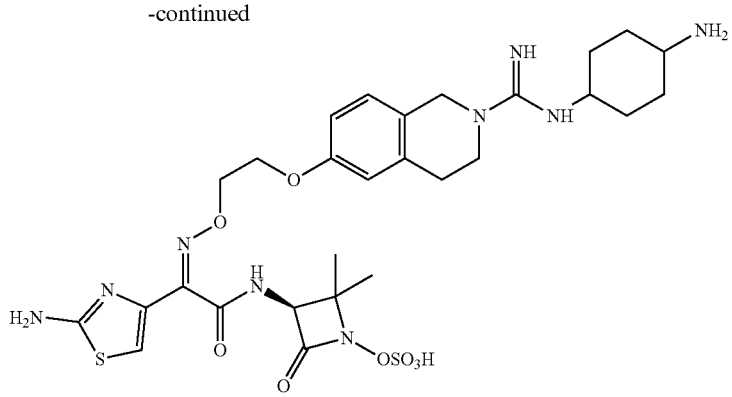

30

Step 1: 20_4 (2.8 g, 6.94 mmol, 1 eq) was added to a solution of compound 4_4 (1.23 g, 6.37 mmol, 1 eq) in DMF (50 mL). The mixture was stirred at 35° C. for 12 hours then poured into water (50 mL) and stirred for another 5 min. The aqueous phase was extracted with ethyl acetate (100 mL×2), the combined organic phase was washed with saline (30 mL*2), dried over anhydrous sodium sulfate, filtered and concentrated under reduced pressure to give compound 301.

Step 2: DIAD (3.83 g, 18.92 mmol, 3.68 mL, eq) was added dropwise to a solution of compound 30_1 (5 g, 9.46 mmol, 1 eq), 2-hydroxyisoindoline-1,3-dione (1.85 g, 11.35 mmol, 1.2 eq) and PPh$_3$ (2.98 g, 11.35 mmol, 1.2 eq) in THF (50 mL) at ° C. The mixture was stirred at 25° C. for 1 hour and concentrated under reduced pressure, the residue was purified by silica gel chromatography (petroleum ether/ethyl acetate=5/1 to 0/1) to give compound 30_2.

Step 3: NH$_2$NH$_2$.H$_2$O (174.84 mg, 2.97 mmol, 169.75 μL, 85% purity, 1 eq) was added to a solution of compound 30_2 (2 g, 2.97 mmol, 1 eq) in EtOH (20 mL). The mixture was stirred at 25° C. for 2 hours and concentrated under reduced pressure. The residue was diluted with dichloromethane/water (30 mL/10 mL), then extracted with DCM (100 mL). The combined organic phase was washed with saturated sodium chloride (20 mL), dried over anhydrous sodium sulfate, filtered and concentrated under reduced pressure to give compound 30_3.

Step 4: intermediate A2 (1.03 g, 2.48 mmol, 0.9 eq) was added to a solution of compound 30_3 (1.5 g, 2.76 mmol, 1 eq) in MeOH (6 mL) and CH$_2$Cl$_2$ (2 mL). The mixture was stirred at 25° C. for 30 mins and concentrated under reduced pressure to give compound 30_4. LCMS (ESI) m/z: 940.4 (M+1).

Step 5: potassium carbonate (749.67 mg, 5.42 mmol, 3 eq) was added to a solution of compound 30_4 (2.4 g, 1.81 mmol, 1 eq) in MeOH (25 mL). The mixture was stirred at 25° C. for 2 hours, then stirred at 40° C. for another 12 hours. The mixture was concentrated under reduced pressure, and the residue was poured into water, dilute hydrochloric acid (30 mL, 1M) was added thereto and stirred for 5 min. The aqueous phase was extracted with DCM (100 mL*2), the organic phases were combined and washed with saturated sodium chloride (30 mL), dried over anhydrous sodium sulfate, filtered and concentrated under reduced pressure, the residue was washed with ethyl acetate (30 mL) under stirring, filtered and the filter cake was collected to give compound 30_5. LCMS (ESI) m/z: 844.3 (M+1).

Step 6: DIC (119.17 mg, 944.28 μmol, 146.22 μL, 2 eq) and HOBt (127.59 mg, 944.28 μmol, 2 eq) were added to a solution of compound 30_5 (500 mg, 472.14 μmol, 1 eq) in DMF (5 mL). The mixture was stirred at 25° C. for 30 min, then intermediate A1 (129.02 mg, 613.78 μmol, 1.3 eq) and NaHCO$_3$ (158.65 mg, 1.89 mmol, 73.45 μL, 4 eq) were added thereto, the mixture was stirred at 25° C. for 12 hours, then water (30 mL) was added and stirred for another 5 min, the mixture was filtered, and the filter cake was purified by silica gel chromatography (DCM/MeOH=50/1 to 10/1) to give compound 30_6.

Step 7: TFA (3.08 g, 27.01 mmol, 2 mL) was added to a solution of compound 30_6 (300 mg, 289.51 μmol, 1 eq) in DCM (2 mL). The mixture was stirred at 0° C. for 30 min, then ethyl acetate/petroleum ether (30 mL, 1/1) was added thereto and stirred for another 5 min, the mixture was filtered, and the obtained filter cake was purified by preparative HPLC (column: Phenomenex Synergi C18 150*25*10 μm; mobile phase: [water (0.1% TFA)-ACN]; acetonitrile %: 4%-34%, 12 min) to give compound 30.

Embodiment 31
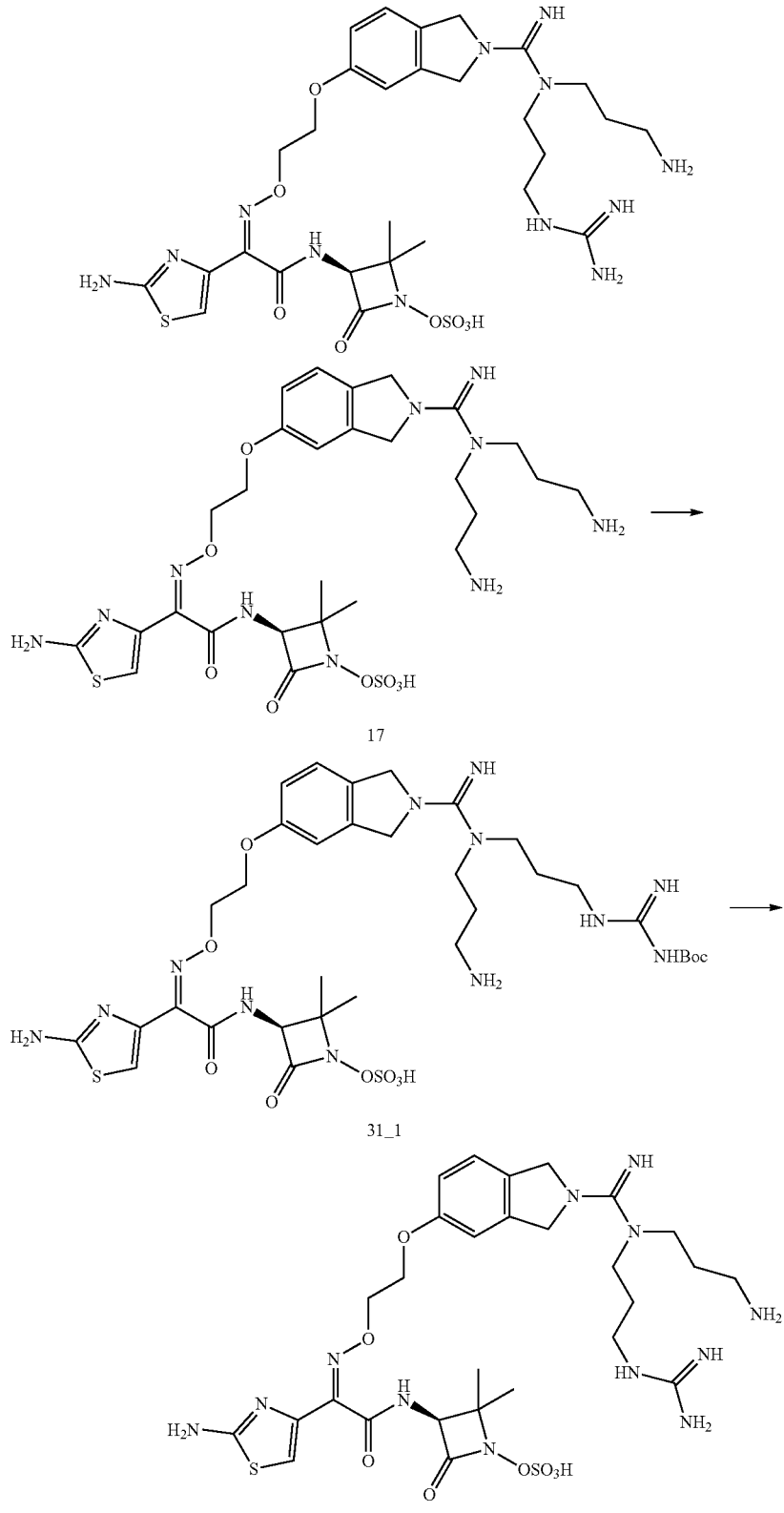

Step 1: triethylamine (116.89 mg, 1.16 mmol, 4 eq) and tert-butyl N-[(tert-butoxycarbonylamino)-pyrazol-1-yl-methylene] carbamate (107.55 mg, 346.53 µmol, 1.2 eq) were added to a solution of compound 17 (300 mg, 288.78 µmol, 1 eq, 3TFA) in DMF (5 mL). The mixture was stirred at 40° C. for 12 hours, then purified by preparative HPLC (column: Phenomenex Synergi C18 150×25×10 µm; mobile phase: [water (0.1% TFA)-ACN]; acetonitrile %: 15%-45%, 11 min) to give a trifluoroacetate of compound 31_1. LCMS (ESI) m/z: 839.5 (M+1).

Step 2: TFA (1.54 g, 13.51 mmol, 1 mL, 160.12 eq) was added to a solution of compound 31_1 (90 mg, 84.35 µmol, 1 eq, 2TFA) in DCM (2 mL). The mixture was stirred at 0° C. for 3 hours, then concentrated under reduced pressure to remove the solvent, the residue was purified by preparative HPLC (column: Boston pH-lex 150×25×10 µm; mobile phase: [water (0.1% TFA)-ACN]; acetonitrile %: 8%-38%, 9 min) to give compound 31.

LCMS (ESI) m/z: 739.3 (M+1); $^1$H NMR (400 MHz, DMSO-$d_6$+$D_2O$) δ=7.28 (br d, J=8.6 Hz, 1H), 6.96-6.89 (m, 2H), 6.81 (s, 1H), 4.66 (br d, J=17.9 Hz, 4H), 4.58 (s, 1H), 4.46-4.38 (m, 2H), 4.19 (br s, 2H), 3.35-3.22 (m, 2H), 3.15 (br t, J=6.9 Hz, 2H), 2.99-2.87 (m, 4H), 1.88-1.73 (m, 4H), 1.37 (s, 3H), 1.15 (s, 3H) ppm.

Embodiment 32

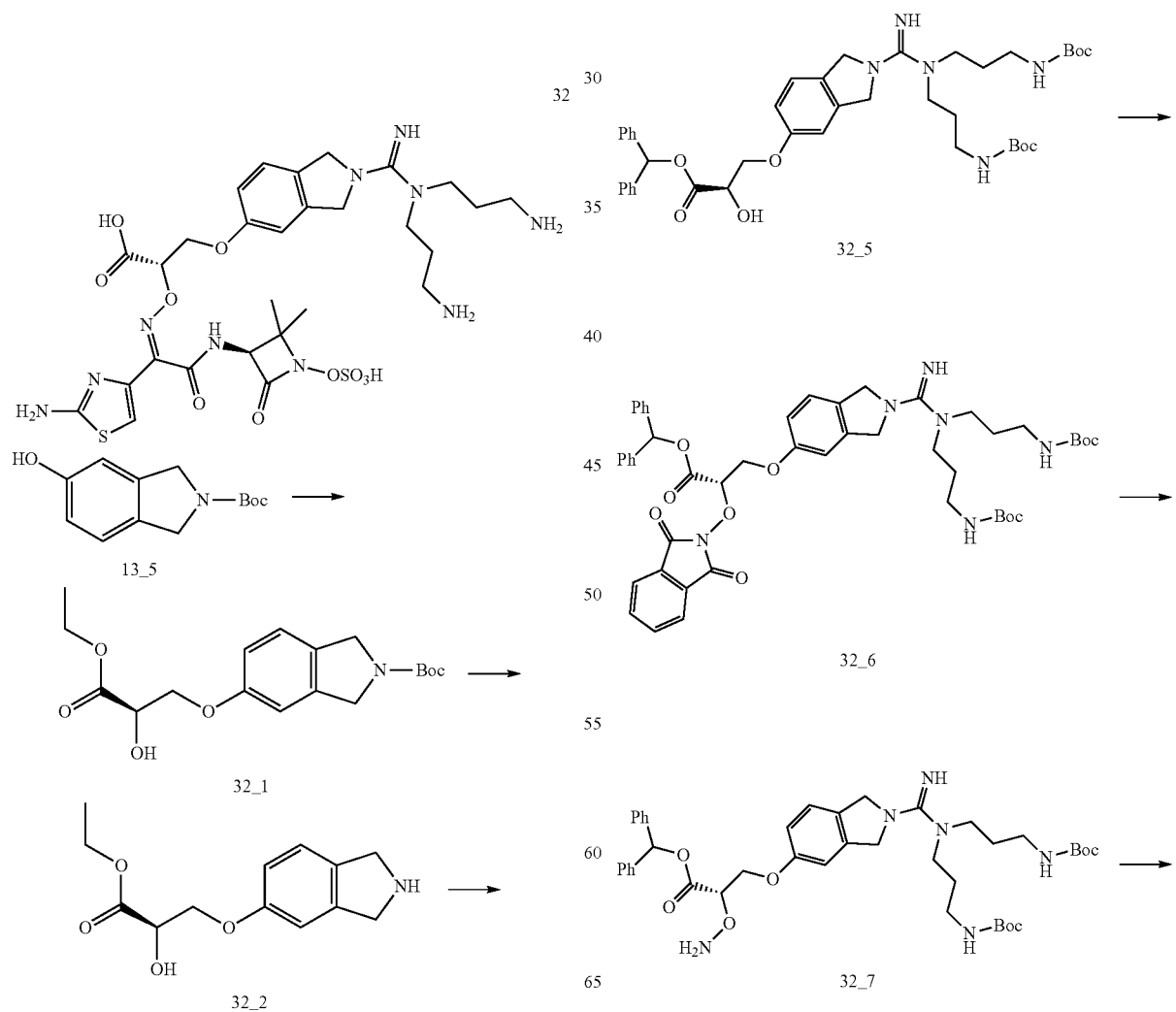

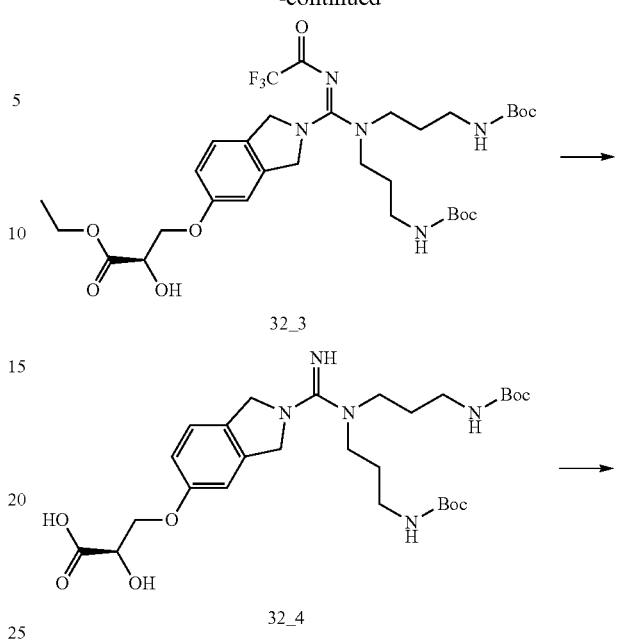

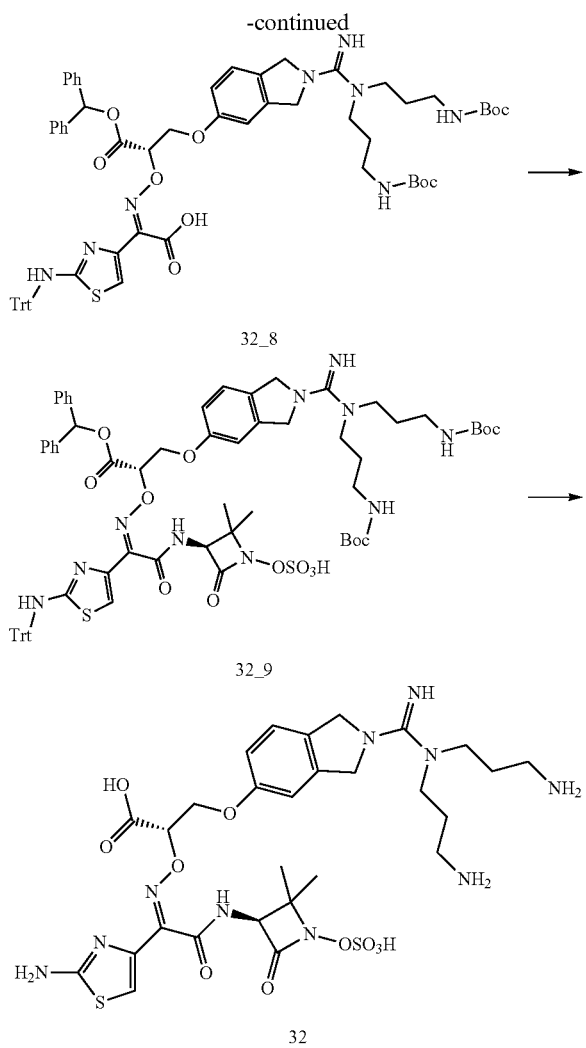

Step 1: catalyst A8 (673.34 mg, 800.64 µmol, 0.03 eq) was added to a solution of intermediate 13_5 (6.8 g, 26.69 mmol, 1 eq), ethyl oxirane-2-carboxylate (7.75 g, 66.72 mmol, 2.5 eq), 4 Å molecular sieve (8 g) in MTBE (10 mL), the mixture was ventilated with nitrogen for 3 times, then stirred at 20° C. for 12 hours. The reaction mixture was diluted with ethyl acetate (30 mL) and filtered, the filtrate was concentrated under reduced pressure then purified by column chromatography (SiO₂, petroleum ether/ethyl acetate=6/1 to 3/1 (v/v)) to give compound 32_1.

Step 2: TFA (14.88 g, 130.51 mmol, 9.66 mL, 7.53 eq) was added to a solution of compound 32_1 (6.3 g, 17.32 mmol, 1 eq) in DCM (20 mL) at 0° C., the mixture was stirred at 20° C. for 1 hour then concentrated under reduced pressure to give a trifluoroacetate of compound 32_2.

Step 3: triethylamine (2.95 g, 29.20 mmol, 4.06 mL, 4 eq) and the trifluoroacetate of compound 32_2 (5.33 g, 14.60 mmol, 2 eq) were added to a solution of intermediate A6 (3.8 g, 7.30 mmol, 1 eq) in DMF (30 mL). The mixture was stirred at 45° C. for 2 hours and concentrated under reduced pressure to remove DMF, the residue was diluted with water (50 mL) and extracted with ethyl acetate (50 mL). The organic phases were combined and washed with saturated sodium chloride aqueous solution (25 mL), dried over anhydrous sodium sulfate, filtered and concentrated under reduced pressure to give a residue, which was purified by column chromatography (SiO₂, petroleum ether/ethyl acetate=1/1 to 0/1) to give compound 32_3.

Step 4: NaOH (378.39 mg, 9.46 mmol, 2.1 eq) was added to a solution of compound 32_3 (3.3 g, 4.50 mmol, 1 eq) in MeOH (20 mL). The mixture was stirred at 20° C. for 17 hours and the pH value was adjusted to 3-4 with dilute hydrochloric acid (2 M), then concentrated under reduced pressure, the residue was diluted with methanol (20 mL) and filtered, then concentrated under reduced pressure to give compound 32_4.

Step 5: diphenyl diazomethane (1.34 g, 6.90 mmol, 2 eq) was added to a solution of compound 32_4 (2 g, 3.45 mmol, 1 eq) in MeOH (20 mL). The mixture was stirred at 20° C. for 12 hours, then concentrated under reduced pressure, the residue was diluted with water (20 mL) and extracted with DCM (40 mL). The combined organic phase was washed with saturated sodium chloride aqueous solution (10 mL), dried over anhydrous sodium sulfate and filtered, then concentrated under reduced pressure, the residue was purified by column chromatography (SiO₂, DCM/MeOH=20/1 to 10/1 (v/v)) to give compound 32_5.

Step 6: PPh₃ (560.04 mg, 2.14 mmol, 1.5 eq) and DIAD (431.75 mg, 2.14 mmol, 415.15 µL, 1.5 equivalent) were added to a solution of compound 32_5 (1.2 g, 1.42 mmol, 1 eq) and 2-hydroxyisoindoline-1,3-dione (278.65 mg, 1.71 mmol, 1.2 eq) in THF (12 mL) at 0° C. The mixture was stirred at 20° C. for 1 hour and concentrated under reduced pressure to remove THF, the residue was purified by column chromatography (SiO₂, DCM/EtOH=20/1 to 10/1 (v/v)) to give compound 32_6.

Step 7: NH₂NH₂·H₂O (77.95 mg, 1.32 mmol, 75.68 µL, 85% purity, 1.2 eq) was added to a solution of compound 32_6 (1 g, 1.10 mmol, 1 eq) in EtOH (10 mL). The mixture was stirred at 20° C. for 30 mins and filtered, then concentrated under reduced pressure, the residue was diluted with water (10 mL) and extracted with DCM (20 mL), the organic phases were combined and dried over anhydrous sodium sulfate. The mixture was filtered and concentrated under reduced pressure to give compound 32_7.

Step 8: intermediate A2 (416.01 mg, 1.00 mmol, 1 eq) was added to a solution of compound 32_7 (900 mg, 1.00 mmol, 1 eq) in DCM (5 mL) and EtOH (5 mL), the mixture was stirred at 20° C. for 1 hour under nitrogen atmosphere, and the reaction mixture was concentrated under reduced pressure, the residue was purified by column chromatography (SiO₂, DCM/MeOH=20/1 to 10/1 (v/v)) to give compound 32_8.

Step 9: N,N'-diisopropylcarbodiimide (41.24 mg, 326.77 µmol, 2 eq) and HOBt (44.15 mg, 326.77 µmol, 2 eq) were added to a solution of compound 32_8 (200 mg, 163.39 µmol, 1 eq) in DMF (2 mL). The mixture was stirred at 20° C. for 1 hour, then intermediate A1 (48.08 mg, 228.74 µmol, 1.4 eq) and NaHCO₃ (54.90 mg, 653.55 µmol, 25.42 µL, 4 eq) were added thereto, and stirred at 20° C. for 11 hours. The reaction mixture was diluted with water (8 mL) and filtered, the solid was collected to give compound 32_9.

Step 10: TFA (1.54 g, 13.51 mmol, 1 mL, 82.85 eq) was added to a solution of compound 32_9 (220 mg, 163.01 µmol, 1 eq) in DCM (1 mL) at 0° C. and stirred for 1 hour. The reaction mixture was diluted with petroleum ether/ethyl acetate (10 mL, 4/1) and filtered, the solid was collected and purified by preparative HPLC (TFA, column: Phenomenex Synergi C18 150×25×10 µm; mobile phase: [water (0.1% TFA)-acetonitrile]; acetonitrile %: 1%-30%, 9 min) to give compound 32.

¹H NMR (400 MHz, D₂O) δ=7.23 (d, J=8.4 Hz, 1H), 7.10 (s, 1H), 6.93-6.85 (m, 2H), 5.19 (dd, J=2.0, 5.7 Hz, 1H), 4.87-4.76 (m, 4H), 4.64 (s, 1H), 4.54-4.48 (m, 1H), 4.44-4.37 (m, 1H), 3.43 (br t, J=7.3 Hz, 4H), 3.04-2.91 (m, 4H), 1.98 (quin, J=7.6 Hz, 4H), 1.41 (s, 3H), 0.97 (s, 3H) ppm; LCMS (ESI) m/z: 741.3 (M+1).
Embodiment 33
Step 1: DIC (41.24 mg, 326.78 50 mmol, 2 eq) and HOBt (44.15 mg, 326.78 μmol, 2 eq) were added to a solution of compound 32_8 (200 mg, 163.39 μmol, 1 eq) in DMF (2 mL). The mixture was stirred at 20° C. for 1 hour, then intermediate A3 (44.16 mg, 245.08 μmol, 1.5 eq) and NaHCO$_3$ (54.90 mg, 653.56 μmol, 25.42 μL, 4 eq) were added thereto, and stirred at 20° C. for 11 hours. The reaction
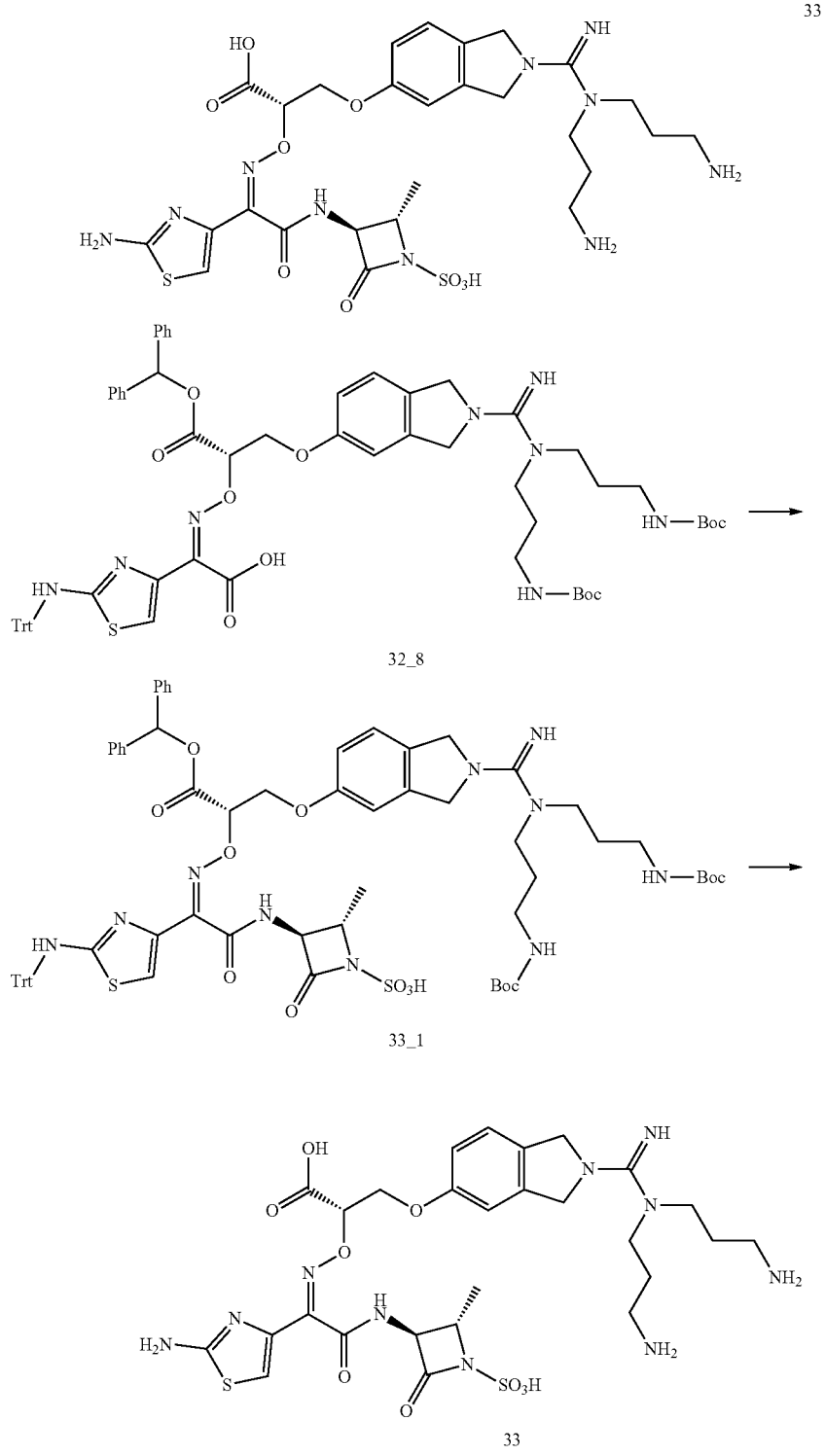

mixture was diluted with water (8 mL) and filtered, the solid was collected to give compound 33_1.

Step 2: TFA (1.54 g, 13.50 mmol, 1 mL, 82.85 eq) was added to a solution of compound 33_1 (215 mg, 162.94 μmol, 1 eq) in DCM (1 mL) at 0° C. The mixture was stirred at 0° C. for 1 hour, diluted with petroleum ether/ethyl acetate (10 mL, 4/1) and filtered, the solid was collected and purified by preparative HPLC (TFA, column: Phenomenex Synergi C18 150×25×10 μm; mobile phase: [water (0.1% TFA)-ACN]; acetonitrile %: 1%-30%, 9 min) to give compound 33.

$^1$H NMR (400 MHz, D$_2$O) δ=7.23 (d, J=8.1 Hz, 1H), 7.05 (s, 1H), 6.97-6.88 (m, 2H), 5.07 (br d, J=3.9 Hz, 1H), 4.87-4.76 (m, 4H), 4.57 (br d, J=11.6 Hz, 1H), 4.50-4.41 (m, 1H), 4.32 (br s, 1H), 3.52-3.33 (m, 5H), 2.97 (br t, J=7.8 Hz, 4H), 1.97 (quin, J=7.4 Hz, 4H), 1.13 (br d, J=6.0 Hz, 3H) ppm; LCMS (ESI) m/z: 711.3 (M+1).

Embodiment 34

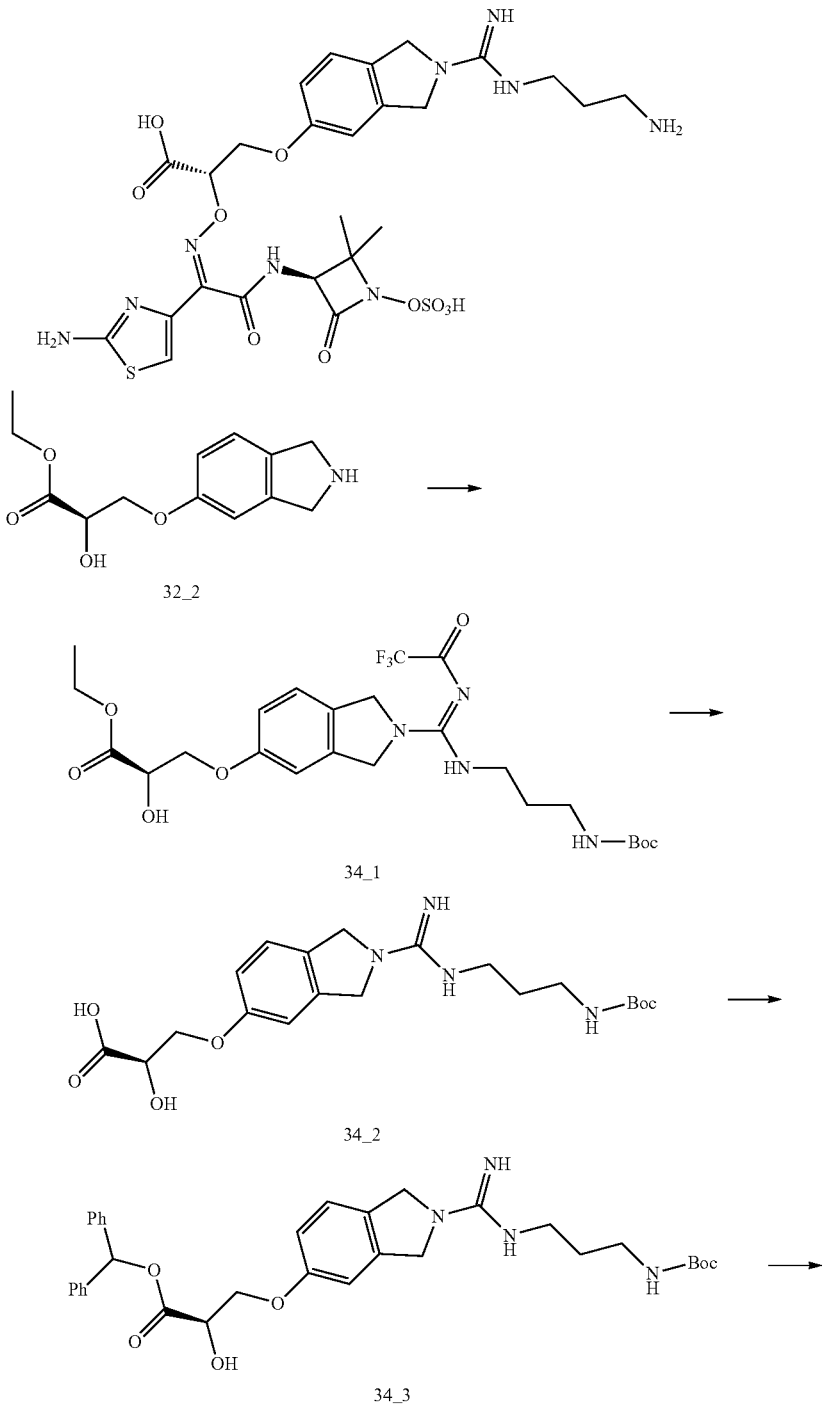

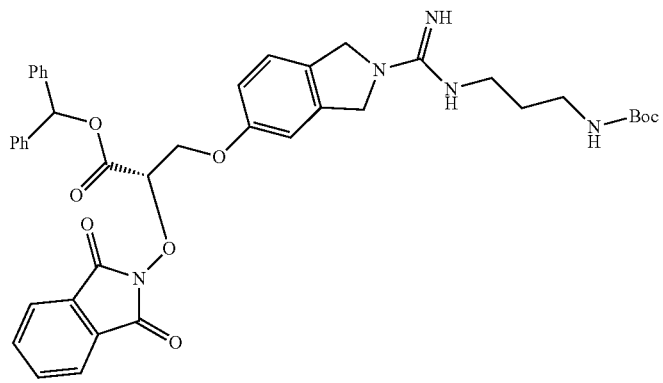
34_4
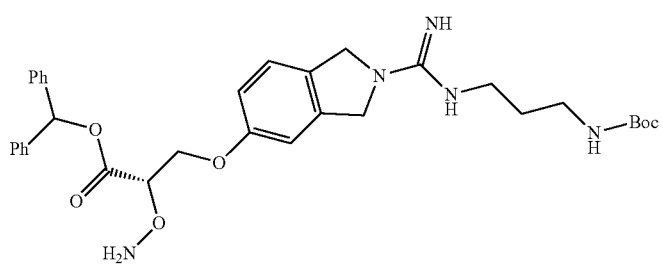
34_5
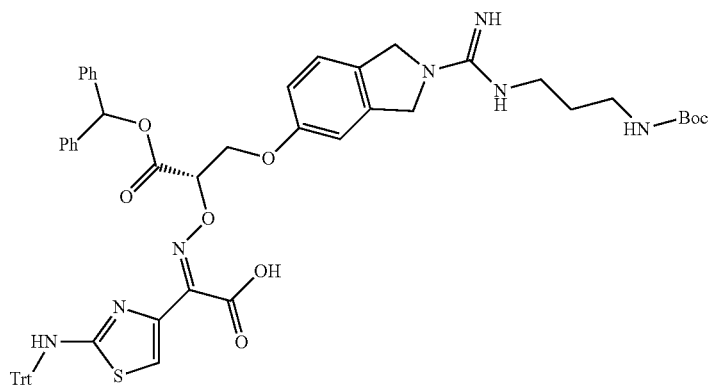
34_6
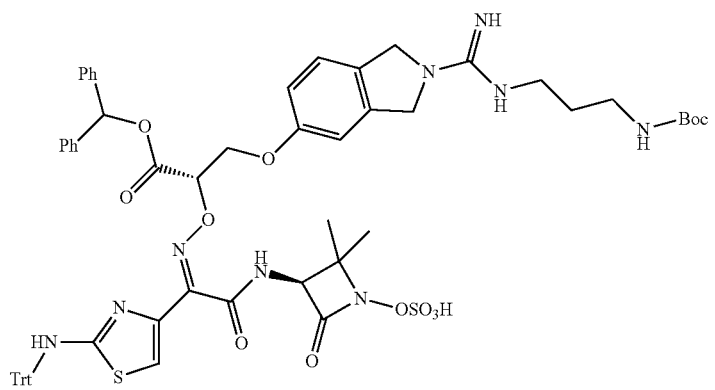
34_7

-continued

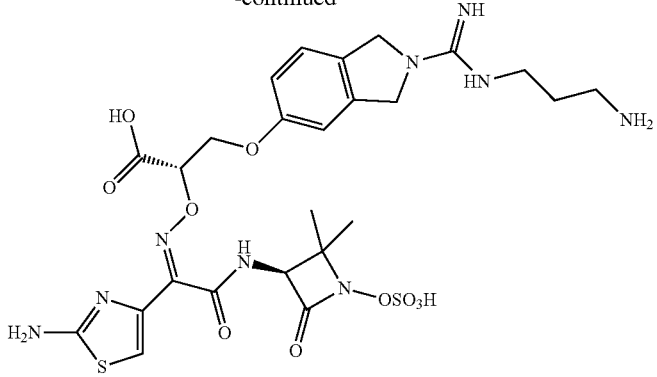

34

Step 1: triethylamine (2.16 g, 41.06 mmol, 5.72 mL, 5 eq) and 32_2 (3 g, 8.21 mmol, 8.21 eq) were added to solution of intermediate A4 (3 g, 8.26 mmol, 1.01 eq) in DMF (30 mL), the mixture was stirred at 40° C. for 12 hours then cooled to room temperature, and then the residue was poured into water (50 mL) and stirred for 5 min. The aqueous phase was extracted with ethyl acetate (200 mL*2). The combined organic phase was washed with saturated sodium chloride (50 mL), dried over anhydrous sodium sulfate, filtered and concentrated under reduced pressure. The residue was purified by silica gel chromatography (petroleum ether/ethyl acetate=10/1 to 0/1) to give compound 34_1.

Step 2: sodium hydroxide (337.06 mg, 8.43 mmol, 2.5 eq) was added to a solution of compound 34_1 (2.2 g, 3.37 mmol, 1 eq) in methanol (20 mL). The mixture was stirred at 15° C. for 14 hours then sodium hydroxide (337.06 mg, 8.43 mmol, 2.5 eq) was further added thereto, the mixture was stirred at 15° C. for 17 hours. The mixture was cooled down to room temperature and the pH value was adjusted to 6-7, and concentrated under reduced pressure at 33° C. to give compound 34_2.

Step 3: diphenyl diazomethane (1.79 g, 9.23 mmol, 3 eq) was added to a solution of compound 34_2 (1.3 g, 3.08 mmol, eq) in methanol (15 mL). The mixture was stirred at 15° C. for 12 hours and concentrated under reduced pressure. The residue was purified by silica gel chromatography (dichloromethane/methanol=30/1 to 10/1) to give compound 34_3.

Step 4: diisopropyl azodiformate (783.15 mg, 3.87 mmol, 753.03 μL, 2 eq) and triphenylphosphine (609.50 mg, 2.32 mmol, 1.2 eq) were added to a solution of compound 34_3 (1.14 g, 1.94 mmol, 1 eq) and 2-hydroxyisoindoline-1,3-dione (379.08 mg, 2.32 mmol, 1.2 eq) in tetrahydrofuran (15 mL). The mixture was stirred at 15° C. for 3 hours and concentrated under reduced pressure, the residue was purified by silica gel chromatography (dichloromethane/methanol=1/0 to 10/1) to give compound 34_4.

Step 5: $NH_2NH_2 \cdot H_2O$ (112.36 mg, 1.91 mmol, 109.09 μL, 85% purity, 1 eq) was added to a solution of compound 34_4 (1.4 g, 1.91 mmol, 1 eq) in ethanol (25 mL). The mixture was reacted at 15° C. for 30 mins and then filtered, the filtrate was collected and concentrated under reduced pressure to give compound 34_5.

Step 6: intermediate A2 (679.69 mg, 1.64 mmol, 0.9 eq) was added to a solution of compound 34_5 (1.1 g, 1.82 mmol, 1 eq) in methanol (6 mL) and dichloromethane (2 mL). The mixture was stirred at 15° C. for 1 hour and concentrated under reduced pressure, the residue was washed with (petroleum ether/ethyl acetate=1/2, 30 mL*2) to give compound 34_6.

Step 7: HOBt (81.06 mg, 599.90 μmol, 2 eq) and N,N'-diisopropylcarbodiimide (75.71 mg, 599.90 μmol, 92.89 μL, 2 eq) were added to a solution of compound 34_6 (300 mg, 299.95 mol, 1 eq) in DMF (3 mL). The mixture was stirred at 10° C. for 1 hour, then intermediate A1 (81.97 mg, 389.94 μmol, 1.3 eq) and $NaHCO_3$ (100.79 mg, 1.20 mmol, 46.66 μL, 4 eq) were added thereto. The mixture was stirred at 30° C. for 11 hours, water (5 mL) was added thereto and stirred for 5 min, the mixture was filtered and the filter cake was collected to give compound 34_7.

Step 8: trifluoroacetic acid (4.62 g, 40.52 mmol, 3 mL, 161.04 eq) was added to a solution of compound 34_7 (300 mg, 251.60 μmol, 1 eq) in dichloromethane (1 mL). The mixture was stirred at 0° C. for 1 hour, then petroleum ether/ethyl acetate (10 mL, 1/3) was added thereto and stirred for 5 min, the mixture was filtered, and the filter cake was purified by preparative HPLC (column: Phenomenex Synergi C18 150×25×10 μm; mobile phase: [water (0.1% trifluoroacetic acid)-acetonitrile]; acetonitrile %: 1%-30%, 9 min) to give compound 34.

$^1H$ NMR (400 MHz, $D_2O$) δ=7.25-7.16 (m, 1H), 7.04 (s, 1H), 6.86 (br s, 2H), 5.06 (br d, J=4.2 Hz, 1H), 4.61 (br s, 1H), 4.55 (br d, J=7.1 Hz, 4H), 4.46 (br d, J=9.7 Hz, 1H), 4.40-4.32 (m, 1H), 3.33 (br t, J=6.8 Hz, 2H), 3.07-2.94 (m, 2H), 1.99-1.83 (m, 2H), 1.37 (s, 3H), 0.94 (s, 3H) ppm; LCMS (ESI) m/z: 684.7 (M+1).

Embodiment 35

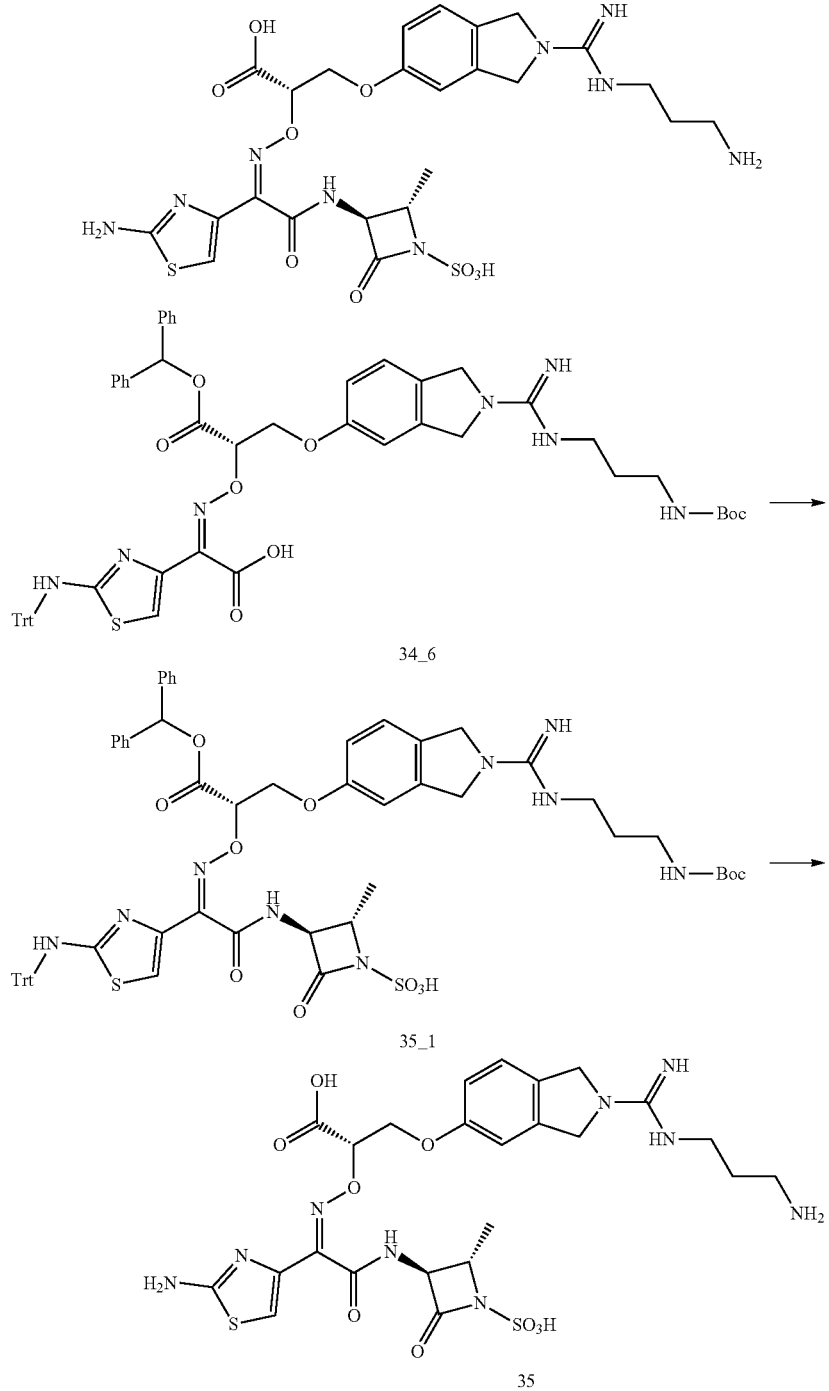

Step 1: HOBt (81.06 mg, 599.90 µmol, 2 eq) and N,N'-diisopropylcarbodiimide (75.71 mg, 599.90 µmol, 92.89 µL, 2 eq) were added to a solution of intermediate 34_6 (300 mg, 299.95 µmol, 1 eq) in DMF (3 mL). The mixture was stirred at 10° C. for 1 hour, then intermediate A3 (64.85 mg, 359.94 µmol, 1.2 eq) and sodium bicarbonate (100.79 mg, 1.20 mmol, 46.66 µL, 4 eq) were added thereto, the mixture was stirred at 30° C. for 11 hours, then water (5 mL) was added thereto and stirred for 5 min, the mixture was stirred and the filter cake was collected to give compound 35_1.

Step 2: trifluoroacetic acid (29.43 mg, 258.10 µmol, 19.11 µL, 1 eq) was added to a solution of compound 35_1 (300 mg, 258.10 µmol, 1 eq) in dichloromethane (1 mL). The mixture was stirred at 0° C. for 1 hour, then petroleum ether/ethyl acetate (10 mL, 1/3) was added thereto and stirred for 5 min, the mixture was filtered and the filter cake was collected and purified by preparative HPLC (column: Phenomenex Synergi C18 150×25×10 μm; mobile phase: [water (0.1% trifluoroacetic acid)-acetonitrile]; acetonitrile %: 1%-30%, 9 min) to give compound 35.
$^1$H NMR (400 MHz, D$_2$O) δ=7.17 (d, J=9.2 Hz, 1H), 7.01 (s, 1H), 6.92-6.78 (m, 2H), 5.06 (br s, 1H), 4.57-4.43 (m, 1H), 4.58-4.37 (m, 5H), 4.28 (br s, 1H), 3.29 (br t, J=6.7 Hz, 2H), 3.04-2.92 (m, 2H), 1.96-1.83 (m, 2H), 1.12 (br d, J=4.9 Hz, 3H) ppm; LCMS (ESI) m/z: 654.3 (M+1).
Embodiment 36
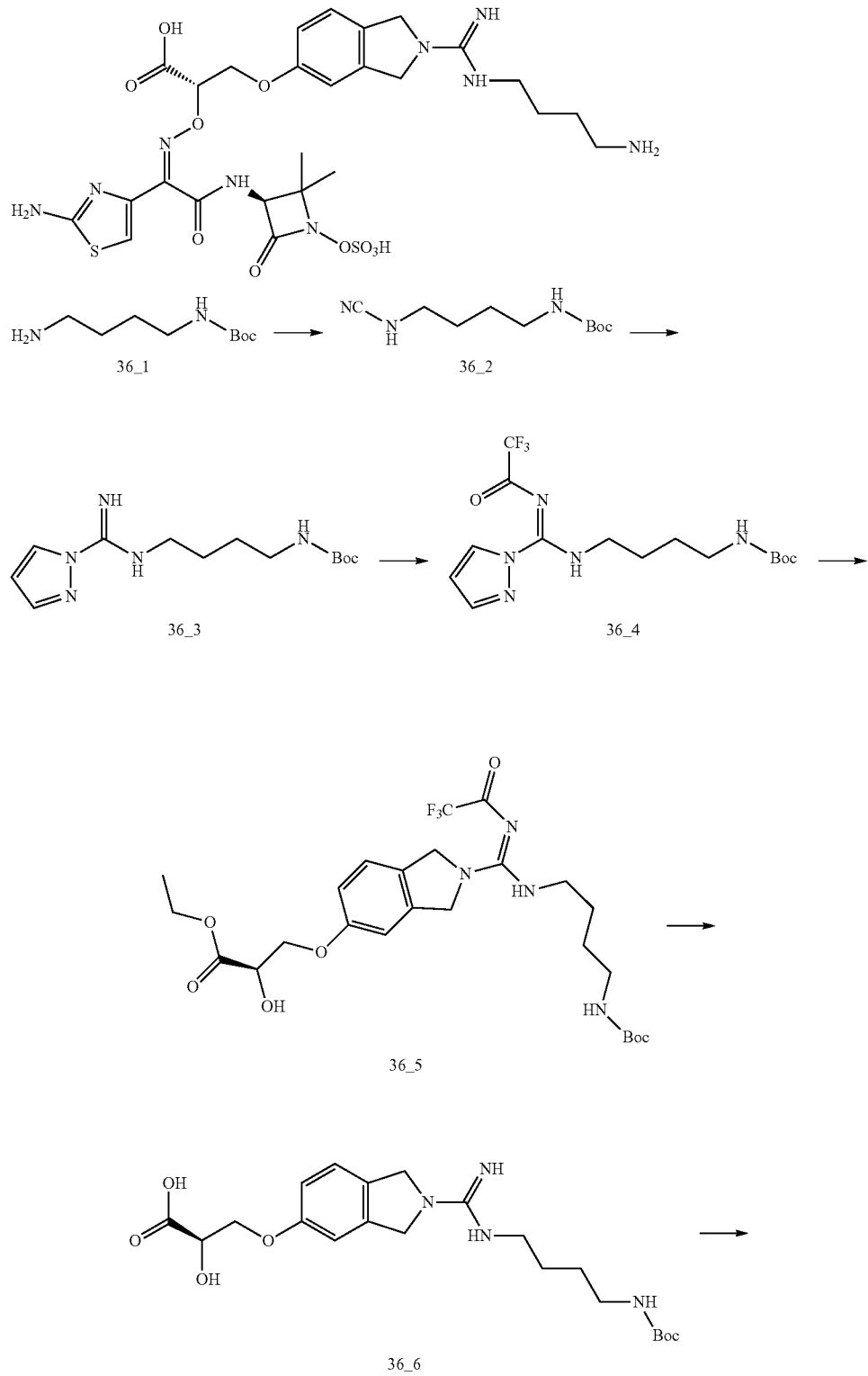

-continued
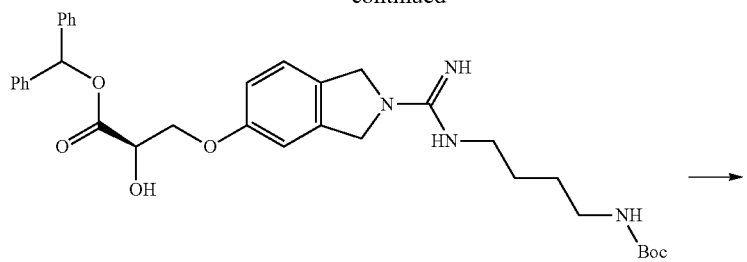
36_7
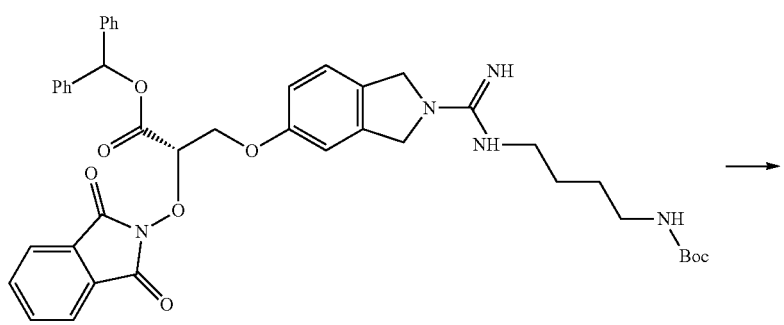
36_8
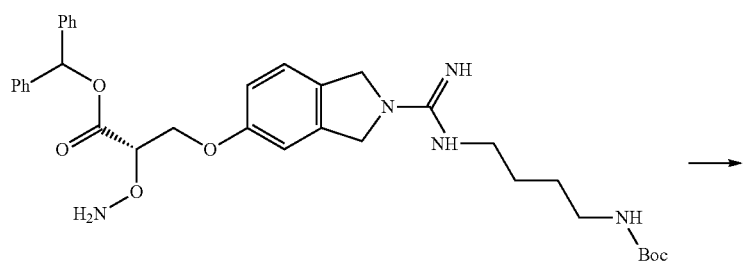
36_9
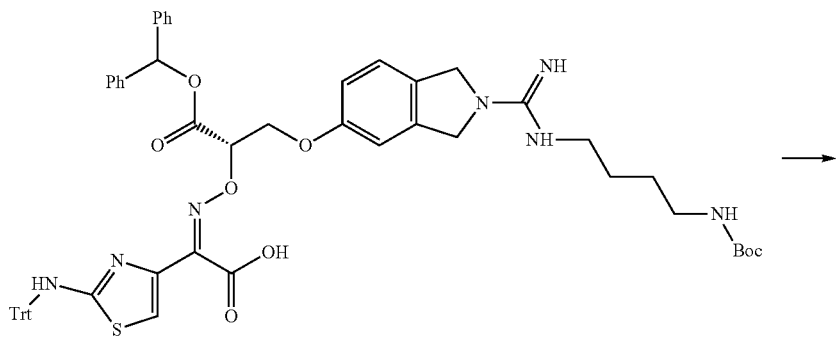
36_10
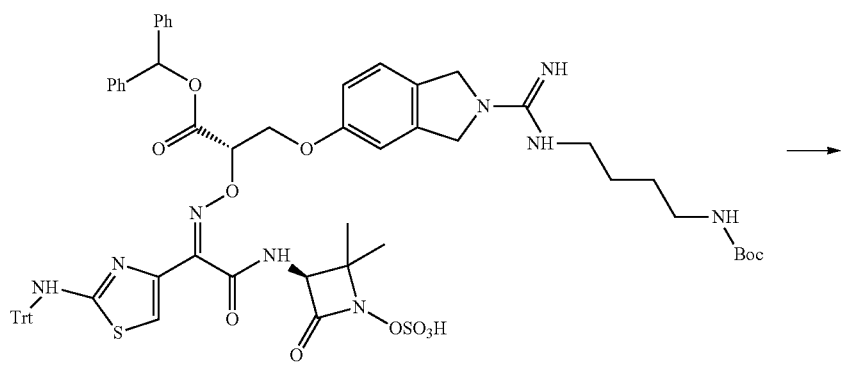
36_11

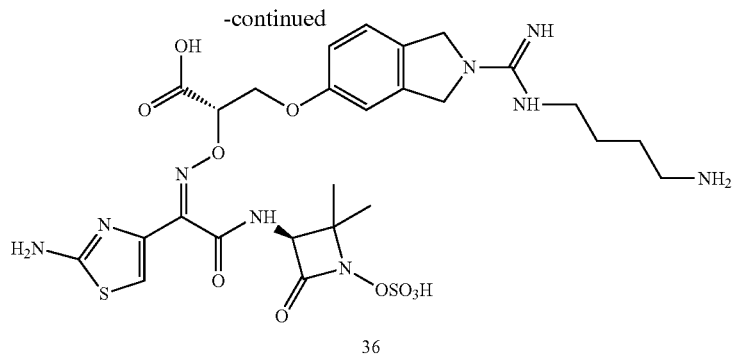

36

Step 1: sodium acetate (5.45 g, 66.40 mmol, 2.5 eq) and cyanogen bromide (5.63 g, 53.12 mmol, 2 eq) were added to a solution of 36_1 (5 g, 26.56 mmol, 1 eq) in methanol (50 mL). The mixture was stirred at 10° C. for 3 hours, then poured into saturated sodium bicarbonate solution (20 mL) and stirred for 5 min, then extracted with ethyl acetate (100 mL*2). The combined organic phase was washed with saturated sodium chloride (20 mL), dried over anhydrous sodium sulfate and filtered, then concentrated in vacuum, the residue was purified by silica gel chromatography (petroleum ether/ethyl acetate=3/1 to 0/1) to give compound 36_2.

Step 2: pyrazole hydrochloride (2.74 g, 26.26 mmol, 1 eq) was added to a solution of compound 36_2 (5.6 g, 26.26 mmol, 1 eq) in tetrahydrofuran (50 mL). The mixture was stirred at 70° C. for 12 hours and filtered, the filter cake was collected to give compound 36_3.

Step 3: trifluoroacetic anhydride (3.97 g, 18.88 mmol, 2.63 mL, 1 eq) and triethylamine (3.82 g, 37.76 mmol, 5.26 mL, 2 eq) were added to a solution of compound 36_3 (6 g, 18.88 mmol, 1 eq, HCl) in dichloromethane (60 mL). The mixture was stirred at 0° C. for 30 mins then poured into water (20 mL) and stirred for 5 min. The aqueous phase was extracted with dichloromethane (100 mL), the combined organic phase was washed with saturated sodium chloride (20 mL), dried over anhydrous sodium sulfate, filtered and concentrated under reduced pressure to give compound 36_4.

Step 4: triethylamine (2.08 g, 20.55 mmol, 5 eq) and compound 36_4 (1.55 g, 4.11 mmol, 1 eq) were added to a solution of compound 32_2 (1.5 g, 4.11 mmol, 1 eq, TFA) in DMF (15 mL). The mixture was stirred at 40° C. for 12 hours then poured into water (30 mL) and stirred for 5 min. The aqueous phase of the mixture was extracted with ethyl acetate (100 mL*2). The combined organic phase was washed with saturated sodium chloride (30 mL), dried over anhydrous sodium sulfate, filtered and concentrated under reduced pressure, the residue was purified by silica gel chromatography (petroleum ether/ethyl acetate=10/1 to 0/1) to give compound 36_5.

Step 5: sodium hydroxide (178.39 mg, 4.46 mmol, 2.5 eq) was added to a solution of compound 36_5 (1 g, 1.78 mmol, 1 eq) in methanol (15 mL). The mixture was stirred at 15° C. for 12 hours then sodium hydroxide (178.39 mg, 4.46 mmol, 2.5 eq) was added thereto, the mixture was then stirred at 15° C. for 17 hours and the pH value was adjusted to 6-7, then the mixture was concentrated under reduced pressure to give compound 36_6.

Step 6: diphenyl diazomethane (1.03 g, 5.29 mmol, 3 eq) was added to a solution of compound 36_6 (770 mg, 1.76 mmol, 1 eq) in MeOH (10 mL). The mixture was stirred at 15° C. for 12 hours and concentrated under reduced pressure, the residue was purified by silica gel chromatography (dichloromethane/methanol=50/1 to 10/1) to give compound 36_7.

Step 7: triphenylphosphine (326.38 mg, 1.24 mmol, 1.5 eq) and diisopropyl azodicarboxylate (335.49 mg, 1.66 mmol, 2 eq) were added to a solution of compound 36_7 (500 mg, 829.57 μmol, 1 eq) and 2-hydroxyisoindoline-1,3-dione (202.99 mg, 1.24 mmol, 1.5 eq) in tetrahydrofuran (5 mL). The mixture was stirred at 15° C. for 12 hours and concentrated under reduced pressure, the residue was purified by silica gel chromatography (petroleum ether/ethyl acetate=10/1 to 0/1) to give compound 36_8.

Step 8: NH$_2$NH$_2$.H$_2$O (24.08 mg, 408.91 μmol, 23.38 μL, 85% purity, 1 eq) was added to a solution of compound 36_8 (400 mg, 408.91 μmol, 1 eq) in ethanol (4 mL). The mixture was stirred at 15° C. for 30 mins and filtered, and the filtrate was concentrated under reduced pressure, the residue was poured into water (10 mL) and stirred for 5 min, then extracted with dichloromethane (100 mL). The combined organic phase was washed with saturated sodium chloride (20 mL), dried over anhydrous sodium sulfate and filtered, then concentrated under reduced pressure to give compound 36_9.

Step 9: intermediate A2 (138.89 mg, 335.10 μmol, 0.9 eq) was added to a solution of compound 36_9 (230 mg, 372.33 μmol, eq) in methanol (3 mL) and dichloromethane (1 mL). The mixture was stirred at 15° C. for 30 mins and concentrated under reduced pressure to give compound 36_10.

Step 10: N,N'-diisopropylcarbodiimide (49.77 mg, 394.40 μmol, 61.07 eq) and HOBt (53.29 mg, 394.40 μmol, 2 eq) were added to a solution of compound 36_10 (200 mg, 197.20 μmol, 1 eq) in DMF (2 mL). The mixture was stirred at 15° C. for 1 hour then intermediate A1 (62.18 mg, 295.80 μmol, 1.5 eq) and sodium bicarbonate (66.26 mg, 788.80 μmol, 4 eq) were added thereto. The mixture was stirred at 15° C. for 15 hours, then poured into water (10 mL) and stirred for 5 min. The mixture was filtered and the filter cake was collected to give compound 36_11.

Step 11: triethylamine (21.74 mg, 190.65 μmol, 14.12 μL, 1 eq) was added to a solution of compound 36_11 (230.00 mg, 190.65 μmol, 1 eq) in dichloromethane (1 mL). The mixture was stirred at 0° C. for 1 hour, then petroleum ether/ethyl acetate (10 mL, 1/3) was added and stirred for another 5 min, the mixture was filtered, and the filter cake was purified by preparative HPLC (column: Boston Green ODS 150×30 5; mobile phase: [water (0.1% trifluoroacetic acid)-acetonitrile]; acetonitrile %: 1%-30%, 10 min) to give compound 36.

$^1$H NMR (400 MHz, D$_2$O) δ=7.23 (br d, J=8.9 Hz, 1H), 7.07 (s, 1H), 6.89 (br s, 2H), 5.07 (br d, J=5.7 Hz, 1H), 4.65-4.55 (m, 5H), 4.52-4.32 (m, 2H), 3.29 (br s, 2H), 2.99 (br t, J=6.4 Hz, 2H), 1.68 (br s, 4H), 1.41-1.36 (m, 3H), 1.01 (s, 3H) ppm; LCMS (ESI) m/z: 698.4 (M+1).

Embodiment 37

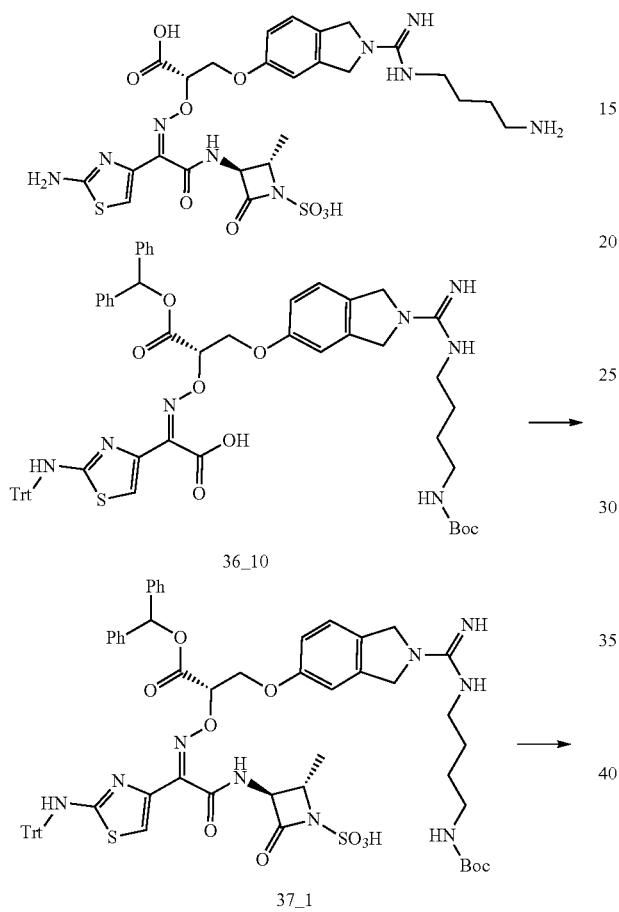

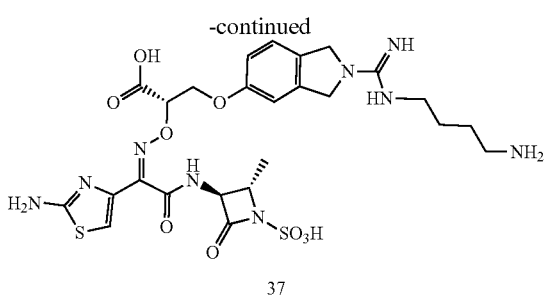

Step 1: N,N'-diisopropylcarbodiimide (29.86 mg, 236.64 μmol, 36.64 2 eq) and HOBt (31.98 mg, 236.64 μmol, 2 eq) were added to a solution of compound 36_10 (120 mg, 118.32 μmol, 1 eq) in DMF (1 mL). The mixture was stirred at 15° C. for 1 hour, then intermediate A3 (25.58 mg, 141.99 μmol, 1.2 eq) and sodium bicarbonate (39.76 mg, 473.28 μmol, 18.41 μL, 4 eq) were added thereto. The mixture was stirred at 15° C. for 11 hours, then water (10 mL) was added and stirred for 5 min, the mixture was filtered and the filter cake was collected to give compound 37_1.

Step 2: trifluoroacetic acid (3.08 g, 27.01 mmol, 2 mL, 317.76 eq) was added to a solution of compound 37_1 (100 mg, 85.01 μmol, 1 eq) in dichloromethane (1 mL). The mixture was stirred at 0° C. for 1 hour, petroleum ether/ethyl acetate (10 mL, 1/3) was added thereto and stirred for 5 min, the mixture was filtered and the filter cake was purified by preparative HPLC (column: Phenomenex Synergi C18 150× 25×10 μm; mobile phase: [water (0.1% trifluoroacetic acid)-acetonitrile]; acetonitrile %: 1%-30%, 9 min) to give compound 37.

$^1$H NMR (400 MHz, D$_2$O) δ=7.22 (br d, J=9.2 Hz, 1H), 7.06 (s, 1H), 6.92 (br s, 2H), 5.09 (br s, 1H), 4.63-4.51 (m, 5H), 4.49-4.41 (m, 1H), 4.33 (br s, 1H), 3.63 (br s, 1H), 3.27 (br t, J=6.1 Hz, 2H), 2.98 (br t, J=6.7 Hz, 2H), 1.66 (br s, 4H), 1.17 (br d, J=6.1 Hz, 3H) ppm; LCMS (ESI) m/z: (M+1).

Embodiment 38

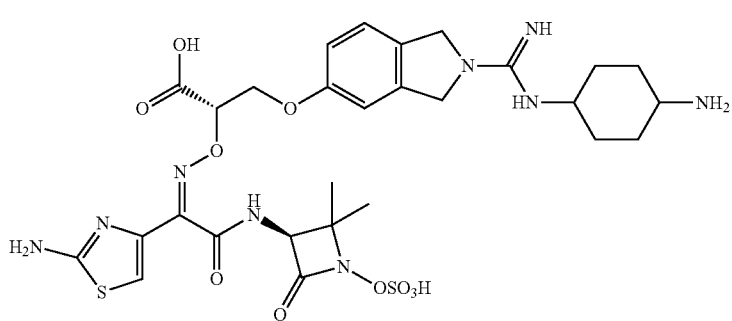

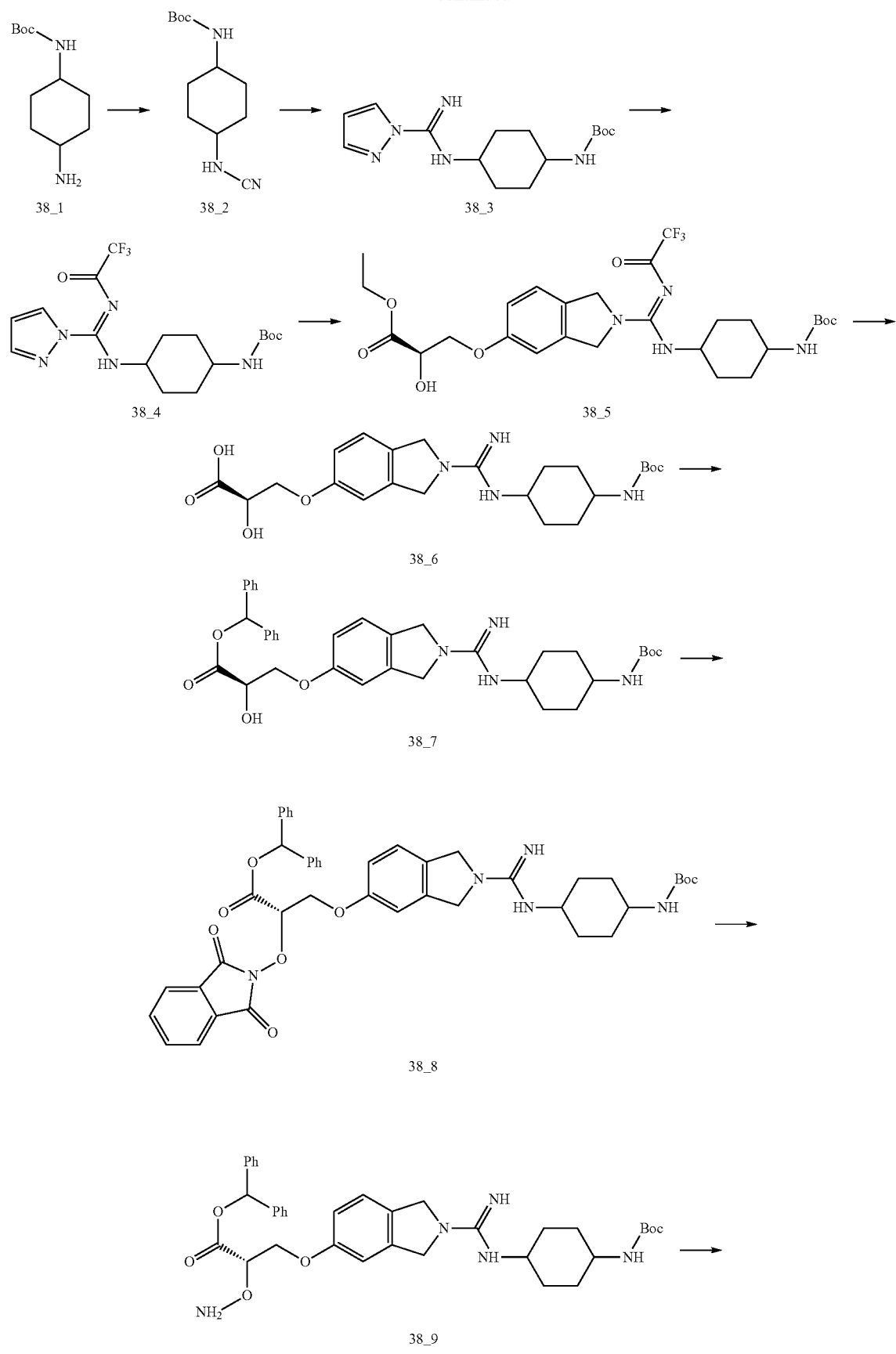
-continued

-continued

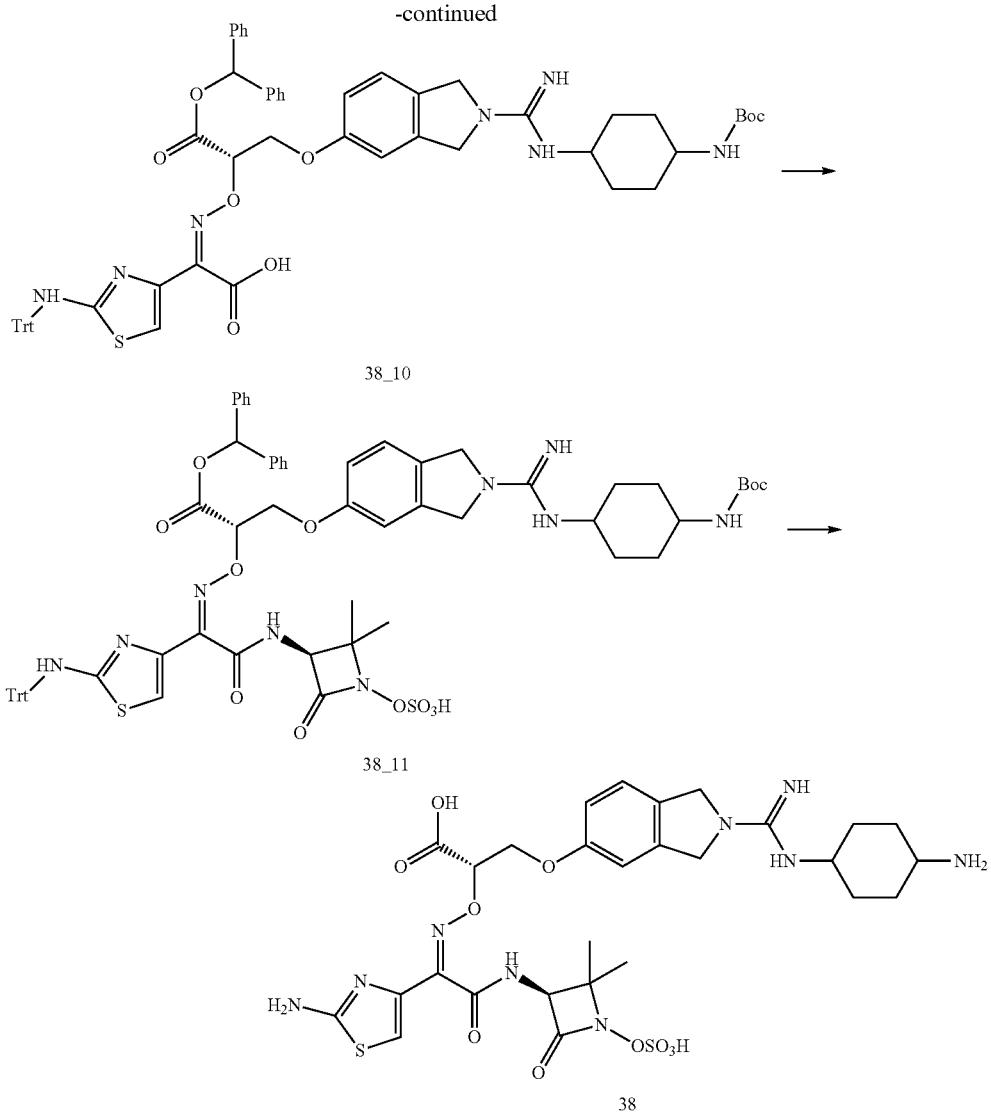

Step 1: sodium acetate (4.50 g, 54.83 mmol, 2.5 eq) and cyanogen bromide (4.65 g, 43.86 mmol, 2 eq) were added to a solution of compound 38_1 (4.7 g, 21.93 mmol, 1 eq) in methanol (50 mL). The mixture was stirred at 10° C. for 3 hours then poured into saturated sodium bicarbonate (20 mL) and stirred for 5 min. The aqueous phase was extracted with ethyl acetate (100 mL*2). The combined organic phase was washed with saturated sodium chloride (20 mL), dried over anhydrous sodium sulfate, filtered and concentrated under reduced pressure to give compound 38_2.

Step 2: pyrazole hydrochloride (2.27 g, 21.73 mmol, 1 eq) was added to a solution of compound 382 (5.2 g, 21.73 mmol, 1 eq) in THF (50 mL). The mixture was stirred at 70° C. for 12 hours then cooled down, the mixture was filtered and the filter cake was collected to give compound 38_3.

Step 3: trifluoroacetic anhydride (4.03 g, 19.19 mmol, 2.67 mL, 1 eq) and triethylamine (3.88 g, 38.39 mmol, 5.34 mL, 2 eq) were added to a solution of compound 38_3 (6.6 g, 19.19 mmol, 1 eq, HCl) in dichloromethane (60 mL). The mixture was stirred at 0° C. for 30 mins then poured into water (20 mL) and stirred for 5 min. The aqueous phase was extracted with dichloromethane (100 mL). The combined organic phase was washed with saturated sodium chloride (20 mL), dried over anhydrous sodium sulfate, filtered and concentrated under reduced pressure to give compound 38_4.

Step 4: triethylamine (4.16 g, 41.06 mmol, 5.72 mL, 5 eq) and the trifluoroacetate of 32_2 (3 g, 8.21 mmol, 1 eq) were added to a solution of compound 38_4 (2 g, 4.96 mmol, 0.60 eq) in DMF (30 mL). The mixture was stirred at 40° C. for 12 hours then poured into water (100 mL) and stirred for 5 min. The mixture extracted with ethyl acetate (200 mL), the obtained organic phase was washed with saturated sodium chloride (30 mL), dried over anhydrous sodium sulfate, filtered and concentrated under reduced pressure, the residue was purified by silica gel chromatography (petroleum ether/ethyl acetate=10/1 to 0/1) to give compound 38_5.

Step 5: sodium hydroxide (306.83 mg, 7.67 mmol, 2.5 eq) was added to a solution of compound 38_5 (1.8 g, 3.07 mmol, 1 eq) in methanol (20 mL), the mixture was stirred at 15° C. for 15 hours, then NaOH (306 mg) was added thereto and stirred for another 12 hours, then the pH value was adjusted to 5-6 by using dilute hydrochloric acid, and the mixture was concentrated under reduced pressure to give compound 38_6.

Step 6: diphenyl diazomethane (1.76 g, 9.08 mmol, 3 eq) was added to a solution of compound 38_6 (1.4 g, 3.03 mmol, 1 eq) in methanol (15 mL). The mixture was stirred at 15° C. for 12 hours and concentrated under reduced pressure, the residue was purified by silica gel chromatography (dichloromethane/methanol=50/1 to 10/1) to give compound 38_7.

Step 7: triphenylphosphine (425.49 mg, 1.62 mmol, 1.5 eq) and diisopropyl azodicarboxylate (437.38 mg, 2.16 mmol, 420.55 μL, 2 eq) were added to a solution of compound 38_7 (680 mg, 1.08 mmol, 1 eq) and 2-hydroxyisoindoline-1,3-dione (264.64 mg, 1.62 mmol, 1.5 eq) in THF (8 mL). The mixture was stirred at 15° C. for 12 hours and concentrated under reduced pressure, the residue was purified by silica gel chromatography (dichloromethane/methanol=50/1 to 10/1) to give compound 38_8.

Step 8: $NH_2NH_2 \cdot H_2O$ (38.05 mg, 646.10 μmol, 36.94 μL, 85% purity, 1 eq) was added to a solution of compound 38_8 (500 mg, 646.10 μmol, 1 eq) in ethanol (2 mL). The mixture was stirred at 15° C. for 30 mins and concentrated under reduced pressure to give compound 38_9.

Step 9: intermediate A2 (289.72 mg, 699.01 μmol, 0.9 eq) was added to a solution of compound 38_9 (500 mg, 776.67 μmol, 1 eq) in dichloromethane (2 mL) and methanol (6 mL). The mixture was stirred at 15° C. for 30 mins and concentrated under reduced pressure to give compound 38_10.

Step 10: N,N'-diisopropylcarbodiimide (48.53 mg, 2 eq) and HOBt (51.96 mg, 2 eq) was added to a solution of compound 38_10 (200 mg, 192.26 μmol, 1 eq) in DMF (2 mL). The mixture was stirred at 15° C. for 1 hour, then intermediate A1 (60.62 mg, 288.40 μmol, 1.5 eq) and sodium bicarbonate (64.61 mg, 769.06 μmol, 29.91 μL, 4 eq) were added thereto, the mixture was stirred at 15° C. for 11 hours, water (10 mL) was added and stirred for 5 min, the mixture was filtered in vacuum and the filter cake was collected and dried to give compound 38_11.

Step 11: trifluoroacetic acid (3.08 g, 27.01 mmol, 2 mL, 166.45 eq) was added to a solution of compound 38_11 (200 mg, 162.28 μmol, 1 eq) in dichloromethane (1 mL). The mixture was stirred at 0° C. for 1 hour and petroleum ether/ethyl acetate (10 mL, 1/3) was added, the mixture was filtered and the filter cake was purified by preparative HPLC (column: Boston Prime C18 150*30 mm 5 μm water (0.1% trifluoroacetic acid)-acetonitrile) to give compound 38.

$^1$H NMR (400 MHz, $D_2O$) δ=7.23 (br d, J=9.0 Hz, 1H), 7.08 (s, 1H), 6.94-6.86 (m, 2H), 5.10 (br s, 1H), 4.61 (br s, 1H), 4.58 (br s, 3H), 4.50 (br d, J=9.5 Hz, 2H), 4.46-4.36 (m, 1H), 3.44 (br s, 1H), 3.19 (br s, 1H), 2.10 (br d, J=5.6 Hz, 4H), 1.51 (br t, J=9.1 Hz, 4H), 1.43 (s, 3H), 1.05 (s, 3H) ppm; LCMS (ESI) m/z: 724.3 (M+1).

Embodiment 39

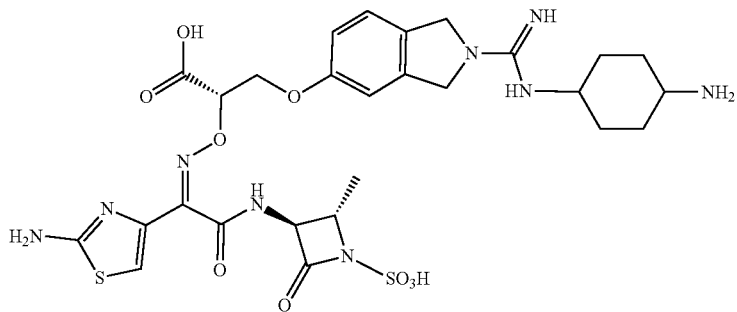

39

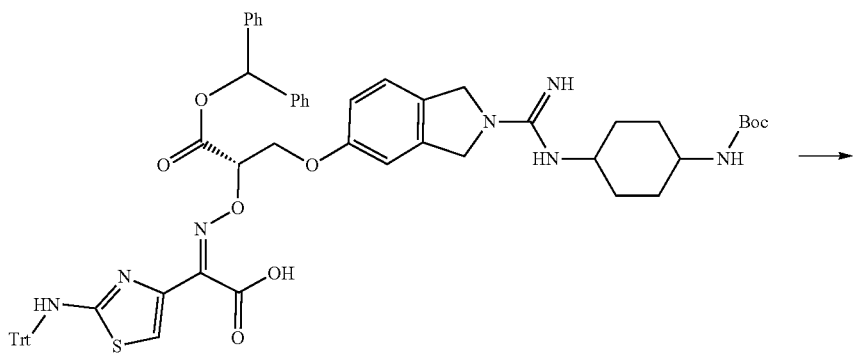

38_10

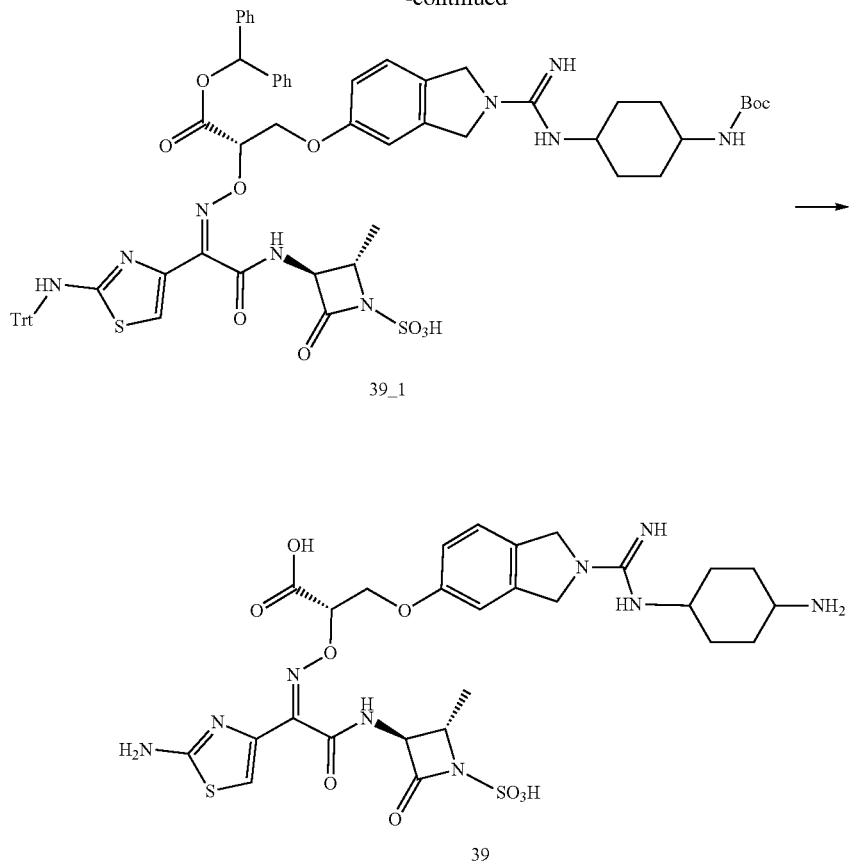

39_1

39

Step 1: N,N'-diisopropylcarbodiimide (24.26 mg, 192.27 μmol, 29.77 2 eq) and HOBt (25.98 mg, 192.27 μmol, 2 eq) were added to a solution of compound 38_10 (100 mg, 96.13 μmol, 1 eq) in DMF (1 mL). The mixture was stirred at 15° C. for 1 hour, then intermediate A3 (20.79 mg, 115.36 μmol, 1.2 eq) and sodium bicarbonate (32.30 mg, 384.53 μmol, 14.96 μL, 4 eq) were added, the mixture was stirred at 15° C. for 11 hours then water (10 mL) was added, the mixture was filtered and the filter cake was collected to give compound 39_1.

Step 2: trifluoroacetic acid (3.08 g, 27.01 mmol, 2 mL, 324.79 eq) was added to a solution of compound 39_1 (100 mg, 83.17 mol, 1 eq) in dichloromethane (1 mL). The mixture was stirred at 0° C. for 1 hour then petroleum ether/ethyl acetate (10 mL, 1/3) was added thereto, the mixture was filtered, and the filter cake was purified by preparative HPLC (column: Boston Prime C18 150×30 mm 5 μm; mobile phase: [water (0.1% trifluoroacetic acid)-acetonitrile]; acetonitrile %: 10%-27%, 7 min) to give compound 39.

$^1$H NMR (400 MHz, D$_2$O) δ=7.31-7.18 (m, 1H), 7.04 (s, 1H), 6.94 (br s, 2H), 5.00 (br s, 1H), 4.53 (br d, J=11.7 Hz, 3H), 4.46-4.39 (m, 2H), 4.34 (m, 2H), 3.76-3.56 (m, 1H), 3.43 (br s, 1H), 3.18 (br s, 1H), 2.17-1.99 (m, 4H), 1.49 (br s, 4H), 1.18 (br d, J=2.9 Hz, 3H) ppm; LCMS (ESI) m/z: 694.4 (M+1).

Embodiment 40

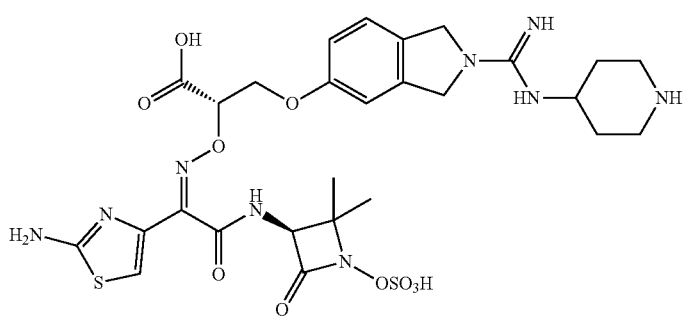

40

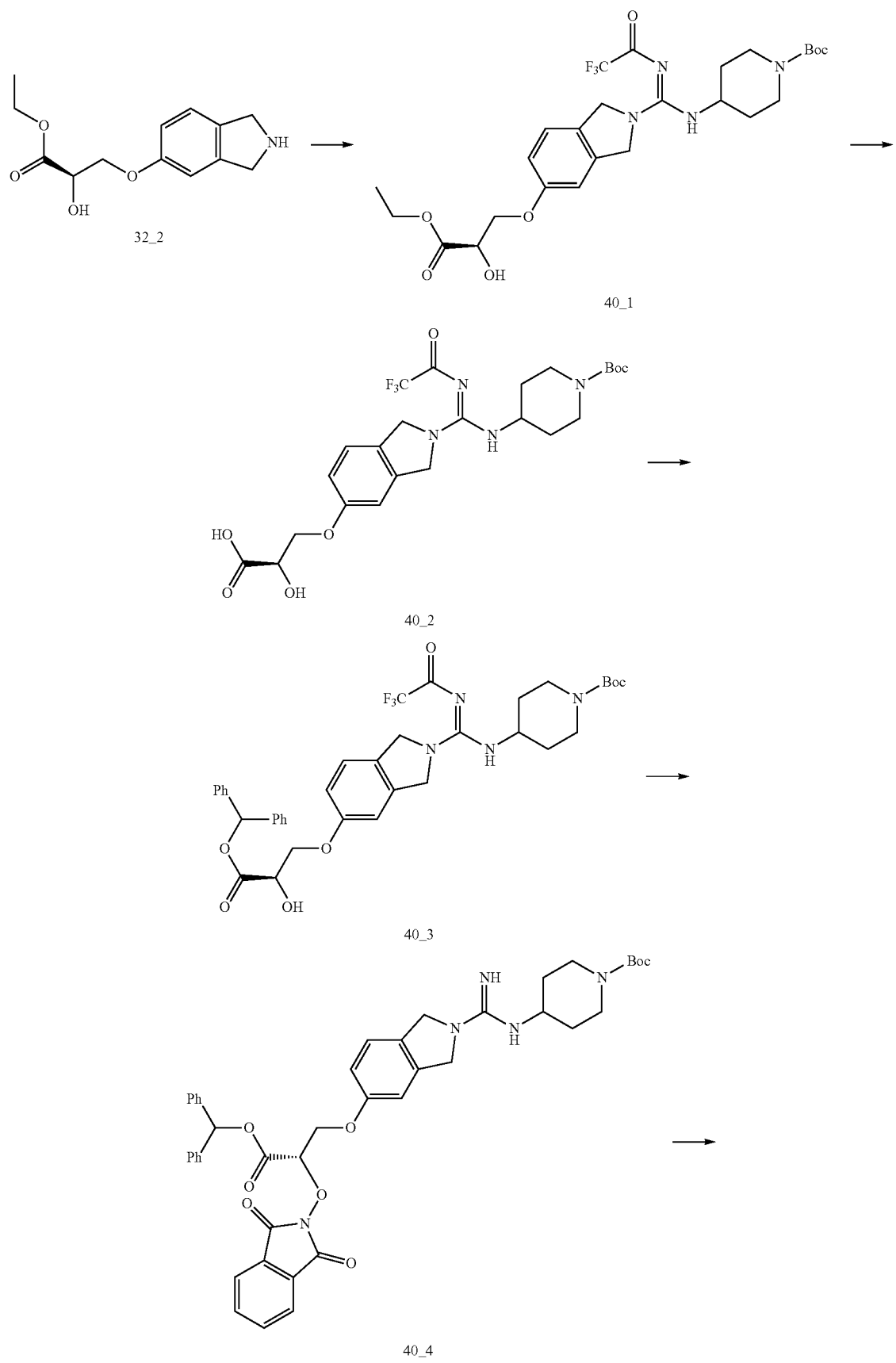

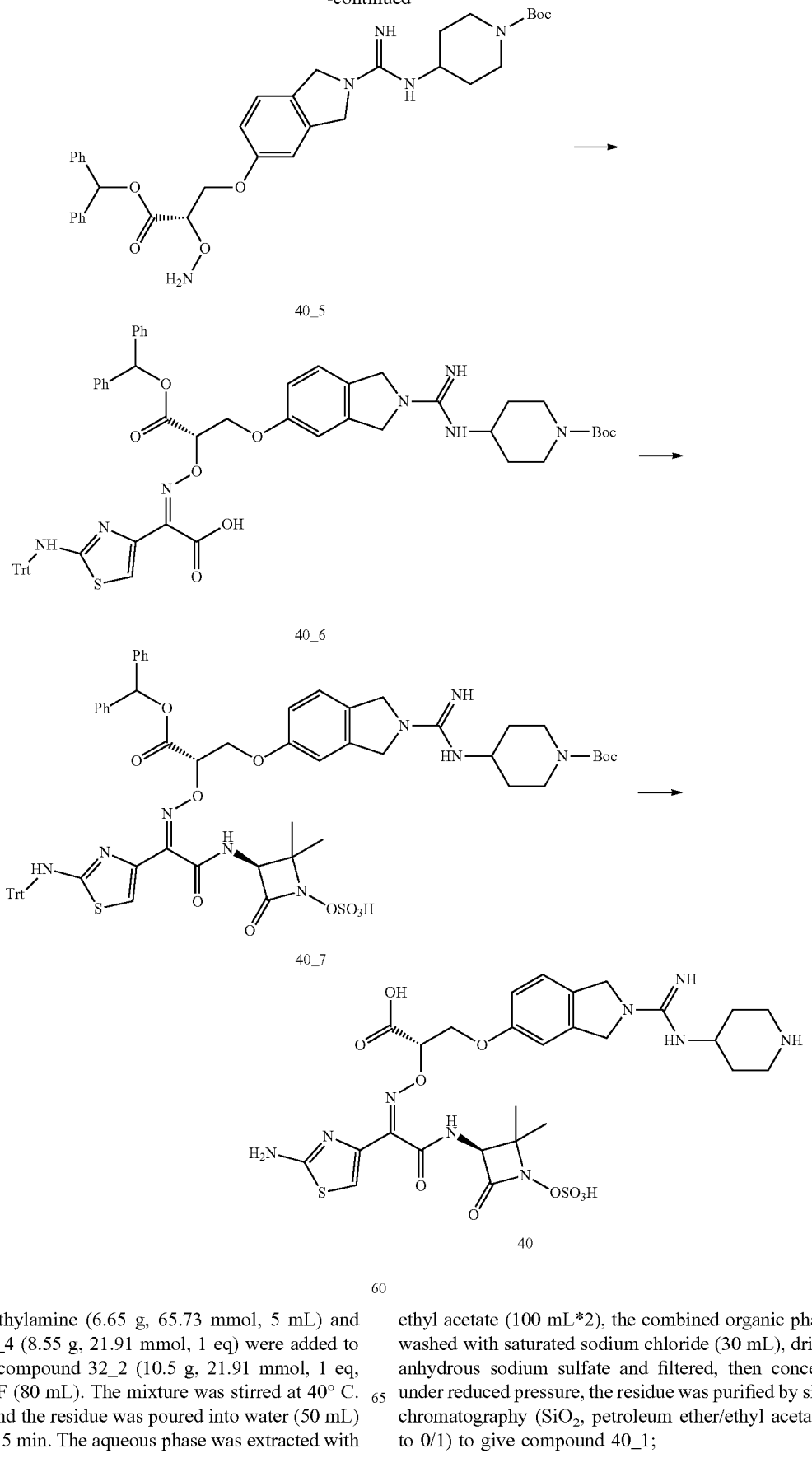

Step 1: triethylamine (6.65 g, 65.73 mmol, 5 mL) and compound 12_4 (8.55 g, 21.91 mmol, 1 eq) were added to a solution of compound 32_2 (10.5 g, 21.91 mmol, 1 eq, 2TFA) in DMF (80 mL). The mixture was stirred at 40° C. for 14 hours and the residue was poured into water (50 mL) and stirred for 5 min. The aqueous phase was extracted with ethyl acetate (100 mL*2), the combined organic phase was washed with saturated sodium chloride (30 mL), dried over anhydrous sodium sulfate and filtered, then concentrated under reduced pressure, the residue was purified by silica gel chromatography (SiO$_2$, petroleum ether/ethyl acetate=10/1 to 0/1) to give compound 40_1;

Step 2: sodium hydroxide (1.40 g, 34.93 mmol, 4 eq) was added to a solution of compound 40_1 (5 g, 8.73 mmol, 1 eq) in methanol (50 mL). The mixture was stirred at 25° C. for 14 hours, the pH value was adjusted to 3-5, the mixture was stirred at 40° C. then concentrated under reduced pressure to give compound 40_2;

Step 3: diphenyl diazomethane (4.5 g, 23.17 mmol, 2.66 eq) was added in batches to a solution of compound 40_2 (3.9 g, 8.70 mmol, 1 eq) in methanol (40 mL). The mixture was stirred at 20° C. for 12 hours and concentrated under reduced pressure, the residue was purified by silica gel chromatography (SiO$_2$, dichloromethane/methanol=1/0 to 10/1) to give compound 40_3;

Step 4: triphenylphosphine (1.92 g, 7.32 mmol, 1.5 eq) and DIAD (1.97 g, 9.76 mmol, 1.90 mL, 2 eq) were added to a solution of compound 40_3 (3 g, 4.88 mmol, 1 eq) and 2-hydroxyisoindoline-1,3-dione (875.72 mg, 5.37 mmol, 1.1 eq) in tetrahydrofuran (30 mL). The mixture was stirred at 25° C. for 12 hours then concentrated in vacuum, the residue was purified by silica gel chromatography (SiO$_2$, dichloromethane/methanol=50/1 to 10/1) to give compound 40_4. LCMS (ESI) m/z: 760.4 (M+1);

Step 5: NH$_2$NH$_2$.H$_2$O (193.77 mg, 3.29 mmol, 188.13 µL, 85% purity, 1 eq) was added to a solution of compound 40_4 (2.5 g, 3.29 mmol, 1 eq) in ethanol (25 mL). The mixture was stirred at 15° C. for 30 mins and concentrated under reduced pressure, the residue was filtered and the filtrate was concentrated in vacuum to give compound 40_5.

Step 6: intermediate A2 (1.19 g, 2.86 mmol, 0.9 eq) was added to a solution of compound 40_5 (2 g, 3.18, 1 eq) in methanol (12 mL) and dichloromethane (4 mL). The mixture was stirred at 15° C. for 30 mins and concentrated under reduced pressure to give compound 40_6. LCMS (ESI) m/z: 1026.6 (M+1);

Step 7: N,N'-diisopropylcarbodiimide (737.01 mg, 5.84 mmol, 904.30 µL, 2 eq) and HOBt (789.10 mg, 5.84 mmol, 2 eq) were added to a solution of compound 40_6 (3 g, 2.92 mmol, 1 eq) in DMF (30 mL). The mixture was stirred at 25° C. for 1 hour then intermediate A1 (920.71 mg, 4.38 mmol, 1.5 eq) and sodium bicarbonate (981.20 mg, 11.68 mmol, 4 eq) were added thereto, the mixture was stirred at 25° C. for 12 hours, then poured into water (20 mL) and stirred for 5 min. The mixture was filtered and the filter cake was collected and dried to give compound 40_7.

Step 8: trifluoroacetic acid (46.20 g, 405.18 mmol, 30.00 mL, 123.42 eq) was added to a solution of compound 40_7 (4.00 g, 3.28 mmol, 1 eq) in dichloromethane (30 mL). The mixture was stirred at 0° C. for 1 hour, then petroleum ether/ethyl acetate (50 mL, v/v=1/2) was added thereto and stirred for 5 min. The mixture was filtered and the filter cake was collected, which was purified by preparative HPLC (column: Phenomenex Synergi Max-RP 250*50 mm*10 µm; mobile phase: [water (0.1% trifluoroacetic acid)-acetonitrile]; acetonitrile %: 5%-35%, 20 min) to give compound 40.

$^1$H NMR (400 MHz, d$_6$-DMSO) δ=7.28-7.21 (m, 1H), 7.08 (d, J=2.3 Hz, 1H), 6.91 (br s, 2H), 5.09 (br s, 1H), 4.69-4.68 (m, 1H), 4.68-4.65 (m, 1H), 4.62 (br s, 2H), 4.60 (s, 1H), 4.54-4.47 (m, 1H), 4.43 (br s, 1H), 3.84-3.72 (m, 1H), 3.50 (br d, J=13.8 Hz, 2H), 3.08 (br t, J=12.1 Hz, 2H), 2.24 (br d, J=13.7 Hz, 2H), 1.93-1.77 (m, 2H), 1.42 (s, 3H), 1.01 (s, 3H) ppm; LCMS (ESI) m/z: 710.3 (M+1).

Embodiment 41

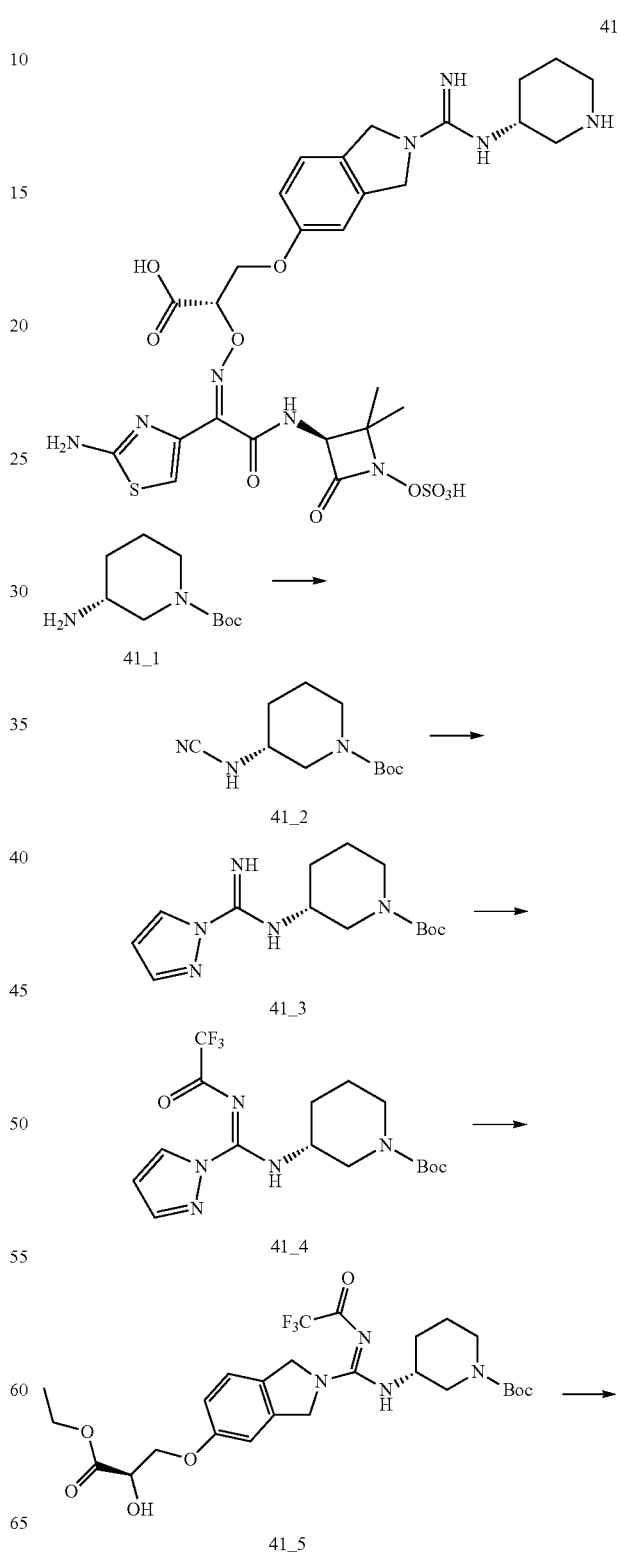

201
-continued

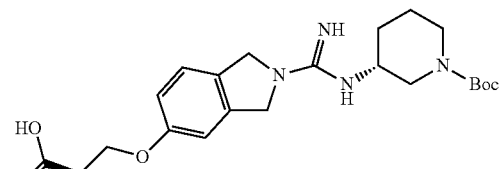
41_6

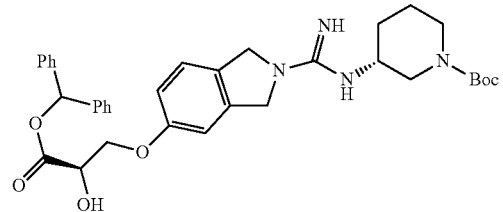
41_7

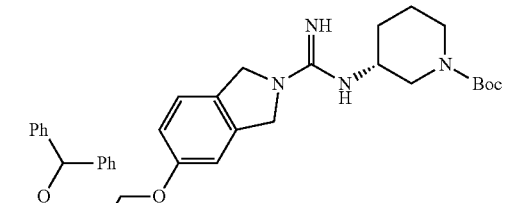
41_8

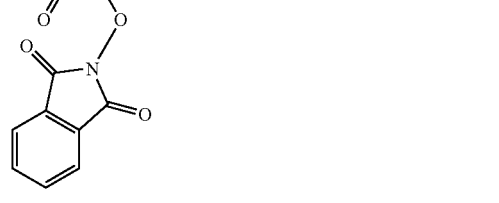
41_9

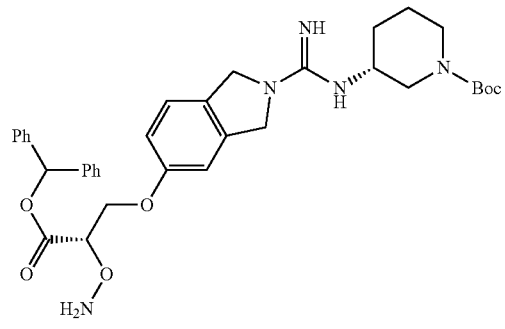
41_10

202
-continued

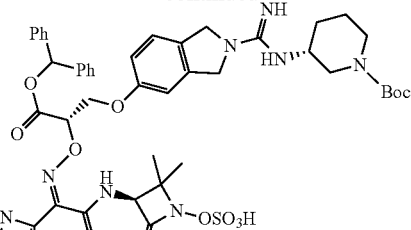
41_11

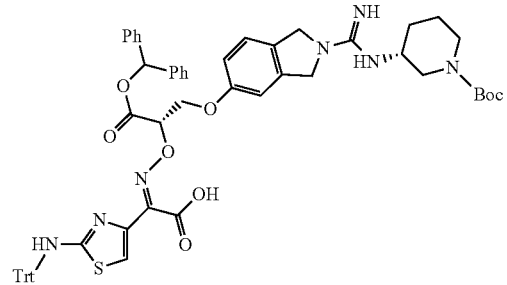
41

Step 1: cyanogen bromide (11 g, 103.85 mmol, 7.64 mL, 2.08 eq) and sodium acetate (10.24 g, 124.83 mmol, 2.5 eq) were added to a solution of compound 41_1 (10 g, 49.93 mmol, 1 eq) in methanol (10 mL). The mixture was stirred at 20° C. for 1 hour, then poured into water (50 mL) and stirred for 5 min, the aqueous phase was extracted with ethyl acetate (100 mL*3), the combined organic phase was washed with saturated sodium chloride (30 mL), dried over anhydrous sodium sulfate, the mixture was filtered and concentrated under reduced pressure to give compound 41_2;

Step 2: pyrazole hydrochloride (5.61 g, 53.71 mmol, 1.1 equivalent) was added to a solution of compound 41_2 (11 g, 48.83 mmol, 1 eq) in tetrahydrofuran (80 mL). The mixture was stirred at 70° C. for 12 hours and filtered, the filtrate was concentrated under reduced pressure to give compound 41_3; LCMS (ESI) m/z: 294.0 (M+1);

Step 3: trifluoroacetic anhydride (7.88 g, 37.50 mmol, 5.22 mL, 1 eq) and triethylamine (7.59 g, 74.99 mmol, 10.44 mL, 2 eq) were added to a solution of compound 41_3 (11 g, 37.50 mmol, 1 eq) in dichloromethane (100 mL). The mixture was stirred at 15° C. for 1 hour then poured into water (50 mL) and stirred for 5 min. The aqueous phase was extracted with dichloromethane (100 mL*2), the combined organic phase was washed with saturated sodium chloride (30 mL), dried over anhydrous sodium sulfate, filtered and concentrated under reduced pressure to give compound 41_4;

Step 4: triethylamine (11.08 g, 109.50 mmol, 15.24 mL, 4 eq) and compound 41_4 (10 g, 25.68 mmol, 0.94 eq) were added to a solution of the trifluoroacetate of compound 32_2 (10 g, 27.37 mmol, 1 eq) in DMF (100 mL). The mixture was stirred at 40° C. for 12 hours then poured into water (50 mL) and stirred for 5 min. The aqueous phase was extracted with ethyl acetate (200 mL*2), the combined organic phase was washed with saline (50 mL), dried over anhydrous sodium sulfate, filtered and concentrated under reduced pressure, the residue was purified by silica gel chromatography (SiO₂, petroleum ether/ethyl acetate=1/0 to 0/1) to give compound 41_5.

Step 5: sodium hydroxide (1.68 g, 41.92 mmol, 4 eq) was added to a solution of compound 41_5 (6 g, 10.48 mmol, 1 eq) in methanol (60 mL). The mixture was stirred at 20° C. for 12 hours, then stirred at 35° C. for another 3 hours, the pH value was adjusted to 4-5, and the mixture was concentrated under reduced pressure to give compound 41_6.

Step 6: a solution of compound 41_6 (4.7 g, 10.48 mmol, 1 eq) in methanol (60 mL) was added dropwise to a solution of diphenyl diazomethane (5.9 g, 30.38 mmol, 2.90 eq) in dichloromethane (60 mL). The mixture was stirred at 20° C. for 1 hour, and extracted with dichloromethane (100 mL). The combined organic phase was washed with saturated sodium chloride (100 mL*2), dried over anhydrous sodium sulfate, filtered and concentrated under reduced pressure, the residue was purified by silica gel chromatography (SiO₂, dichloromethane/methanol=1/0 to 10/1) to give compound 41_7.

Step 7: 2-hydroxyisoindoline-1,3-dione (835.91 mg, 5.12 mmol, 1.05 eq), triphenylphosphine (1.92 g, 7.32 mmol, 1.5 eq) and DIAD (1.97 g, 9.76 mmol, 1.90 mL, 2 eq) were added to a solution of compound 41_7 (1.92 g, 7.32 mmol, 1.5 eq) in tetrahydrofuran (30 mL). The mixture was stirred at 20° C. for 12 hours, then concentrated under reduced pressure, the residue was purified by silica gel chromatography (SiO₂, dichloromethane/methanol=50/1 to 20/1) to give compound 41_8. LCMS (ESI) m/z: 760.6 (M+1).

Step 8: NH₂NH₂·H₂O (174.64 mg, 2.97 mmol, 169.55 μL, 85% purity, 1 eq) was added to a solution of compound 41_8 (2.7 g, 2.97 mmol, 1 eq) in ethanol (30 mL). The mixture was stirred at 20° C. for 20 mins and concentrated under reduced pressure to give compound 41_9.

Step 9: intermediate A2 (1.24 g, 3.00 mmol, 0.9 eq)) was added to a solution of compound 41_9 (1.24 g, 3.00 mmol, 3.13 mmol, 1 eq) in methanol (27 mL) and dichloromethane (9 mL). The mixture was stirred at 20° C. for 30 mins and concentrated under reduced pressure, the obtained solid was washed with petroleum ether/ethyl acetate (30 mL, v/v=1/1) to give compound 41_10. LCMS (ESI) m/z: 1026.4 (M+1);

Step 10: HOBt (682.58 mg, 5.05 mmol, 2 eq) and DIC (637.52 mg, 5.05 mmol, 782.23 μL, 2 eq) were added to a solution of compound 41_10 (3 g, 2.53 mmol, 1 eq) in DMF (30 mL). The mixture was stirred at 20° C. for 1 hour, then intermediate A1 (796.42 mg, 3.79 mmol, 1.5 eq) and sodium bicarbonate (848.77 mg, 10.10 mmol, 392.95 μL, 4 eq) were added thereto, the mixture was stirred at 20° C. for 12 hours, then poured into water (30 mL) and stirred for 5 min, the mixture was filtered and the filter cake was collected to give compound 41_11.

Step 11: trifluoroacetic acid (13.48 g, 118.18 mmol, 8.75 mL, 41.14 eq) was added to a solution of compound 41_11 (3.5 g, 2.87 mmol, 1 eq) in dichloromethane (10 mL). The mixture was stirred at 0° C. for 1 hour, then petroleum ether/ethyl acetate (30 mL, v/v=1/3) was added and stirred for 5 min, the mixture was filtered and the filter cake was collected. The residue was purified by preparative HPLC (column: Kromasil 250*50 mm*10 um; mobile phase: [water (0.1% trifluoroacetic acid)-acetonitrile]; acetonitrile %: 2%-30%, 25 min) to give compound 41. ¹H NMR (400 MHz, d₆-DMSO) δ=7.26 (br d, J=8.8 Hz, 1H), 7.10 (br s, 1H), 6.92 (br s, 2H), 5.21-5.09 (m, 1H), 5.06-4.92 (m, 1H), 4.62-4.60 (m, 2H), 4.57 (br s, 2H), 4.47-4.37 (m, 2H), 3.96-3.81 (m, 1H), 3.54 (br d, J=12.2 Hz, 1H), 3.34 (br d, J=12.8 Hz, 1H), 3.07-2.91 (m, 2H), 2.17 (br s, 1H), 2.03 (br d, J=9.7 Hz, 1H), 1.87-1.64 (m, 2H), 1.42 (s, 3H), 1.00 (br s, 3H) ppm; LCMS (ESI) m/z: 710.4 (M+1).

Embodiment 42

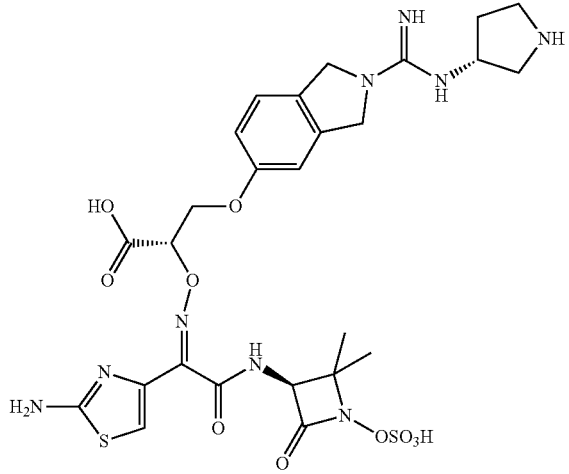

41

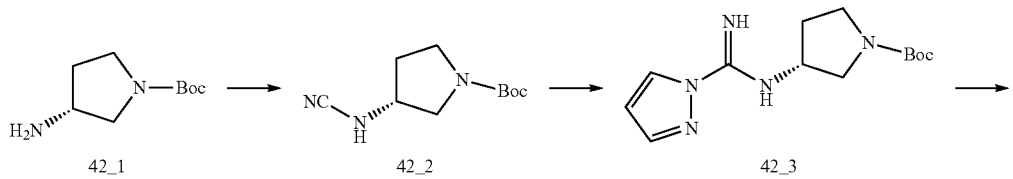

42_1    42_2    42_3

-continued
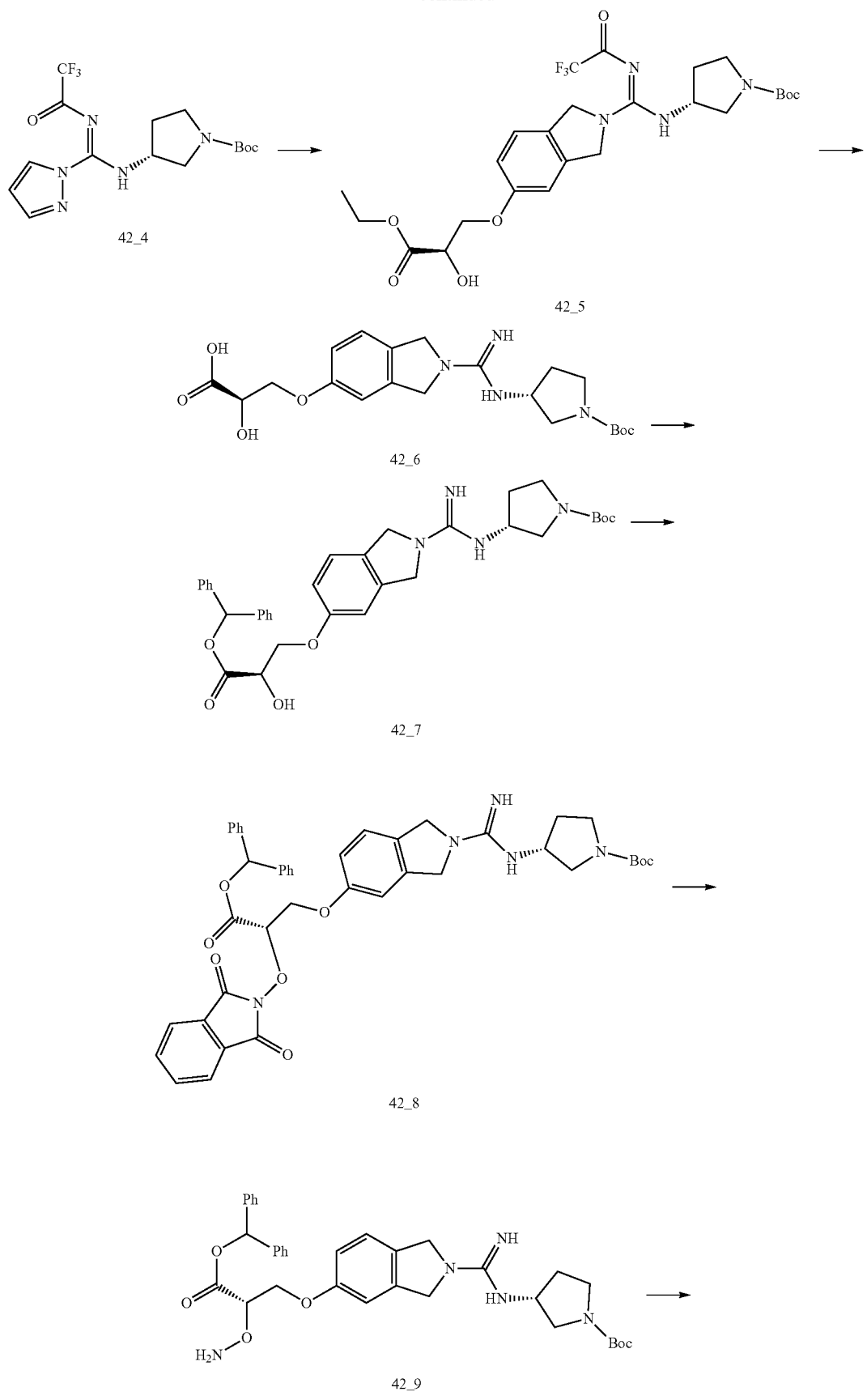

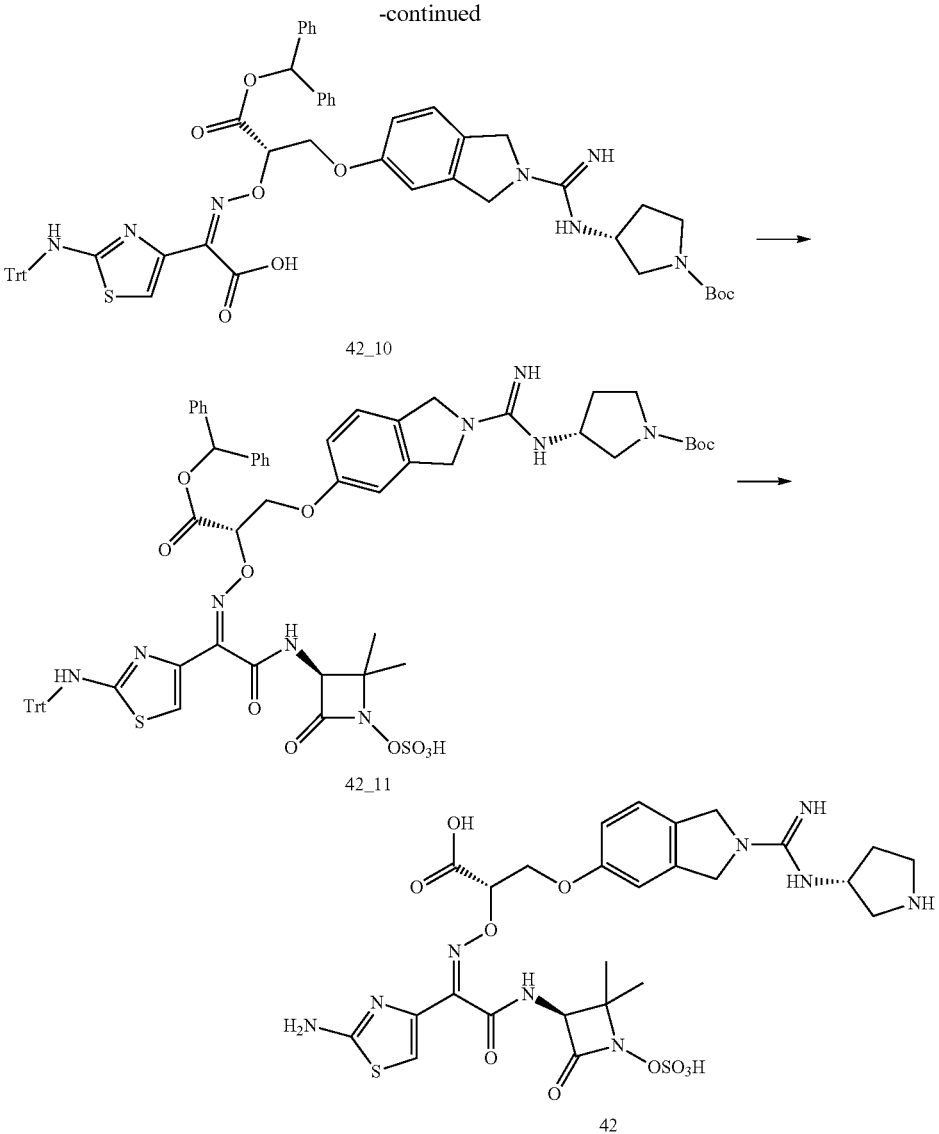

Step 1: cyanogen bromide (6.82 g, 64.43 mmol, 4.74 mL, 2 eq), sodium acetate (13.21 g, 161.07 mmol, 5 eq) was added to a solution of compound 42_1 (6 g, 32.21 mmol, 5.45 mL, 1 eq) in methanol (50 mL). The reaction mixture was stirred at room temperature (15-25° C.) for 2 hours and diluted with water (50 mL), the mixture was extracted with ethyl acetate (50 mL*2), the combined organic phase was washed with saturated sodium chloride aqueous solution, dried over anhydrous sodium sulfate and filtered, the mixture was then concentrated under reduced pressure to give compound 42_2;

Step 2: pyrazole hydrochloride (2.26 g, 21.58 mmol, 0.65 eq) was added to a solution of compound 42_2 (7 g, 33.13 mmol, 1 eq) in tetrahydrofuran (50 mL). The mixture was stirred at 65° C. for 12 hours, then concentrated under reduced pressure to remove the solvent to give compound 42_3;

Step 3: trifluoroacetic anhydride (6.65 g, 31.67 mmol, 4.40 mL, 1 eq) and triethylamine (9.61 g, 95.00 mmol, 13.22 mL, 3 eq) were added to a solution of compound 42_3 (10 g, 31.67 mmol, 1 eq, HCl) in dichloromethane (100 mL). The mixture was stirred at 0° C. for 1 hour, then poured into water (30 mL) and stirred for 5 min, the aqueous phase was extracted with dichloromethane (100 mL), the combined organic phase was washed with dilute hydrochloric acid (30 mL, 0.5 M) and saturated sodium chloride saline (30 mL), dried over anhydrous sodium sulfate, filtered and concentrated under reduced pressure to give compound 42_4;

Step 4: triethylamine (6.98 g, 68.98 mmol, 4 eq) and compound 42_4 (5.83 g, 15.52 mmol, 0.9 eq) were added to a solution of compound 32_2 (6.3 g, 17.25 mmol, 1 eq, TFA) in DMF (60 mL). The mixture was stirred at 20° C. for 2 hours and concentrated under reduced pressure, the residue was poured into water (20 mL) and stirred for 5 min. The aqueous phase was extracted with ethyl acetate (100 mL*2), the combined organic phase was washed with saturated sodium chloride (30 mL*2), dried over anhydrous sodium sulfate, then the mixture was filtered and concentrated under reduced pressure, the residue was purified by silica gel chromatography ($SiO_2$, petroleum ether/ethyl acetate=5/1 to 0/1) to give compound 42_5;

Step 5: sodium hydroxide (1.35 g, 33.66 mmol, 4 eq) was added to a methanol solution of compound 42_5 (4.7 g, 8.41 mmol, 1 eq), the mixture was stirred at 20° C. for 14 hours, then the pH value was adjusted to 4-5 and concentrated under reduced pressure at 40° C. to give compound 42_6;

Step 6: a solution of diphenyl diazomethane (4.83 g, 24.87 mmol, 3 eq) in dichloromethane (50 mL) was added dropwise to a solution of compound 42_6 (3.6 g, 8.29 mmol, 1 eq) in methanol (30 mL). The mixture was stirred at 20° C. for 12 hours and concentrated under reduced pressure, the residue was purified by silica gel chromatography ($SiO_2$, dichloromethane/methanol=50/1 to 10/1) to give compound 42_7;

Step 7: triphenylphosphine (1.05 g, 4.00 mmol, 1.5 eq) and DIAD (1.08 g, 5.33 mmol, 1.04 mL, 2 eq) were added to a solution of compound 42_7 (1.6 g, 2.66 mmol, 1 eq) and 2-hydroxyisoindoline-1,3-dione (477.95 mg, 2.93 mmol, 1.1 eq) in tetrahydrofuran (20 mL). The mixture was stirred at 20° C. for 12 hours and concentrated under reduced pressure, the residue was purified by silica gel chromatography ($SiO_2$, dichloromethane/methanol=50/1 to 10/1) to give compound 42_8;

Step 8: $NH_2NH_2 \cdot H_2O$ (94.76 mg, 1.61 mmol, 92.00 µL, 85% purity, 1 eq) was added to a solution of compound 42_8 (1.2 g, 1.61 mmol, 1 eq) ethanol (10 mL), the mixture was stirred at 20° C. for 1 hour and concentrated under reduced pressure, then filtered and concentrated under reduced pressure again to remove the solvent to give compound 42_9;

Step 9: intermediate A2 (545.26 mg, 1.32 mmol, 1 eq) was added to a solution of compound 42_9 (810 mg, 1.32 mmol, 1 eq) in methanol (6 mL) and dichloromethane (2 mL). The mixture was stirred at 20° C. for 30 mins and concentrated under reduced pressure to give compound 42_10;

Step 10: DIC (299.23 mg, 2.37 mmol, 367.16 µL, 2 eq) and HOBt (320.39 mg, 2.37 mmol, 2 eq) were added to a solution of compound 42_10 (1.2 g, 1.19 mmol, 1 eq) in DMF (12 mL). The mixture was stirred at 20° C. for 1 hour, then intermediate A1 (373.82 mg, 1.78 mmol, 1.5 eq) and sodium bicarbonate (398.38 mg, 4.74 mmol, 4 eq) were added thereto, the mixture was stirred at 20° C. for 12 hours, then poured into water (30 mL) and stirred for 5 min, the mixture was filtered and the filter cake was collected and dried to give compound 42_11;

Step 11: trifluoroacetic acid (15.40 g, 135.06 mmol, 10 mL, 116.19 eq) was added to a solution of compound 42_11 (1.4 g, 1.16 mmol, 1 eq) in dichloromethane (10 mL). The mixture was stirred at 0° C. for 1 hour, then poured into petroleum ether/ethyl acetate (30 mL, v/v=1/4) and stirred for 5 min, the mixture was then filtered and the filter cake was collected, which was purified by preparative HPLC column (Phenomenex Synergi C18 150×25×10 µm; mobile phase: [water (0.1% trifluoroacetic acid)-acetonitrile]; acetonitrile %: 5%-35%, 9 min) to give compound 42. LCMS (ESI) m/z: 696.6 (M+1). $^1$H NMR (400 MHz, $D_2O$) δ=7.24 (br d, J=9.0 Hz, 1H), 7.09 (s, 1H), 6.94-6.88 (m, 2H), 5.15 (br d, J=5.9 Hz, 2H), 4.64-4.63 (m, 1H), 4.60 (s, 2H), 4.53 (br s, 1H), 4.50 (br s, 1H), 4.47-4.40 (m, 2H), 3.64 (dd, J=6.7, 12.7 Hz, 1H), 3.58-3.49 (m, 1H), 3.47-3.40 (m, 2H), 2.48-2.36 (m, 1H), 2.21 (dt, J=5.8, 13.4 Hz, 1H), 1.42 (s, 3H), 1.00 (s, 3H) ppm.

Embodiment 43

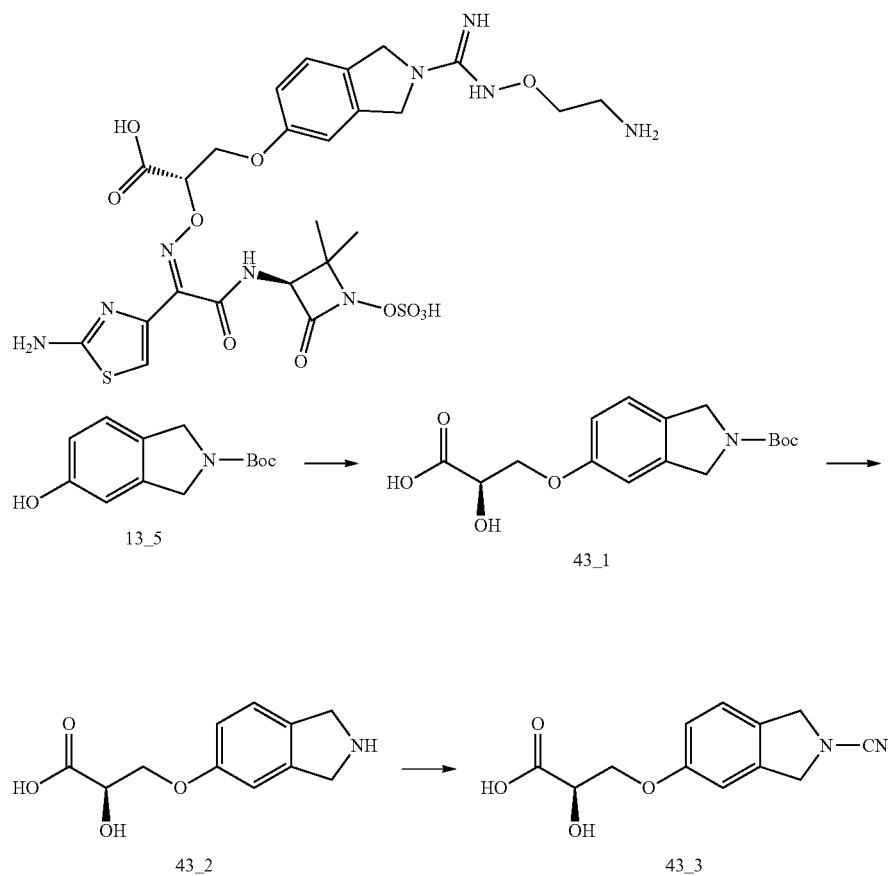

-continued
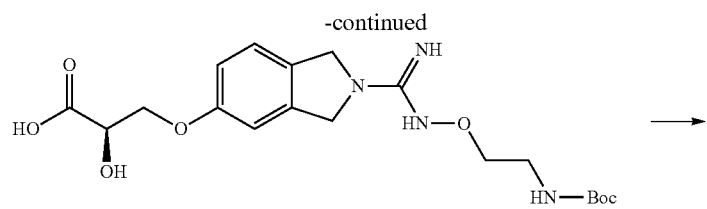
43_4
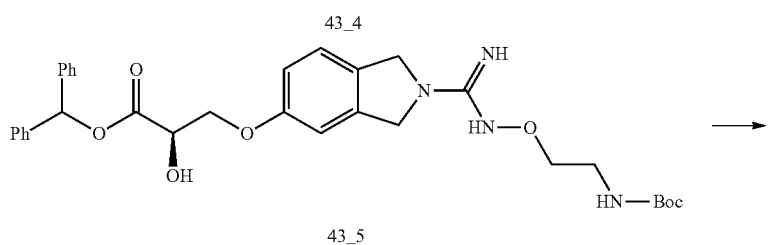
43_5
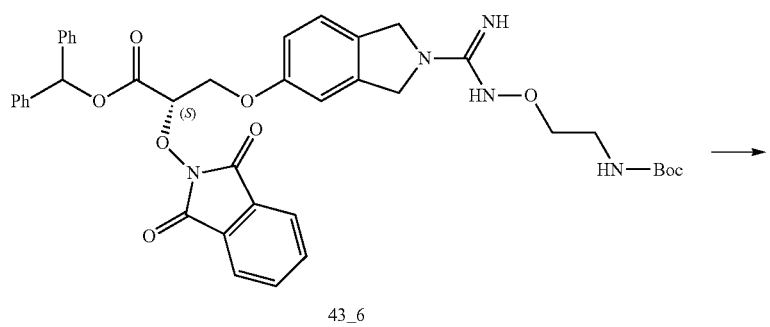
43_6
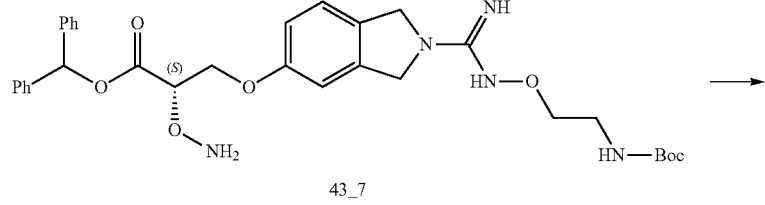
43_7
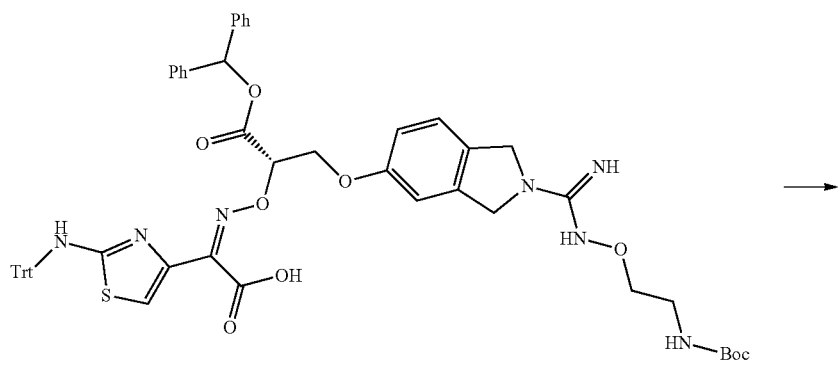
43_8

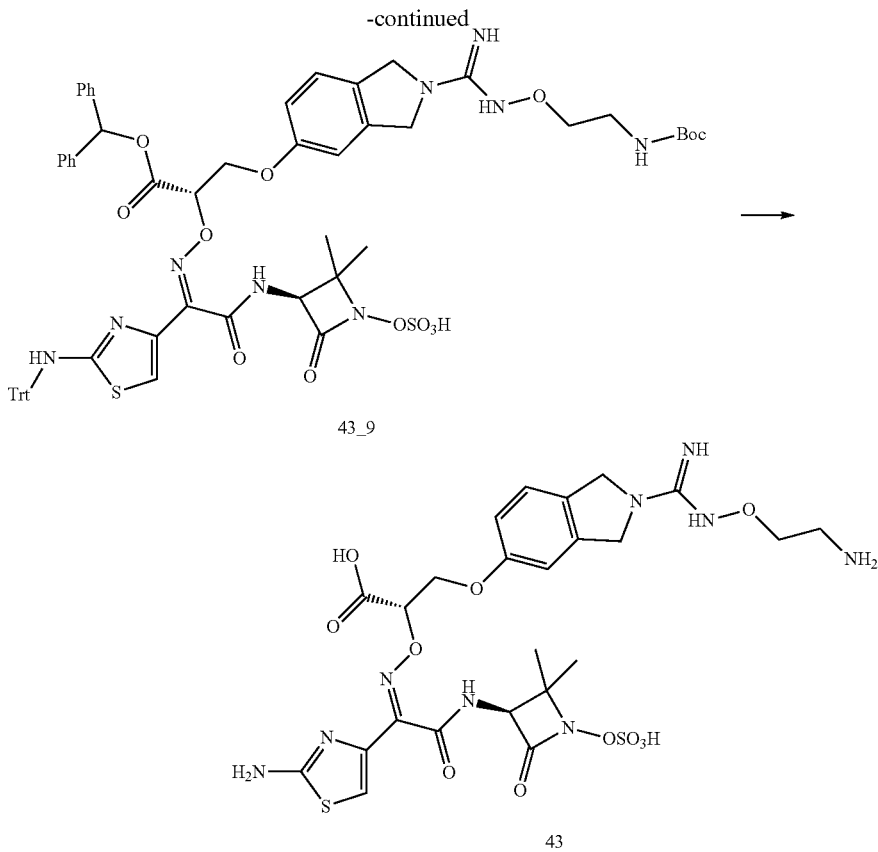

43_9

43

Step 1. NaH (38.22 g, 955.67 mmol, 60% purity, 1.88 eq) was added to a solution of compound 13_5 (130 g, 508.33 mmol, 1 eq) in TH (1200 mL) and DMF (300 mL) at −30 to −10° C., the mixture was stirred for 15 mins and intermediate A10 (53.80 g, 432.08 mmol, 0.85 eq) was added slowly in batches into the reaction mixture, the mixture was reacted at 70-75° C. for 3 hours and then cooled to room temperature, the mixture was diluted with water (1500 mL) and washed with ethyl acetate (500 mL*2), the combined organic phase was washed with water (500 mL), the combined aqueous phase was acidified to pH=1 by dilute hydrochloric acid (1 M), then extracted with ethyl acetate (700 mL*3), the organic phases were combined and washed with saline (500 mL) and concentrated, then ethyl acetate/petroleum ether (1500 mL, 1/1) was added to the residue under stirring until a large amount of solid precipitated, the mixture was filtered and the solid was collected to give compound 43_1.

Step 2: trifluoroacetic acid (215.60 g, 1.89 mol, 140 mL, 10.19 eq) was added to a solution of compound 43_1 (60 g, 185.56 mmol, 1 eq) in DCM (420 mL) at 0-5° C., the mixture was stirred for 1.5 hours and concentrated under reduced pressure to give compound 43_2.

Step 3: sodium bicarbonate (64.95 g, 773.17 mmol, 5 equivalent) was added to a solution of compound 43_2 (52.15 g, 154.63 mmol, 1 eq, TFA) in water (500 mL), then the mixture was cooled to 0-5° C., BrCN (19.65 g, 185.56 mmol, 13.65 mL, 1.2 eq) was added at one time to the mixture and stirred for 3 hours, then DCM (1500 mL) was added thereto, the mixture was then acidified to pH=1 by dilute hydrochloric acid (1 M), a large amount of gray solid was precipitated, the mixture was filtered and the solid was collected, the aqueous phase extracted with ethyl acetate (500 mL*3), the combined organic phase was dried over anhydrous sodium sulfate and filtered, and the filtrate was concentrated to about 200 mL while a solid was precipitated, the mixture was filtered and the solid was collected, and two parts of solid was combined and dried to give compound 43_3.

Step 4: A10_2 (2.48 g, 14.10 mmol, 1.0 eq) and A10 (3.00 g, 14.10 mmol, 1.0 eq, HCl) were added to a solution of compound 43_3 (3.5 g, 14.10 mmol, 1 eq) in ethanol (35 mL), the mixture was stirred at 90° C. for 12 hours under nitrogen atmosphere and filtered, the solid was collected to give compound 43_4; LCMS (ESI) m/z: 425.2 (M+1).

Step 5: a solution of diphenyl diazomethane (1.78 g, 9.18 mmol, 4 eq) in dichloromethane (10 mL) was added to a solution of compound 43_4 (1.3 g, 2.30 mmol, 1 eq) in methanol (20 mL). The mixture was stirred at 25° C. for 1 hour and concentrated under reduced pressure, the residue was purified by column chromatography (SiO₂, DCM/MeOH=30/1 to 10/1) to give compound 43_5; LCMS (ESI) m/z: 591.3 (M+1).

Step 6: 2-hydroxyisoindoline-1,3-dione (272.75 mg, 1.67 mmol, 1.1 eq), triphenylphosphine (438.54 mg, 1.67 mmol, 1.1 eq) and DIAD (307.36 mg, 1.52 mmol, 295.53 μL, 1 eq) were added to a solution of compound 43_5 (900 mg, 1.52 mmol, 1 eq) in THE (10 mL). The mixture was stirred at room temperature (10-15° C.) for 12 hours and concentrated under reduced pressure, the residue was purified by column chromatography (SiO₂, DCM/MeOH=50/1 to 10/1) to give compound 43_6.

Step 7: NH₂NH₂.H₂O (37.62 mg, 638.78 g 50), 36.528 g, 85% purity, 1 eq) was added to a solution of compound 43_6

(470 mg, 638.78 μmol, 1 eq) in ethanol (2 mL) and dichloromethane (2 mL). The mixture was stirred at room temperature (15-20° C.) for 1 hour and filtered, the filtrate was concentrated under reduced pressure, and the residue was diluted with dichloromethane (5 mL) and washed with saline, dried over anhydrous sodium sulfate, concentrated under reduced pressure to give compound 43_7.

Step 8: intermediate A2 (266.88 mg, 1 eq) was added to a solution of compound 43_7 (390 mg, 1 eq) in ethanol (3 mL) and dichloromethane (2 mL). The mixture was stirred at room temperature (15-20° C.) for 1 hour and concentrated under reduced pressure, the residue was stirred in petroleum ether/ethyl acetate (10 mL, 4/1) and filtered to give compound 43_8.

Step 8: intermediate A2 (266.88 mg, 643.90 mg compound, 1 eq) was added to a solution of compound 43_7 (390 mg, 643.90 obtained compound, 1 eq) in ethanol (3 mL) and dichloromethane (2 mL). The mixture was stirred at room temperature (15-20° C.) for 1 hour and concentrated under reduced pressure, the residue was stirred in petroleum ether/ethyl acetate (10 mL, 4/1) and filtered to give compound 43_8.

Step 9: diisopropylcarbodiimide (138.52 mg, 1.10 mmol, 169.97 μL, 2 eq) and HOBt (148.32 mg, 1.10 mmol, 2 eq) were added to a solution of compound 43_8 (550 mg, 1 eq) in DMF (3 mL), the mixture was stirred at 20° C. for 1 hour, then intermediate A1 (161.51 mg, 1.4 eq) and $NaHCO_3$ (184.42 mg, 2.20 mmol, 4 eq) were added thereto, the mixture was stirred at 20° C. for 11 hours, then poured into water (20 mL) and the mixture was filtered, the solid collected was dissolved in dichloromethane (100 mL) and dried over anhydrous sodium sulfate and filtered, then concentrated under reduced pressure, the residue was purified by column chromatography ($SiO_2$, DCM/MeOH=30/1 to 20/1) to give compound 43_9; LCMS (ESI) m/z: 1194.9 (M+1).

Step 10: trifluoroacetic acid (924.00 mg, 8.10 mmol, 0.6 mL) was added to a solution of compound 43_9 (120 mg, 1 eq) in dichloromethane (0.6 mL) at 0° C., the mixture was stirred at 0° C. for 1 hour, then diluted with petroleum ether/ethyl acetate (20 mL, 1/4) and stirred for 10 min, the mixture was filtered and the solid was purified by preparative HPLC (trifluoroacetic acid column: Phenomenex luna C18 150×25 mm×10 μm; mobile phase: [water (0.1% trifluoroacetic acid)-acetonitrile]; acetonitrile %: 2%-25%, 10 min) to give compound 43.

$^1$H NMR (400 MHz, $d^6$-DMSO) δ=7.22 (br d, J=9.1 Hz, 1H), 7.04 (s, 1H), 6.92-6.86 (m, 2H), 5.04 (br s, 1H), 4.76 (d, J=3.8 Hz, 3H), 4.59 (s, 2H), 4.46 (br d, J=10.9 Hz, 1H), 4.40-4.32 (m, 1H), 4.21-4.14 (m, 2H), 3.32 (t, J=4.6 Hz, 2H), 1.38 (s, 3H), 0.94 (s, 3H); LCMS (ESI) m/z: 686.5 (M+1).

Embodiment 44

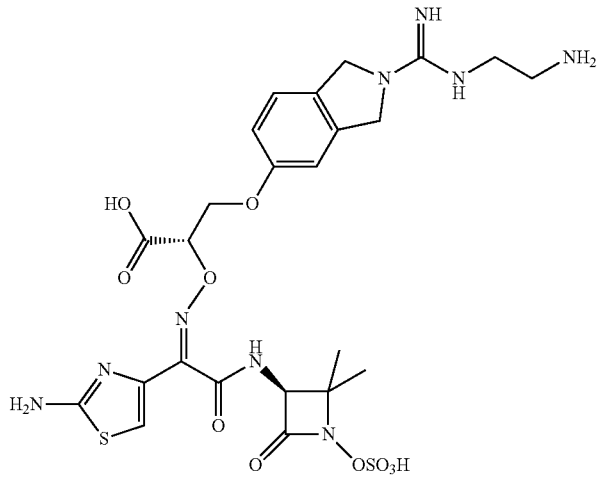

44

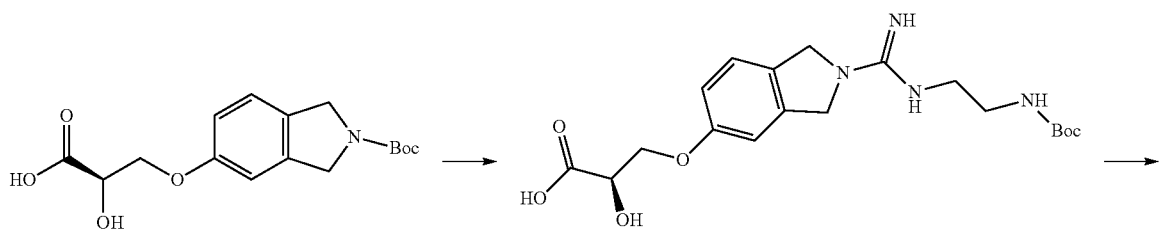

-continued
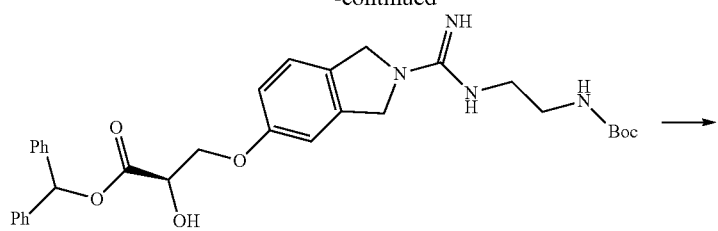
44_2
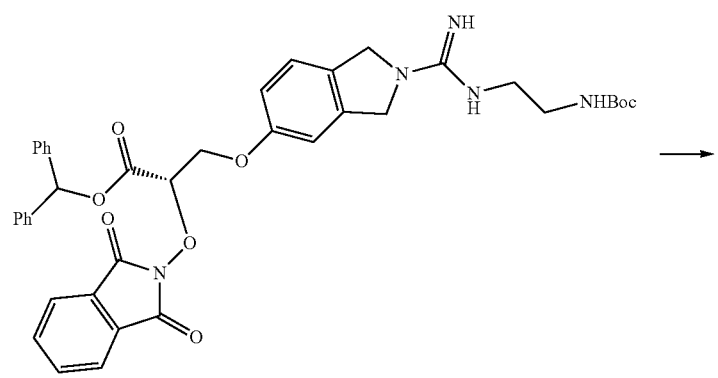
44_3
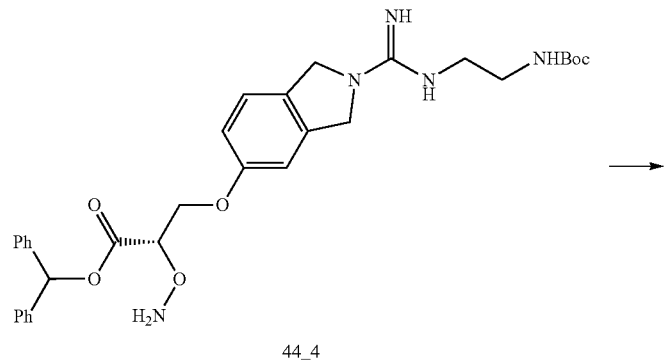
44_4
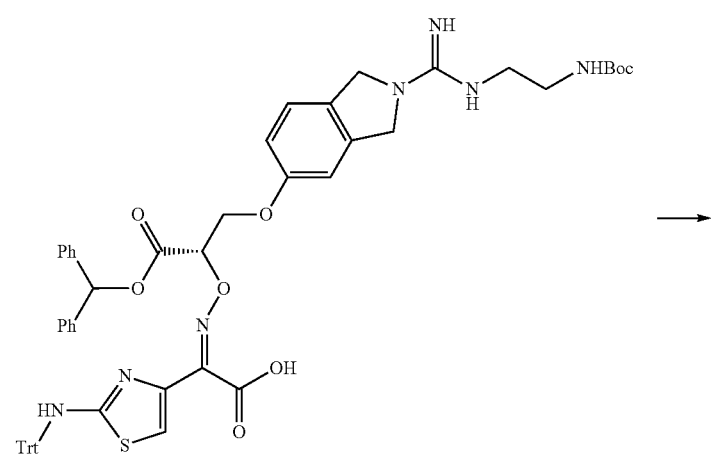
44_5

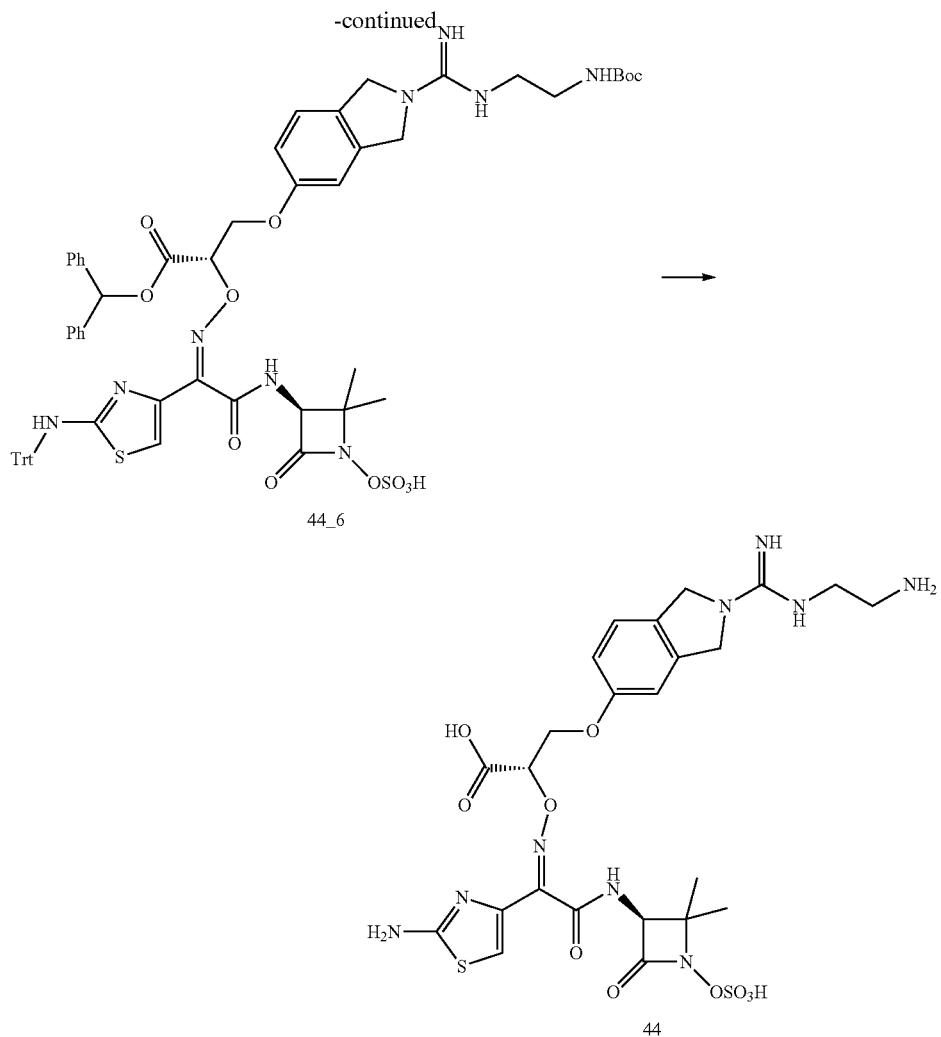

Step 1: N-tert-butyl (2-aminoethyl)carbamate (2.38 g, 12.09 mmol, 2.33 mL, 1 eq, HCl) and tert-butyl N (2-aminoethyl)carbamate (1.94 g, 12.09 mmol, 1.90 mL, 1 eq) were added to a solution of compound 43_3 (3 g, 12.09 mmol, 1 eq) in ethanol (30 mL). The mixture was stirred at 90° C. for 12 hours, then ethyl acetate (30 mL) was added, the mixture was stirred for 5 mins and filtered, the solid was collected to give compound 44_1; LCMS (ESI) m/z: 409.1 (M+1).

Step 2: dilute hydrochloric acid (8.00 mL, 0.5 M) and diphenyl diazomethane (3.04 g, 15.67 mmol, 2 eq) were added dropwise to a solution of compound 44_1 (4 g, 7.83 mmol, 1 eq) in methanol (40 mL). The mixture was stirred at 25° C. for 30 mins then extracted with dichloromethane (50 mL*2) to obtain an aqueous phase. The combined organic phase was washed with saturated sodium chloride (30 mL), dried over anhydrous sodium sulfate, filtered and concentrated under reduced pressure, the residue was purified by column chromatography (SiO$_2$, DCM/MeOH=50/1 to 10/1) to give compound 44_2; LCMS (ESI) m/z: 575.3 (M+1).

Step 2: dilute hydrochloric acid (8.00 mL, 0.5 M) and diphenyl diazomethane (3.04 g, 15.67 mmol, 2 eq) were added dropwise to a solution of compound 44_1 (4 g, 7.83 mmol, 1 eq) in methanol (40 mL). The mixture was stirred at 25° C. for 30 mins then extracted with dichloromethane (50 mL*2) to obtain an aqueous phase. The combined organic phase was washed with saturated sodium chloride (30 mL), dried over anhydrous sodium sulfate, filtered and concentrated under reduced pressure, the residue was purified by column chromatography (SiO$_2$, DCM/MeOH=50/1 to 10/1) to give compound 44_2; LCMS (ESI) m/z: 575.3 (M+1).

Step 3: 2-hydroxyisoindoline-1,3-dione (1.11 g, 6.79 mmol, 1.1 eq), triphenylphosphine (2.43 g, 9.26 mmol, 1.5 eq) and DIAD (2.50 g, 12.35 mmol, 2.40 mL, 2 eq) were added to a solution of compound 44_2 (3.7 g, 6.17 mmol, 1 eq) in THF (40 mL). The mixture was stirred at 25° C. for 1 hour and concentrated under reduced pressure, the residue was purified by silica gel chromatography (SiO$_2$, DCM/MeOH=50/1 to 10/1) to give compound 44_3.

Step 4: NH$_2$NH$_2$.H$_2$O (312.26 mg, 6.11 mmol, 98% purity, 1 eq) was added to a solution of compound 44_3 (4.4 g, 6.11 mmol, 1 eq) in ethanol (45 mL). The mixture was stirred at 25° C. for 30 mins and filtered, and the filtrate was concentrated under reduced pressure to give compound 44_4.

Step 5: intermediate A2 (2.02 g, 4.88 mmol, 0.8 eq) was added to a solution of compound 44_4 (3.6 g, 6.11 mmol, 1 eq) in methanol (24 mL) and dichloromethane (8 mL). The mixture was stirred at 25° C. for 30 mins and concentrated under reduced pressure, the residue was washed with petroleum ether/ethyl acetate (30 mL, 1/1), the mixture was filtered and the solid was collected to give compound 44_5.

Step 6: DIC (639.86 mg, 5.07 mmol, 785.11 μL, 2 eq) and HOBt (685.11 mg, 5.07 mmol, 2 eq) were added to a solution of compound 44_5 (2.5 g, 2.54 mmol, 1 eq) in DMF (25 mL). The mixture was stirred at 25° C. for 1 hour, then sodium bicarbonate (851.87 mg, 10.14 mmol, 4 eq) and intermediate A1 (639.49 mg, 3.04 mmol, 1.2 eq) were added thereto. The mixture was stirred at 25° C. for 11 hours then poured into water (50 mL), the mixture was stirred for 5 mins and filtered, the solid was collected to give compound 44_6.

Step 7: trifluoroacetic acid (30.80 g, 270.12 mmol, 20.00 mL, 109.76 eq) was added in batches to a solution of compound 44_6 (2.9 g, 2.46 mmol, 1 eq) in dichloromethane (10 mL) at −40° C., the mixture was stirred at 0° C. for 1 hour, then petroleum ether/ethyl acetate (30 mL, v/v=1/2) was added thereto and stirred for 5 min, the mixture was then filtered and the filter cake was collected and purified by preparative HPLC (column: Phenomenex Luna C18 250×50 mm×10 μm; mobile phase: [water (0.1% trifluoroacetic acid)-acetonitrile]; acetonitrile %: 1%-25%, 10 min) to give compound 44.

$^1$H NMR (400 MHz, d$^6$-DMSO) δ=7.26 (br d, J=8.4 Hz, 1H), 7.13-7.02 (m, 1H), 6.92 (s, 2H), 5.10 (br s, 1H), 4.94 (br s, 2H), 4.62 (br s, 2H), 4.54-4.46 (m, 2H), 4.39 (br s, 1H), 3.62 (br t, J=5.9 Hz, 2H), 3.24 (br t, J=5.7 Hz, 2H), 1.42 (s, 3H), 0.98 (s, 3H); LCMS (ESI) m/z: 670.2 (M+1).

Embodiment 45

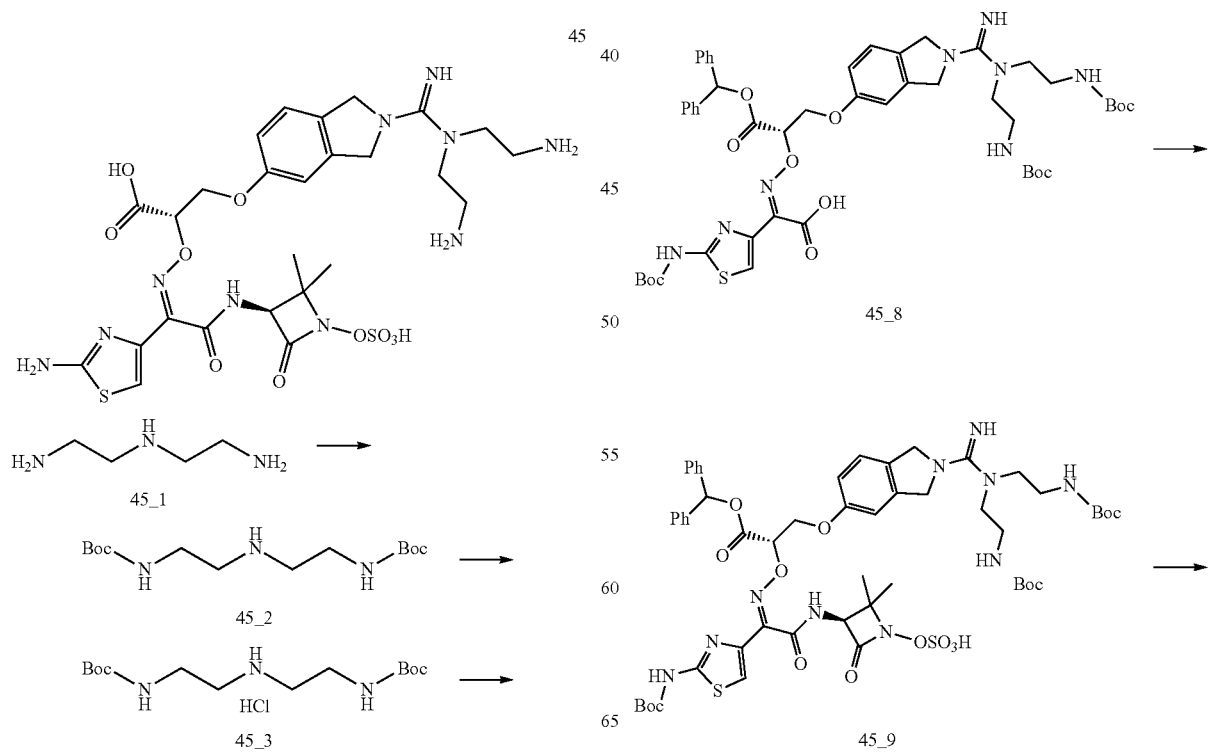

-continued

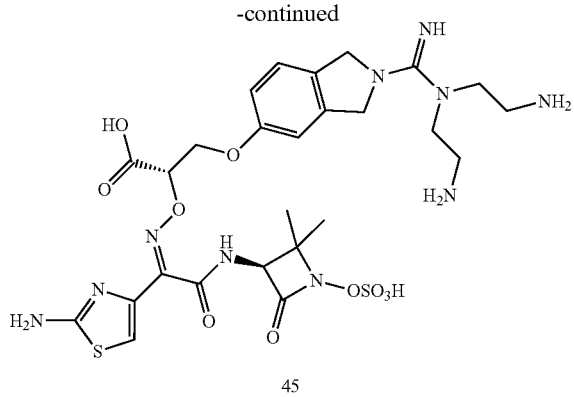

45

Step 1: tert-Butyl imidazole-1-carboxylate (78.26 g, 465.27 mmol, 2 eq) was added to a solution of compound 45_1 (24 g, 232.63 mmol, 25.13 mL, 1 eq) in THF (250 mL). The mixture was stirred at 60° C. for 12 hours and concentrated under reduced pressure, the residue was diluted with water (50 mL) and extracted with ethyl acetate (100 mL). The organic phase was washed with saturated sodium chloride (150 mL*2), dried over anhydrous sodium sulfate and filtered, then concentrated under reduced pressure, the residue was washed with petroleum ether/methyl tert-butyl ether (200 mL, 1/1) under stirring, the mixture was filtered and the solid was collected to give compound 45_2; $^1$H NMR (400 MHz, CDCl$_3$) δ=4.97 (br s, 1H), 3.22 (q, J=5.7 Hz, 2H), 2.74 (t, J=5.8 Hz, 2H), 1.46 (s, 9H).

Step 2: HCl/EtOAc (8.24 mL, 4 M, 1 eq) solution was slowly added dropwise to a solution of compound 45_2 (10 g, 32.96 mmol, 1 eq) in ethyl acetate (100 mL) at 0° C. The mixture was stirred at 0° C. for 10 mins and filtered, the solid was collected to give compound 45_3.

Step 3: compound 45_2 (3.88 g, 12.79 mmol, 1 eq) and compound 45_3 (4.35 g, 12.79 mmol, 1 eq) were added to a solution of compound 433 (3.2 g, 12.79 mmol, 1 eq) in tert-butanol (40 mL), the mixture was stirred at 100° C. for 12 hours under nitrogen atmosphere and concentrated under reduced pressure, the obtained crude product was diluted with water (50 mL) and the pH value was adjusted to 9-10 by dilute lithium hydroxide, the mixture was washed with ethyl acetate (50 mL*2), the aqueous phase was cooled to 0° C. and the pH was adjusted to 3-4 by using dilute hydrochloric acid (0.5 M), the aqueous phase was freeze-dried to give compound 45_4. LCMS (ESI) m/z: 552.4 (M+1).

Step 4: a solution of diphenyl diazomethane (4.58 g, 23.57 mmol, 2 eq) in dichloromethane (50 mL) was added to a solution of compound 45_4 (6.5 g, 11.78 mmol, 1 eq) in methanol (70 mL). The mixture was stirred at 25° C. for 1 hour and concentrated under reduced pressure, the obtained residue was diluted with water (50 mL), the mixture was extracted with dichloromethane (100 mL), the combined organic phase was dried over anhydrous sodium sulfate, filtered and concentrated under reduced pressure, the obtained residue was purified by column chromatography (SiO$_2$, DCM/MeOH=20/1 to 10/1) to give compound 45_5. LCMS (ESI) m/z: 718.4 (M+1).

Step 5: 2-hydroxyisoindoline-1,3-dione (312.38 mg, 1.91 mmol, 2 eq), triphenylphosphine (502.26 mg, 1.91 mmol, 2 eq) and DIAD (387.21 mg, 1.91 mmol, 2 eq) were added to a solution of compound 45_5 (1.3 g, 957.46 μmol, 1 eq) in THF (15 mL). The mixture was stirred at 20° C. for 0.5 hour and concentrated under reduced pressure, the obtained residue was purified by column chromatography (SiO$_2$, DCM/MeOH=20/1 to 10/1) to give compound 45_6. LCMS (ESI) m/z: 863.5 (M+1).

Step 6: NH$_2$NH$_2$.H$_2$O (64.87 mg, 1.30 mmol, 1.2 eq) was added to a solution of compound 45_6 (1.2 g, 1.08 mmol, 1 eq) in ethanol (15 mL). The mixture was stirred at 20° C. for 1 hour and filtered, then the filtrate was concentrated, the obtained residue was dissolved in dichloromethane (20 mL), dried over anhydrous sodium sulfate, filtered and concentrated under reduced pressure to give compound 45_7. LCMS (ESI) m/z: 733.4 (M+1).

Step 7: intermediate A2 (357.95 mg, 1 eq) was added to a solution of compound 45_7 (850 mg, 1 eq) in ethanol (8 mL) and dichloromethane (8 mL), the mixture was stirred at 20° C. for 1 hour under nitrogen atmosphere and concentrated under reduced pressure, the obtained residue was purified by column chromatography (SiO$_2$, DCM/MeOH=20/1 to 10/1) to give compound 45_8. LCMS (ESI) m/z: 1129.6 (M+1).

Step 7: HOBt (186.65 mg, 1.38 mmol, 2 eq) and DIC (174.33 mg, 1.38 mmol, 2 eq) were added to a solution of compound 45_8 (780 mg, 1 eq) in DMF (5 mL), the mixture was stirred at room temperature for 1 hour, then intermediate A2 (217.78 mg, 1.04 mmol, 1.5 eq) and sodium bicarbonate (232.09 mg, 2.76 mmol, 4 eq) were added. The mixture was stirred at 20° C. for 11 hours and poured into water (50 mL), then the mixture was stirred for 10 mins and filtered, the obtained solid was dissolved in dichloromethane (20 mL), dried over anhydrous sodium sulfate and filtered, then concentrated under reduced pressure to give compound 45_9. LCMS (ESI) m/z: 1322.3 (M+1).

Step 8: trifluoroacetic acid (4.62 g, 40.52 mmol, 3 mL, 58.84 eq) was added to a solution of compound 45_9 (910 mg, 1 eq) in dichloromethane (6 mL) at 0° C. The mixture was stirred at 0° C. for 1 hour and diluted with petroleum ether/ethyl acetate (60 mL, 1/4), then the mixture was filtered, the solid was collected and purified by preparative HPLC (trifluoroacetic acid, column: Phenomenex luna C18 250*50 mm*10 μm; mobile phase: [water (0.1% trifluoroacetic acid)-acetonitrile]; acetonitrile %: 1%-30%, 10 min) to give compound 45.

$^1$H NMR (400 MHz, DEUTERIUM OXIDE) δ=7.25 (br d, J=8.1 Hz, 1H), 7.09 (s, 1H), 6.96-6.88 (m, 2H), 5.13 (br s, 1H), 4.94-4.82 (m, 4H), 4.64 (s, 1H), 4.51 (br d, J=10.8 Hz, 1H), 4.42-4.34 (m, 1H), 3.70 (br t, J=6.8 Hz, 4H), 3.28 (br t, J=6.8 Hz, 4H), 1.42 (s, 3H), 0.97 (s, 3H); LCMS (ESI) m/z: 713.3 (M+1).

225
Embodiment 46
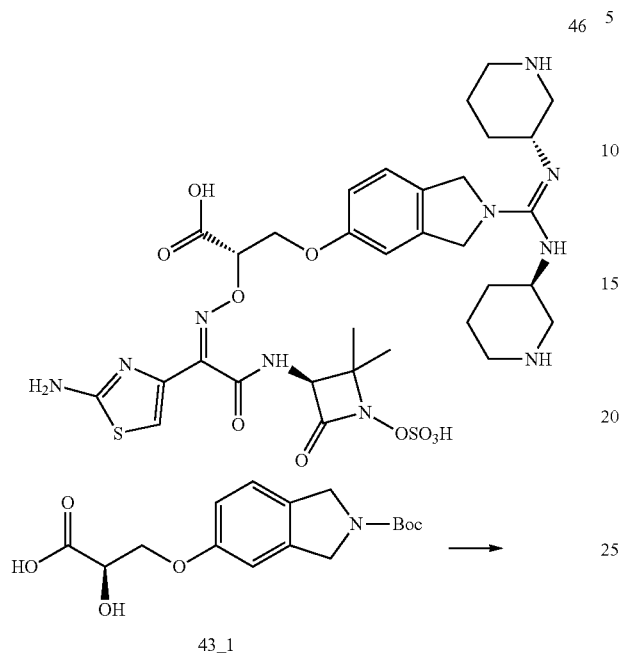
226
-continued
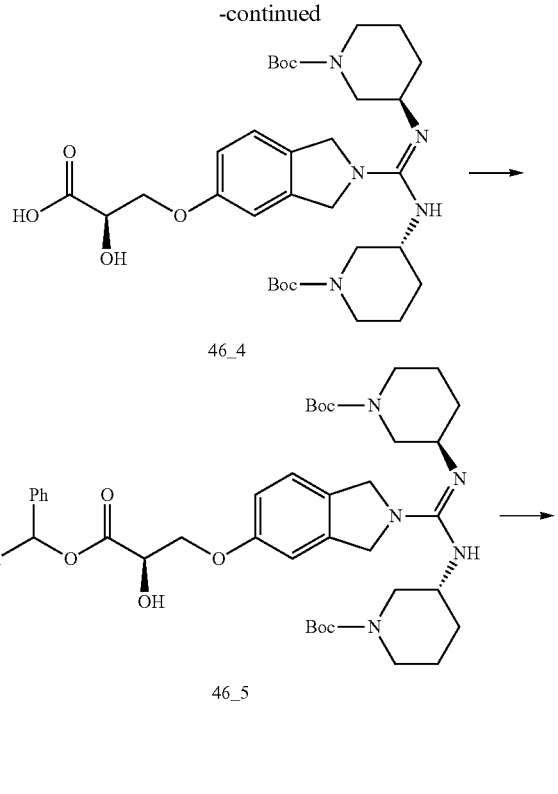
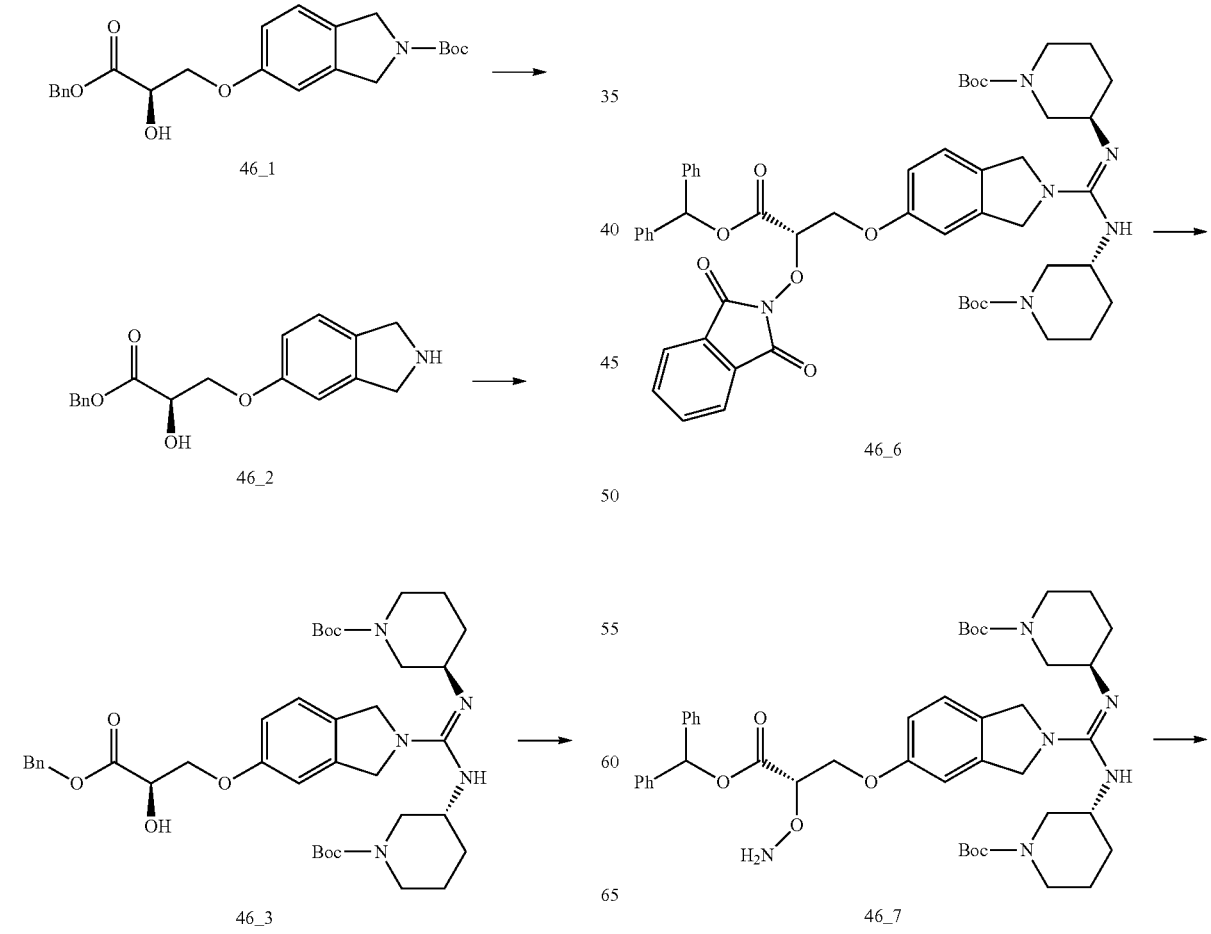

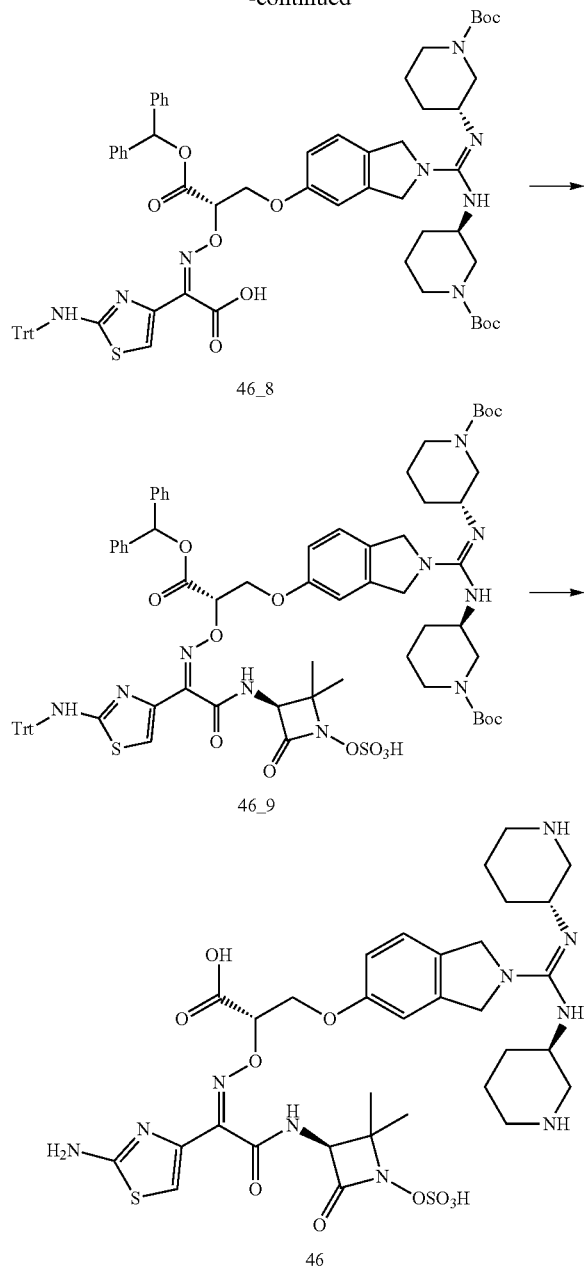

Step 3: diisopropylamine (6.64 g, 51.40 mmol, 8.95 mL, 1.5 eq) and intermediate A11 (14.65 g, 34.27 mmol, 1 eq, trifluoroacetic acid) were added to a solution of compound 46_2 (14 g, 34.27 mmol, 1 eq) in dioxane (140 mL). The mixture was stirred at 60° C. for 1 hour and concentrated under reduced pressure, the residue was purified by column chromatography (SiO$_2$, petroleum ether/ethyl acetate=1/0 to 8/1) to give compound 46_3; LCMS (ESI) m/z: 722.3 (M+1).

Step 4: sodium hydroxide (753.59 mg, 18.84 mmol, 2 eq) was added to a solution of compound 46_3 (6.8 g, 9.42 mmol, 1 eq) in MeOH (50 mL). The reaction mixture was stirred at room temperature (10-15° C.) for 1 hour, then the pH value was adjusted to 3-4 with dilute hydrochloric acid (1 M) to give a solution of compound 46_4 in methanol; LCMS (ESI) m/z: 633.1 (M+1).

Step 5: a solution of diphenyl diazomethane (8 g, 12.66 mmol, 1 eq) in dichloromethane (50 mL) was added dropwise to the above solution of compound 46_4 (4.92 g, 25.32 mmol, 2 eq) in methanol. The mixture was stirred at room temperature (10-20° C.) for 1 hour and concentrated under reduced pressure, the residue was diluted with dichloromethane (50 mL), the organic phase was washed with water (30 mL), saturated sodium chloride aqueous solution, dried over anhydrous sodium sulfate and filtered, the filtrate was concentrated under reduced pressure, the residue was purified by column chromatography (SiO$_2$, DCM/MeOH=100/1 to 10/1) to give compound 46_5; LCMS (ESI) m/z: 798.5 (M+1).

Step 6: triphenylphosphine (2.96 g, 11.28 mmol, 1.5 eq) and DIAD (2.28 g, 11.28 mmol, 2.19 mL, 1.5 eq) was added to a solution of compound 46_5 (6 g, 7.52 mmol, 1 eq) and 2-hydroxyisoindole-1,3-dione (1.47 g, 9.02 mmol, 1.2 eq) in THF (60 mL). The mixture was stirred at room temperature (10-15° C.) for 1 hour and concentrated under reduced pressure, the residue was purified by column chromatography (SiO$_2$, DCM/MeOH=50/1 to 10/1) to give compound 46_6; LCMS (ESI) m/z: 944.3 (M+1).

Step 7: NH$_2$NH$_2$.H$_2$O (291.95 mg, 5.83 mmol, 1.1 eq) was added to a solution of compound 46_6 (5.00 g, 5.30 mmol, 1 eq) in ethanol (50 mL). The mixture was stirred at 20° C. for 1 hour and concentrated under reduced pressure, the residue was dissolved in dichloromethane (70 mL) and washed with water (20 mL*2), dried over anhydrous sodium sulfate and filtered, the residue was concentrated under reduced pressure to give compound 46_7; LCMS (ESI) m/z: 813.4 (M+1).

Step 8: intermediate A2 (4.7 g, 5.78 mmol, 1 eq) was added to a solution of compound 46_7 (1.92 g, 4.62 mmol, 0.8 eq) in EtOH (20 mL) and DCM (20 mL). The mixture was stirred at 20° C. for 1 hour and concentrated under reduced pressure to give compound 46_8; LCMS (ESI) m/z: 967.4 (M-243+1).

Step 9: HOBt (167.58 mg, 1.24 mmol, 1.5 eq) and DIC (156.52 mg, 1.24 mmol, 1.5 eq) were added to a solution of compound 46_8 (1 g, 1 eq) in DMF (10 mL). The mixture was stirred at the temperature for 1 hour, then (225.95 mg, 1.07 mmol, 1.3 eq) and sodium bicarbonate (277.83 mg, 3.31 mmol, 4 eq) were added thereto. The obtained mixture was diluted with water (80 mL) at 25° C. for 11 hours, the mixture was filtered and the filter cake was dried under reduced pressure to give compound 46_9.

Step 10: trifluoroacetic acid (6.16 g, 54.02 mmol, 4 mL, 63.10 eq) was added to a DCM (6 mL) solution of compound 46_9 (1.2 g, 856.14 μmol, 1 eq). The mixture was stirred at 20° C. for 1 hour and concentrated under reduced pressure, the residue was purified by preparative HPLC (column:

Step 1: BnBr (11.64 g, 68.04 mmol, 8.08 mL, 1.1 eq) and potassium carbonate (17.10 g, 123.71 mmol, 2 eq) were added to a solution of compound 43_1 (20 g, 61.85 mmol, 1 eq) in DMF (200 mL). The mixture was stirred at room temperature (20-25° C.) for 12 hours, then poured into water (200 mL), the mixture was extracted with methyl tert-butyl ether (100 mL*3), the combined organic phase was washed with water (100 mL*2) and saturated sodium chloride (100 mL), dried over anhydrous sodium sulfate, the residue was concentrated under reduced pressure to give compound 46_1.

Step 2: trifluoroacetic acid (20 mL) was added dropwise to a solution of compound 46_1 (10 g, 24.19 mmol, 1 eq) in dichloromethane (50 mL) at 0° C. The reaction mixture was stirred at room temperature (15-20° C.) for 1 hour and concentrated under reduced pressure to give compound 46_2.

Luna C18 150×25 mm×5 μm; mobile phase: [water (0.075% trifluoroacetic acid)-acetonitrile]; acetonitrile %: 1%-30%, 9 min) to give compound 46; LCMS (ESI) m/z: 793.2 (M+1); $^1$H NMR (400 MHz, d$^6$-DMSO+D$_2$O) δ=7.30 (d, J=8.4 Hz, 1H), 7.00-6.90 (m, 2H), 6.81 (s, 1H), 4.99-4.70 (m, 5H), 4.57-4.50 (m, 1H), 4.33 (br s, 2H), 3.60 (br s, 2H), 3.29 (br d, J=12.1 Hz, 2H), 2.90-2.65 (m, 5H), 2.33 (br s, 2H), 2.17 (br s, 2H), 1.92 (br s, 2H), 1.67 (br d, J=8.1 Hz, 4H), 1.37 (s, 3H), 1.02 (s, 3H).

Experimental Example 1: Detection of Antibacterial Activity of the Compounds

Three strains of *Klebsiella pneumonia*, *K. pneumoniae* ATCC BAA-205 (TEM-1/SHV-1/SHV-12), *K. pneumoniae* ATCC BAA-1705 (KPC-2), *K. pneumoniae* ATCC BAA-2470 (NDM-1); three strains of *Pseudomonas aeruginosa*, *P. aeruginosa* NCTC13437 (VIM-10; VEB-1), *P. aeruginosa* PA 14 and *P. aeruginosa* ATCC 35151; four strains of *Escherichia coli*, *E. coli* NCTC 13476 (IMP-1 type), *E. coli* ATCC BAA-2523 (OXA-48), *E. coli* MG1655Δtol C, *E. coli* ATCC 25922; one strain of *Acinetobacter baumannii*, *A. baumannii* ATCC 17978 and one strain of *Staphylococcus aureus*, *S. aureus* NRS384 were used to determine the minimum inhibitory concentration (MIC) of the compounds by micro-liquid dilution method according to the Institute of Clinical and Laboratory Standard (CLSI) requirements. A 2-fold serial dilution compound (final concentration range from 0.125 μg/ml to 128 g/ml) was added to a round-bottom 96-well plate (Catalog #3788, Corning), fresh monoclonal bacteria were selected from an overnight cultured Mueller Hinton II Agar medium plate (MHA, Cat. No. 211438, BD BBLTM) and suspended in a sterile physiological saturated sodium chloride aqueous solution, the concentration was adjusted to 1×10$^8$ CFU/ml, and then the solution was diluted by using a cation-adjusted Hinton Miller Cation-Adjusted Mueller Hinton II Broth (MHB, Catalog #212332, BD BBLTM) to a concentration of 5×10$^5$ CFU/ml, and 100 μl of the solution was added to a round bottom 96-well plate containing the drugs. The plate was placed upside down at 37° C. and the MIC value was read after 20-24 h of incubation, and the lowest drug concentration that inhibited the growth of bacteria was set as MIC. The specific test results are shown in Table 1.

TABLE 1

Detection result of antibacterial activity of the compounds

| Bacteria | MIC (μg/mL) | | | | | | | | | | |
| --- | --- | --- | --- | --- | --- | --- | --- | --- | --- | --- | --- |
| | Compound 3 | Compound 4 | Compound 6 | Compound 7 | Compound 10 | Compound 11 | Compound 12 | Compound 17 | Aztreonam | Sulbactam | Meropenem |
| *K. pneumoniae* ATCCBAA-205 | 8 | 8 | 16 | 8 | 16 | 16 | 16 | 2 | >128 | 64 | <=0.125 |
| *K. pneumoniae* ATCCBAA-1705 | 4 | 1 | 4 | 4 | 4 | 1 | 1 | 0.25 | >128 | >128 | 128 |
| *K. pneumoniae* ATCCBAA-2470 | 2 | 0.5 | 4 | 2 | 4 | 1 | 1 | 0.25 | >128 | >128 | >128 |
| *P. aeruginosa* PA 14 | 4 | 1 | 16 | 16 | 8 | 4 | 2 | 0.5 | 8 | 8 | 0.5 |
| *P. aeruginosa* ATCC35151 | 0.0625 | <=0.125 | 0.5 | 0.5 | 0.25 | <=0.125 | <=0.125 | — | <=0.125 | 64 | <=0.125 |
| *A. baumannii* ATCC17978 | 2 | 0.5 | 4 | 1 | 4 | 2 | 0.5 | ≤0.125 | 32 | 2 | 0.25 |
| *E. coli* NCTC13476 | N.T. | 0.25 | 1 | 1 | 2 | 0.5 | 0.25 | — | 0.25 | >128 | 32 |
| *E. coli* ATCCBAA-2523 | 0.25 | <=0.125 | 0.25 | 0.25 | 0.25 | <=0.125 | <=0.125 | <=0.125 | 16 | 64 | 2 |
| *E. coli* MG1655AA-252 | <=0.0039 | <=0.125 | <=0.125 | <=0.125 | <=0.125 | <=0.125 | <=0.125 | — | <=0.125 | 32 | <=0.125 |
| *E. coli* ATCC25922 | 0.25 | <=0.125 | 0.5 | 0.5 | 1 | 0.25 | <=0.125 | — | 0.25 | 64 | <=0.125 |

Experimental results show that the compound of the present disclosure (MIC range from <=0.125 to 16 μg/mL) has better antibacterial activity relative to aztreonam, meropenem and sulbactam (MIC range is 16→128 μg/mL) against *K. pneumoniae* ATCC BAA-205, *K. pneumoniae* ATCC BAA-1705, *K. pneumoniae* ATCC BAA-2470 and *E. coli* ATCC BAA-2523. The activity data also shows that the compound of the present disclosure has better antibacterial activity against various Gram-negative bacteria; the novel monocyclic β-lactam compound designed and synthesized by the present disclosure can effectively improve the antibacterial activity of the monocyclic β-lactam and has a good antibacterial effect on Gram-negative bacteria.

Experimental Example 2: Detection of Antibacterial Activity of the Compounds on *Acinetobacter baumannii*

Twelve strains of *Acinetobacter baumannii*, *A. baumannii* ATCC 17978 (ATCC-BAA-1605, ATCC-BAA-1789, ATCC-BAA-1790, ATCC-BAA-1791, ATCC-BAA-1792, ATCC-BAA-1793, ATCC-BAA-1794, ATCC-BAA-1795, ATCC-BAA-1799, ATCC-BAA-1800, ATCC 19606, ATCC 17978) were used to determine the minimum inhibitory concentration (MIC) of the compounds by micro-liquid dilution method according to the Institute of Clinical and Laboratory Standard (CLSI) requirements. A 2-fold serial dilution compound (final concentration range from 0.125 μg/mL to 128 μg/mL) was added to a round-bottom 96-well plate, fresh monoclonal bacteria were selected from an overnight cultured Mueller Hinton II Agar medium plate (MHA, Cat. No. 211438, BD BBLTM) and suspended in a sterile normal saline, the concentration was adjusted to $1\times10^8$ CFU/mL, and then the solution was diluted by using a cation-adjusted Hinton Miller Cation-Adjusted Mueller Hinton II Broth (MHB, BD BBLTM) to a concentration of $5\times10^5$ CFU/mL, and 100 μL of the solution was added to a round bottom 96-well plate containing the drugs. The plate was placed upside down at 37° C. and the MIC value was read after 20-24 h of incubation, and the lowest drug concentration that inhibited the growth of bacteria was set as MIC. The specific test results are shown in Table 2.

Experimental results show that the compound of the present disclosure (MIC range from 0.25 to 16 μg/mL) has obvious advantage in antibacterial activity relative to meropenem, imipenem and aztreonam (MIC range is 0.25→128 μg/mL) against *Acinetobacter baumannii*; the activity data also shows that the novel monocyclic β-lactam compound designed and synthesized by the present disclosure can effectively solve the drug resistance issues of the *Acinetobacter baumannii* on aztreonam, meropenem and imipenem.

TABLE 2

Detection of antibacterial activity of the compounds on *Acinetobacter baumannii*

| | *Acinetobacter baumannii* (μg/mL) | | | | | | | | | | | |
|---|---|---|---|---|---|---|---|---|---|---|---|---|
| Compound | ATCC-BAA-1605 | ATCC-BAA-1789 | ATCC-BAA-1790 | ATCC-BAA-1791 | ATCC-BAA-1792 | ATCC-BAA-1793 | ATCC-BAA-1794 | ATCC-BAA-1795 | ATCC-BAA-1799 | ATCC-BAA-1800 | ATCC-19606 | ATCC-17978 |
| 3 | 16 | 16 | 16 | 16 | 16 | 8 | 8 | 8 | 16 | 8 | 8 | 4 |
| 4 | 8 | 4 | 4 | 2 | 4 | 4 | 4 | 4 | 4 | 8 | 8 | 0.5 |
| 5 | 16 | 8 | 8 | 2 | 16 | 16 | 16 | 16 | 16 | 16 | 16 | 1 |
| 6 | 16 | 8 | 8 | 4 | 8 | 8 | 8 | 8 | 8 | 8 | 8 | 2 |
| 7 | 8 | 8 | 8 | 2 | 8 | 4 | 4 | 4 | 8 | 4 | 8 | 2 |
| 17 | 4 | — | — | 0.25 | — | 4 | — | — | — | — | — | — |
| Meropenem | 64 | 64 | 128 | 64 | 128 | >128 | >128 | 4 | 128 | >128 | 2 | 0.5 |
| Imipenem | 32 | 16 | 64 | 32 | 64 | 128 | 32 | 1 | 64 | 128 | 0.5 | 0.25 |
| Aztreonam | 128 | 64 | 32 | 32 | 64 | 64 | 32 | 32 | 128 | 32 | 32 | 32 |

Experimental Example 3: Detection of Antibacterial Activity of the Compounds on Clinically Isolated Bacteria Twenty-five strains of clinically isolated *Acinetobacter baumannii* and twenty-seven strains of *Pseudomonas aeruginosa* were respectively selected and used to determine the minimum inhibitory concentration (MIC) of the compounds by micro-liquid dilution method according to the Institute of Clinical and Laboratory Standard (CLSI) requirements. A 2-fold serial dilution compound (final concentration range from 0.125 μg/mL to 128 μg/mL) was added to a round-bottom 96-well plate, fresh monoclonal bacteria were selected from an overnight cultured Mueller Hinton II Agar medium plate (MHA, BD BBLTM) and suspended in a sterile normal saline, the concentration was adjusted to $1\times10^8$ CFU/mL, and then the solution was diluted by a cation-adjusted Hinton Miller Cation-Adjusted Mueller Hinton II Broth (MHB, BD BBLTM) to a concentration of $5\times10^5$ CFU/mL, and 100 μL of the solution was added to a round bottom 96-well plate containing the drugs. The plate was placed upside down at 37° C. and the MIC value was read after 20-24 h of incubation, and the lowest drug concentration that inhibited the growth of bacteria was set as MIC. The specific test results are shown in Table 3.

TABLE 3

Detection of antibacterial activity of the compounds on clinically isolated *Acinetobacter baumannii*

| Experimental strains/embodiments | Minimum Inhibitory Concentration (MIC) (μg/ml) | | | | | | | | |
|---|---|---|---|---|---|---|---|---|---|
| | 36 | 41 | 44 | 43 | 46 | 45 | Aztreonam | Tigecycline | Meropenem |
| *Acinetobacter baumannii* C181 | 2 | 4 | 2 | >16 | 4 | >16 | 64 | 1 | 128 |
| *Acinetobacter baumannii* C241 | 2 | 4 | 2 | >16 | 4 | >16 | 128 | 2 | 64 |
| *Acinetobacter baumannii* C251 | 16 | 8 | 4 | 8 | >16 | 16 | 32 | 8 | 64 |
| *Acinetobacter baumannii* C270 | 2 | 2 | 1 | 8 | 4 | 16 | 64 | 1 | 64 |
| *Acinetobacter baumannii* C279 | 2 | 2 | 1 | 8 | 4 | 16 | 64 | 1 | 64 |
| Acinetobacter baumannii C281 | 2 | 2 | 1 | 8 | 4 | 16 | 64 | 1 | 64 |
| *Acinetobacter baumannii* C283 | 2 | 2 | 1 | 8 | 4 | 16 | 64 | 1 | 64 |
| *Acinetobacter baumannii* C312 | 2 | 2 | 1 | 8 | 4 | 16 | 64 | 1 | 64 |
| *Acinetobacter baumannii* C313 | 2 | 2 | 1 | 8 | 4 | 16 | 64 | 1 | 64 |
| *Acinetobacter baumannii* C315 | 2 | 2 | 1 | 8 | 4 | 16 | 64 | 1 | 64 |
| *Acinetobacter baumannii* C319 | 2 | 2 | 1 | 8 | 4 | 16 | 64 | 1 | 64 |
| *Acinetobacter baumannii* C328 | 2 | 2 | 1 | 8 | 4 | 16 | 64 | 1 | 32 |
| *Acinetobacter baumannii* C330 | 2 | 2 | 1 | 8 | 4 | 16 | 64 | 1 | 64 |
| *Acinetobacter baumannii* C332 | 2 | 2 | 1 | 8 | 4 | 16 | 64 | 1 | 64 |
| *Acinetobacter baumannii* C333 | 2 | 2 | 2 | 8 | 4 | 16 | 64 | 1 | 64 |
| Acinetobacter baumannii C357 | 2 | 2 | 1 | 8 | 4 | 8 | 32 | 1 | 64 |
| Acinetobacter baumannii C361 | 2 | 1 | 1 | 8 | 4 | 8 | 32 | 1 | 64 |
| *Acinetobacter baumannii* C390 | 2 | 2 | 1 | 8 | 4 | 16 | 64 | 1 | 64 |
| *Acinetobacter baumannii* C394 | 2 | 2 | 1 | 8 | 4 | 16 | 64 | 1 | 64 |
| *Acinetobacter baumannii* C395 | 2 | 2 | 1 | 8 | 4 | 8 | 32 | 1 | 32 |
| *Acinetobacter baumannii* C401 | 1 | 1 | 1 | 8 | 4 | 8 | 32 | 1 | 128 |
| *Acinetobacter baumannii* C402 | 2 | 2 | 1 | 8 | 4 | 8 | 32 | 1 | 64 |
| *Acinetobacter baumannii* C403 | 2 | 4 | 2 | 16 | 4 | 16 | 64 | 1 | 64 |
| *Acinetobacter baumannii* C408 | 2 | 2 | 1 | 8 | 4 | 8 | 32 | 1 | 128 |
| *Acinetobacter baumannii* C427 | 2 | 4 | 2 | 16 | 4 | 16 | 64 | 1 | 64 |

TABLE 4

Detection of antibacterial activity of the compounds on clinically isolated *Pseudomonas aeruginosa*

| Experimental strains/embodiments | MIC (µg/ml) | | | | | | | | |
|---|---|---|---|---|---|---|---|---|---|
| | 36 | 41 | 44 | 43 | 46 | 45 | Aztreonam | Tigecycline | Meropenem |
| *Pseudomonas aeruginosa* W47 | 0.5 | 2 | 2 | 8 | 1 | 16 | 16 | 16 | 4 |
| *Pseudomonas aeruginosa* W23 | 0.25 | 0.5 | 0.5 | 1 | 0.25 | 4 | 16 | 16 | 16 |
| *Pseudomonas aeruginosa* W21 | 0.25 | 0.5 | 0.5 | 1 | 0.25 | 4 | 16 | 8 | 16 |
| *Pseudomonas aeruginosa* W29 | 0.5 | 1 | 2 | 8 | 1 | 16 | 32 | 16 | 4 |
| *Pseudomonas aeruginosa* W28 | 4 | 4 | 4 | 8 | 4 | >16 | 32 | >16 | 32 |
| *Pseudomonas aeruginosa* W24 | 0.5 | 2 | 2 | 8 | 1 | 16 | 32 | 16 | 16 |
| *Pseudomonas aeruginosa* W27 | 0.5 | 4 | 4 | 8 | 1 | 16 | 32 | 16 | 32 |
| *Pseudomonas aeruginosa* W46 | 0.25 | 2 | 1 | 4 | 0.5 | 8 | 16 | 8 | 2 |
| *Pseudomonas aeruginosa* W1 | 0.5 | 2 | 2 | 8 | 1 | 16 | 32 | 16 | 4 |
| *Pseudomonas aeruginosa* M4 | 1 | 0.5 | 0.5 | 0.25 | 1 | 0.25 | <0.25 | 4 | 0.5 |
| *Pseudomonas aeruginosa* M1 | 0.5 | 1 | 0.5 | 1 | 1 | 4 | 8 | 16 | 4 |
| *Pseudomonas aeruginosa* W32 | 1 | 4 | 2 | 8 | 1 | 16 | 32 | 16 | 4 |
| *Pseudomonas aeruginosa* W42 | 0.25 | 0.5 | 0.5 | 1 | 0.5 | 4 | 16 | 8 | 1 |
| *Pseudomonas aeruginosa* W35 | 0.125 | 0.5 | 0.25 | 1 | 0.25 | 2 | 2 | 8 | 16 |
| *Pseudomonas aeruginosa* W13 | 0.25 | 0.5 | 0.5 | 1 | 0.25 | 4 | 16 | 8 | 16 |
| *Pseudomonas aeruginosa* W20 | 0.5 | 4 | 2 | 8 | 1 | 16 | 32 | 16 | 8 |
| *Pseudomonas aeruginosa* W9 | 0.5 | 4 | 4 | 8 | 1 | 16 | 32 | 16 | 16 |
| *Pseudomonas aeruginosa* W19 | 0.25 | 1 | 1 | 4 | 0.5 | 8 | 16 | 8 | 1 |
| *Pseudomonas aeruginosa* W6 | 0.5 | 4 | 4 | 8 | 1 | >16 | 32 | 16 | 32 |
| *Pseudomonas aeruginosa* W4 | 1 | 0.5 | 0.5 | 0.5 | 1 | 2 | 4 | 8 | 2 |
| *Pseudomonas aeruginosa* C763 | 4 | 4 | 2 | 8 | 4 | >16 | 32 | >16 | 32 |
| *Pseudomonas aeruginosa* C762 | 8 | 8 | 4 | 16 | 8 | >16 | 128 | >16 | 32 |
| *Pseudomonas aeruginosa* C745 | 8 | 4 | 4 | 8 | 4 | >16 | 32 | >16 | 32 |
| *Pseudomonas aeruginosa* C755 | 0.25 | 0.5 | 0.5 | 1 | 0.5 | 4 | 4 | 4 | <0.25 |
| *Pseudomonas aeruginosa* C761 | 0.25 | 1 | 1 | 2 | 0.25 | 8 | 8 | 16 | <0.25 |
| *Pseudomonas aeruginosa* C754 | 0.25 | 0.5 | 0.5 | 1 | 0.5 | 4 | 4 | 8 | <0.25 |
| *Aeruginosa* ATCC27853 | 0.25 | 0.5 | 0.5 | 1 | 0.5 | 2 | 2 | 8 | <0.25 |

Conclusions: the compound of the present disclosure has obvious advantage in antibacterial activity relative to meropenem, tigecycline and aztreonam (MIC range is 32→128 µg/mL) against *Acinetobacter baumannii* and *Pseudomonas aeruginosa*. The activity data also shows that the novel monocyclic β-lactam compound designed and synthesized by the present disclosure can effectively solve the drug resistance issues of the *Acinetobacter baumannii* on aztreonam, meropenem and tigecycline.

Experimental Example 4: Antibacterial Activity of the Compounds on *Acinetobacter baumannii* (ATCC 17978) Lung Infection Model Four days before administration: thirty CD-1 female mice were divided into 6 cages, 5 mice per cage (marked according to the table below); immunosuppressant cyclophosphamide (150 mpk) was injected intraperitoneally.

| Group | Test compound | |
|---|---|---|
| 1 | 2h Control group | |
| 2 | Infected group | |
| 3 | Embodiment 32 | 150 mpk |
| 4 | Embodiment 34 | 150 mpk |
| 5 | Embodiment 13 | 150 mpk |
| 6 | Tigecycline | 15 mpk |

One day before administration: the mice of the seven cages were injected intraperitoneally with immunosuppressant cyclophosphamide (100 mpk); MHA plate recovery strain ATCC-17978.

On the day of administration: the recovered bacterial colonies were selected and dissolved in normal saline to prepare a ATCC-17978 bacterial liquid with a concentration of 1.0E+09 CFU/ml, which is used for lung infection in mice. The experimental mice were infected by nasal drip, the amount of infected bacterial liquid was 50 µL/mouse, the actual bacterial concentration was 4.40E+09 CFU/ml, and the infection amount of each mouse was 2.20E+08 CFU/mouse.

2 hours after infection, lung tissues of mice in the control group were placed in 5 mL normal saline, the lung tissues were homogenized, and the plates were diluted by gradient dilution;

The mice were administrated according to the above grouping, specific administration delivery was carried out as follows:

(1) 2, 4, 6, 8 hours after infection: the second, third, fourth, fifth and sixth cages of mice were injected intraperitoneally with normal saline, compound 32 at 150 mpk, compound 34 at 150 mpk, and compound 13 at 150 mpk, respectively.

(2) 2, 10 hours after infection: mice in the seventh cage were injected intraperitoneally with Timpcyclin at 15 mpk.

One day after administration: At the end of 24 h infection of mice in the second to seventh cages, lung tissues were placed in 5 mL normal saline, homogenized and the plates were diluted by gradient dilution, the operation was duplicated to each mouse.

Two days after administration: the bacterial load in the lung tissues of the mice was counted, and the experimental results were sorted out. The experimental results are shown in FIG. 1.

Conclusion: The compound of the present disclosure has an in vivo therapeutic effect on lungs of immunosuppressed mice infected with *Acinetobacter baumannii* caused by cyclophosphamide in, which can significantly reduce the bacteria load of lung tissue.

Experimental Example 5: Antibacterial Activity of Compounds on *Escherichia coli* (ATCC 25922) Thigh Muscle Infection Model Four days before administration: fifteen CD-1 female mice were divided into 5 cages, 3 mice per cage (marked according to the table below); immunosuppressant cyclophosphamide (150 mpk) was injected intraperitoneally.

| Group | Test compounds | |
|---|---|---|
| 1 | 2h Control group | |
| 2 | Infected group | |
| 3 | Ciprofloxacin | 20 mpk |
| 4 | Embodiment 32 | 45 mpk |
| 5 | Embodiment 34 | 45 mpk |

One day before administration: 5 cages of mice were injected intraperitoneally with the immunosuppressant cyclophosphamide (100 mpk) for another time; MHA plate recovered strain ATCC-25922.

On the day of administration: the recovered bacterial colonies were selected and dissolved in normal saline to prepare a ATCC-25922 bacterial solution with a concentration of 1.0E+07 CFU/mL, which is used for thigh muscle infection in mice. The amount of bacterial solution injected into the thigh muscle of the experimental mice was 100 µL/mouse, the actual bacterial concentration was 1.0E+07 CFU/mL, and the infection amount of each mouse was 2.20E+08 CFU/mouse.

2 h after infection, thigh muscle tissues of the mice in the control group were placed in 10 mL normal saline, the thigh muscle tissues were homogenized, and the plates were diluted by gradient dilution;

The mice were grouped according to the above table and administrated, specific administration delivery was carried out as follows:

(1) 2 hours after infection: the third, fourth and fifth cages of mice were intraperitoneally injected with 20 mpk, compound 32 at 45 mpk, and compound 34 at 45 mpk, respectively;

(2) 4, 8 hours after infection: the fourth and fifth cages of mice were injected intraperitoneally with compound 32 at 45 mpk and Compound 34 at 45 mpk, respectively;

(3) 10 hours after infection: the third, fourth and fifth cages of mice were intraperitoneally injected with ciprofloxacin at 20 mpk, compound 32 at 45 mpk, and compound 34 at 45 mpk, respectively.

One day after administration: At the end of 24 hours infection of mice in the second to fifth cages, thigh muscle tissues were placed in 10 mL normal saline, homogenized and the plates were diluted by gradient dilution, the operation was duplicated to each mouse.

Two days after administration: the bacterial load in the thigh muscle tissues of the mice was counted, and the experimental results were sorted out.

Experimental Results

Conclusions: The compound of the present disclosure has an in vivo therapeutic effect on thigh muscle of immunosuppressed mice infected with *Escherichia coli* caused by cyclophosphamide, which can significantly reduce the bacteria load in muscle tissue.

Experimental Example 6: Pharmacokinetic Experiment of the Compounds in Mice

Experimental Design and Operation:

In this experiment, six CD-1 mice (males) were divided into 2 groups (2 groups) according to their similar body weight. Group 1 and Group 2 were given respectively a single intravenous and intraperitoneal injection of the compounds of embodiment 13, embodiment 17, embodiment 32 and embodiment 34, each compound was at 2 mg/kg. The vehicles for intravenous and intraperitoneal injections were 5% dimethyl sulfoxide/95% water (10% polyoxyethylene castor oil), K2-EDTA (anticoagulant).

The details of administration and blood collection are shown in Tables 5 and 6 below.

About 0.02 mL of blood samples from the saphenous vein were collected from all experimental animals, and the actual blood collection time was recorded. In this experiment, the deviation between the actual blood collection time and the theoretical blood collection time was in accordance with the regulations (the deviation of time points within 1 hour after administration were within 1 minute, and other deviations were within 5% of the theoretical time). After the blood samples were collected, they were immediately transferred to labeled centrifuge tubes containing K2 EDTA (0.5 M), followed by centrifugation (3,000 g, 4° C., 15 minutes) and the plasma was collected. The plasma was transferred to pre-cooled centrifuge tubes, quickly frozen in dry ice, and stored in an ultra-low temperature refrigerator at −60° C. or lower until LC-MS/MS analysis.

TABLE 5

| Group | Number of animal in each group Male | Dosage (mg/kg) | Concentration (mg/mL) | Administration volume (mL/kg) | Vehicle | Administration route | Administration frequency |
|---|---|---|---|---|---|---|---|
| 1 | 3 | 1 | 0.2 | 5 | 5% dimethyl sulfoxide/ 95% water (10% polyoxyethylene castor oil) | intravenous injection | Single |
| 2 | 3 | 2 | 0.4 | 5 | 5% dimethyl sulfoxide/ 95% water (10% polyoxyethylene castor oil) | intravenous injection | Single |
| 3 | 3 | 2 | 0.4 | 5 | 5% dimethyl sulfoxide/ 95% water (10% polyoxyethylene castor oil) | intraperitoneal injection | Single |

TABLE 6

| Group | Medium | Time point |
|---|---|---|
| 1 | plasma | Before administration, and 0.083 (5 min), 0.25 (15 min), 0.5 (30 min), 1, 2, 4, 8 and 24 hour after administration |
| 2 | plasma | Before administration, and 0.083 (5 min), 0.25 (15 min), 0.5 (30 min), 1, 2, 4, 8 and 24 hour after administration |
| 3 | plasma | Before administration, and 0.083 (5 min), 0.25 (15 min), 0.5 (30 min), 1, 2, 4, 8 and 24 hour after administration |

TABLE 7

Pharmacokinetic data of the compounds in mice

| | Experimental method | Embodiment 13 | Embodiment 17 | Embodiment 32 | Embodiment 34 |
|---|---|---|---|---|---|
| Male CD-1 mice, fasting, intravenous injection; vehicle: 0.20 mg/mL in 5% dimethyl sulfoxide/95% water (10% polyoxyethylene | dosage | 2 mpk | 2 mpk | 2 mpk | 2 mpk |
| | Clearance rate Cl | 8.51 | 4.6 | 1.57 | 10.4 |
| | Apparent distribution volume $Vd_{ss}$ (L/kg) | 0.281 | 0.237 | 0.0636 | 0.274 |
| | Exposure $AUC_{0\text{-}last}$ (nM.hr) | 6728 | 11007 | 5773 | 4948 |

TABLE 7-continued

Pharmacokinetic data of the compounds in mice

| Experimental method | | Embodiment 13 | Embodiment 17 | Embodiment 32 | Embodiment 34 |
|---|---|---|---|---|---|
| castor oil), clear solution | Initial concentration $C_0$ (nM) | 18850 | 16991 | 11290 | 14409 |
| | Half-life period $T_{1/2}$ (hr) | 0.477 | 0.596 | 0.513 | 0.376 |
| Male CD-1 mice, fasting, intravenous injection; vehicle: 0.20 mg/mL in 5% dimethyl sulfoxide/95% water (10% polyoxyethylene castor oil), clear solution | dosage | 2 mpk | 2 mpk | 2 mpk | 2 mpk |
| | Exposure $AUC_{0-last}$ | 6059 | 14657 | 8765 | 4723 |
| | Maximum concentration $C_{max}$ (nM) | 5760 | 10577 | 7997 | 5550 |
| | Half-life period $T_{1/2}$ | 0.439 | 0.569 | 0.540 | 0.378 |
| | Bioavailability (%) | 88.4 | 131 | 140 | 93.3 |

Conclusion: The compound of the present disclosure has low clearance rate, high blood exposure and high bioavailability for intraperitoneal administration in mice, and has good pharmacokinetic properties.

Experimental Example 7: Compounds Experiment on the Lungs of Mice Infected with *Pseudomonas aeruginosa* (1)

1. Experimental Strain

*Pseudomonas aeruginosa* PA14.

2. Test Drugs (1) Test compounds: Embodiment 32, Embodiment 34
(2) Reference compounds: I-g (WO2018065636), aztreonam (product of Dalian Meilune Biotechnology Co., Ltd.).

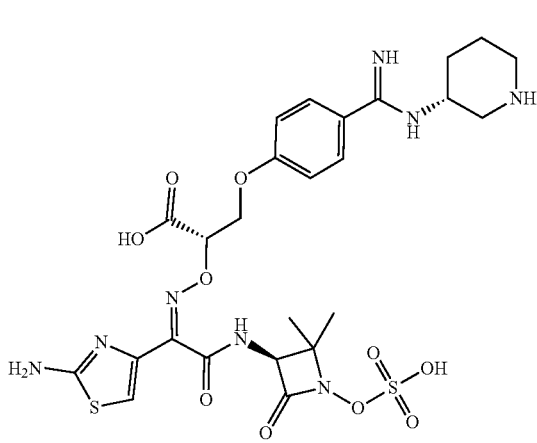

I-g

3. Medium

Mueller-Hinton agar (MHA) and TSA medium, purchased from BD Company.

4. Experimental Animals

CD-1 (ICR) mice, provided by Beijing Charles River Laboratory Animal Technology Co., Ltd., weighing 23-27 g, 7 weeks old, female, a total of 64 mice.

3. Experimental Method (1) Intraperitoneal Injection of Cyclophosphamide to Give Immunosuppressed Mice 64 mice were intraperitoneally injected with 150 mg/kg cyclophosphamide on the first day and the fourth day to give immunosuppressed mice.

(2) Experimental Grouping

Ten groups were set in the experiment, namely the high-, medium-, and low-dose groups of embodiment 34, the high-, medium-, and low-dose groups of embodiment 32, the high- and medium-dose groups of novel antibiotic 3, the aztreonam group, and the model group, 6 animals in each group, and the lung tissues of the remaining four animals were taken to count the bacteria after lung infection for 2 hours. The specific grouping is shown in the table below.

TABLE 8

Grouping of *Pseudomonas aeruginosa* infection experiment in mice

| Group | Drug | Dosage (mg/kg.day) | Administration method | Number of animal |
|---|---|---|---|---|
| A: High-dose group of embodiment 34 | Embodiment 34 | 200 | 2 h, 4 h, 6 h, 8 h; ip | 6 |
| B: Medium-dose group of embodiment 34 | Embodiment 34 | 120 | 2 h, 4 h, 6 h, 8 h; ip | 6 |
| C: Low-dose group of embodiment 34 | Embodiment 34 | 60 | 2 h, 4 h, 6 h, 8 h; ip | 6 |
| D: High-dose group of embodiment 32 | Embodiment 32 | 200 | 2 h, 4 h, 6 h, 8 h; ip | 6 |
| E: Medium-dose group of embodiment 32 | Embodiment 32 | 120 | 2 h, 4 h, 6 h, 8 h; ip | 6 |
| F: Low-dose group of embodiment 32 | Embodiment 32 | 60 | 2 h, 4 h, 6 h, 8 h; ip | 6 |
| G: High-dose group of I-g | I-g | 200 | 2 h, 4 h, 6 h, 8 h; ip | 6 |

TABLE 8-continued

Grouping of *Pseudomonas aeruginosa* infection experiment in mice

| Group | Drug | Dosage (mg/kg.day) | Administration method | Number of animal |
|---|---|---|---|---|
| H: Medium-dose group of I-g | I-g | 120 | 2 h, 4 h, 6 h, 8 h; ip | 6 |
| I: Aztreonam group | Aztreonam | 400 | 2 h, 4 h, 6 h, 8 h; ip | 6 |
| J: Model group | Normal saline (NS) | — | 2 h, 4 h, 6 h, 8 h; ip | 10 |

(3) Lung Infection with *Pseudomonas aeruginosa*

The mice were injected with 50 μL of bacterial solution ($2\times10^3$ CFU) through the airway. 2 hours after the infection, 4 mice in the model group was sacrificed by removing cervical vertebra.

(4) Administration

Two hours after infection, the drugs were administered by groups, and the mice were administered intraperitoneally once at 2 hours, 4 hours, 6 hours, and 8 hours, a total of 4 times.

(5) Bacteria Count

Mice of each group were sacrificed by removing cervical vertebra 24 hours after infection, lung and kidney tissues were taken aseptically and put into sterilized tissue homogenate tubes, weighed, and an appropriate amount of normal saline (NS) was added, the mixture was homogenized by a homogenizer for 1 min, the lung tissues of the model group were diluted $10^4$, $10^5$, $10^6$ times, the lung tissues of each administration group were diluted 10, 100 times, the kidney tissues of the model group were diluted $10^2$, $10^1$, $10^4$ times, and the lung tissues of each administration group were diluted 10 times, the obtained mixtures were coated on TSA plates using spiral coater, then incubated at 37° C. overnight, and the CFU was counted with a colony counter.

(6) Weight

The mice were weighed every day after the start of the experiment and the weight changes were recorded.

(7) Data Processing

Graphpad Prism mapping software was used to make scatter plots of lung tissue CFU. SPSS19.0 software was used to count CFU and average body weight, and analysis of variance was used to analyze differences between groups.

4. Experimental Results (1) Bacterial load in the lungs of immunosuppressed mice infected with *Pseudomonas aeruginosa*

The number of *Pseudomonas aeruginosa* PA14 infected in the lungs of the 4 immunosuppressed mice injected twice with cyclophosphamide through intraperitoneal injection was about $1.06\times10^4$ CFU. After 2 hours, the lung tissues were homogenized to count the bacteria, and the bacterial load of the mice was calculated, the average load was in the range of $5.10\times10^3$ CFU.

(2) Changes in body weight: the weight of animals in each group is shown in Table 9.

The body weight of the animals in each administration group did not change significantly, indicating that the compound of the present disclosure is safe.

TABLE 9

Animal weight changes of the animal in the novel monocyclic β-lactam antibiotics in vivo protection test

| Group | The number of animal | Body weight on the first day (g) | Body weight on the fourth day (g) | Body weight on the fifth day (g) |
|---|---|---|---|---|
| Model group | 10 | 27.01 ± 1.37 | 26.25 ± 2.43 | 26.19 ± 2.43 |
| High-dose group of embodiment 34 | 6 | 27.15 ± 0.85 | 27.32 ± 0.86 | 26.50 ± 1.40 |
| Medium-dose group of embodiment 34 | 6 | 27.11 ± 0.93 | 27.45 ± 2.54 | 27.25 ± 1.52 |
| Low-dose group of embodiment 34 | 4 | 27.11 ± 0.87 | 27.45 ± 0.76 | 27.05 ± 0.57 |
| High-dose group of embodiment 32 | 6 | 26.91 ± 1.03 | 28.03 ± 2.15 | 25.40 ± 2.75 |
| Medium-dose group of embodiment 32 | 6 | 26.47 ± 1.65 | 28.33 ± 1.14 | 28.01 ± 1.35 |
| Low-dose group of embodiment 32 | 6 | 26.14 ± 1.21 | 27.76 ± 0.43 | 26.77 ± 1.02 |
| High-dose group of I-g | 6 | 27.25 ± 1.14 | 28.39 ± 1.60 | 26.43 ± 1.06 |
| Medium-dose group of I-g | 6 | 27.02 ± 1.12 | 28.21 ± 1.16 | 27.20 ± 0.96 |
| Azetreonam | 6 | 27.16 ± 1.74 | 27.80 ± 2.37 | 28.02 ± 1.08 |

(3) Lung Tissues Bacterial Load in Mice after Administration

Novel monocyclic β-lactam antibiotics of embodiment 32, embodiment 34, Ig and aztreonam were injected intraperitoneally at 2 hours, 4 hours, 6 hours and 8 hours after infection, animals were sacrificed at 24 hours, lung tissues were taken aseptically and soaked in normal saline (NS), the tissues were homogenized and after proper dilution, 50 μL of the mixtures were evenly coated on TSA plates, then incubated overnight in a 37° C. incubator, the number of colonies were counted and converted to CFU per milliliter according to the dilution ratio, and then the bacteria load was calculated as a logarithm based on 10, the means and standard deviations were compared between each group, the results are shown in Table 10 and FIG. 1. The 24 hours bacterial load in the model group increased from $1.06\times10^4$ CFU to $3.34\times10^8$ CFU (the $LOG_{10}$ of the bacterial load was 8.14), and the bacterial load in each administration group was significantly lower than that in the model group, indicating the bacteria was basically eliminated, the bacteria in the high-, medium- and low-dose groups of novel antibiotic 2 were completely eliminated.

TABLE 10

Lung bacterial load after administration of the immunosuppressive mice with lung *Pseudomonas* infection

| Group | Drug | Total dosage (mg/kg, day) | Number of animals ( ) | $LOG_{10}$-of bacterial load |
|---|---|---|---|---|
| Model group | — | — | 4 | 8.14 ± 0.85 |
| High-dose group of Embodiment 34 | Embodiment 34 | 200 | 6 | 1.10 ± 1.75** |
| Medium-dose group of embodiment 34 | | 120 | 6 | 0** |
| Low-dose group of embodiment 34 | | 60 | 4 | 0** |
| High-dose group of embodiment 32 | Embodiment 32 | 200 | 6 | 0** |

TABLE 10-continued

Lung bacterial load after administration of the immunosuppressive mice with lung Pseudomonas infection

| Group | Drug | Total dosage (mg/kg, day) | Number of animals ( ) | LOG$_{10}$-of bacterial load |
|---|---|---|---|---|
| Medium-dose group of embodiment 32 | | 120 | 6 | 0** |
| Low-dose group of embodiment 32 | | 60 | 6 | 0** |
| High-dose group of I-g | Compound I-g | 200 | 6 | 0** |
| Medium-dose group of I-g | | 120 | 6 | 1.58 ± 2.45** |
| Aztreonam | Aztreonam | 400 | 5 | 1.62 ± 2.22** |

Note:
**Compared with the model group, p < 0.01, indicating a very significant difference Experimental Conclusions The compound of the present disclosure has an in vivo therapeutic effect on the lungs of immunosuppressed mice infected with Pseudomonas aeruginosa caused by cyclophosphamide, which can significantly reduce the bacterial load in lung tissue and eliminate Pseudomonas aeruginosa from the infection lung.

Experimental Example 8: Compounds Experiment on the Lungs of Mice Infected with Pseudomonas aeruginosa (2)

1. Experimental Strain

Pseudomonas aeruginosa PA14.

2. Test Drugs (1) Test compounds: Embodiment 41, Embodiment 44, Embodiment 46

(2) Reference compounds: I-g, aztreonam (product of Dalian Meilune Biotechnology Co., Ltd.).

3. Medium

Mueller-Hinton agar (MHA) and TSA medium were purchased from BD Company.

4. Experimental Animals

CD-1 (ICR) mice, provided by Beijing Charles River Laboratory Animal Technology Co., Ltd., weighing 23-27 g, 7 weeks old, female, a total of 64 mice.

3. Experimental Method (1) Intraperitoneal Injection of Cyclophosphamide to Give Immunosuppressed Mice 60 mice were intraperitoneally injected with 150 mg/kg cyclophosphamide on day 1 and day 4 to give immunosuppressed mice.

(2) Experimental Grouping

Eight groups were set in the experiment, namely the high- and low-dose groups of embodiment 41, the high- and low-dose groups of embodiment 44, the high- and low-dose groups of embodiment 46, the reference compound group, the aztreonam group, 6 animals in each group, and further the model group was set with 12 animals, among which 6 of animals was in 2 hours model group. The specific grouping is shown in the table 11.

TABLE 11

Grouping of protective experiment of novel antibiotics on mice infected with Pseudomonas aeruginosa in lungs

| Group | Drug | Dosage (mg/kg.day) | Administration method | Number of animal |
|---|---|---|---|---|
| A: High-dose group Embodiment 41 | Embodiment 41 | 60 | 2 h, 4 h, 6 h, 8 h; ip | 6 |
| B: Low-dose group of Embodiment 41 | Embodiment 41 | 20 | 2 h, 4 h, 6 h, 8 h; ip | 6 |
| C: High-dose group of Embodiment 44 | Embodiment 44 | 60 | 2 h, 4 h, 6 h, 8 h; ip | 6 |
| D: Low-dose group of Embodiment 44 | Embodiment 44 | 20 | 2 h, 4 h, 6 h, 8 h; ip | 6 |
| E: High-dose group Embodiment 46 | Embodiment 46 | 60 | 2 h, 4 h, 6 h, 8 h; ip | 6 |
| F: Low-dose group of Embodiment 46 | Embodiment 46 | 20 | 2 h, 4 h, 6 h, 8 h; ip | 6 |
| G: Reference compound group | Reference compound | 60 | 2 h, 4 h, 6 h, 8 h; ip | 6 |
| H: Aztreonam | Aztreonam | 100 | 2 h, 4 h, 6 h, 8 h; ip | 6 |
| I: 2h model group | — | — | — | 6 |
| J: Model group | 25% sulfobutyl β cyclodextrin | — | 2 h, 4 h, 6 h, 8 h; ip | 6 |

(3) Lung Infection with Pseudomonas aeruginosa

The mice were injected with 50 μL of bacterial solution ($2 \times 10^3$ CFU) through the airway. 2 hours after the infection, 4 mice in the model group was sacrificed by removing cervical vertebra.

(4) Administration

Two hours after infection, the drugs were administered by groups, and the mice were administered intraperitoneally once at 2 hours, 4 hours, 6 hours, and 8 hours, a total of 4 times.

(5) Bacteria Count

Mice of each group were sacrificed by removing cervical vertebra 24 hours after infection, lung and kidney tissues were taken aseptically and put into a sterilized tissue homogenate tube, weighed, and an appropriate amount of normal saline (NS) was added, the mixture was homogenized by a homogenizer for 1 min, the lung tissues of the model group were diluted $10^4$, $10^5$, $10^6$ times, the lung tissues of each administration group were diluted 10, 100 times, the kidney tissues of the model group were diluted $10^2$, $10^3$, $10^4$ times, and the lung tissues of each administration group were diluted 10 times, the obtained mixtures were coated on TSA plates using spiral coater, then incubated at 37° C. overnight, and the CFU was counted with a colony counter.

(6) Weight

The mice were weighed every day after the start of the experiment and the weight changes were recorded.

(7) Data Processing

Graphpad Prism mapping software was used to make scatter plots of lung tissue CFU. SPSS19.0 software was used to count CFU and average body weight, and analysis of variance was used to analyze differences between groups.

4. Experimental Results

Figure 2:
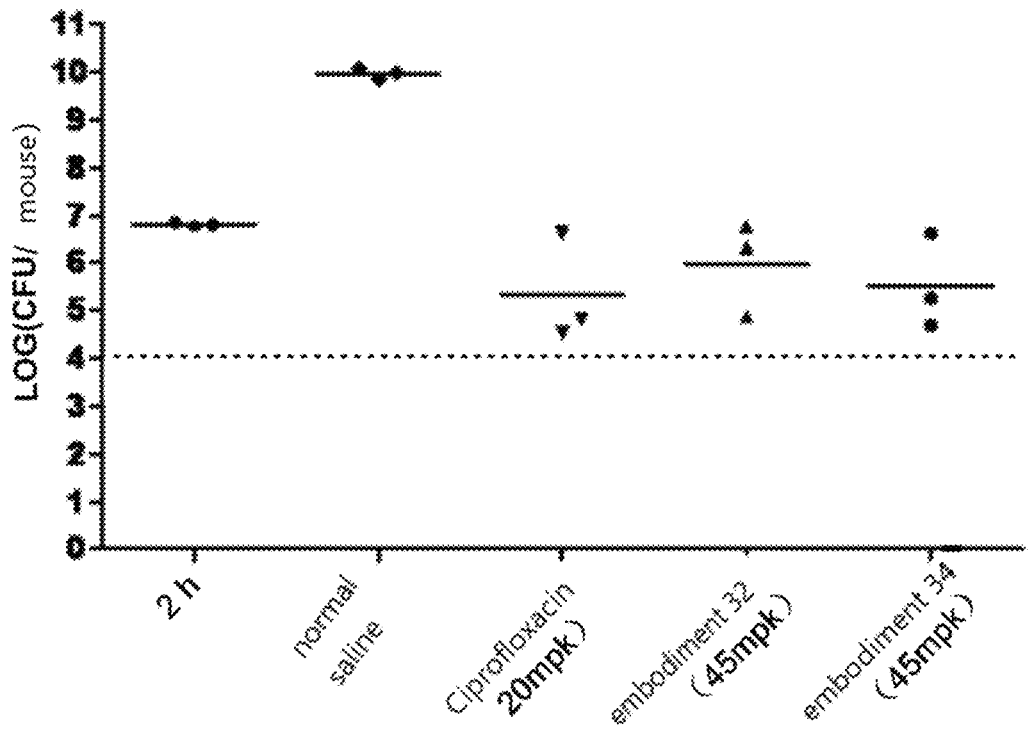
FIG. 2 shows the results of the in vivo efficacy test of the compound on thigh muscle infection in mice.
Figure 3:
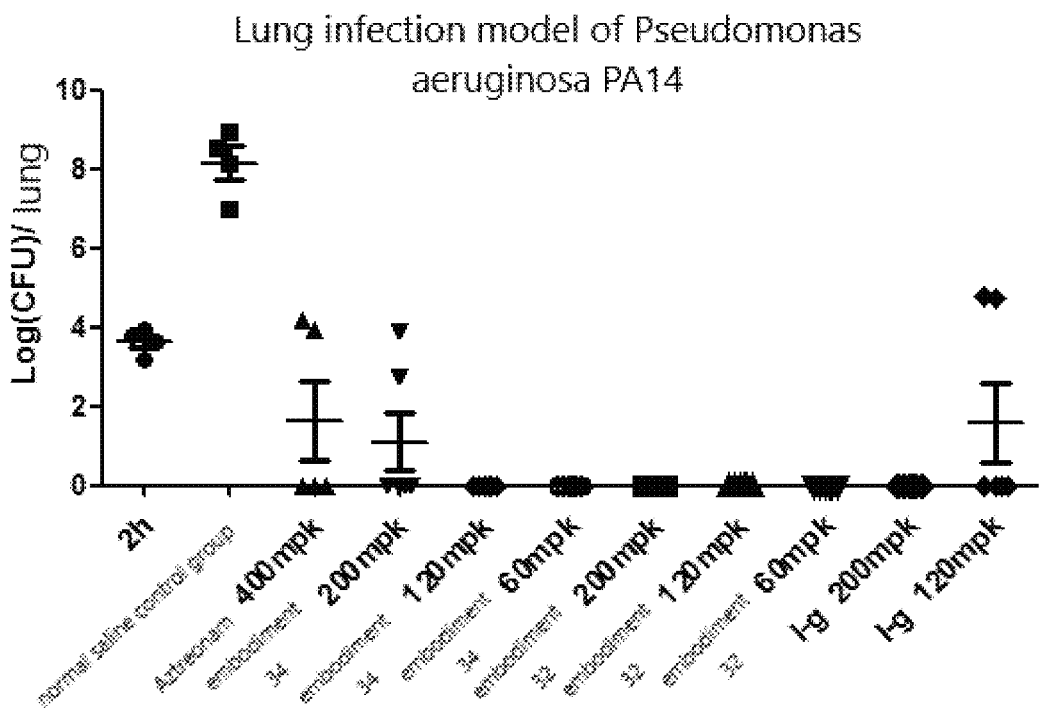
FIGS. 3 and 4 show the lung bacteria load of immunosuppressive mice with *Pseudomonas* infection after drug administration.
Figure 4:
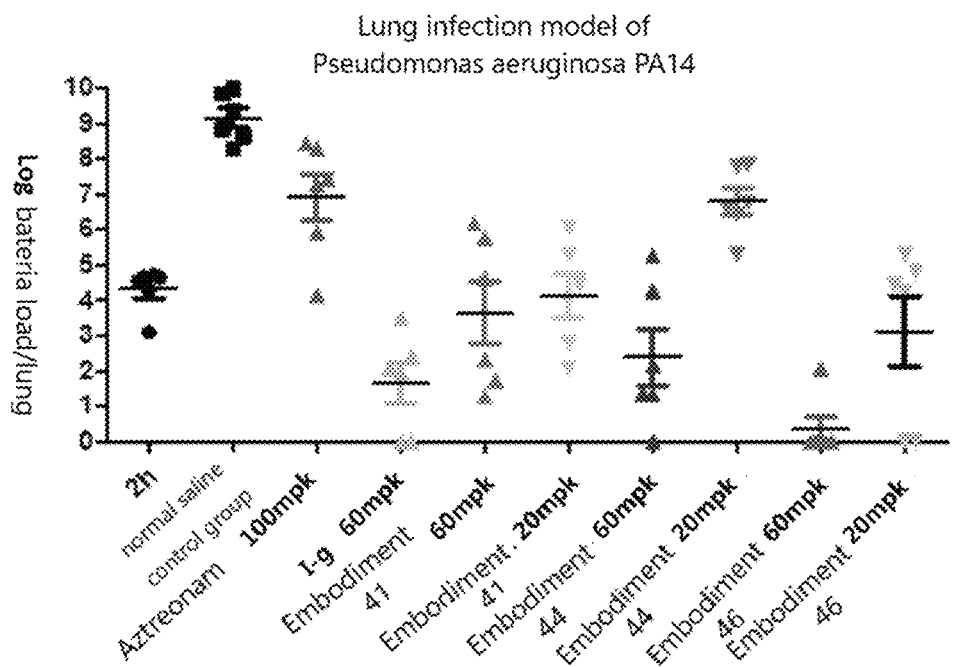

Novel monocyclic β-lactam antibiotics of embodiment 41, embodiment 44, embodiment 61, I-g and aztreonam were injected intraperitoneally at 2 hours, 4 hours, 6 hours and 8 hours after infection, animals were sacrificed at 24 hours, lung tissues were taken aseptically and soaked in normal saline (NS), the tissues were homogenized and after proper dilution, 50 μL of the mixtures were evenly coated on TSA plates, then incubated overnight in a 37° C. incubator, the number of colonies were counted and converted to CFU per milliliter according to the dilution ratio, and then the bacteria load was calculated as a logarithm based on 10, the means and standard deviations were compared between each group, the results are shown in Table 12 and FIG. 2. The 24 hours bacterial load in the model group increased from $3.31 \times 10^4$ CFU to $3.40 \times 10^8$ CFU (the $LOG_{10}$ of the bacterial load was 9.53), and the bacterial load in each administration group was significantly lower than that in the model group. The bacteria in the high and low dose groups of novel antibiotic WXFL70050164 were significantly lower than that of other drug groups, indicating that its efficacy in the body was more better.

TABLE 12

Lung bacterial load of the immunosuppresive mice with *Pseudomonas* infection treated with novel monocyclic β-lactam antibiotics

| Group | Drug | Total dosage (mg/kg, day) | Number of animals ( ) | $LOG_{10}$-of bacterial load |
|---|---|---|---|---|
| Model group | — | — | 6 | 9.16 ± 0.68 |
| High-dose group of embodiment 41 | Embodiment 41 | 60 | 6 | 3.65 ± 2.15** |
| Low-dose group of embodiment 41 | | 20 | 6 | 4.12 ± 1.50** |
| High-dose group embodiment 44 | Embodiment 44 | 60 | 6 | 2.40 ± 1.99** |
| Low-dose group of embodiment 44 | | 20 | 5 | 6.80 ± 0.94** |
| High-dose group of Embodiment 46 | Embodiment 46 | 60 | 6 | 0.34 ± 0.85** |
| Low-dose group of embodiment 46 | | 20 | 6 | 3.13 ± 2.45** |
| High-dose group of the reference compound | Reference compound | 60 | 6 | 1.65 ± 1.39** |
| Aztreonam group | Aztreonam | 100 | 6 | 6.91 ± 1.63** |

Note:
** Compound with the model group. p < 0.01, indicating a very significant difference.

Experimental Conclusion

The compound of the present disclosure has an in vivo therapeutic effect on the lungs of immunosuppressed mice infected with *Pseudomonas aeruginosa* caused by cyclophosphamide, which can significantly reduce the bacterial load of lung tissue and eliminate *Pseudomonas aeruginosa* from the infection lung.

What is claimed is:

1. A compound of formula (I') or formula (II'), a tautomer thereof, a stereoisomer thereof or a pharmaceutically acceptable salt thereof,

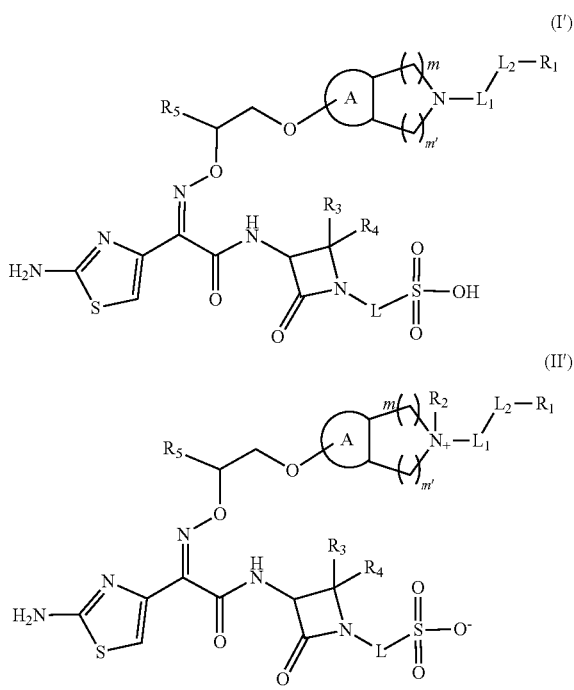

wherein, ring A is phenyl or 5-6 membered heteroaryl;

each of m and m' is independently 1 or 2;

each of $L_1$ and $L_2$ is independently single bond, —NH—, —C(=NH)—, —C(=NR$_6$)NH—, —CH=N— or —(CH$_2$)$_n$—;

$R_6$ is H or 3-6 membered heterocycloalkyl optionally substituted by one, two or three R;

n is 1, 2, 3 or 4;

$R_1$ is H, NH$_2$, C$_{1-6}$ alkyl, C$_{1-6}$ heteroalkyl, C$_{3-6}$ cycloalkyl or 3-6 membered heterocycloalkyl, where each of the C$_{1-6}$ alkyl, C$_{1-6}$ heteroalkyl, C$_{3-6}$ cycloalkyl and 3-6 membered heterocycloalkyl is independently optionally substituted by one, two or three R;

R is selected from F, Cl, Br, I, CH$_3$, NH$_2$,

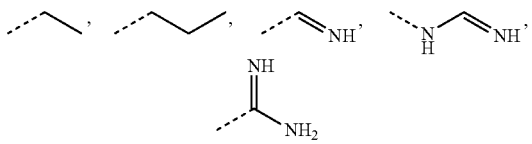

and 5-6 membered heterocycloalkyl, where each of CH$_3$, NH$_2$,

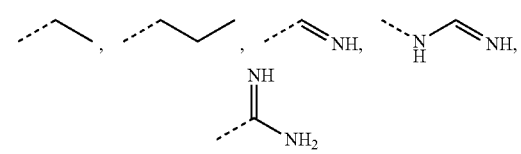

and 5-6 membered heterocycloalkyl is independently optionally substituted by one, two or three R';

R' is selected from F, Cl, Br, I, CH$_3$, NH$_2$,

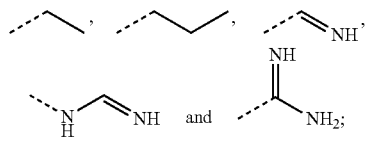

R$_2$ is C$_{1-3}$ alkyl;

each of R$_3$ and R$_4$ is independently H or C$_{1-3}$ alkyl optionally substituted by one, two or three R;

L is single bond or —O—;

R$_5$ is H, COOH, OH, C(=O)NH$_2$, C(=O)CH$_3$ or C(=O)OCH$_3$;

the "hetero" represents for heteroatom or heteroatom group, the "hetero" in 5-6 membered heteroaryl, C$_{1-6}$ heteroalkyl, 3-6 membered heterocycloalkyl, 5-6 membered heterocycloalkyl is independently selected from N, —NH—, —C(=NH)—, —C(=NH)NH—, —O—, —S—, N, =O, =S and —C(=O)—;

in 5-6 membered heteroaryl, 3-6 membered heterocycloalkyl, C$_{1-6}$ heteroalkyl and 5-6 membered heterocycloalkyl, the number of the heteroatom or heteroatom group is independently 1, 2 or 3.

2. The compound as defined in claim 1, the tautomer thereof, the stereoisomer thereof or the pharmaceutically acceptable salt thereof, wherein, R is selected from F, Cl, Br, I, CH$_3$, NH$_2$,

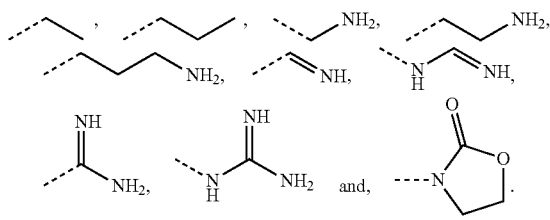

3. The compound as defined in claim 1, the tautomer thereof, the stereoisomer thereof or the pharmaceutically acceptable salt thereof, wherein, R$_1$ is H, NH$_2$, C$_{1-4}$ alkyl, C$_{1-4}$ heteroalkyl, C$_{3-6}$ cycloalkyl or 3-6 membered heterocycloalkyl, where each of the C$_{1-4}$ alkyl, C$_{1-4}$ heteroalkyl, C$_{3-6}$ cycloalkyl and 3-6 membered heterocycloalkyl is independently optionally substituted by one, two or three R.

4. The compound as defined in claim 3, the tautomer thereof, the stereoisomer thereof or the pharmaceutically acceptable salt thereof, wherein, R$_1$ is H, NH$_2$, CH$_3$, OCH$_2$CH$_3$,

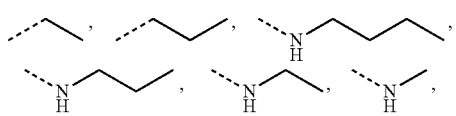

cyclohexyl, pyrrolidinyl, piperidinyl or piperazinyl, where each of the NH$_2$, CH$_3$, OCH$_2$CH$_3$,

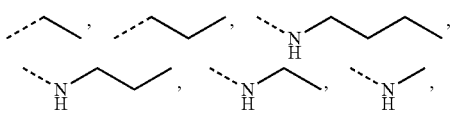

cyclohexyl, pyrrolidinyl, piperidinyl and piperazinyl is independently optionally substituted by one, two or three R.

5. The compound as defined in claim 4, the tautomer thereof, the stereoisomer thereof or the pharmaceutically acceptable salt thereof, wherein, R$_1$ is H, CH$_3$, OCH$_2$CH$_2$(NH$_2$), NH$_2$,

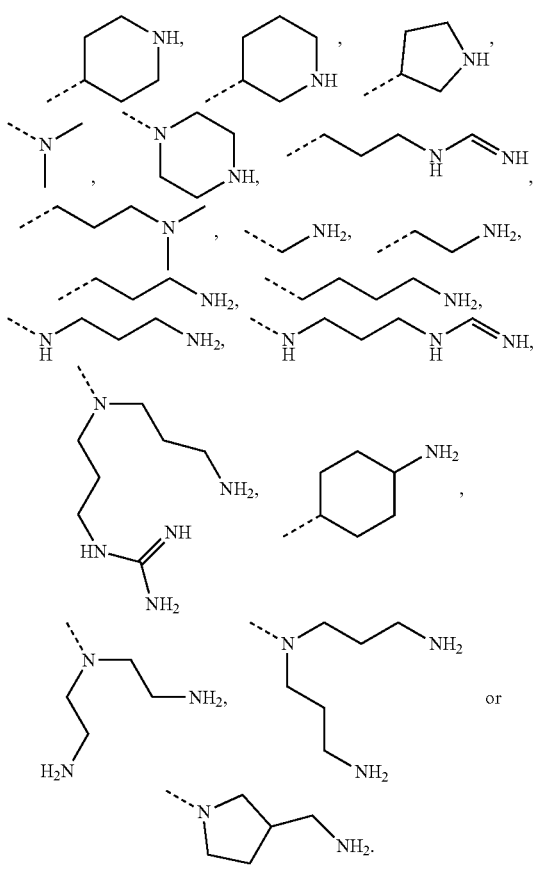

6. The compound as defined in claim 1, the tautomer thereof, the stereoisomer thereof or the pharmaceutically acceptable salt thereof, wherein, R$_6$ is H or piperidinyl optionally substituted by one, two or three R.

7. The compound as defined in claim 6, the tautomer thereof, the stereoisomer thereof or the pharmaceutically acceptable salt thereof, wherein, R$_6$ is H or

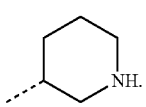

8. The compound as defined in claim 1, the tautomer thereof, the stereoisomer thereof or the pharmaceutically acceptable salt thereof, wherein, the moiety

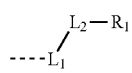
is H, CH₃,
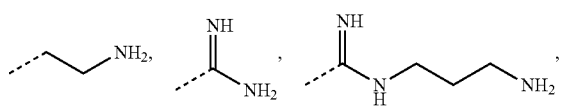
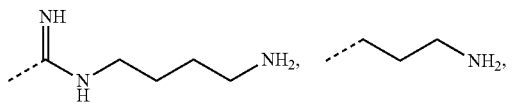
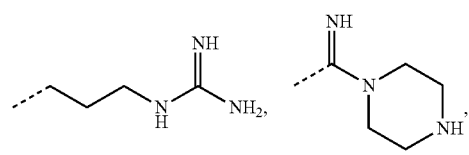
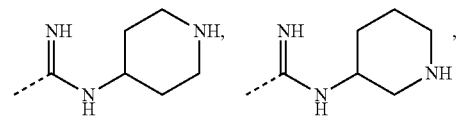
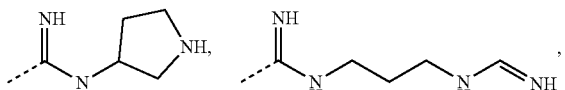
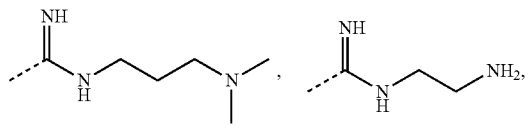
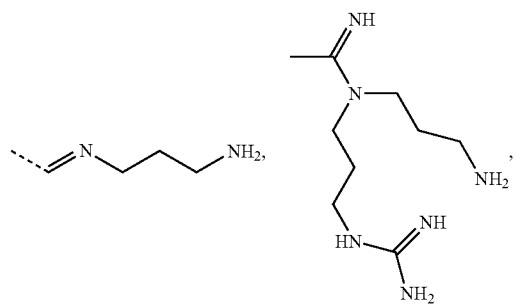
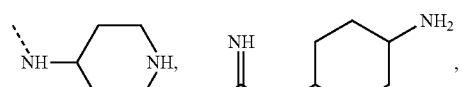
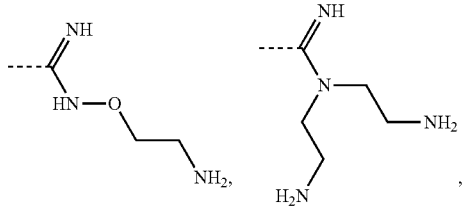
-continued
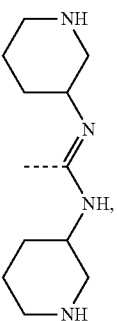
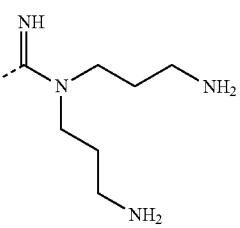
or
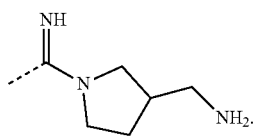
9. The compound as defined in claim 1, the tautomer thereof, the stereoisomer thereof or the pharmaceutically acceptable salt thereof, wherein, R₂ is CH₃;
or ring A is phenyl;
or the moiety
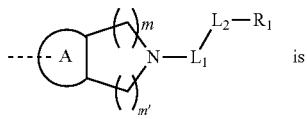 is
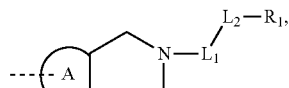
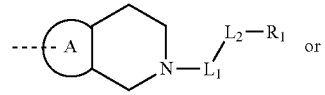 or
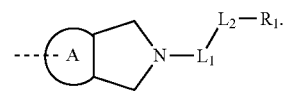
10. The compound as defined in claim 1, the tautomer thereof, the stereoisomer thereof or the pharmaceutically acceptable salt thereof, wherein, the moiety
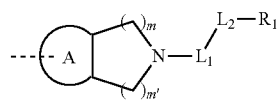
is
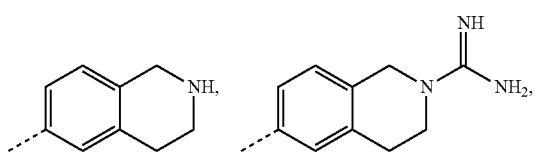

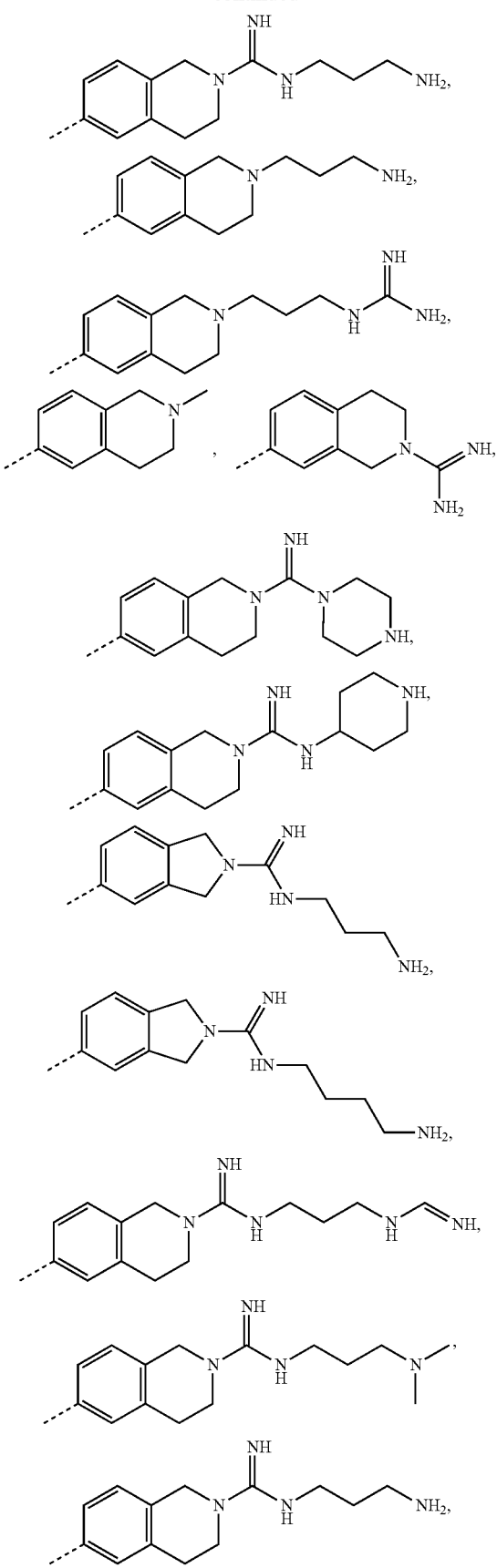
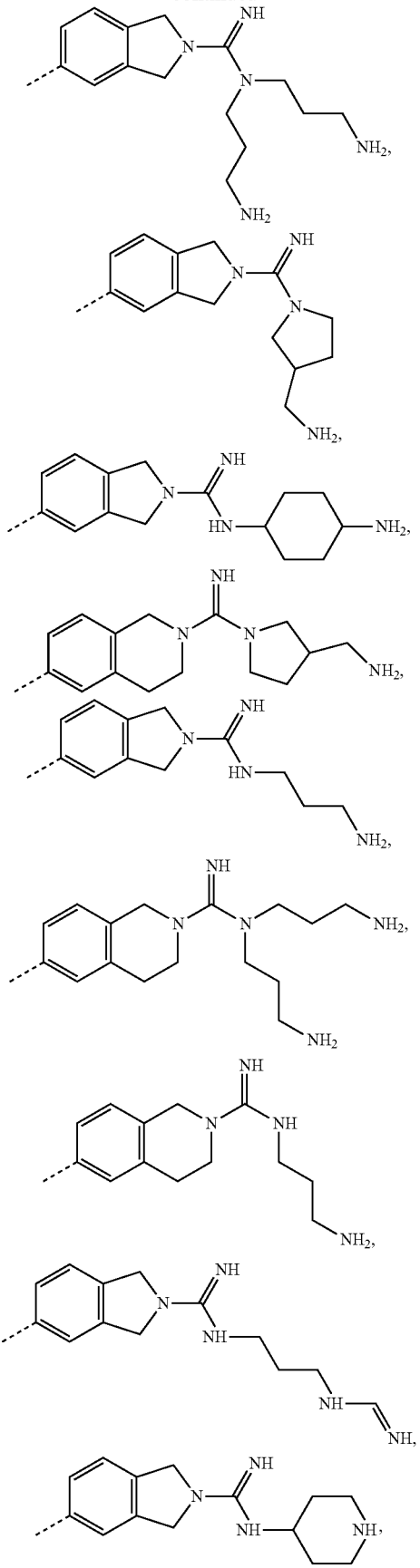

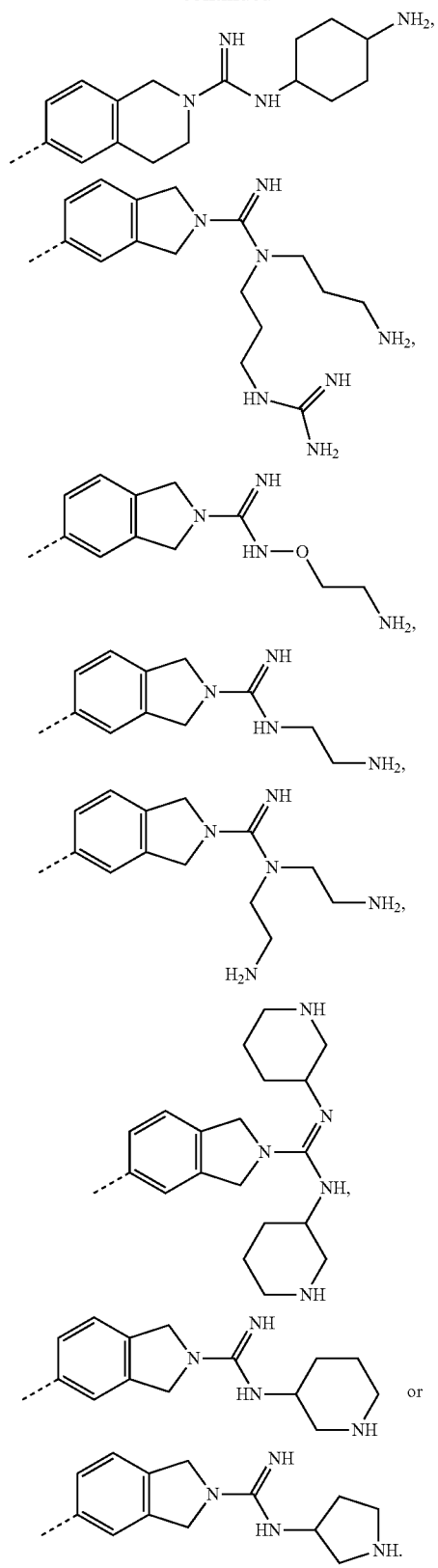

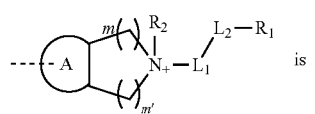

is

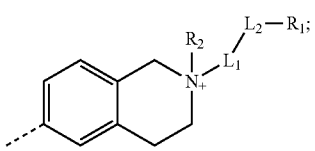

or, the moiety

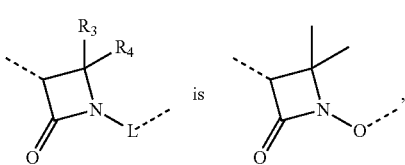

is

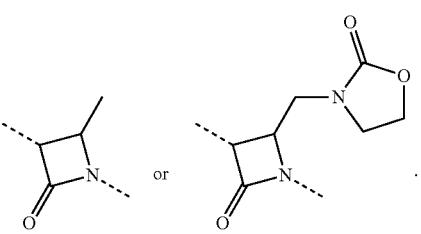

12. The compound as defined in claim 1, the tautomer thereof, the stereoisomer thereof or the pharmaceutically acceptable salt thereof, wherein, the moiety

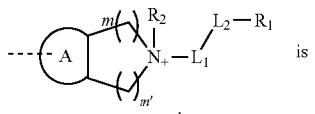

is

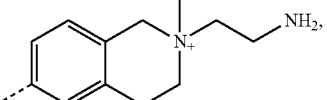

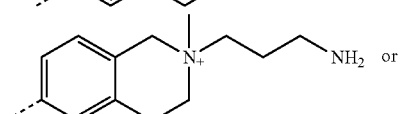

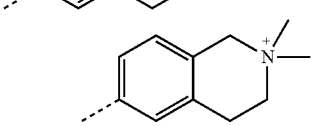

11. The compound as defined in claim 1, the tautomer thereof, the stereoisomer thereof or the pharmaceutically acceptable salt thereof, wherein, the moiety

13. The compound as defined in claim 1, the tautomer thereof, the stereoisomer thereof or the pharmaceutically acceptable salt thereof, wherein, the compound is selected from:

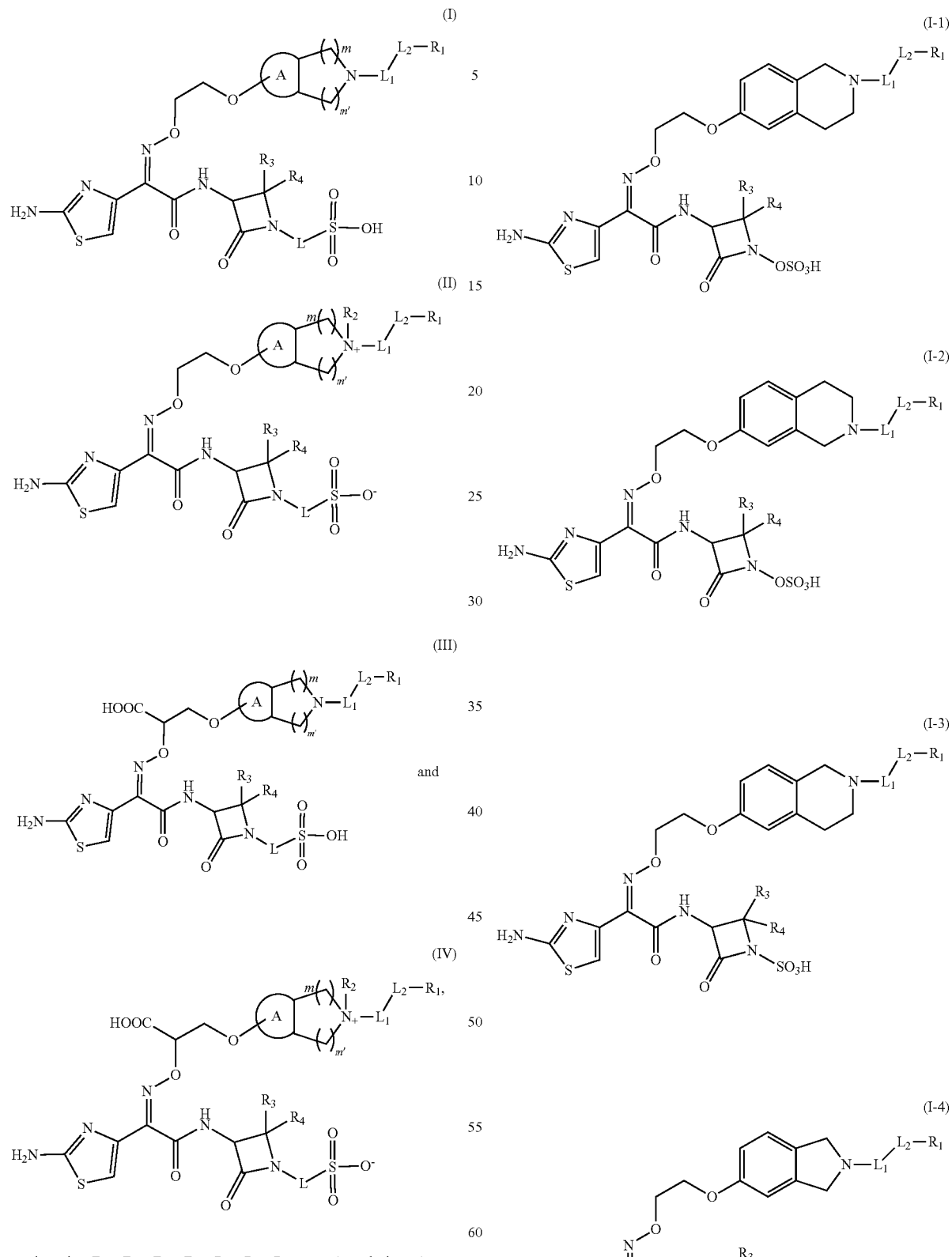
wherein, $R_1$, $R_2$, $R_3$, $R_4$, $L_1$, $L_2$, $L$, $m$, $m'$ and ring A are as defined above.
14. The compound as defined in claim 13, the tautomer thereof, the stereoisomer thereof or the pharmaceutically acceptable salt thereof, wherein, the compound is selected from:

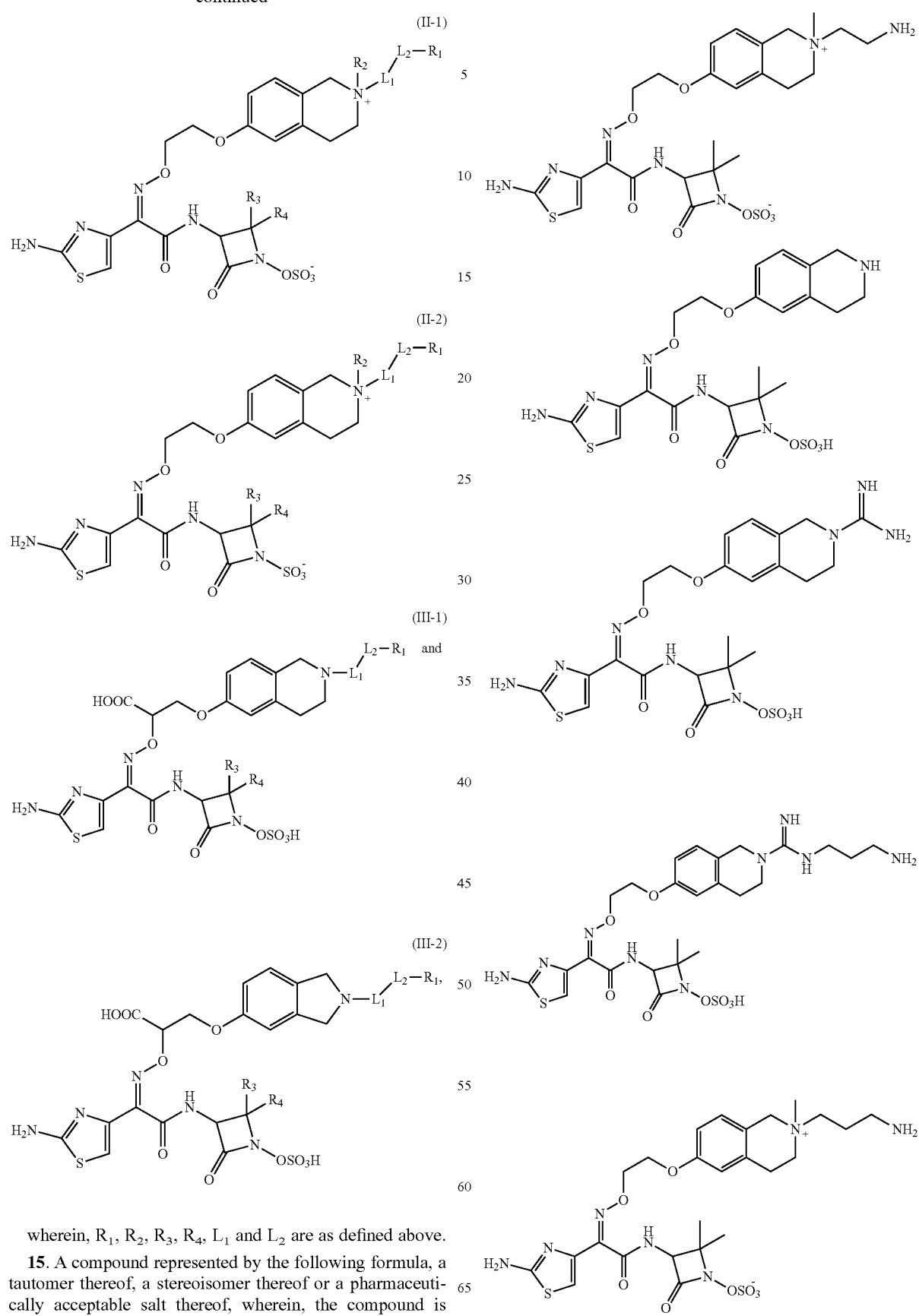
wherein, $R_1$, $R_2$, $R_3$, $R_4$, $L_1$ and $L_2$ are as defined above.
15. A compound represented by the following formula, a tautomer thereof, a stereoisomer thereof or a pharmaceutically acceptable salt thereof, wherein, the compound is selected from 261
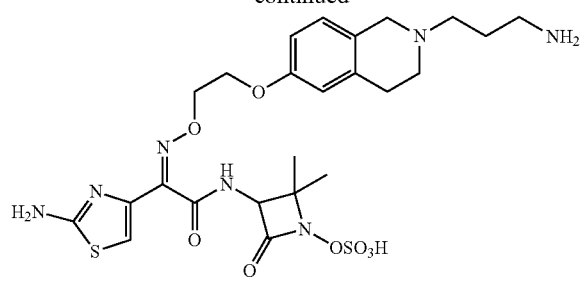
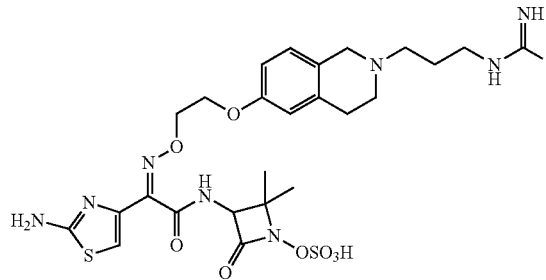
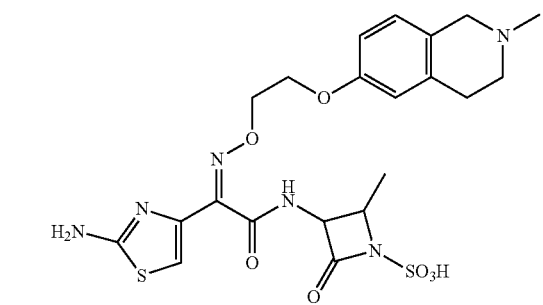
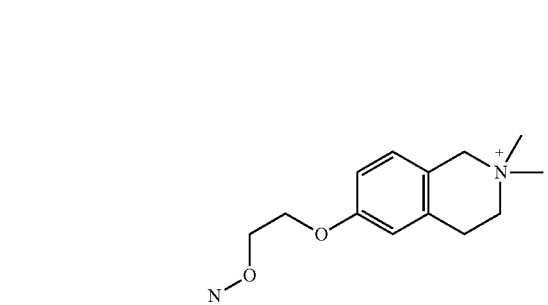
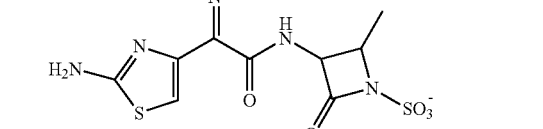
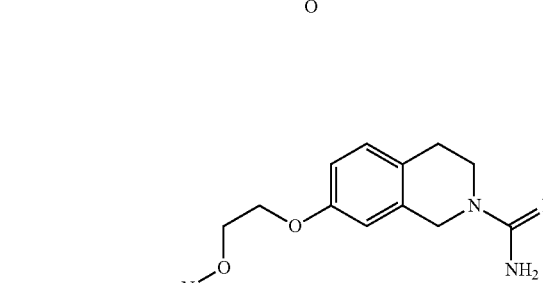
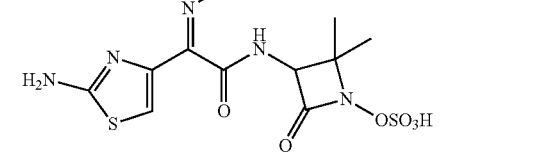
262
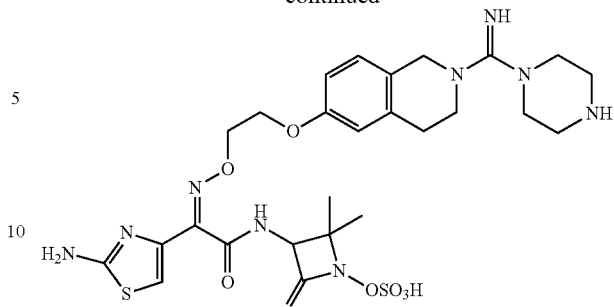
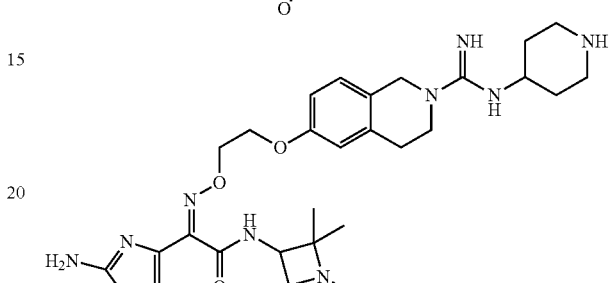
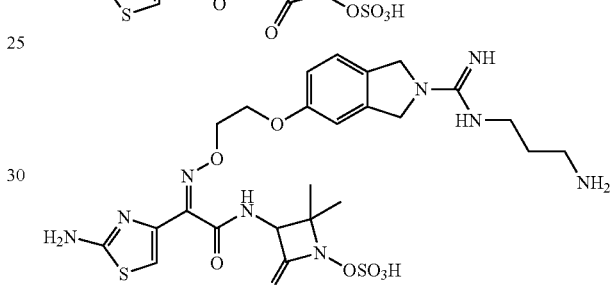
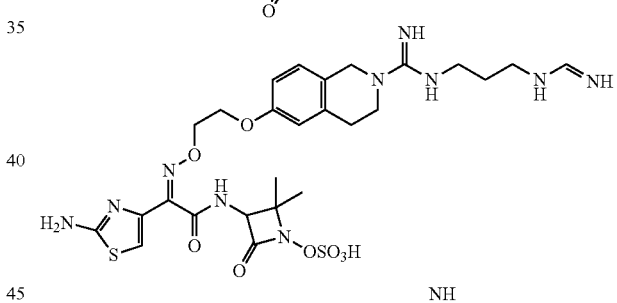
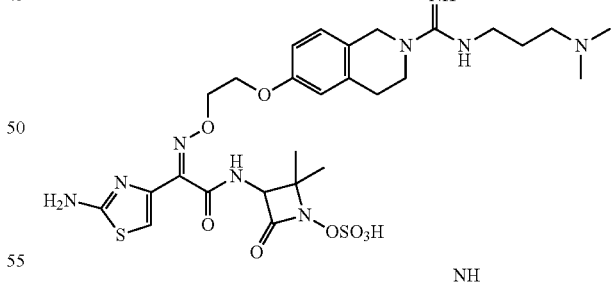
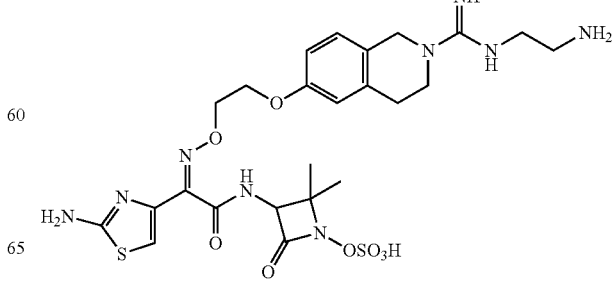

263
-continued
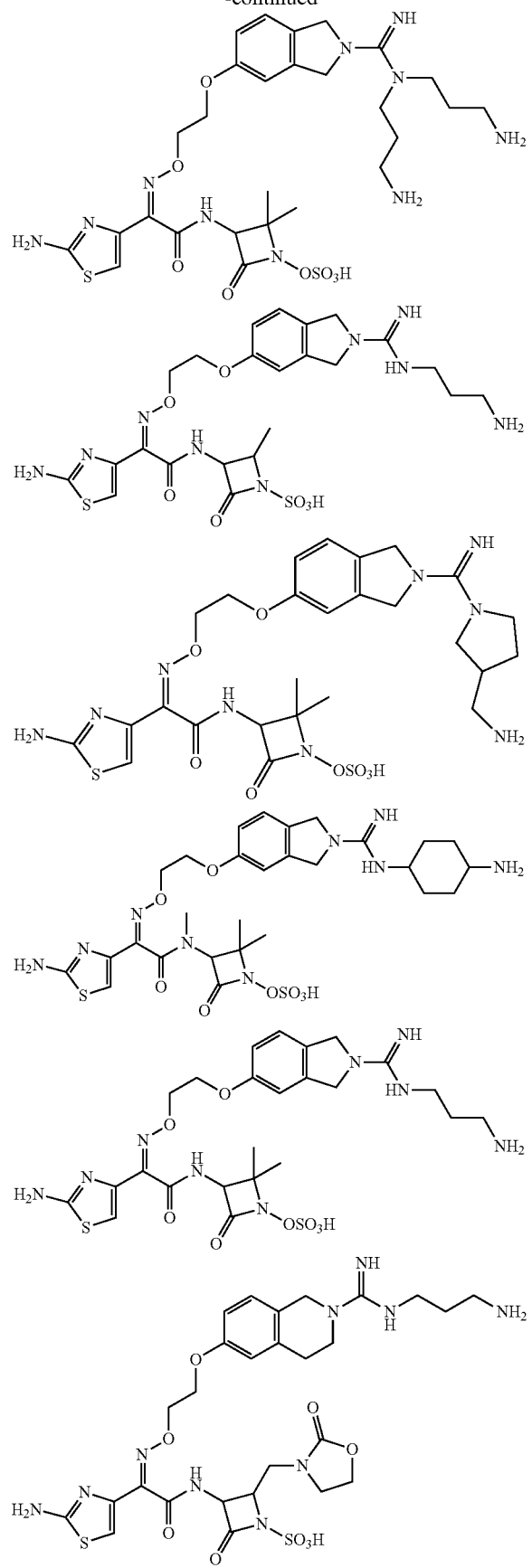
264
-continued
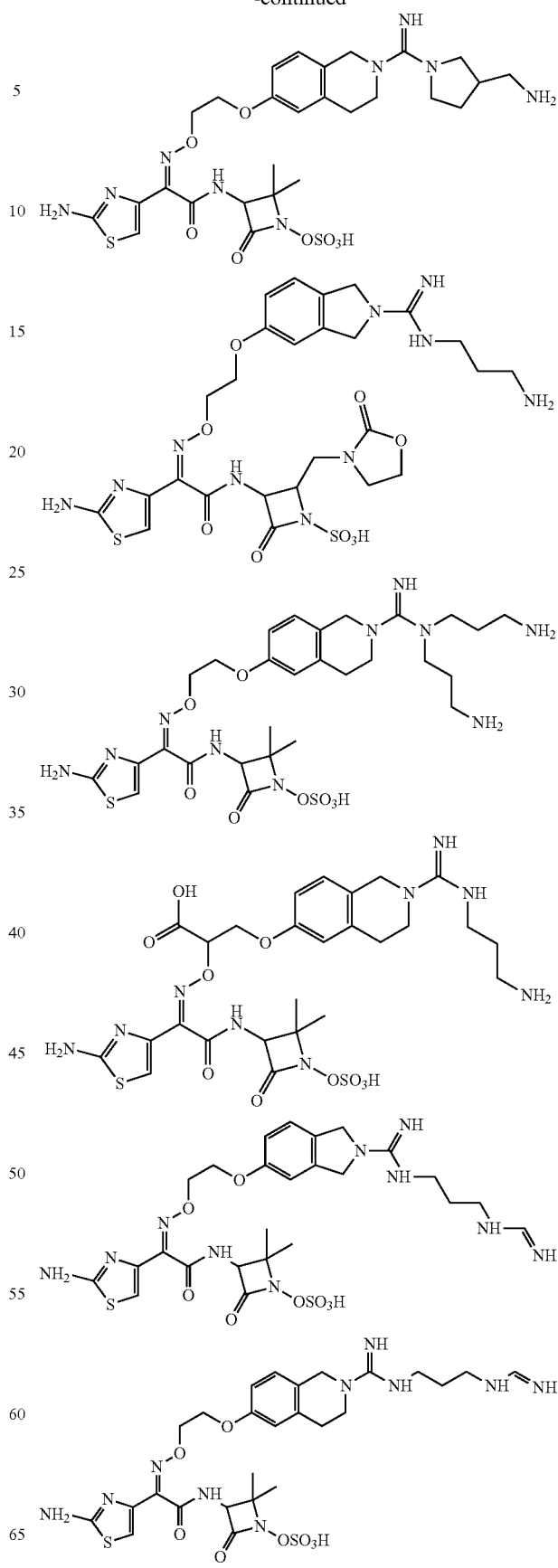

265
-continued
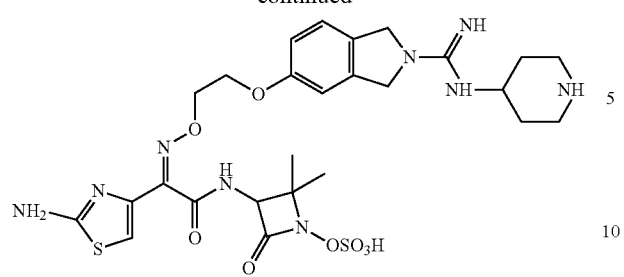
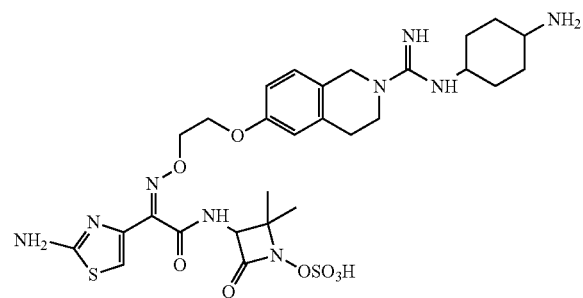
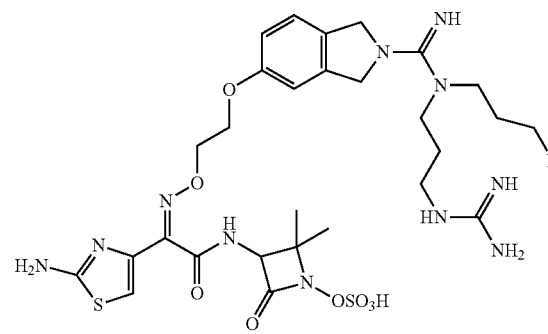
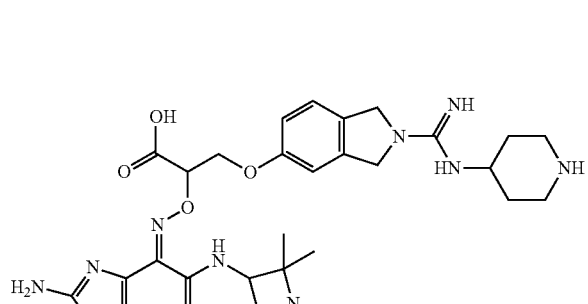
266
-continued
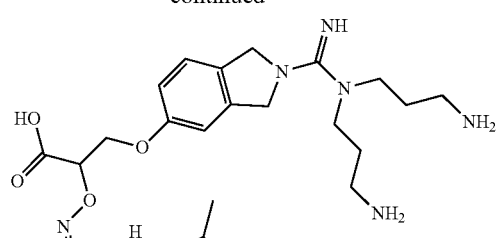
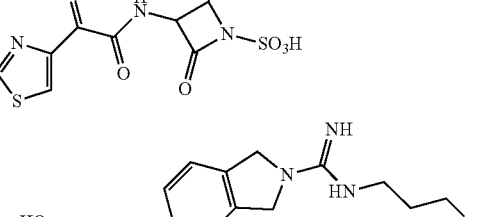
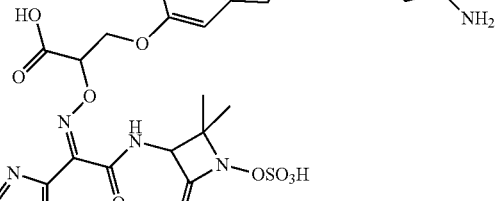
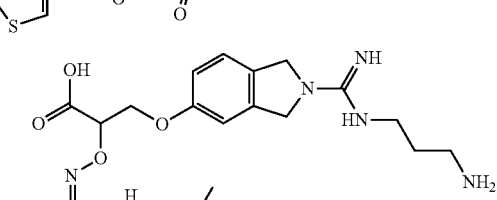
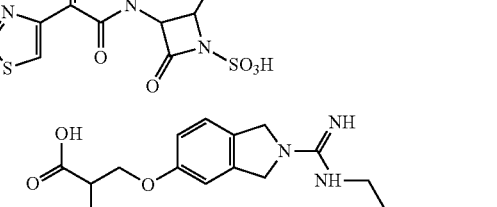
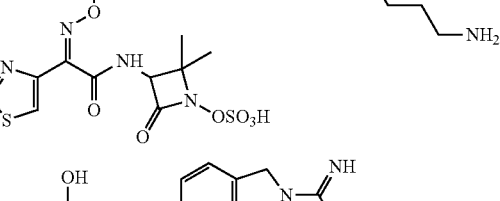
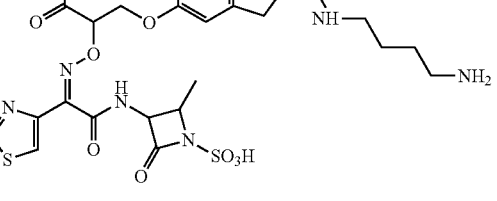
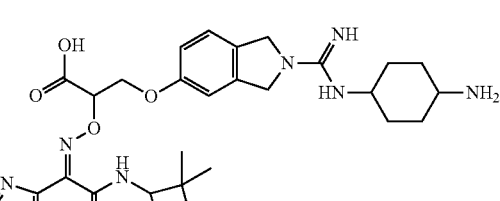

267
-continued
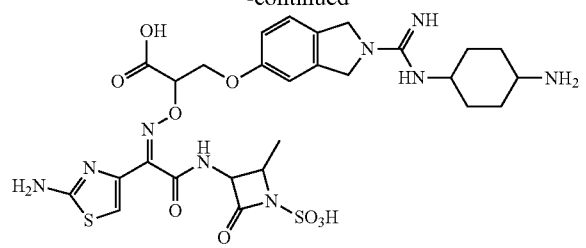
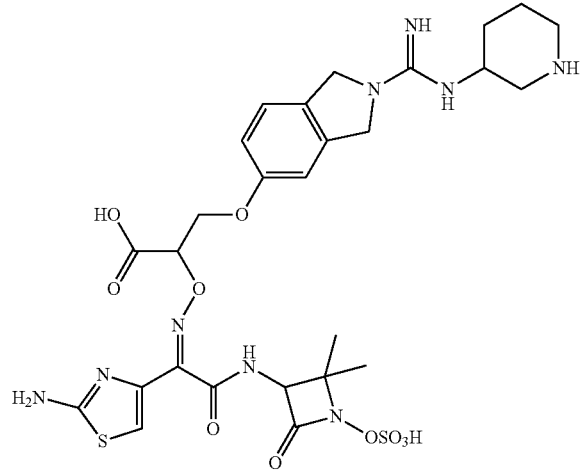
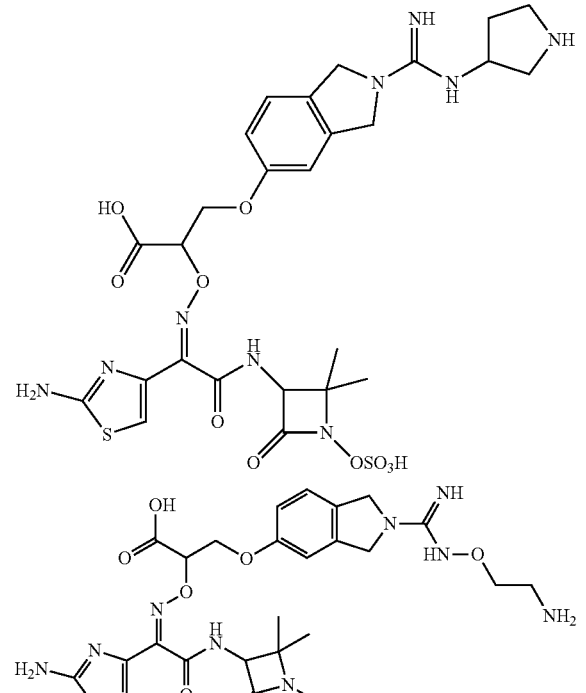
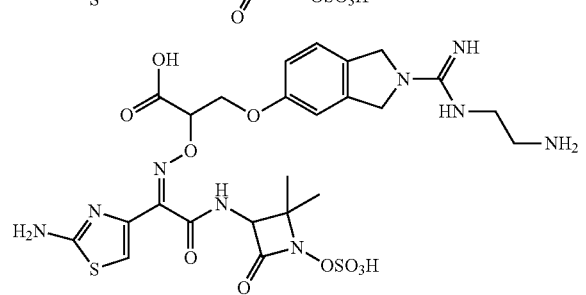
268
-continued
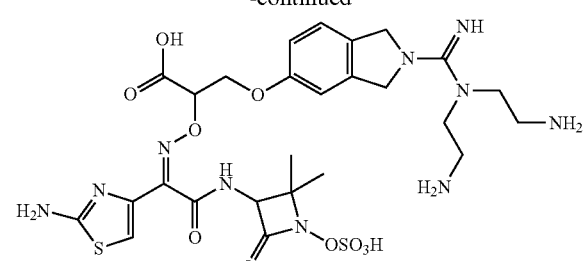
and
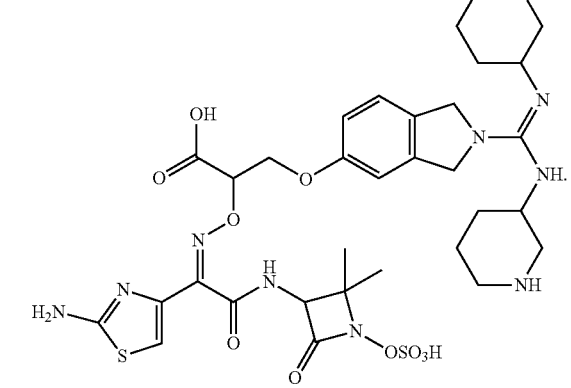
16. The compound as defined in claim 15, the tautomer thereof, the stereoisomer thereof or the pharmaceutically acceptable salt thereof, wherein, the compound is selected from
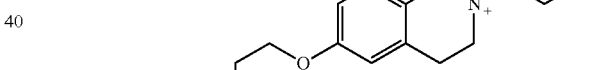
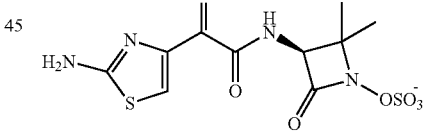
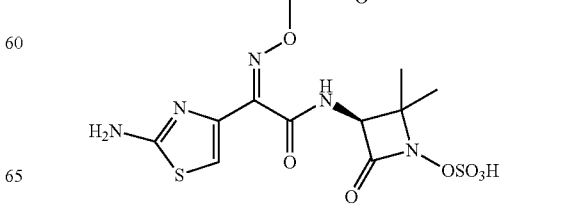

269
-continued
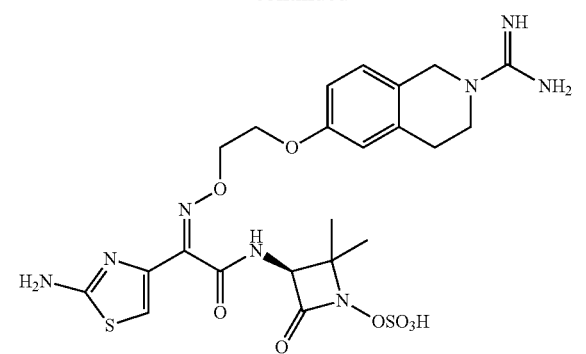
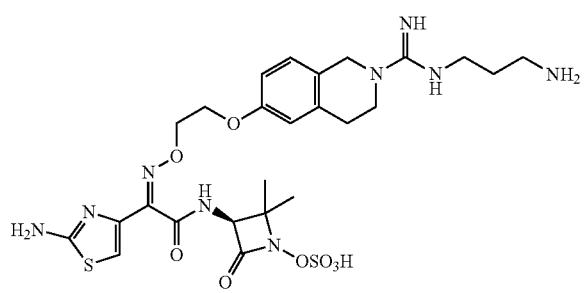
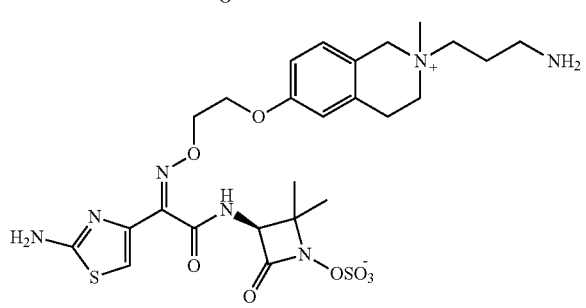
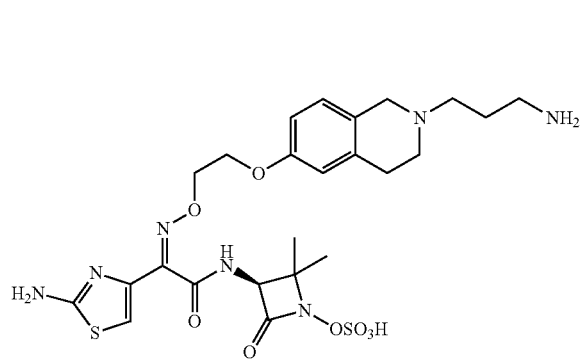
270
-continued
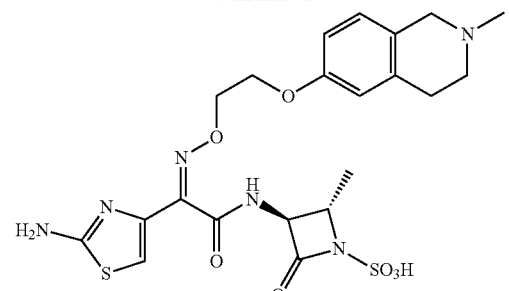
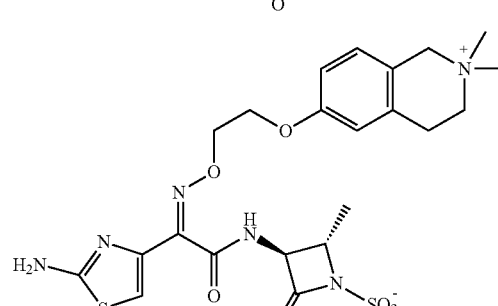
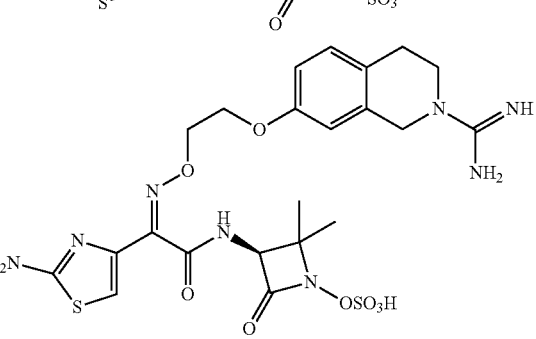
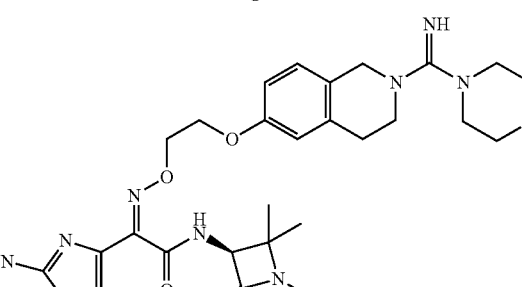
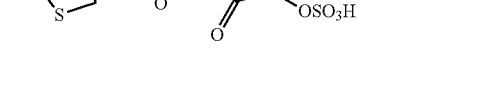

271
-continued
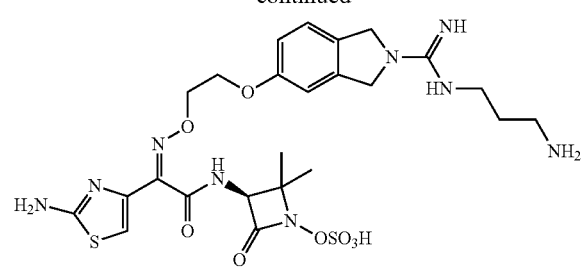
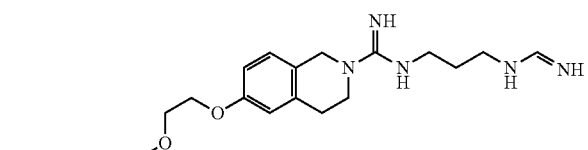
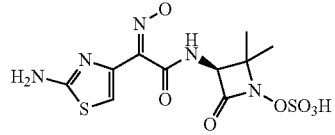
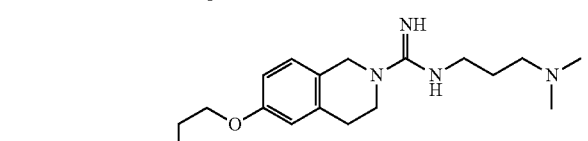
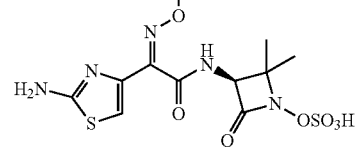
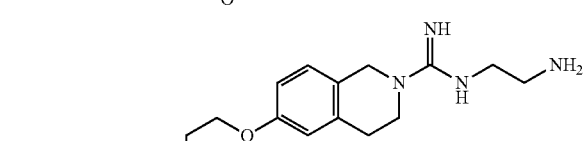
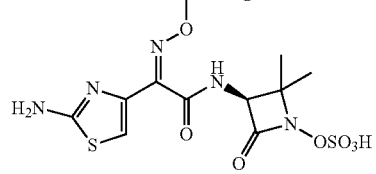
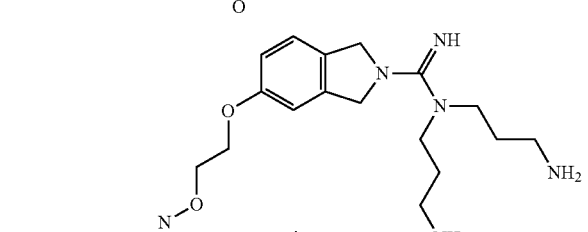
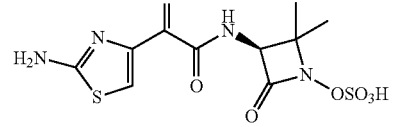
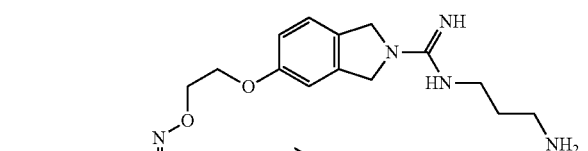
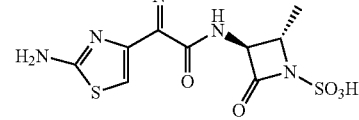
272
-continued
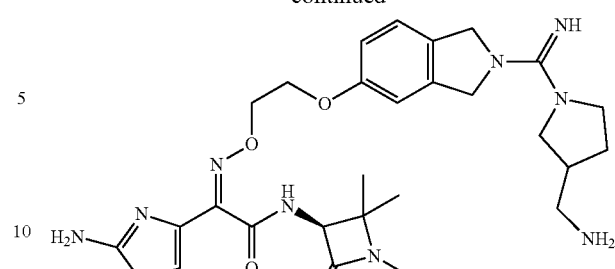
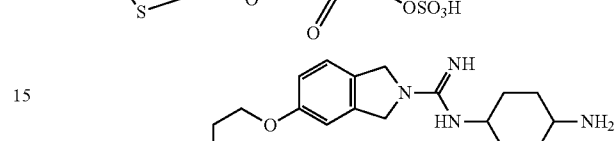
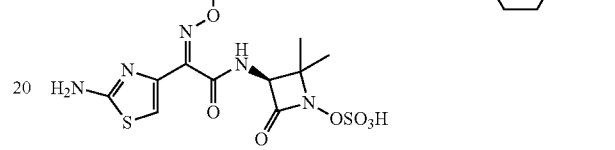
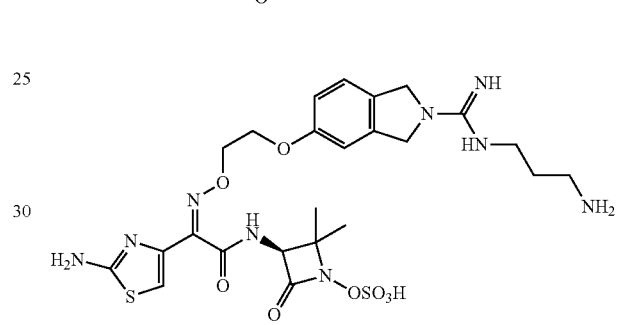
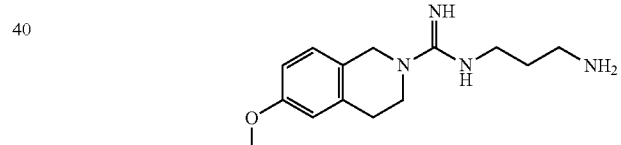
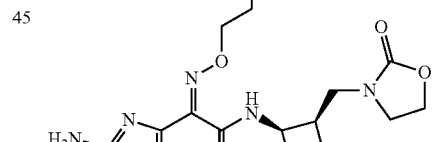
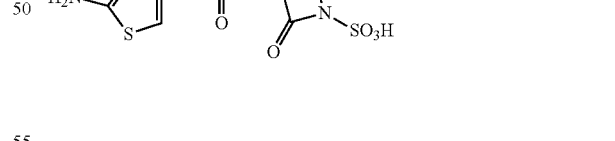
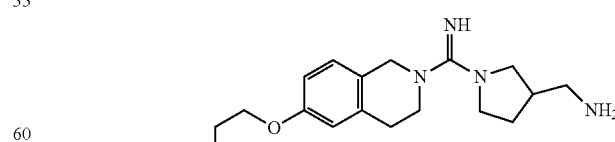
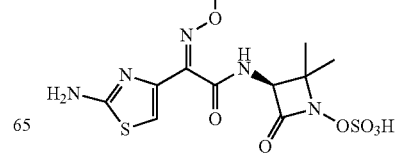

273
-continued
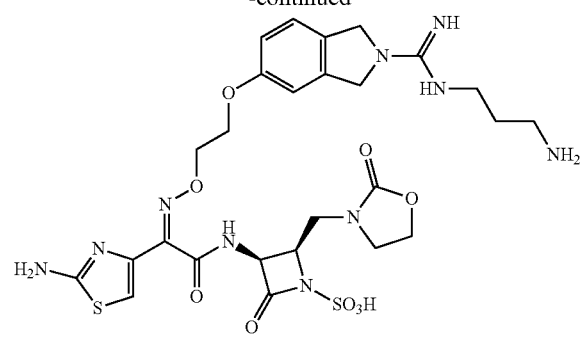
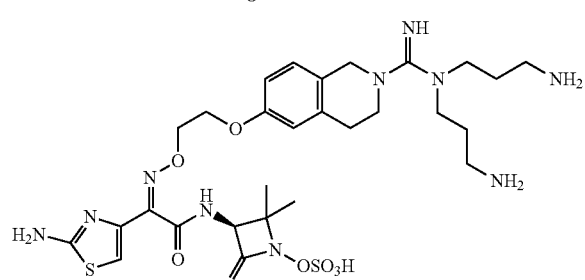
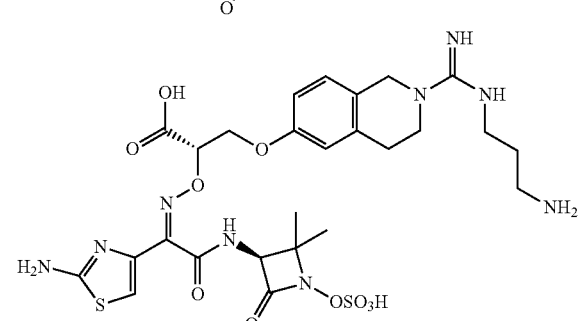
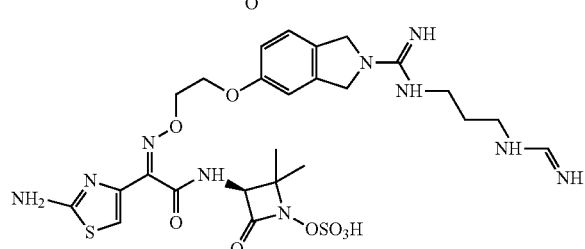
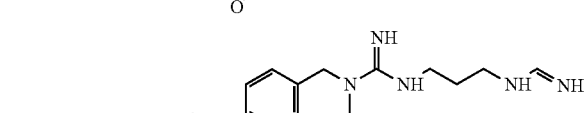
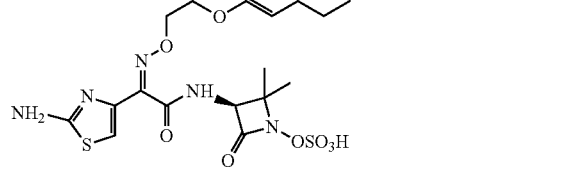
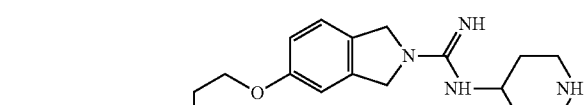
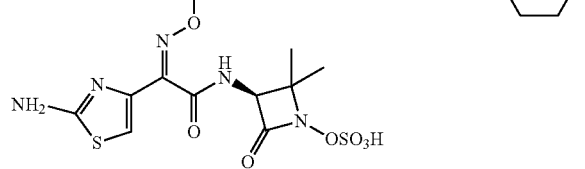
274
-continued
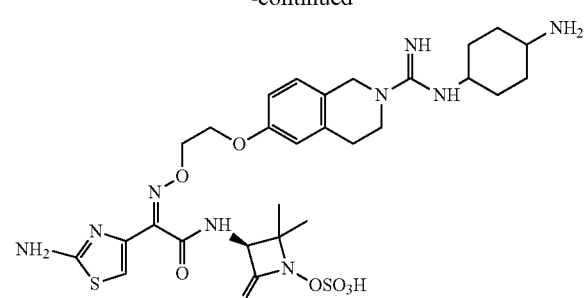
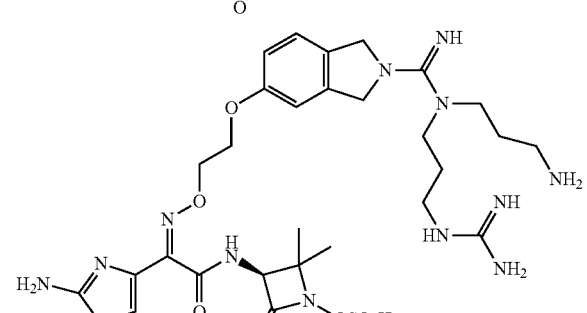
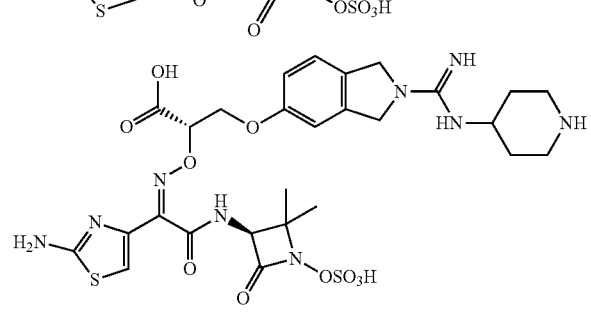
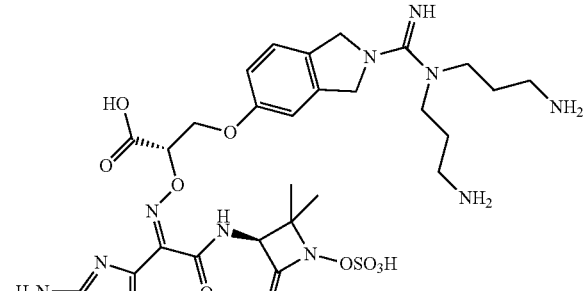
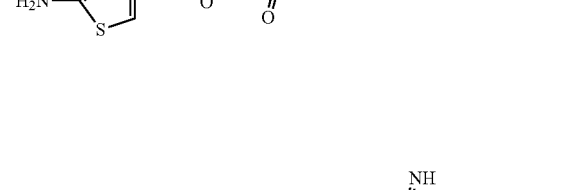
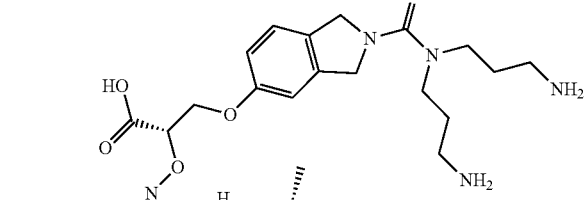
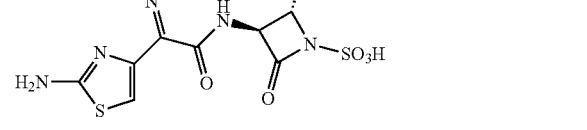

275
-continued
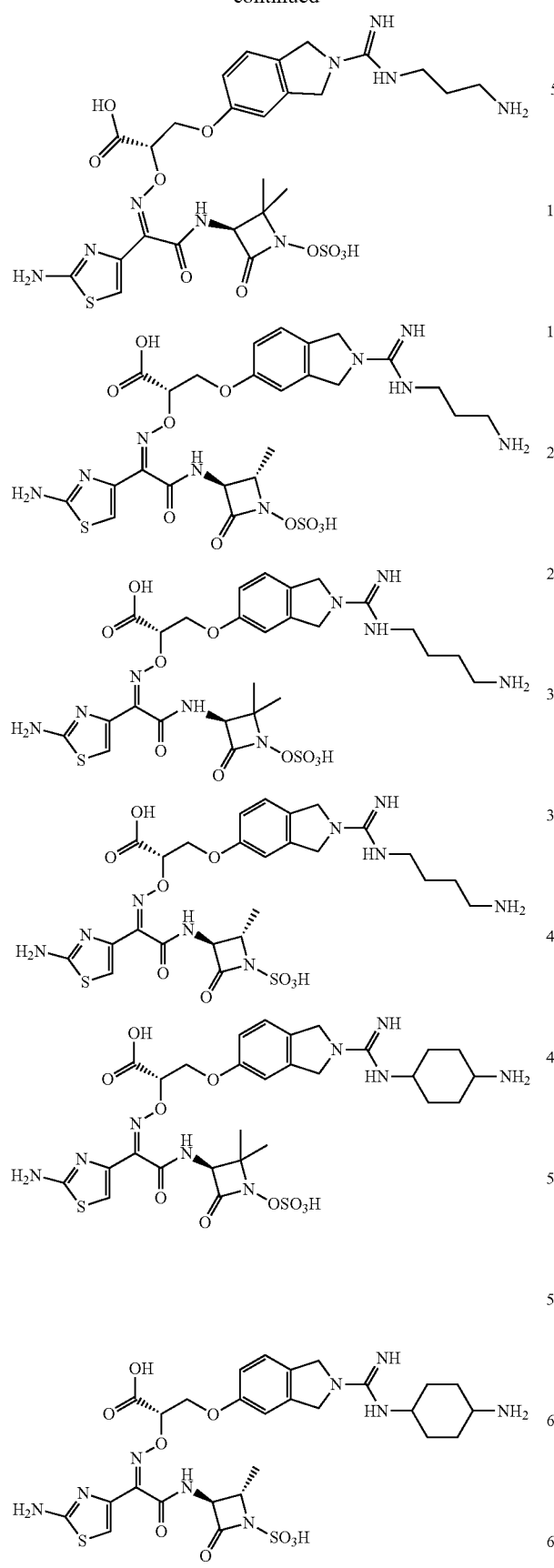
276
-continued
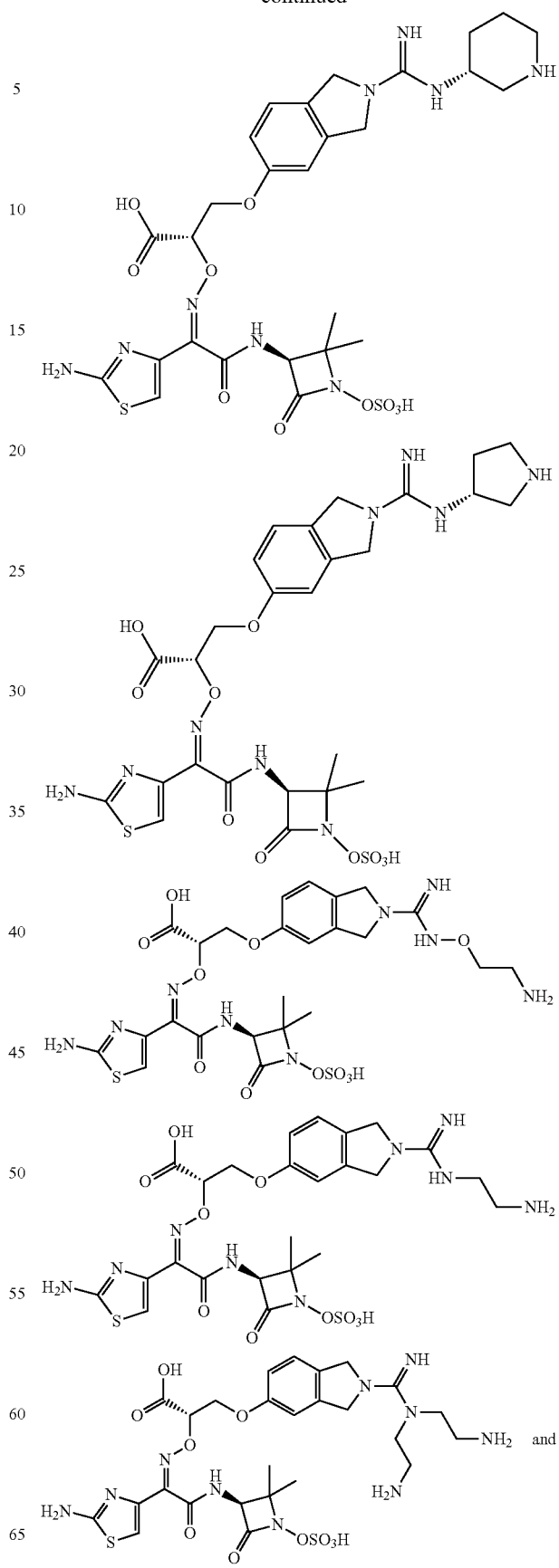

-continued

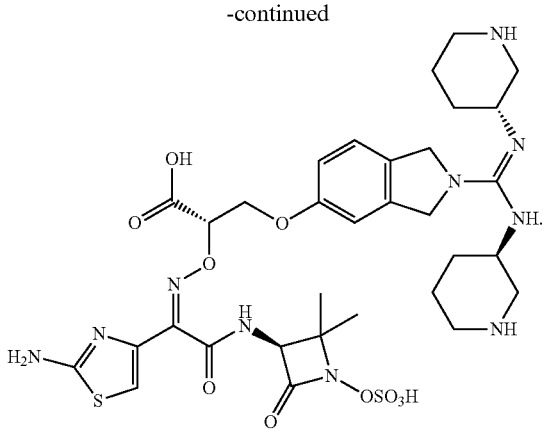

17. A pharmaceutical composition, comprising a therapeutically effective amount of the compound as defined in claim 1, the tautomer thereof, the stereoisomer thereof or the pharmaceutically acceptable salt thereof as an active ingredient and a pharmaceutically acceptable carrier.

18. A method for treating a disease related to bacterial infection in a subject in need thereof, comprising administrating an effective amount of compound as defined in claim 1, the tautomer thereof, the stereoisomer or the pharmaceutically acceptable salt thereof to the subject.

19. The method as defined in claim 18, wherein the bacteria is Gram-negative bacteria.

20. The method as defined in claim 18, wherein the bacteria is *Acinetobacter baumannii*, *Pseudomonas aeruginosa* or *Klebsiella*.

* * * * *